United States Patent
De La Rosa et al.

(10) Patent No.: US 9,029,391 B2
(45) Date of Patent: May 12, 2015

(54) ISOQUINOLINE COMPOUNDS AND METHODS FOR TREATING HIV

(75) Inventors: Martha Alicia De La Rosa, Durham, NC (US); Simon Haydar, Durham, NC (US); Brian Alvin Johns, Durham, NC (US); Emile Johann Velthuisen, Durham, NC (US)

(73) Assignee: ViiV Healthcare UK Limited, Brentford (GB)

( * ) Notice: Subject to any disclaimer, the term of this patent is extended or adjusted under 35 U.S.C. 154(b) by 135 days.

(21) Appl. No.: 13/980,085

(22) PCT Filed: Jan. 23, 2012

(86) PCT No.: PCT/US2012/022161
§ 371 (c)(1),
(2), (4) Date: Jul. 17, 2013

(87) PCT Pub. No.: WO2012/102985
PCT Pub. Date: Aug. 2, 2012

(65) Prior Publication Data
US 2013/0289027 A1     Oct. 31, 2013

Related U.S. Application Data

(60) Provisional application No. 61/435,783, filed on Jan. 24, 2011, provisional application No. 61/510,534, filed on Jul. 22, 2011.

(51) Int. Cl.
| | | |
|---|---|---|
| *A61K 31/472* | (2006.01) | |
| *A61K 31/4725* | (2006.01) | |
| *A61K 31/5377* | (2006.01) | |
| *A61K 31/541* | (2006.01) | |
| *A61K 45/06* | (2006.01) | |
| *C07D 401/12* | (2006.01) | |
| *C07D 217/24* | (2006.01) | |
| *C07D 401/04* | (2006.01) | |
| *C07D 401/14* | (2006.01) | |
| *C07D 405/04* | (2006.01) | |
| *C07D 413/14* | (2006.01) | |
| *C07D 405/14* | (2006.01) | |

(52) U.S. Cl.
CPC ............ *C07D 217/24* (2013.01); *C07D 401/04* (2013.01); *C07D 401/14* (2013.01); *C07D 405/04* (2013.01); *C07D 405/14* (2013.01); *C07D 413/14* (2013.01); *A61K 31/472* (2013.01); *A61K 31/4725* (2013.01); *A61K 31/5377* (2013.01); *A61K 31/541* (2013.01); *A61K 45/06* (2013.01); *C07D 401/12* (2013.01)

(58) Field of Classification Search
CPC . A61K 31/472; A61K 31/4725; C07D 217/24
USPC ............................ 514/307; 544/128; 546/41
See application file for complete search history.

(56) References Cited

U.S. PATENT DOCUMENTS

| | | | |
|---|---|---|---|
| 6,534,520 B2 | 3/2003 | Bedard et al. | |
| 6,841,558 B2 | 1/2005 | Anthony et al. | |

OTHER PUBLICATIONS

Ryu et al. "Crystal Structure of the HIV-Binding Recombinant Fragment of Human CD4." Nature, 1990, vol. 348, pp. 319-426.

*Primary Examiner* — Kendra D Carter
(74) *Attorney, Agent, or Firm* — Robert H. Brink

(57) ABSTRACT

Provided are compounds and pharmaceutically acceptable salts thereof, their pharmaceutical compositions, their methods of preparation, and their use for treating viral infections mediated by a member of the retrovirus family of viruses such as the Human Immunodeficiency Virus (HIV).

5 Claims, No Drawings

ISOQUINOLINE COMPOUNDS AND METHODS FOR TREATING HIV

CROSS-REFERENCE TO RELATED APPLICATIONS

This application is filed pursuant to 35 USC 371 as a United States National Phase Application of International Patent Application Serial No. PCT/US2012/022161 filed on Jan. 23, 2012, which claims priority from 61/435,783 filed on Jan. 24, 2011 and 61/510,534 filed on Jul. 22, 2011 in the United States.

FIELD OF THE INVENTION

The present invention relates to substituted isoquinoline compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Presently, long-term suppression of viral replication with antiretroviral drugs is the only option for treating HIV-1 infection. To date, a number of approved drugs have been shown to greatly increase patient survival. However, therapeutic regimens known as highly active antiretroviral therapy (HAART) are often complex because a combination of different drugs must be administered to the patient to avoid the rapid emergence of drug-resistant HIV-1 variants. Despite the positive impact of HAART on patient survival, drug resistance can still occur.

The emergence of multidrug-resistant (MDR) HIV-1 isolates has serious clinical consequences and must be suppressed with a new drug regimen, known as salvage therapy. Current guidelines recommend that salvage therapy includes at least two, and preferably three, fully active drugs. Typically, first-line therapies combine three to four drugs targeting the viral enzymes RT and protease (PR). One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase (IN) inhibitors. However, resistance to all three new drug classes has already been reported both in vitro and in vivo. Sustained successful treatment of HIV-1-infected patients with antiretroviral drugs will therefore require the continued development of new and improved drugs with new targets and mechanisms of action.

SUMMARY OF THE INVENTION

In accordance with one embodiment of the present invention, there is provided a compound of Formula I:

Formula I

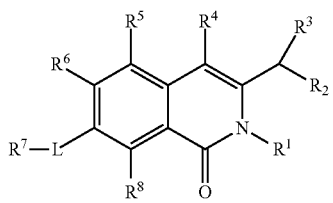

(I)

or a pharmaceutically acceptable salt thereof, wherein:

L is linker that is selected from the group consisting of a direct bond, a branched or straight chain $(C_1\text{-}C_6)$alkylene, $-SO_2-$, and $-C(O)NH-$;

$R^1$ is selected from $(C_1\text{-}C_6)$alkyl or $(C_3\text{-}C_7)$cycloalkyl;

$R^2$ is selected from the group consisting of $-CO_2R^9$, $-C(O)R^{15}$,

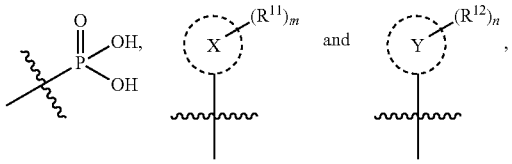

wherein the X and Y rings indicated by a dashed circle are as defined below and wherein the X and Y individual rings each form a monocyclic ring comprised of the indicated rings;

$R^3$ is selected from the group consisting of $(C_1\text{-}C_6)$alkyl, $-OR^{10}$, and $-(C_3\text{-}C_7)$cycloalkyl$(R^{10})$;

$R^4$ is selected from the group consisting of $(C_5\text{-}C_{14})$aryl, $(C_3\text{-}C_7)$cycloalkyl, $(C_2\text{-}C_9)$heterocycle, and $(C_2\text{-}C_9)$heteroaryl, wherein the heterocycle and heteroaryl each comprise one to three heteroatoms selected from S, N and O;

$R^5$, $R^6$, $R^7$, and $R^8$ are independently selected from $-H$, $(C_1\text{-}C_6)$alkyl, $(C_1\text{-}C_6)$alkoxy, halo, nitrile, $(C_3\text{-}C_7)$cycloalkyl, $-OR^{10}(C_5\text{-}C_{14})$aryl, $-OR^{10}R^{14}$, $-OR^{10}(C_5\text{-}C_{14})$aryl$(R^{11})_m$, $-R^{10}(Y)(R^{12})_n$, $-OR^{10}R^{17}$, $-R^{10}R^{17}$, $-R^{17}R^{15}$, $-OR^{10}(R^{14})_q$, $-OR^{10}(Y)$, $-OR^{10}R^{18}$, $-OSO_2R^{15}$, $-R^{15}$, $-(C_5\text{-}C_{14})$aryl, $-(Y)$, $-(Y)(R^{12})_n$, $-C(O)(Y)$, $-C(O)R^{15}$, $-R^{10}(C_5\text{-}C_{14})$aryl, $-R^{10}R^{15}$, and $-(C_5\text{-}C_{14})$aryl$R^{15}$;

$R^9$ is independently selected from $-H$ or $(C_1\text{-}C_6)$alkyl;

$R^{10}$ is $(C_1\text{-}C_6)$alkyl;

$R^{11}$, $R^{12}$, and $R^{13}$ are independently selected from the group consisting of $-H$, $(C_1\text{-}C_6)$alkyl, $(C_1\text{-}C_6)$alkoxy, oxo, halo, $-R^{10}(R^{14})_q$, $-OR^{10}(R^{14})_q$, $-SO_2R^{10}$; $-C(O)R^{10}$, $-C(O)R^{15}$, and $-R^{10}R^{17}$;

$R^{14}$ is halo;

$R^{15}$ is $-N(R^{16})_2$;

$R^{16}$ is independently selected from the group consisting of $-H$, $(C_1\text{-}C_6)$alkyl, hydroxyl, $-SO_2R^{10}$, $-SO_2N(R^{10})_2$, $-C(O)NHR^{10}$, $-C(O)R^{18}$, and $-(C_5\text{-}C_{14})$aryl$(R^{11})$;

$R^{17}$ is $-OR^9$;

$R^{18}$ is $-CO_2R^9$;

X is $(C_5\text{-}C_{14})$aryl;

Y is independently selected from $(C_2\text{-}C_9)$heterocycle or $(C_2\text{-}C_9)$heteroaryl, each having one to four heteroatoms selected from S, N and O, wherein X and Y are optionally substituted by one to four $R^{11}$ groups;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

In another embodiment of the present invention, there is provided a compound of Formula I:

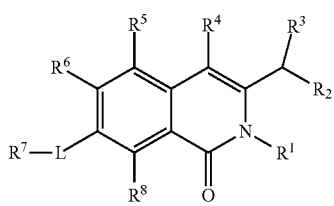

Formula I or a pharmaceutically acceptable salt thereof, wherein:

L is linker that is selected from the group consisting of a direct bond, a branched or straight chain $(C_1-C_6)$alkylene, —$SO_2$—, and —C(O)NH—;

$R^1$ is selected from $(C_1-C_6)$alkyl or $(C_3-C_7)$cycloalkyl;

$R^2$ is selected from the group consisting of —$CO_2R^9$, —$C(O)R^{15}$,

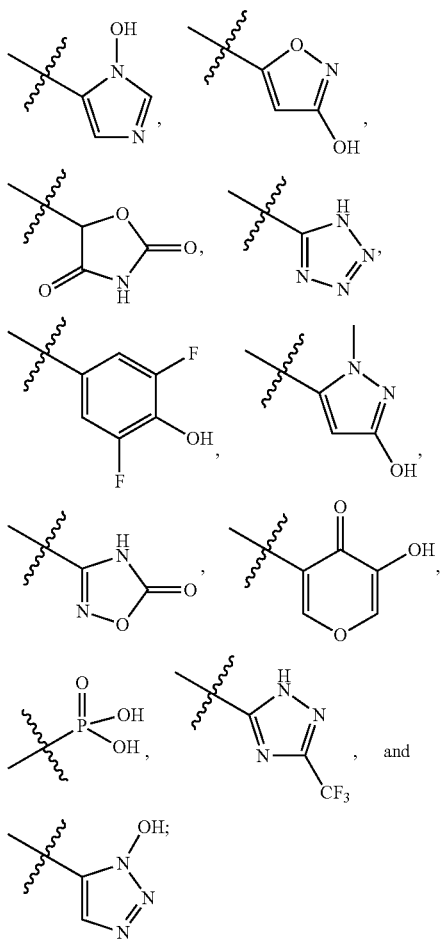

$R^3$ is selected from the group consisting of $(C_1-C_6)$alkyl, —$OR^{10}$, and —$(Z)R^{10}$;

$R^4$ is selected from the group consisting of —$NR^9(X)$, tetrahydropyridoquinolinyl,

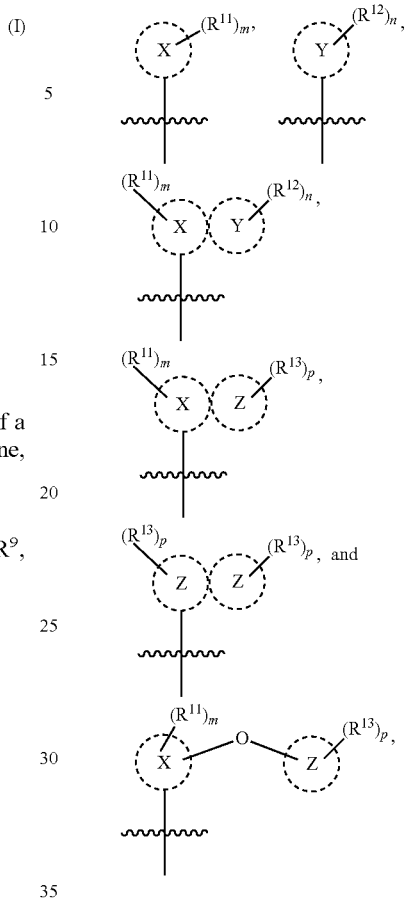

wherein the X, Y, Z, XY, XZ, and ZZ rings indicated by a dashed circle are as defined below and wherein the XY, XZ, ZZ rings each together form a bicyclic fused ring system comprised of the indicated rings and wherein the X, Y, and Z individual rings each form a monocyclic ring comprised of the indicated rings;

$R^5$, $R^6$, and $R^7$ are independently selected from the group consisting of —H, —OH, $(C_1-C_6)$alkyl, $(C_1-C_6)$alkoxy, halo, nitrile, $(C_3-C_7)$cycloalkyl, —$OR^{10}(X)$, —$OR^{10}R^{14}$, —$OR^{10}(X)(R^{11})_m$, —$R^{10}(Y)(R^{12})_n$, —$OR^{10}R^{17}$, —$R^{10}R^{17}$, —$R^{17}R^{15}$, —$OR^{10}(R^{14})_q$, —$OR^{10}(Y)$, —$OR^{10}R^{18}$, —$OSO_2R^{15}$, —$R^{15}$, —(X), —(Y), —$(Y)(R^{12})_n$, —C(O)(Y), —$C(O)R^{15}$, —$R^{10}(X)$, —$R^{10}R^{15}$, and —$(X)R^{15}$;

$R^9$ is independently selected from the group consisting of H and $(C_1-C_6)$alkyl;

$R^{10}$ is $(C_1-C_6)$alkyl;

$R^{11}$, $R^{12}$, and $R^{13}$ are independently selected from the group consisting of —H, $(C_1-C_6)$alkyl, $(C_1-C_6)$alkoxy, oxo, halo, —$R^{10}(R^{14})_q$, —$OR^{10}(R^{14})_q$, —$SO_2R^{10}$, —$C(O)R^{10}$, —$C(O)R^{15}$, and —$R^{10}R^{17}$;

$R^{14}$ is halo;

$R^{15}$ is —$N(R^{16})_2$;

$R^{16}$ is independently selected from the group consisting of —H, $(C_1-C_6)$alkyl, hydroxyl, —$SO_2R^{10}$, —$SO_2N(R^{10})_2$, —$C(O)NHR^{10}$, —$C(O)R^{18}$, and —$(X)(R^{11})$;

$R^{17}$ is —$OR^9$;

$R^{18}$ is —$CO_2R^9$;

X is $(C_5-C_{14})$aryl;

Y is independently selected from $(C_2-C_9)$heterocycle or $(C_2-C_9)$heteroaryl, each having one to three heteroatoms selected from S, N and O;

Z is $(C_3-C_7)$cycloalkyl;
m is zero or an integer selected from 1, 2, 3, or 4;
n is zero or an integer selected from 1, 2, or 3;
p is zero or an integer selected from 1, 2, or 3; and
q is an integer selected from 1, 2, or 3.

In another embodiment of the present invention, there is provided a compound of Formula I:

Formula I

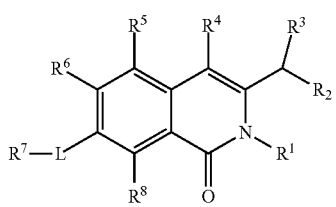

or a pharmaceutically acceptable salt thereof, wherein:

L is linker that is selected from the group consisting of a direct bond, a branched or straight chain $(C_1-C_6)$alkylene, $-SO_2-$, and $-C(O)NH-$;

$R^1$ is selected from the group consisting of $-H$, $(C_1-C_6)$alkyl and $(C_3-C_7)$cycloalkyl;

$R^2$ is selected from the group consisting of $-CO_2R^9$, $-C(O)R^{15}$,

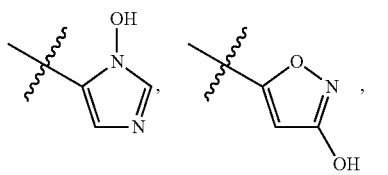

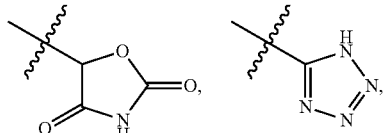

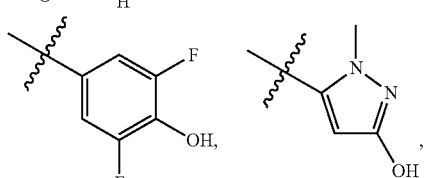

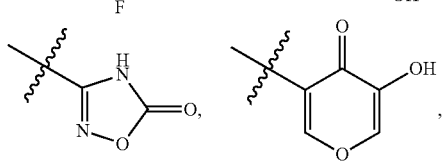

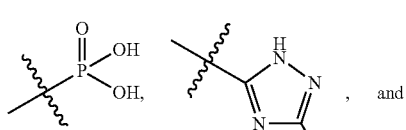, and

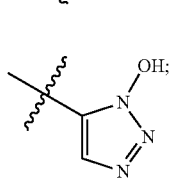

$R^3$ is selected from the group consisting of $(C_1-C_6)$alkyl, $-OR^{10}$, and $-(C_3-C_7)$cycloalkyl$R^{10}$;

$R^4$ is selected from the group consisting of:

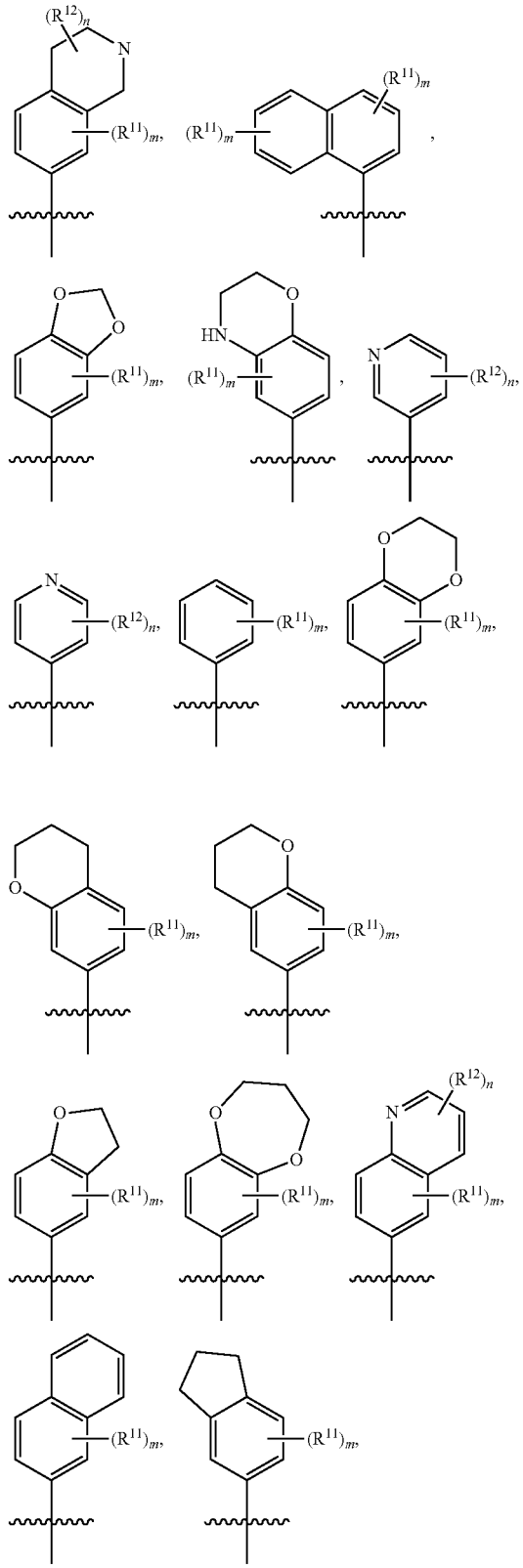

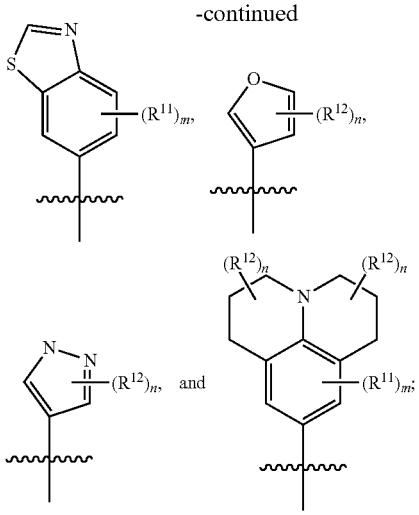

$R^5$, $R^6$, $R^7$, and $R^8$ are independently selected from —H, —OH, $(C_1\text{-}C_6)$alkyl, $(C_1\text{-}C_6)$alkoxy, halo, nitrile, $(C_3\text{-}C_7)$ cycloalkyl, —$OR^{10}(X)$, —$OR^{10}R^{14}$, —$OR^{10}(X)(R^{11})_m$, —$R^{10}(Y)(R^{12})_n$, —$OR^{10}R^{17}$, $R^{10}R^{17}$, $R^{17}R^{15}$, —$OR^{10}$ $(R^{14})_q$, —$OR^{10}(Y)$, —$OR^{10}R^{18}$, —$OSO_2R^{15}$, —$R^{15}$, —(X), —(Y), —$(Y)(R^{12})_n$, —$C(O)(Y)$, —$C(O)R^{15}$, —$R^{10}(X)$, —$R^{10}R^{15}$, and —$(X)R^{15}$;

$R^9$ is independently selected from the group consisting of —H and $(C_1\text{-}C_6)$alkyl;

$R^{10}$ is $(C_1\text{-}C_6)$alkyl;

$R^{11}$, $R^{12}$, and $R^{13}$ are independently selected from the group consisting of —H, $(C_1\text{-}C_6)$alkyl, $(C_1\text{-}C_6)$alkoxy, oxo, halo, —$R^{10}(R^{14})_q$, —$OR^{10}(R^{14})_q$, —$SO_2R^{10}$; —$C(O)R^{10}$, —$C(O)R^{15}$, and —$R^{10}R^{17}$;

$R^{14}$ is halo;

$R^{15}$ is —$N(R^{16})_2$;

$R^{16}$ is independently selected from the group consisting of —H, $(C_1\text{-}C_6)$alkyl, hydroxyl, —$SO_2R^{10}$, —$SO_2N(R^{10})_2$, —$C(O)NHR^{10}$, —$C(O)R^{18}$, and —$(X)(R^{11})$;

$R^{17}$ is —$OR^9$;

$R^{18}$ is —$CO_2R^9$;

X is $(C_5\text{-}C_{14})$aryl;

Y is independently selected from $(C_2\text{-}C_9)$heterocycle or $(C_2\text{-}C_9)$heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

In another embodiment of the present invention, there is provided a compound of Formula (II):

Formula II

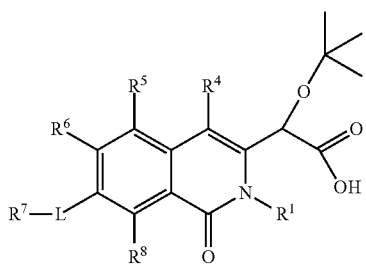

(II)

or a pharmaceutically acceptable salt thereof, wherein:

L is linker that is selected from the group consisting of a direct bond, methylene, —$SO_2$—, and —$C(O)NH$—;

X is phenyl;

$R^4$ is selected from the group consisting of phenyl, dihydrobenzopyranyl, naphthalenyl, pyridinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, and tetrahydropyridoquinolinyl;

$R^5$, $R^6$, and $R^7$ are independently selected from H, methyl, ethyl, propyl, butyl, hydroxyl, fluoro, chloro, bromo, methoxy, ethoxy, propoxy, methoxyethoxy, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, and dimethylisoxazolyl;

$R^9$ is independently selected from the group consisting of —H, methyl, ethyl, propyl, isopropyl, butyl, isobutyl, tert-butyl, pentyl, and septyl;

$R^{10}$ is selected from the group consisting of —H, methyl, ethyl, propyl, isopropyl, butyl, isobutyl, tert-butyl, penty, and septyl;

$R^{11}$, $R^{12}$, and $R^{13}$ are independently selected from the group consisting of —H, methyl, ethyl, methoxy, ethoxy, oxo, chloro, fluoro, bromo, trifluoromethyl, trifluoromethoxy, methylsulfonyl, —$C(O)$methyl, —$C(O)R^{15}$, and methylmethoxy;

$R^{14}$ is selected from the group consisting of chloro, fluoro, and bromo.

$R^{15}$ is —$N(R^{16})_2$;

$R^{16}$ is independently selected from the group consisting of —H, methyl, ethyl, hydroxyl, methylsulfonyl, —$SO_2N$(methyl)$_2$, —$C(O)NH$methyl, —$C(O)R^{18}$, and —$(X)(R^{11})$;

$R^{17}$ is —$OR^9$; and $R^{18}$ is —$CO_2R^9$.

Also provided is a pharmaceutical composition comprising a pharmaceutically acceptable carrier or excipient and a therapeutically effective amount of a compound of Formula I, or a pharmaceutically acceptable salt thereof.

Also provided are synthetic intermediates, methods for preparing the compounds of Formula I, or a pharmaceutically acceptable salt or solvate thereof, and compositions thereof and for their therapeutic uses.

In some embodiments, provided is a method for treating a viral infection in a patient mediated at least in part by a virus in the retrovirus family of viruses, comprising administering to said patient a composition comprising a compound of any of Formula I, or a pharmaceutically acceptable salt thereof. In some embodiments, the viral infection is mediated by the HIV virus. Those and other embodiments are further described in the text that follows.

In another aspect, a particular embodiment of the present invention provides a method of treating a subject infected with HIV comprising administering to the subject a therapeutically effective amount of the compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of the compound of Formula I, or a pharmaceutically acceptable salt thereof.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to a monovalent saturated aliphatic hydrocarbyl group having from 1 to 14 carbon atoms and, in some embodiments, from 1 to 6 carbon atoms. "$(C_x-C_y)$alkyl" refers to alkyl groups having from x to y carbon atoms. The term "alkyl" includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylidene" or "alkylene" refers to divalent saturated aliphatic hydrocarbyl groups having from 1 to 10 carbon atoms and, in some embodiments, from 1 to 6 carbon atoms. "$(C_{u-v})$alkylene" refers to alkylene groups having from u to v carbon atoms. The alkylidene and alkylene groups include branched and straight chain hydrocarbyl groups. For example "$(C_{1-6})$alkylene" is meant to include methylene, ethylene, propylene, 2-methypropylene, pentylene, and so forth.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $(C_x-C_y)$alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}$C(O)alkyl, —$NR^{20}$C(O)cycloalkyl, —$NR^{20}$C(O)alkenyl, —$NR^{20}$C(O)alkynyl, —$NR^{20}$C(O)aryl, —$NR^{20}$C(O)heteroaryl, and —$NR^{20}$C(O)heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$ where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)$NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8tetrahydronaphthalene-2-yl is an aryl group as its point of attachment is at the 2-position of the aromatic phenyl ring).

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below:

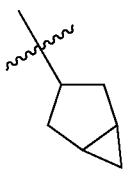 [SMILES: *C1CC2CC2C1]

bicyclohexyl, and

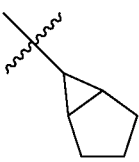 [SMILES: *C1C2CCCC12]

bicyclohexyl.

"(C$_u$-C$_v$)cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

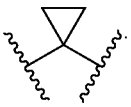 [SMILES: *C1(*)CC1]

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

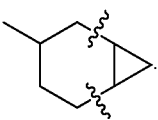

"Halo" or "halogen" refers to fluoro, chloro, bromo, and iodo.

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., C$_3$-C$_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

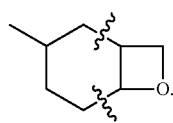

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {N$^+$—O$^-$} and sulfur such as S(O) and S(O)$_2$, and the quaternized form of any basic nitrogen.

"Oxazolidinone" refers to a 5-membered heterocyclic ring containing one nitrogen and one oxygen as heteroatoms and also contains two carbons and is substituted at one of the two carbons by a carbonyl group as exemplified by any of the following structures, wherein the oxazolidinone groups shown here are bonded to a parent molecule, which is indicated by a wavy line in the bond to the parent molecule:

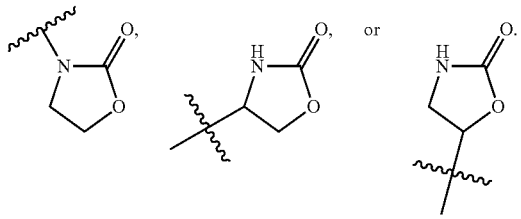 [SMILES: *N1CCOC1=O ; *C1COC(=O)N1 ; *C1CNC(=O)O1]

"Racemates" refers to a mixture of enantiomers. In an embodiment of the invention, the compounds of Formulas I or II, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species (Eliel, E. and Wilen, S. (1994) Stereochemistry of Organic Compounds, John Wiley & Sons, Inc.). One skilled in the art will recognize that upon installing a nonsymmetrical R$^4$, the formation of atropisomers is possible. In addition, once a second chiral center is installed in a given molecule containing an atropisomer, the two chiral elements taken together can create diastereomeric and enantiomeric stereochemical species. Depending upon the substitution about the R$^4$ axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C(R$^x$)$_2$—", it should be understood that the two R$^x$ groups can be the same, or they can be different if R$^x$ is defined as having more than one possible identity. In addition, certain substituents are drawn as —R$^x$R$^y$, where the "—" indicates a bond adjacent to the parent molecule and R$^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In accordance with one preferred embodiment of the present invention, there is provided a compound of Formula I:

Formula I

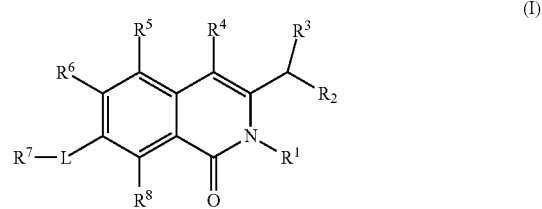

(I)

or a pharmaceutically acceptable salt thereof, wherein:

L is linker that is selected from the group consisting of a direct bond, a branched or straight chain $(C_1-C_6)$alkylene, $-SO_2-$, and $-C(O)NH-$;

$R^1$ is selected from $(C_1-C_6)$alkyl or $(C_3-C_7)$cycloalkyl;

$R^2$ is selected from the group consisting of $-CO_2R^9$, $-C(O)R^15$,

[chemical structures shown]

wherein the X and Y rings indicated by a dashed circle are as defined below and wherein the X and Y individual rings each form a monocyclic ring comprised of the indicated rings;

$R^3$ is selected from the group consisting of $(C_1-C_6)$alkyl, $-OR^{10}$, and $-(C_3-C_7)$cycloalkyl$(R^{10})$;

$R^4$ is selected from the group consisting of $(C_5-C_{14})$aryl, $(C_3-C_7)$cycloalkyl, $(C_2-C_9)$heterocycle, and $(C_2-C_9)$heteroaryl, wherein the heterocycle and heteroaryl each comprise one to three heteroatoms selected from S, N and O;

$R^5$, $R^6$, $R^7$, and $R^8$ are independently selected from $-H$, $(C_1-C_6)$alkyl, $(C_1-C_6)$alkoxy, halo, nitrile, $(C_3-C_7)$cycloalkyl, $-OR^{10}(C_5-C_{14})$aryl, $-OR^{10}R^{14}$, $-OR^{10}(C_5-C_{14})$aryl$(R^{11})_m$, $-R^{10}(Y)(R^{12})_n$, $-OR^{10}R^{17}$, $-R^{10}R^{17}$, $-R^{17}R^{15}$, $-OR^{10}(R^{14})_q$, $-OR^{10}(Y)$, $-OR^{10}R^{18}$, $-OSO_2R^{15}$, $-R^{15}$, $-(C_5-C_{14})$aryl, $-(Y)$, $-(Y)(R^{12})_n$, $-C(O)(Y)$, $-C(O)R^{15}$, $-R^{10}(C_5-C_{14})$aryl, $-R^{10}R^{15}$, and $-(C_5-C_{14})$aryl$R^{15}$;

$R^9$ is independently selected from $-H$ or $(C_1-C_6)$alkyl;

$R^{10}$ is $(C_1-C_6)$alkyl;

$R^{11}$, $R^{12}$, and $R^{13}$ are independently selected from the group consisting of $-H$, $(C_1-C_6)$alkyl, $(C_1-C_6)$alkoxy, oxo, halo, $-R^{10}(R^{14})_q$, $-OR^{10}(R^{14})_q$, $-SO_2R^{10}$; $-C(O)R^{10}$, $-C(O)R^{15}$, and $-R^{10}R^{17}$;

$R^{14}$ is halo;

$R^{15}$ is $-N(R^{16})_2$;

$R^{16}$ is independently selected from the group consisting of $-H$, $(C_1-C_6)$alkyl, hydroxyl, $-SO_2R^{10}$, $-SO_2N(R^{10})_2$, $-C(O)NHR^{10}$, $-C(O)R^{18}$, and $-(C_5-C_{14})$aryl$(R^{11})$;

$R^{17}$ is $-OR^9$;

$R^{18}$ is $-CO_2R^9$;

X is $(C_5-C_{14})$aryl;

Y is independently selected from $(C_2-C_9)$heterocycle or $(C_2-C_9)$heteroaryl, each having one to four heteroatoms selected from S, N and O, wherein X and Y are optionally substituted by one to four $R^{11}$ groups;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

In another embodiment of the present invention, there is provided a compound of Formula I, wherein L is selected from the group consisting of a bond, $-C(O)NH-$, $-SO_2-$, methylene, and ethylene.

In another embodiment of the present invention, there is provided a compound of Formula I, wherein L is selected from a bond or methylene.

In another embodiment of the present invention, there is provided a compound of Formula I, wherein L is a bond.

In another embodiment of the present invention, there is provided a compound of Formula I, wherein L is methylene.

In another embodiment of the present invention, there is provided a compound of Formula I, wherein $R^1$ is selected from the group consisting of methyl, ethyl, and cyclopropyl.

In another embodiment of the present invention, there is provided a compound of Formula I, wherein $R^1$ is methyl.

In another embodiment of the present invention, there is provided a compound of Formula I, wherein $R^2$ is selected from the group consisting of carboxyl, hydroxyamide, hydroxymethylamide, methylsulfonylamide,

[chemical structures shown]

In another embodiment of the present invention, there is provided a compound of Formula I, wherein $R^2$ is carboxyl.

In another embodiment of the present invention, there is provided a compound of Formula I, wherein $R^3$ is selected from the group consisting of methyl, ethyl, propyl, butyl, methoxy, ethoxy, propoxy, butoxy, pentoxy, and methylcyclobutoxy.

In another embodiment of the present invention, there is provided a compound of Formula I, wherein $R^3$ is butoxy.

In another embodiment of the present invention, there is provided a compound of Formula I, $R^3$ is tert-butoxy.

In another embodiment of the present invention, there is provided a compound of Formula I, wherein $R^4$ is selected from the group consisting of $(C_5-C_{14})$aryl, $(C_3-C_7)$cycloalkyl, $(C_2-C_8)$heterocycle, and $(C_2-C_8)$heteroaryl, wherein the heterocycle and heteroaryl each comprise one to four heteroatoms selected from S, N and O.

In another embodiment of the present invention, there is provided a compound of Formula I, wherein $R^4$ is selected from the group consisting of phenyl, dihydrobenzopyranyl, naphthalenyl, pyridinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, and tetrahydropyridoquinolinyl.

In another embodiment of the present invention, there is provided a compound of Formula I, wherein $R^4$ is selected from phenyl or dihydrobenzopyranyl.

In another embodiment of the present invention, there is provided a compound of Formula I, wherein $R^4$ is dihydrobenzopyranyl.

In another embodiment of the present invention, there is provided a compound of Formula I, wherein $R^4$ is phenyl.

In another embodiment of the present invention, there is provided a compound of Formula I, wherein $R^4$ is optionally substituted by one to three groups selected from methyl, ethyl, oxo, methoxy, ethoxy, propoxy, methoxymethyl, fluoro, chloro, bromo, trifluoromethoxy, trifluoromethyl, methylsulfonyl, dimethylamide, cyclohexyloxy, acetyl, and fluoromethyl.

In another embodiment of the present invention, there is provided a compound of Formula I, wherein $R^4$ is optionally substituted by one to three groups selected from methyl, methoxy, fluoro, chloro, trifluoromethoxy, trifluoromethyl, acetyl.

In another embodiment of the present invention, there is provided a compound of Formula I, wherein $R^4$ is substituted by one to two groups selected from methyl, fluoro, chloro.

In another embodiment of the present invention, there is provided a compound of Formula I, wherein $R^4$ is substituted by one to two groups selected from methyl and fluoro.

In another embodiment of the present invention, there is provided a compound of Formula I, wherein $R^4$ is substituted by one to two methyl groups.

In another embodiment of the present invention, there is provided a compound of Formula I, wherein $R^4$ is substituted by one or two fluoro groups.

In another embodiment of the present invention, there is provided a compound of Formula I, wherein $R^4$ is substituted by one to two chloro groups.

In another embodiment of the present invention, there is provided a compound of Formula I, wherein $R^4$ is substituted by one to two methoxy groups.

In another embodiment of the present invention, there is provided a compound of Formula I, wherein $R^5$, $R^6$, $R^7$, and $R^8$ are independently selected from the group consisting of —H, methyl, ethyl, propyl, butyl, hydroxyl, fluoro, chloro, bromo, methoxy, ethoxy, propoxy, methoxyethoxy, cyclopropyl, cyclohexyl, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, and dimethylisoxazolyl.

In another embodiment of the present invention, there is provided a compound of Formula I, wherein $R^9$ is independently selected from the group consisting of —H, methyl, ethyl, propyl, isopropyl, butyl, isobutyl, tert-butyl, pentyl and septyl.

In another embodiment of the present invention, there is provided a compound of Formula I, wherein $R^9$ is —H.

In another embodiment of the present invention, there is provided a compound of Formula I, wherein $R^9$ is independently selected from the group consisting of methyl, ethyl, propyl, isopropyl, butyl, isobutyl, tert-butyl, pentyl and septyl.

In another embodiment of the present invention, there is provided a compound of Formula I, wherein $R^{10}$ is independently selected from the group consisting of methyl, ethyl, propyl, isopropyl, butyl, isobutyl, tert-butyl, pentyl and septyl.

In another embodiment of the present invention, there is provided a compound of Formula I, wherein $R^{11}$, $R^{12}$, and $R^{13}$ are independently selected from the group consisting of —H, methyl, ethyl, methoxy, ethoxy, oxo, chloro, fluoro, bromo, trifluoromethyl, trifluoromethoxy, methylsulfonyl, —C(O)methyl, —C(O)$R^{15}$, and methylmethoxy.

In another embodiment of the present invention, there is provided a compound of Formula I, wherein $R^{16}$ is independently selected from the group consisting of —H, methyl, ethyl, hydroxyl, methylsulfonyl, —SO$_2$N(methyl)$_2$, —C(O)NHmethyl, —C(O)$R^{18}$, and —(X)($R^{11}$).

In another embodiment of the present invention, there is provided a compound of Formula I:

Formula I

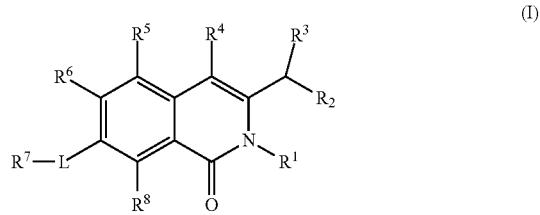

(I)

or a pharmaceutically acceptable salt thereof, wherein:

L is linker that is selected from the group consisting of a direct bond, a branched or straight chain (C$_1$-C$_6$)alkylene, —SO$_2$—, and —C(O)NH—;

$R^1$ is selected from (C$_1$-C$_6$)alkyl or (C$_3$-C$_7$)cycloalkyl;

$R^2$ is selected from the group consisting of —CO$_2R^9$, —C(O)$R^{15}$,

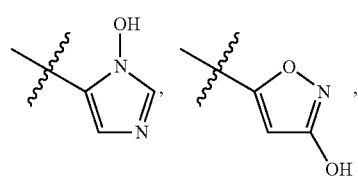

-continued

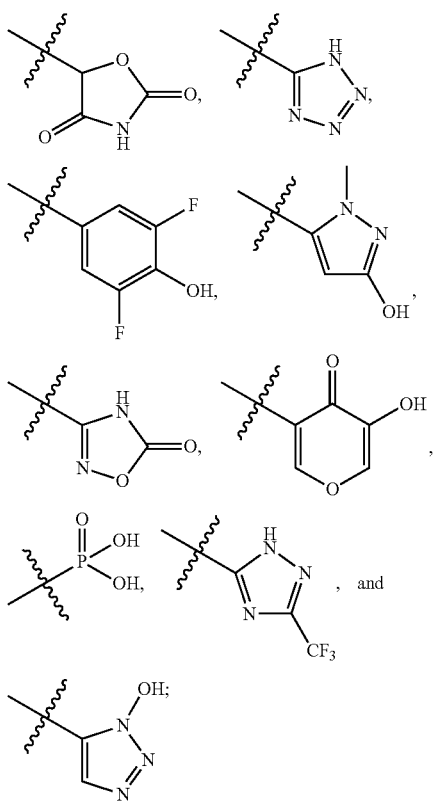

$R^3$ is selected from the group consisting of $(C_1-C_6)$alkyl, —$OR^{10}$, and —(Z)$R^{10}$;

$R^4$ is selected from the group consisting of —$NR^9$(X), tetrahydropyridoquinolinyl,

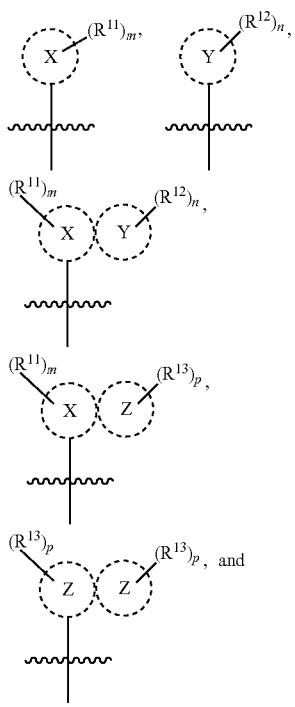

-continued

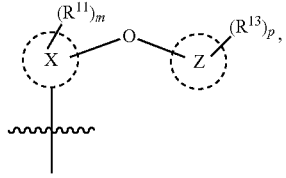

wherein the X, Y, Z, XY, XZ, and ZZ rings indicated by a dashed circle are as defined below and wherein the XY, XZ, ZZ rings each together form a bicyclic fused ring system comprised of the indicated rings and wherein the X, Y, and Z individual rings each form a monocyclic ring comprised of the indicated rings;

$R^5$, $R^6$, and $R^7$ are independently selected from the group consisting of —H, —OH, $(C_1-C_6)$alkyl, $(C_1-C_6)$alkoxy, halo, nitrile, $(C_3-C_7)$cycloalkyl, —$OR^{10}$(X), —$OR^{10}R^{14}$, —$OR^{10}$(X)($R^{11}$)$_m$, —$OR^{10}$(Y)($R^{12}$)$_n$, —$OR^{10}R^{17}$, —$R^{10}R^{17}$, —$R^{17}R^{15}$, —$OR^{10}(R^{14})_q$, —$OR^{10}$(Y), —$OR^{10}R^{18}$, —$OSO_2R^{15}$, —$R^{15}$, —(X), —(Y), —(Y)($R^{12}$)$_n$, —C(O)(Y), —C(O)$R^{15}$, —$R^{10}$(X), —$R^{10}R^{15}$, and —(X)$R^{15}$;

$R^9$ is independently selected from the group consisting of H and $(C_1-C_6)$alkyl;

$R^{10}$ is $(C_1-C_6)$alkyl;

$R^{11}$, $R^{12}$, and $R^{13}$ are independently selected from the group consisting of —H, $(C_1-C_6)$alkyl, $(C_1-C_6)$alkoxy, oxo, halo, —$R^{10}(R^{14})_q$, —$OR^{10}(R^{14})_q$, —$SO_2R^{10}$; —C(O)$R^{10}$, —C(O)$R^{15}$, and —$R^{10}R^{17}$;

$R^{14}$ is halo;

$R^{15}$ is —N($R^{16}$)$_2$;

$R^{16}$ is independently selected from the group consisting of —H, $(C_1-C_6)$alkyl, hydroxyl, —$SO_2R^{10}$, —$SO_2N(R^{10})_2$, —C(O)NH$R^{10}$, —C(O)$R^{18}$, and —(X)($R^{11}$);

$R^{17}$ is —$OR^9$;

$R^{18}$ is —$CO_2R^9$;

X is $(C_5-C_{14})$aryl;

Y is independently selected from $(C_2-C_9)$heterocycle or $(C_2-C_9)$heteroaryl, each having one to three heteroatoms selected from S, N and O;

Z is $(C_3-C_7)$cycloalkyl;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

In another embodiment of the present invention, there is provided a compound of Formula I:

Formula I

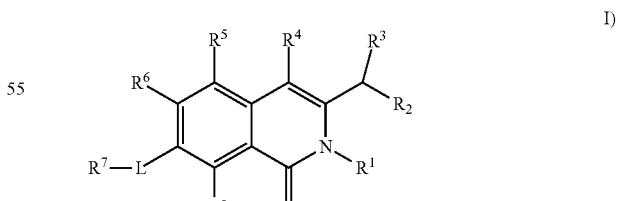

or a pharmaceutically acceptable salt thereof, wherein:

L is linker that is selected from the group consisting of a direct bond, a branched or straight chain $(C_1-C_6)$alkylene, —$SO_2$—, and —C(O)NH—;

$R^1$ is selected from the group consisting of —H, $(C_1-C_6)$alkyl and $(C_3-C_7)$cycloalkyl;

R² is selected from the group consisting of —CO₂R⁹, —C(O)R¹⁵,

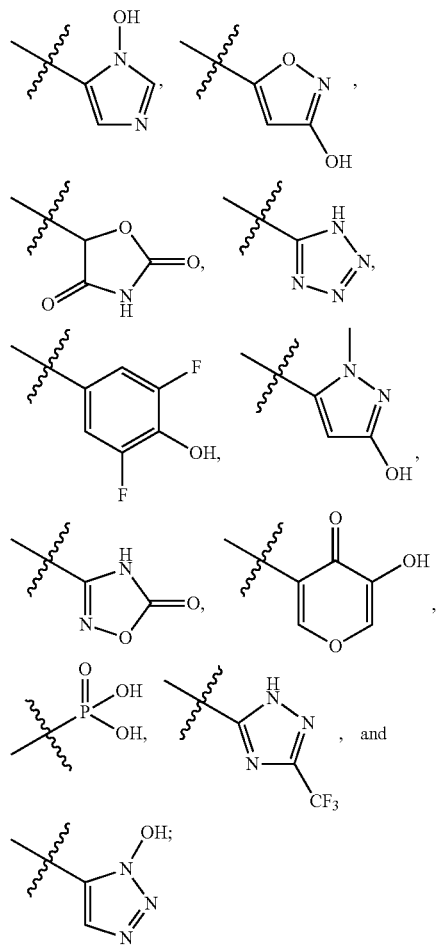

R³ is selected from the group consisting of (C₁-C₆)alkyl, —OR¹⁰, and —(C₃-C₇)cycloalkylR¹⁰;

R⁴ is selected from the group consisting of:

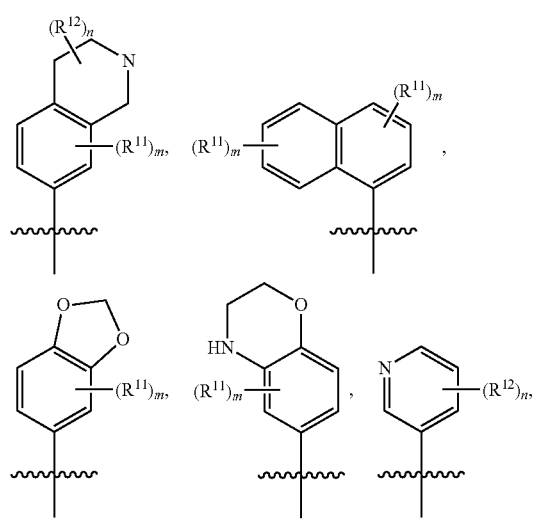

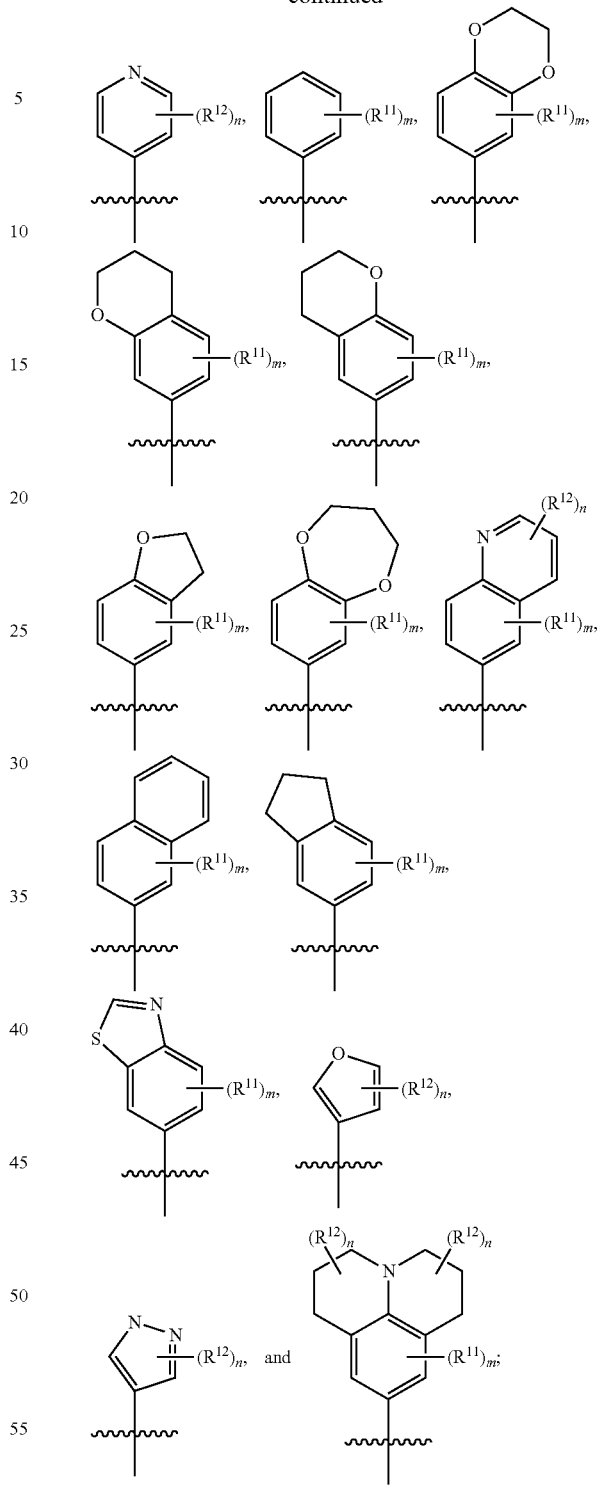

R⁵, R⁶, R⁷, and R⁸ are independently selected from —H, —OH, (C₁-C₆)alkyl, (C₁-C₆)alkoxy, halo, nitrile, (C₃-C₇)cycloalkyl, —OR¹⁰(X), —OR¹⁰R¹⁴, —OR¹⁰(X)(R¹¹)ₙ, —R¹⁰(Y)(R¹²)ₙ, —OR¹⁰R¹⁷, R¹⁰R¹⁷, R¹⁷R¹⁵, —OR¹⁰(R¹⁴)q, —OR¹⁰(Y), —OR¹⁰R¹⁸, —OSO₂R¹⁵, —R¹⁵, —(X), —(Y), —(Y)(R¹²)ₙ, —C(O)(Y), —C(O)R¹⁵, —R¹⁰(X), —R¹⁰R¹⁵, and —(X)R¹⁵;

R⁹ is independently selected from the group consisting of —H and (C₁-C₆)alkyl;

$R^{10}$ is $(C_1-C_6)$alkyl;

$R^{11}$, $R^{12}$, and $R^{13}$ are independently selected from the group consisting of —H, $(C_1-C_6)$alkyl, $(C_1-C_6)$alkoxy, oxo, halo, —$R^{10}(R^{14})_q$, —$OR^{10}(R^{14})_q$, —$SO_2R^{10}$; —$C(O)R^{10}$, —$C(O)R^{15}$, and —$R^{10}R^{17}$;

$R^{14}$ is halo;

$R^{15}$ is —$N(R^{16})_2$;

$R^{16}$ is independently selected from the group consisting of —H, $(C_1-C_6)$alkyl, hydroxyl, —$SO_2R^{10}$, —$SO_2N(R^{10})_2$, —$C(O)NHR^{10}$, —$C(O)R^{18}$, and —$(X)(R^{11})$;

$R^{17}$ is —$OR^9$;

$R^{18}$ is —$CO_2R^9$;

X is $(C_5-C_{14})$aryl;

Y is independently selected from $(C_2-C_9)$heterocycle or $(C_2-C_9)$heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

In another embodiment of the present invention, there is provided a compound of Formula (II):

Formula II

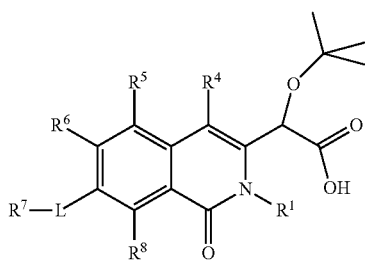

(II)

or a pharmaceutically acceptable salt thereof, wherein:

L is linker that is selected from the group consisting of a direct bond, methylene, —$SO_2$—, and —$C(O)NH$—;

X is phenyl;

$R^4$ is selected from the group consisting of phenyl, dihydrobenzopyranyl, naphthalenyl, pyridinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, and tetrahydropyridoquinolinyl;

$R^5$, $R^6$, and $R^7$ are independently selected from H, methyl, ethyl, propyl, butyl, hydroxyl, fluoro, chloro, bromo, methoxy, ethoxy, propoxy, methoxyethoxy, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, and dimethylisoxazolyl;

$R^9$ is independently selected from the group consisting of —H, methyl, ethyl, propyl, isopropyl, butyl, isobutyl, tert-butyl, pentyl, and septyl;

$R^{10}$ is selected from the group consisting of —H, methyl, ethyl, propyl, isopropyl, butyl, isobutyl, tert-butyl, penty, and septyl;

$R^{11}$, $R^{12}$, and $R^{13}$ are independently selected from the group consisting of —H, methyl, ethyl, methoxy, ethoxy, oxo, chloro, fluoro, bromo, trifluoromethyl, trifluoromethoxy, methylsulfonyl, —$C(O)$methyl, —$C(O)R^{15}$, and methylmethoxy;

$R^{14}$ is selected from the group consisting of chloro, fluoro, and bromo.

$R^{15}$ is —$N(R^{16})_2$;

$R^{16}$ is independently selected from the group consisting of —H, methyl, ethyl, hydroxyl, methylsulfonyl, —$SO_2N(methyl)_2$, —$C(O)NH$methyl, —$C(O)R^{18}$, and —$(X)(R^{11})$;

$R^{17}$ is —$OR^9$; and $R^{18}$ is —$CO_2R^9$.

In another embodiment of the present invention, there is provided a compound that is selected from the group consisting of:

2-(tert-butoxy)-2-{2-methyl-1-oxo-4-[4-(trifluoromethoxy)phenyl]-1,2-dihydroisoquinolin-3-yl}acetic acid, 2-(tert-butoxy)-2-[4-(3,5-difluorophenyl)-2-methyl-1-oxo-1,2-dihydroisoquinolin-3-yl]acetic acid, 2-(tert-butoxy)-2-[2-methyl-4-(4-methylphenyl)-1-oxo-1,2-dihydroisoquinolin-3-yl]acetic acid, 2-(tert-butoxy)-2-[4-(4-methoxyphenyl)-2-methyl-1-oxo-1,2-dihydroisoquinolin-3-yl]acetic acid, 2-(tert-butoxy)-2-[4-(4-fluorophenyl)-2-methyl-1-oxo-1,2-dihydroisoquinolin-3-yl]acetic acid, 2-(tert-butoxy)-2-[4-(3,5-dimethylphenyl)-2-methyl-1-oxo-1,2-dihydroisoquinolin-3-yl]acetic acid, 2-(tert-butoxy)-2-[4-(3,4-dichlorophenyl)-2-methyl-1-oxo-1,2-dihydroisoquinolin-3-yl]acetic acid, 2-(tert-butoxy)-2-[4-(3,5-dichlorophenyl)-2-methyl-1-oxo-1,2-dihydroisoquinolin-3-yl]acetic acid, 2-(tert-butoxy)-2-[4-(2,3-difluorophenyl)-2-methyl-1-oxo-1,2-dihydroisoquinolin-3-yl]acetic acid, 2-(tert-butoxy)-2-{2-methyl-1-oxo-4-[3-(trifluoromethyl)phenyl]-1,2-dihydroisoquinolin-3-yl}acetic acid, 2-(tert-butoxy)-2-[4-(2,5-dichlorophenyl)-2-methyl-1-oxo-1,2-dihydroisoquinolin-3-yl]acetic acid, 2-(tert-butoxy)-2-[4-(3-methoxyphenyl)-2-methyl-1-oxo-1,2-dihydroisoquinolin-3-yl]acetic acid, 2-(tert-butoxy)-2-{2-methyl-1-oxo-4-[3-(trifluoromethoxy)phenyl]-1,2-dihydroisoquinolin-3-yl}acetic acid, 2-(tert-butoxy)-2-{2-methyl-1-oxo-4-[4-(trifluoromethyl)phenyl]-1,2-dihydroisoquinolin-3-yl}acetic acid, 2-(tert-butoxy)-2-[2-methyl-4-(3-methylphenyl)-1-oxo-1,2-dihydroisoquinolin-3-yl]acetic acid, 2-(tert-butoxy)-2-[2-methyl-4-(5-methyl-3,4-dihydro-2H-1-benzopyran-6-yl)-1-oxo-1,2-dihydroisoquinolin-3-yl]acetic acid, 2-(tert-butoxy)-2-[2-methyl-4-(7-methyl-3,4-dihydro-2H-1-benzopyran-6-yl)-1-oxo-1,2-dihydroisoquinolin-3-yl]acetic acid, 2-(tert-butoxy)-2-[4-(5-chloro-3,4-dihydro-2H-1-benzopyran-6-yl)-2-methyl-1-oxo-1,2-dihydroisoquinolin-3-yl]acetic acid, 2-(tert-butoxy)-2-[4-(4-methanesulfonylphenyl)-2-methyl-1-oxo-1,2-dihydroisoquinolin-3-yl]acetic acid, 2-(tert-butoxy)-2-{4-[4-(dimethylcarbamoyl)phenyl]-2-methyl-1-oxo-1,2-dihydroisoquinolin-3-yl}acetic acid,
2-(tert-butoxy)-2-{4-[4-(cyclohexyloxy)phenyl]-2-methyl-1-oxo-1,2-dihydroisoquinolin-3-yl}acetic acid,
2-(tert-butoxy)-2-[4-(3,4-dihydro-2H-1-benzopyran-6-yl)-6-fluoro-2-methyl-1-oxo-1,2-dihydroisoquinolin-3-yl]acetic acid,
2-(tert-butoxy)-2-[6-chloro-4-(3,4-dihydro-2H-1-benzopyran-6-yl)-2-methyl-1-oxo-1,2-dihydroisoquinolin-3-yl]acetic acid,
2-(tert-butoxy)-2-[2-methyl-1-oxo-4-(3,4,5-trimethoxyphenyl)-1,2-dihydroisoquinolin-3-yl]acetic acid,
2-(tert-butoxy)-2-[4-(3,4-dimethylphenyl)-2-ethyl-1-oxo-1,2-dihydroisoquinolin-3-yl]acetic acid,
2-(tert-butoxy)-2-[4-(4-methoxy-3,5-dimethylphenyl)-2-methyl-1-oxo-1,2-dihydroisoquinolin-3-yl]acetic acid,
2-(tert-butoxy)-2-[2-methyl-4-(naphthalen-1-yl)-1-oxo-1,2-dihydroisoquinolin-3-yl]acetic acid,
2-(tert-butoxy)-2-[2-cyclopropyl-4-(3,4-dihydro-2H-1-benzopyran-6-yl)-1-oxo-1,2-dihydroisoquinolin-3-yl]acetic acid,
2-(tert-butoxy)-2-[4-(4-methoxy-2-methylphenyl)-2-methyl-1-oxo-1,2-dihydroisoquinolin-3-yl]acetic acid,
2-(tert-butoxy)-2-[4-(2-methoxyphenyl)-2-methyl-1-oxo-1,2-dihydroisoquinolin-3-yl]acetic acid,
2-(tert-butoxy)-2-[4-(2,4-dimethylphenyl)-2-methyl-1-oxo-1,2-dihydroisoquinolin-3-yl]acetic acid,
2-(tert-butoxy)-2-[4-(3,4-dihydro-2H-1-benzopyran-6-yl)-8-fluoro-2-methyl-1-oxo-1,2-dihydroisoquinolin-3-yl]acetic acid,
2-(tert-butoxy)-2-[4-(3,4-dihydro-2H-1-benzopyran-7-yl)-2-methyl-1-oxo-1,2-dihydroisoquinolin-3-yl]acetic acid,
2-(tert-butoxy)-2-[4-(8-chloro-3,4-dihydro-2H-1-benzopyran-7-yl)-2-methyl-1-oxo-1,2-dihydroisoquinolin-3-yl]acetic acid,
2-[7-(benzyloxy)-2-methyl-4-(5-methyl-3,4-dihydro-2H-1-benzopyran-6-yl)-1-oxo-1,2-dihydroisoquinolin-3-yl]-2-(tert-butoxy)acetic acid,
2-(tert-butoxy)-2-[7-(2-fluoroethoxy)-2-methyl-4-(5-methyl-3,4-dihydro-2H-1-benzopyran-6-yl)-1-oxo-1,2-dihydroisoquinolin-3-yl]acetic acid,
2-(tert-butoxy)-2-[8-fluoro-4-(8-fluoro-5-methyl-3,4-dihydro-2H-1-benzopyran-6-yl)-2-methyl-1-oxo-1,2-dihydroisoquinolin-3-yl]acetic acid,
2-(tert-butoxy)-2-[6-fluoro-4-(8-fluoro-5-methyl-3,4-dihydro-2H-1-benzopyran-6-yl)-2-methyl-1-oxo-1,2-dihydroisoquinolin-3-yl]acetic acid,
2-(tert-butoxy)-2-[7-fluoro-4-(8-fluoro-5-methyl-3,4-dihydro-2H-1-benzopyran-6-yl)-2-methyl-1-oxo-1,2-dihydroisoquinolin-3-yl]acetic acid,
2-(tert-butoxy)-2-{7-[(4-fluorophenyl)methoxy]-2-methyl-4-(5-methyl-3,4-dihydro-2H-1-benzopyran-6-yl)-1-oxo-1,2-dihydroisoquinolin-3-yl}acetic acid,
(2S)-2-(tert-butoxy)-2-[7-methoxy-2-methyl-4-(5-methyl-3,4-dihydro-2H-1-benzopyran-6-yl)-1-oxo-1,2-dihydroisoquinolin-3-yl]acetic acid,
2-(tert-butoxy)-2-{7-[(2,5-difluorophenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-{7-[(2,3-difluorophenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[2-methyl-4-(5-methyl-3,4-dihydro-2H-1-benzopyran-6-yl)-1-oxo-7-(pyridin-3-ylmethoxy)-1,2-dihydroisoquinolin-3-yl]acetic acid,
2-(tert-butoxy)-2-{7-[(2,6-difluorophenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[2-methyl-4-(5-methyl-3,4-dihydro-2H-1-benzopyran-6-yl)-1-oxo-7-[(2,4,6-trifluorophenyl)methoxy]-1,2-dihydroisoquinolin-3-yl]acetic acid,
2-(tert-butoxy)-2-{7-[(5-fluoropyridin-2-yl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[4-(8-fluoro-5-methyl-3,4-dihydro-2H-1-benzopyran-6-yl)-7-[(5-fluoropyridin-2-yl)methoxy]-2-methyl-1-oxo-1,2-dihydroisoquinolin-3-yl]acetic acid,
2-(tert-butoxy)-2-[2-methyl-4-(5-methyl-3,4-dihydro-2H-1-benzopyran-6-yl)-7-[(3-methylpyridin-2-yl)methoxy]-1-oxo-1,2-dihydroisoquinolin-3-yl]acetic acid,
2-(tert-butoxy)-2-{7-[(2-fluorophenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-{7-[(3-fluorophenyl)methoxy]-2-methyl-4-(5-methyl-3,4-dihydro-2H-1-benzopyran-6-yl)-1-oxo-1,2-dihydroisoquinolin-3-yl}acetic acid,
(2S)-2-(tert-butoxy)-2-{7-[(dimethyl-1,3-oxazol-4-yl)methoxy]-4-(8-fluoro-5-methyl-3,4-dihydro-2H-1-benzopyran-6-yl)-2-methyl-1-oxo-1,2-dihydroisoquinolin-3-yl}acetic acid,
(2S)-2-(tert-butoxy)-2-[4-(8-fluoro-5-methyl-3,4-dihydro-2H-1-benzopyran-6-yl)-7-methoxy-2-methyl-1-oxo-1,2-dihydroisoquinolin-3-yl]acetic acid,
(2S)-2-(tert-butoxy)-2-{7-[(2,4-difluorophenyl)methoxy]-4-(8-fluoro-5-methyl-3,4-dihydro-2H-1-benzopyran-6-yl)-2-methyl-1-oxo-1,2-dihydroisoquinolin-3-yl}acetic acid,
(2S)-2-(tert-butoxy)-2-{7-[(3,4-difluorophenyl)methoxy]-2-methyl-4-(5-methyl-3,4-dihydro-2H-1-benzopyran-6-yl)-1-oxo-1,2-dihydroisoquinolin-3-yl}acetic acid,
(2S)-2-(tert-butoxy)-2-[4-(8-fluoro-5-methyl-3,4-dihydro-2H-1-benzopyran-6-yl)-2-methyl-1-oxo-7-(thiophen-2-ylmethoxy)-1,2-dihydroisoquinolin-3-yl]acetic acid,
(2S)-2-(tert-butoxy)-2-[4-(8-fluoro-5-methyl-3,4-dihydro-2H-1-benzopyran-6-yl)-7-(2-fluoroethoxy)-2-methyl-1-oxo-1,2-dihydroisoquinolin-3-yl]acetic acid,
(2S)-2-(tert-butoxy)-2-{7-[(5-chlorothiophen-2-yl)methoxy]-4-(8-fluoro-5-methyl-3,4-dihydro-2H-1-benzopyran-6-yl)-2-methyl-1-oxo-1,2-dihydroisoquinolin-3-yl}acetic acid,
(2S)-2-(tert-butoxy)-2-[2-methyl-4-(5-methyl-3,4-dihydro-2H-1-benzopyran-6-yl)-1-oxo-7-(thiophen-2-ylmethoxy)-1,2-dihydroisoquinolin-3-yl]acetic acid,
(2S)-2-(tert-butoxy)-2-{7-[(5-chlorothiophen-2-yl)methoxy]-2-methyl-4-(5-methyl-3,4-dihydro-2H-1-benzopyran-6-yl)-1-oxo-1,2-dihydroisoquinolin-3-yl}acetic acid,
(2S)-2-(tert-butoxy)-2-[4-(8-fluoro-5-methyl-3,4-dihydro-2H-1-benzopyran-6-yl)-2-methyl-7-[(5-methylthiophen-2-yl)methoxy]-1-oxo-1,2-dihydroisoquinolin-3-yl]acetic acid,
2-(tert-butoxy)-2-[4-(3,4-difluorophenyl)-2-methyl-1-oxo-1,2-dihydroisoquinolin-3-yl]acetic acid,
2-(tert-butoxy)-2-[4-(3,4-dihydro-2H-1-benzopyran-6-yl)-2-methyl-1-oxo-1,2-dihydroisoquinolin-3-yl]acetic acid,
2-(tert-butoxy)-2-[4-(3-fluorophenyl)-2-methyl-1-oxo-1,2-dihydroisoquinolin-3-yl]acetic acid,
2-(tert-butoxy)-2-[2-methyl-1-oxo-4-(pyridin-3-yl)-1,2-dihydroisoquinolin-3-yl]acetic acid,
2-(tert-butoxy)-2-[4-(4-ethoxyphenyl)-2-methyl-1-oxo-1,2-dihydroisoquinolin-3-yl]acetic acid,
2-(tert-butoxy)-2-[2-methyl-1-oxo-4-(2,4,5-trimethylphenyl)-1,2-dihydroisoquinolin-3-yl]acetic acid, 2-(tert-butoxy)-2-[2-methyl-1-oxo-4-(4-propoxyphenyl)-1,2-dihydroisoquinolin-3-yl]acetic acid, 2-(tert-butoxy)-2-{2-methyl-1-oxo-4-[4-(propan-2-yloxy)phenyl]-1,2-dihydroisoquinolin-3-yl}acetic acid, 2-(tert-butoxy)-2-[4-(2,4-difluorophenyl)-2-methyl-1-oxo-1,2-dihydroisoquinolin-3-yl]acetic acid, 2-(tert-butoxy)-2-[4-(4-ethylphenyl)-2-methyl-1-oxo-1,2-dihydroisoquinolin-3-yl]acetic acid, 2-(tert-butoxy)-2-[2-methyl-1-oxo-4-(pyridin-4-yl)-1,2-dihydroisoquinolin-3-yl]acetic acid, 2-(tert-butoxy)-2-{4-[4-(methoxymethyl)phenyl]-2-methyl-1-oxo-1,2-dihydroisoquinolin-3-yl}acetic acid, 2-(tert-butoxy)-2-[4-(3,4-dimethoxyphenyl)-2-methyl-1-oxo-1,2-dihydroisoquinolin-3-yl]acetic acid, 2-[4-(2H-1,3-benzodioxol-5-yl)-2-methyl-1-oxo-1,2-dihydroisoquinolin-3-yl]-2-(tert-butoxy)acetic acid, 2-(tert-butoxy)-2-[4-(3-methoxy-4-methylphenyl)-2-methyl-1-oxo-1,2-dihydroisoquinolin-3-yl]acetic acid, 2-(tert-butoxy)-2-[4-(2,3-dihydro-1,4-benzodioxin-6-yl)-2-methyl-1-oxo-1,2-dihydroisoquinolin-3-yl]acetic acid, 2-(tert-butoxy)-2-[4-(4-methoxy-3-methylphenyl)-2-methyl-1-oxo-1,2-dihydroisoquinolin-3-yl]acetic acid, 2-(tert-butoxy)-2-[4-(3,4-dimethylphenyl)-2,6-dimethyl-1-oxo-1,2-dihydroisoquinolin-3-yl]acetic acid, 2-(tert-butoxy)-2-[4-(3,4-dimethylphenyl)-6-fluoro-2-methyl-1-oxo-1,2-dihydroisoquinolin-3-yl]acetic acid, 2-(tert-butoxy)-2-[4-(3,4-dihydro-2H-1-benzopyran-6-yl)-7-fluoro-2-methyl-1-oxo-1,2-dihydroisoquinolin-3-yl]acetic acid, 2-(tert-butoxy)-2-[4-(3,4-dihydro-2H-1-benzopyran-6-yl)-2,7-dimethyl-1-oxo-1,2-dihydroisoquinolin-3-yl]acetic acid, 2-(tert-butoxy)-2-[4-(3,4-dimethylphenyl)-8-fluoro-2-methyl-1-oxo-1,2-dihydroisoquinolin-3-yl]acetic acid, 2-(tert-butoxy)-2-[4-(3,4-dimethylphenyl)-2,7-dimethyl-1-oxo-1,2-dihydroisoquinolin-3-yl]acetic acid, 2-(tert-butoxy)-2-[4-(3,4-dihydro-2H-1,5-benzodioxepin-7-yl)-2-methyl-1-oxo-1,2-dihydroisoquinolin-3-yl]acetic acid, 2-(tert-butoxy)-2-[2-methyl-1-oxo-4-(quinolin-6-yl)-1,2-dihydroisoquinolin-3-yl]acetic acid, 2-(tert-butoxy)-2-[4-(2,3-dihydro-1-benzofuran-5-yl)-2-methyl-1-oxo-1,2-dihydroisoquinolin-3-yl]acetic acid, 2-(tert-butoxy)-2-[2-methyl-4-(naphthalen-2-yl)-1-oxo-1,2-dihydroisoquinolin-3-yl]acetic acid,I 2-(tert-butoxy)-2-[4-(3,4-dihydro-2H-1-benzopyran-6-yl)-2-ethyl-1-oxo-1,2-dihydroisoquinolin-3-yl]acetic acid, 2-(tert-butoxy)-2-[4-(4-chloro-3,5-dimethylphenyl)-2-methyl-1-oxo-1,2-dihydroisoquinolin-3-yl]acetic acid, 2-(tert-butoxy)-2-[2,7-dimethyl-4-(5-methyl-3,4-dihydro-2H-1-benzopyran-6-yl)-1-oxo-1,2-dihydroisoquinolin-3-yl]acetic acid, 2-(tert-butoxy)-2-[7-chloro-4-(3,4-dihydro-2H-1-benzopyran-6-yl)-2-methyl-1-oxo-1,2-dihydroisoquinolin-3-yl]acetic acid, 2-(tert-butoxy)-2-[6-fluoro-2-methyl-4-(5-methyl-3,4-dihydro-2H-1-benzopyran-6-yl)-1-oxo-1,2-dihydroisoquinolin-3-yl]acetic acid, 2-(tert-butoxy)-2-[4-(8-chloro-5-methyl-3,4-dihydro-2H-1-benzopyran-6-yl)-2-methyl-1-oxo-1,2-dihydroisoquinolin-3-yl]acetic acid, 2-(tert-butoxy)-2-[2-methyl-4-(2-methylphenyl)-1-oxo-1,2-dihydroisoquinolin-3-yl]acetic acid 2-(tert-butoxy)-2-[4-(3,4-dihydro-2H-1-benzopyran-6-yl)-7-methoxy-2-methyl-1-oxo-1,2-dihydroisoquinolin-3-yl]acetic acid, 2-(tert-butoxy)-2-[4-(2,2-dimethyl-4-oxo-3,4-dihydro-2H-1-benzopyran-6-yl)-2-methyl-1-oxo-1,2-dihydroisoquinolin-3-yl]acetic acid, 2-(tert-butoxy)-2-[4-(3,4-dihydro-2H-1-benzopyran-6-yl)-2,5-dimethyl-1-oxo-1,2-dihydroisoquinolin-3-yl]acetic acid, 2-(tert-butoxy)-2-[7-fluoro-2-methyl-4-(5-methyl-3,4-dihydro-2H-1-benzopyran-6-yl)-1-oxo-1,2-dihydroisoquinolin-3-yl]acetic acid, 2-(tert-butoxy)-2-[7-methoxy-2-methyl-4-(5-methyl-3,4-dihydro-2H-1-benzopyran-6-yl)-1-oxo-1,2-dihydroisoquinolin-3-yl]acetic acid, 2-(tert-butoxy)-2-[2-ethyl-4-(5-methyl-3,4-dihydro-2H-1-benzopyran-6-yl)-1-oxo-1,2-dihydroisoquinolin-3-yl]acetic acid, 2-(tert-butoxy)-2-[4-(2,2-dimethyl-3,4-dihydro-2H-1-benzopyran-6-yl)-2-methyl-1-oxo-1,2-dihydroisoquinolin-3-yl]acetic acid, 2-(tert-butoxy)-2-[7-chloro-2-methyl-4-(5-methyl-3,4-dihydro-2H-1-benzopyran-6-yl)-1-oxo-1,2-dihydroisoquinolin-3-yl]acetic acid, 2-[4-(2-acetyl-1,2,3,4-tetrahydroisoquinolin-7-yl)-2-methyl-1-oxo-1,2-dihydroisoquinolin-3-yl]-2-(tert-butoxy)acetic acid, 2-(tert-butoxy)-2-[7-(2-methoxyethoxy)-2-methyl-4-(5-methyl-3,4-dihydro-2H-1-benzopyran-6-yl)-1-oxo-1,2-dihydroisoquinolin-3-yl]acetic acid, 2-(tert-butoxy)-2-[4-(3,4-dihydro-2H-1,4-benzoxazin-6-yl)-2-methyl-1-oxo-1,2-dihydroisoquinolin-3-yl]acetic acid, 2-(tert-butoxy)-2-[8-fluoro-2-methyl-4-(5-methyl-3,4-dihydro-2H-1-benzopyran-6-yl)-1-oxo-1,2-dihydroisoquinolin-3-yl]acetic acid, 2-(tert-butoxy)-2-[7-hydroxy-2-methyl-4-(5-methyl-3,4-dihydro-2H-1-benzopyran-6-yl)-1-oxo-1,2-dihydroisoquinolin-3-yl]acetic acid, 2-(tert-butoxy)-2-[7-(2-hydroxyethoxy)-2-methyl-4-(5-methyl-3,4-dihydro-2H-1-benzopyran-6-yl)-1-oxo-1,2-dihydroisoquinolin-3-yl]acetic acid, 2-(tert-butoxy)-2-{7-[2-(dimethylamino)ethoxy]-2-methyl-4-(5-methyl-3,4-dihydro-2H-1-benzopyran-6-yl)-1-oxo-1,2-dihydroisoquinolin-3-yl}acetic acid, 2-(tert-butoxy)-2-[4-(5-chloro-3,4-dihydro-2H-1,4-benzoxazin-6-yl)-2-methyl-1-oxo-1,2-dihydroisoquinolin-3-yl]acetic acid, 2-(tert-butoxy)-2-[7-(difluoromethoxy)-2-methyl-4-(5-methyl-3,4-dihydro-2H-1-benzopyran-6-yl)-1-oxo-1,2-dihydroisoquinolin-3-yl]acetic acid, (2S)-2-(tert-butoxy)-2-[2,7-dimethyl-4-(5-methyl-3,4-dihydro-2H-1-benzopyran-6-yl)-1-oxo-1,2-dihydroisoquinolin-3-yl]acetic acid, 2-[4-(4-acetyl-5-chloro-3,4-dihydro-2H-1,4-benzoxazin-6-yl)-2-methyl-1-oxo-1,2-dihydroisoquinolin-3-yl]-2-(tert-butoxy)acetic acid, 2-(tert-butoxy)-2-[2-methyl-4-(5-methyl-3,4-dihydro-2H-1-benzopyran-6-yl)-1-oxo-7-[2-(pyrrolidin-1-yl)ethoxy]-1,2-dihydroisoquinolin-3-yl]acetic acid, 2-(tert-butoxy)-2-(2-methyl-1-oxo-4-{2H,3H,4H-pyrano[2,3-b]pyridin-6-yl}-1,2-dihydroisoquinolin-3-yl)acetic acid, 2-(tert-butoxy)-2-[2-methyl-4-(5-methyl-3,4-dihydro-2H-1-benzopyran-6-yl)-7-[2-(morpholin-4-yl)ethoxy]-1-oxo-1,2-dihydroisoquinolin-3-yl]acetic acid, 2-(tert-butoxy)-2-[7-methoxy-2,6-dimethyl-4-(5-methyl-3,4-dihydro-2H-1-benzopyran-6-yl)-1-oxo-1,2-dihydroisoquinolin-3-yl]acetic acid, 2-(tert-butoxy)-2-[4-(5-ethyl-3,4-dihydro-2H-1-benzopyran-6-yl)-2-methyl-1-oxo-1,2-dihydroisoquinolin-3-yl]acetic acid,
2-({3-[(tert-butoxy)(carboxy)methyl]-2-methyl-4-(5-methyl-3,4-dihydro-2H-1-benzopyran-6-yl)-1-oxo-1,2-dihydroisoquinolin-7-yl}oxy)acetic acid,
2-(tert-butoxy)-2-{7-[(dimethylsulfamoyl)oxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[4-(8-fluoro-5-methyl-3,4-dihydro-2H-1-benzopyran-6-yl)-2,7-dimethyl-1-oxo-1,2-dihydroisoquinolin-3-yl]acetic acid,
2-(tert-butoxy)-2-[4-(8-fluoro-5-methyl-3,4-dihydro-2H-1-benzopyran-6-yl)-7-methoxy-2-methyl-1-oxo-1,2-dihydroisoquinolin-3-yl]acetic acid,
2-(tert-butoxy)-2-[8-fluoro-7-methoxy-2-methyl-4-(5-methyl-3,4-dihydro-2H-1-benzopyran-6-yl)-1-oxo-1,2-dihydroisoquinolin-3-yl]acetic acid,
2-(tert-butoxy)-2-[2-methyl-4-(5-methyl-3,4-dihydro-2H-1-benzopyran-6-yl)-1-oxo-7-(trifluoromethyl)-1,2-dihydroisoquinolin-3-yl]acetic acid,
2-(tert-butoxy)-2-{7-[(4-methanesulfonylphenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[2-methyl-4-(5-methyl-3,4-dihydro-2H-1-benzopyran-6-yl)-1-oxo-7-(pyridin-2-ylmethoxy)-1,2-dihydroisoquinolin-3-yl]acetic acid,
2-(tert-butoxy)-2-[6-chloro-7-methoxy-2-methyl-4-(5-methyl-3,4-dihydro-2H-1-benzopyran-6-yl)-1-oxo-1,2-dihydroisoquinolin-3-yl]acetic acid,
(2S)-2-(tert-butoxy)-2-[4-(8-fluoro-5-methyl-3,4-dihydro-2H-1-benzopyran-6-yl)-2,7-dimethyl-1-oxo-1,2-dihydroisoquinolin-3-yl]acetic acid,
2-(tert-butoxy)-2-[2-methyl-4-(5-methyl-3,4-dihydro-2H-1-benzopyran-6-yl)-1-oxo-7-{[4-(trifluoromethyl)phenyl]methoxy}-1,2-dihydroisoquinolin-3-yl]acetic acid,
2-(tert-butoxy)-2-{7-[(dimethyl-1,3-oxazol-4-yl)methoxy]-4-(8-fluoro-5-methyl-3,4-dihydro-2H-1-benzopyran-6-yl)-2-methyl-1-oxo-1,2-dihydroisoquinolin-3-yl}acetic acid,
2-(tert-butoxy)-2-{7-[(2,4-difluorophenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[2-methyl-4-(5-methyl-3,4-dihydro-2H-1-benzopyran-6-yl)-1-oxo-7-(propan-2-yloxy)-1,2-dihydroisoquinolin-3-yl]acetic acid,
2-(tert-butoxy)-2-{7-[(4-chlorophenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[2-methyl-4-(5-methyl-3,4-dihydro-2H-1-benzopyran-6-yl)-1-oxo-7-(pyrimidin-5-ylmethoxy)-1,2-dihydroisoquinolin-3-yl]acetic acid,
2-(tert-butoxy)-2-{7-[(3,4-difluorophenyl)methoxy]-2-methyl-4-(5-methyl-3,4-dihydro-2H-1-benzopyran-6-yl)-1-oxo-1,2-dihydroisoquinolin-3-yl}acetic acid,
(2S)-2-(tert-butoxy)-2-[7-fluoro-4-(8-fluoro-5-methyl-3,4-dihydro-2H-1-benzopyran-6-yl)-2-methyl-1-oxo-1,2-dihydroisoquinolin-3-yl]acetic acid,
(2S)-2-(tert-butoxy)-2-[7-(2-fluoroethoxy)-2-methyl-4-(5-methyl-3,4-dihydro-2H-1-benzopyran-6-yl)-1-oxo-1,2-dihydroisoquinolin-3-yl]acetic acid,
2-(tert-butoxy)-2-[2-methyl-4-(5-methyl-3,4-dihydro-2H-1-benzopyran-6-yl)-1-oxo-7-(thiophen-2-ylmethoxy)-1,2-dihydroisoquinolin-3-yl]acetic acid,
(2S)-2-(tert-butoxy)-2-[4-(8-fluoro-5-methyl-3,4-dihydro-2H-1-benzopyran-6-yl)-2-methyl-1-oxo-7-(pyridin-2-ylmethoxy)-1,2-dihydroisoquinolin-3-yl]acetic acid,
(2S)-2-(tert-butoxy)-2-[2-methyl-4-(5-methyl-3,4-dihydro-2H-1-benzopyran-6-yl)-1-oxo-7-(pyridin-2-ylmethoxy)-1,2-dihydroisoquinolin-3-yl]acetic acid,
2-(tert-butoxy)-2-[4-(8-fluoro-5-methyl-3,4-dihydro-2H-1-benzopyran-6-yl)-7-[(4-fluorophenyl)methoxy]-2-methyl-1-oxo-1,2-dihydroisoquinolin-3-yl]acetic acid,
2-(tert-butoxy)-2-[2-methyl-4-(5-methyl-3,4-dihydro-2H-1-benzopyran-6-yl)-1-oxo-7-{[4-(trifluoromethoxy)phenyl]methoxy}-1,2-dihydroisoquinolin-3-yl]acetic acid,
(2S)-2-(tert-butoxy)-2-{7-[(4-fluorophenyl)methoxy]-2-methyl-4-(5-methyl-3,4-dihydro-2H-1-benzopyran-6-yl)-1-oxo-1,2-dihydroisoquinolin-3-yl}acetic acid,
(2S)-2-(tert-butoxy)-2-{7-[(2,4-difluorophenyl)methoxy]-2-methyl-4-(5-methyl-3,4-dihydro-2H-1-benzopyran-6-yl)-1-oxo-1,2-dihydroisoquinolin-3-yl}acetic acid,
2-(tert-butoxy)-2-[4-(3,4-dimethylphenyl)-7-fluoro-2-methyl-1-oxo-1,2-dihydroisoquinolin-3-yl]acetic acid,
(2S)-2-(tert-butoxy)-2-[2-methyl-4-(5-methyl-3,4-dihydro-2H-1-benzopyran-6-yl)-1-oxo-1,2-dihydroisoquinolin-3-yl]acetic acid,
[(1,1-dimethylethyl)oxy][2-methyl-4-(4-methyl-3,4-dihydro-2H-chromen-6-yl)-1-oxo-1,2-dihydro-3-isoquinolinyl]acetic acid,
[(1,1-dimethylethyl)oxy][4-(8-fluoro-5-methyl-3,4-dihydro-2H-chromen-6-yl)-2-methyl-1-oxo-1,2-dihydro-3-isoquinolinyl]acetic acid,
[(1,1-dimethylethyl)oxy]{4-[2-fluoro-4-(fluoromethyl)phenyl]-2-methyl-1-oxo-1,2-dihydro-3-isoquinolinyl}acetic acid,
2-(tert-butoxy)-2-(4-(2,3-dihydro-1H-inden-5-yl)-2-methyl-1-oxo-1,2-dihydroisoquinolin-3-yl)acetic acid,
2-(4-(benzo[d]thiazol-6-yl)-2-methyl-1-oxo-1,2-dihydroisoquinolin-3-yl)-2-(tert-butoxy)acetic acid,
[4-(4-chlorophenyl)-2-methyl-1-oxo-1,2-dihydro-3-isoquinolinyl][(1,1-dimethylethyl)oxy]acetic acid,
[(1,1-dimethylethyl)oxy][2-methyl-4-(2-methyl-3-furanyl)-1-oxo-1,2-dihydro-3-isoquinolinyl]acetic acid,
[(1,1-dimethylethyl)oxy](2-methyl-1-oxo-4-phenyl-1,2-dihydro-3-isoquinolinyl)acetic acid,
[(1,1-dimethylethyl)oxy][2-methyl-4-(1-methyl-1H-pyrazol-4-yl)-1-oxo-1,2-dihydro-3-isoquinolinyl]acetic acid,
[(1,1-dimethylethyl)oxy][2-methyl-1-oxo-4-(2,3,6,7-tetrahydro-1H,5H-pyrido[3,2,1-ij]quinolin-9-yl)-1,2-dihydro-3-isoquinolinyl]acetic acid,
(2R)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]acetic acid,
(2S)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]acetic acid,
(2R)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]acetic acid,
(2S)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]acetic acid,
(2S)-2-[4-(8-fluoro-5-methyl-3,4-dihydro-2H-1-benzopyran-6-yl)-2-methyl-1-oxo-1,2-dihydroisoquinolin-3-yl]-2-(1-methylcyclobutoxy)acetic acid,
(2S)(M)-[7-bromo-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid,
(2S)(M)-[7-[(4-chloro-3-fluorophenyl)amino]-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid, (2S)(M)-[(1,1-dimethylethyl)oxy][4-(8-fluoro-5-methyl-3,4-dihydro-2H-chromen-6-yl)-2-methyl-1-oxo-7-(1-piperidinyl)-1,2-dihydro-3-isoquinolinyl]ethanoic acid, (2S)(M)-[(1,1-dimethylethyl)oxy][7-(1,1-dioxido-4-thiomorpholinyl)-4-(8-fluoro-5-methyl-3,4-dihydro-2H-chromen-6-yl)-2-methyl-1-oxo-1,2-dihydro-3-isoquinolinyl]ethanoic acid, (S)(M)-2-(tert-butoxy)-2-(4-(8-fluoro-5-methylchroman-6-yl)-2-methyl-7-morpholino-1-oxo-1,2-dihydroisoquinolin-3-yl)acetic acid, (S)(M)-2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetic acid,

[(1,1-dimethylethyl)oxy]{4-(3,4-dimethylphenyl)-7-[(ethylamino)carbonyl]-2-methyl-1-oxo-1,2-dihydro-3-isoquinolinyl}acetic acid,

[(1,1-dimethylethyl)oxy](4-(3,4-dimethylphenyl)-2-methyl-7-{[4-(methyloxy)phenyl]methyl}-1-oxo-1,2-dihydro-3-isoquinolinyl)acetic acid,

[(1,1-dimethylethyl)oxy][4-(3,4-dimethylphenyl)-2-methyl-7-(2-methylpropyl)-1-oxo-1,2-dihydro-3-isoquinolinyl]acetic acid, (2S)(M)-[(1,1-dimethylethyl)oxy][4-(8-fluoro-5-methyl-3,4-dihydro-2H-chromen-6-yl)-2-methyl-7-(6-methyl-2-pyridinyl)-1-oxo-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-7-(2-methylpropyl)-1-oxo-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-1-oxo-7-(phenylmethyl)-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-1-oxo-7-(2-phenylethyl)-1,2-dihydro-3-isoquinolinyl]ethanoic acid, 7-cyano-4-(3,4-dimethylphenyl)-2-methyl-1-oxo-1,2-dihydro-3-isoquinolinyl][(1,1-dimethylethyl)oxy]acetic acid,

[7-(aminocarbonyl)-4-(3,4-dimethylphenyl)-2-methyl-1-oxo-1,2-dihydro-3-isoquinolinyl][(1,1-dimethylethyl)oxy]acetic acid,

[7-(aminomethyl)-4-(3,4-dimethylphenyl)-2-methyl-1-oxo-1,2-dihydro-3-isoquinolinyl][(1,1-dimethylethyl)oxy]acetic acid-TFA salt, 2,2'-(iminobis{methanediyl[4-(3,4-dimethylphenyl)-2-methyl-1-oxo-1,2-dihydroisoquinoline-7,3-diyl]})bis{[(1,1-dimethylethyl)oxy]acetic acid}, 2-(tert-butoxy)-2-(4-(3,4-dimethylphenyl)-2-methyl-7-(methylsufonamidomethyl)-1-oxo-1,2-dihydroisoquinolin-3-yl)acetic acid, 2-(7-((bis(pyridin-2-ylmethyl)amino)methyl)-4-(3,4-dimethylphenyl)-2-methyl-1-oxo-1,2-dihydroisoquinolin-3-yl)-2-(tert-butoxy)acetic acid, 2-(tert-butoxy)-2-(4-(3,4-dimethylphenyl)-2-methyl-1-oxo-7-(((pyridin-2-ylmethyl)amino)methyl)-1,2-dihydroisoquinolin-3-yl)acetic acid, 2-(7-(acetamidomethyl)-4-(3,4-dimethylphenyl)-2-methyl-1-oxo-1,2-dihydroisoquinolin-3-yl)-2-(tert-butoxy)acetic acid, 2-(tert-butoxy)-2-(4-(3,4-dimethylphenyl)-7-((3-ethylureido)methyl)-2-methyl-1-oxo-1,2-dihydroisoquinolin-3-yl)acetic acid, 2-(tert-butoxy)-2-(7-((carboxyformamido)methyl)-4-(3,4-dimethylphenyl)-2-methyl-1-oxo-1,2-dihydroisoquinolin-3-yl)acetic acid, 2-(tert-butoxy)-2-(4-(3,4-dimethylphenyl)-2-methyl-7-(methylsufonamidomethyl)-1-oxo-1,2-dihydroisoquinolin-3-yl)acetic acid, 2-(tert-butoxy)-2-(4-(3,4-dimethylphenyl)-7-(((N,N-dimethylsulfamoyl)amino)methyl)-2-methyl-1-oxo-1,2-dihydroisoquinolin-3-yl)acetic acid, (S)(M)-2-(tert-butoxy)-2-(4-(8-fluoro-5-methylchroman-6-yl)-2-methyl-7-(morpholinomethyl)-1-oxo-1,2-dihydroisoquinolin-3-yl)acetic acid, (S)(M)-2-(tert-butoxy)-2-(4-(8-fluoro-5-methylchroman-6-yl)-2-methyl-1-oxo-7-(piperidin-1-ylmethyl)-1,2-dihydroisoquinolin-3-yl)acetic acid,

[(1,1-dimethylethyl)oxy][4-(3,4-dimethylphenyl)-2-methyl-7-(1-methyl-1H-pyrrol-2-yl)-1-oxo-1,2-dihydro-3-isoquinolinyl]acetic acid,

[(1,1-dimethylethyl)oxy][4-(3,4-dimethyl phenyl)-2-methyl-7-(1-methyl-1H-pyrazol-4-yl)-1-oxo-1,2-dihydro-3-isoquinolinyl]acetic acid,

[(1,1-dimethylethyl)oxy][4-(3,4-dimethylphenyl)-2-methyl-7-(2-methyl-3-furanyl)-1-oxo-1,2-dihydro-3-isoquinolinyl]acetic acid, (2S)(M)-[(1,1-dimethylethyl)oxy][4-(8-fluoro-5-methyl-3,4-dihydro-2H-chromen-6-yl)-7-(3-furanyl)-2-methyl-1-oxo-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-7-(1-methyl-1H-pyrazol-5-yl)-1-oxo-1,2-dihydro-3-isoquinolinyl]ethanoic acid, 2S)(M)-[(1,1-dimethylethyl)oxy][7-(3,5-dimethyl-1H-pyrazol-4-yl)-4-(8-fluoro-5-methyl-3,4-dihydro-2H-chromen-6-yl)-2-methyl-1-oxo-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-1-oxo-7-(1H-pyrazol-4-yl)-1,2-dihydro-3-isoquinolinyl]ethanoic acid (2S)(M)-[(1,1-dimethylethyl)oxy]{4-(8-fluoro-5-methyl-3,4-dihydro-2H-chromen-6-yl)-2-methyl-7-[6-(methyloxy)-3-pyridinyl]-1-oxo-1,2-dihydro-3-isoquinolinyl}ethanoic acid, (2S)(M)-[7-[4-(dimethylamino)phenyl]-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid, (2S)(M)-[(1,1-dimethylethyl)oxy][4-(8-fluoro-5-methyl-3,4-dihydro-2H-chromen-6-yl)-2-methyl-7-(1-methyl-1H-pyrazol-4-yl)-1-oxo-1,2-dihydro-3-isoquinolinyl]ethanoic acid, (2S)(M)-[(1,1-dimethylethyl)oxy]{4-(8-fluoro-5-methyl-3,4-dihydro-2H-chromen-6-yl)-2-methyl-7-[1-(3-methylbutyl)-1H-pyrazol-4-yl]-1-oxo-1,2-dihydro-3-isoquinolinyl}ethanoic acid, (S)(M)-[(1,1-dimethylethyl)oxy][4-(8-fluoro-5-methyl-3,4-dihydro-2H-chromen-6-yl)-2-methyl-7-(1-methyl-1H-pyrrol-2-yl)-1-oxo-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-7-(2-methyl-3-furanyl)-1-oxo-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-1-oxo-7-phenyl-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-1-oxo-7-(4-pyridinyl)-1,2-dihydro-3-isoquinolinyl]ethanoic acid, (2S)(M)-[(1,1-dimethylethyl)oxy][4-(8-fluoro-5-methyl-3,4-dihydro-2H-chromen-6-yl)-2-methyl-1-oxo-7-(3-pyridinyl)-1,2-dihydro-3-isoquinolinyl]ethanoic acid, (2S)(M)-[(1,1-dimethylethyl)oxy][7-(3,5-dimethyl-4-isoxazolyl)-4-(8-fluoro-5-methyl-3,4-dihydro-2H-chromen-6-yl)-2-methyl-1-oxo-1,2-dihydro-3-isoquinolinyl]ethanoic acid,
(2S)(M)-[(1,1-dimethylethyl)oxy]{4-(8-fluoro-5-methyl-3,4-dihydro-2H-chromen-6-yl)-2-methyl-7-[6-(methyloxy)-2-pyridinyl]-1-oxo-1,2-dihydro-3-isoquinolinyl}ethanoic acid,
(S)(M)-2-(tert-butoxy)-2-(4-(8-fluoro-5-methylchroman-6-yl)-7-(4-fluorophenyl)-2-methyl-1-oxo-1,2-dihydroisoquinolin-3-yl)acetic acid,
(S)(M)-2-(tert-butoxy)-2-(4-(8-fluoro-5-methylchroman-6-yl)-7-(3-fluorophenyl)-2-methyl-1-oxo-1,2-dihydroisoquinolin-3-yl)acetic acid,
(S)(M)-2-(tert-butoxy)-2-(4-(8-fluoro-5-methylchroman-6-yl)-7-(2-fluorophenyl)-2-methyl-1-oxo-1,2-dihydroisoquinolin-3-yl)acetic acid,
2-(tert-Butoxy)-2-(4-((3,4-dimethylphenyl)(methyl)amino)-2-methyl-1-oxo-1,2-dihydroisoquinolin-3-yl)acetic acid,
(S)(M)-2-(tert-butoxy)-2-(4-(8-fluoro-5-methylchroman-6-yl)-2-methyl-1-oxo-1,2-dihydroisoquinolin-3-yl)-N-hydroxyacetamide,
(S)(M)-2-(tert-butoxy)-2-(4-(8-fluoro-5-methylchroman-6-yl)-2-methyl-1-oxo-1,2-dihydroisoquinolin-3-yl)-N-hydroxy-N-methylacetamide,
(2S)(M)-2-[(1,1-dimethylethyl)oxy]-2-[4-(8-fluoro-5-methyl-3,4-dihydro-2H-chromen-6-yl)-2-methyl-1-oxo-1,2-dihydro-3-isoquinolinyl]-N-(methylsulfonyl)ethanamide,
2-[4-(2,4-dimethylphenyl)-2-methyl-1-oxo-1,2-dihydro-3-isoquinolinyl]pentanoic acid,
2-[4-(2,4-dimethylphenyl)-2-methyl-1-oxo-1,2-dihydro-3-isoquinolinyl]-4-methylpentanoic acid,
Methyl [4-(2,4-dimethylphenyl)-2-methyl-1-oxo-1,2-dihydro-3-isoquinolinyl](ethyloxy)acetate,
[(1,1-dimethylethyl)oxy]{4-(2,4-dimethylphenyl)-7-[1-(2-hydroxyethyl)-1H-1,2,3-triazol-4-yl]-2-methyl-1-oxo-1,2-dihydro-3-isoquinolinyl}acetic acid, and
2-(tert-butoxy)-2-(1-(4-fluorobenzyl)-6-methyl-4-(p-tolyl)-1H-pyrrolo[2,3-b]pyridin-5-yl)acetic acid,
and pharmaceutically acceptable salts thereof.

In another embodiment of the present invention, there is provided a compound of Formula I or II, wherein a compound suitable for use with the present invention is selected from the group consisting of those compounds described in Table 1 and/or Table 2.

Such compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formulas I or II, wherein the compound or salt of the compound is used in the manufacture of a medicament for use in the treatment of a viral infection in a human.

In another embodiment of the invention, there is provided a pharmaceutical composition comprising a pharmaceutically acceptable diluent and a therapeutically effective amount of a compound as defined in Formulas I or II.

In one embodiment, the pharmaceutical formulation containing a compound of Formulas I or II, or a salt thereof is a formulation adapted for parenteral administration. In another embodiment, the formulation is a long-acting parenteral formulation. In a further embodiment, the formulation is a nanoparticle formulation.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formulas I or II, or salts thereof and the other pharmaceutically active agent(s) and the relative timings of administration will be selected in order to achieve the desired combined therapeutic effect.

As such, the compounds of the present invention may be used in combination with one or more agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Inteqrase inhibitors such as raltegravir, elvitegravir, GSK1349572, GSK1265744 and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methyethyl)-1-1 [2-(1-methylethyl)-4-thiazolyl]-3,6-dioxo-8,11-bis(phenylmethyl)-2,4,7,12-tetraazamidecan-13-oic acid, 5-thiazolylmethyl ester, [5S-(5S*,8R*,10R*,11R*)] and is available from Abbott Laboratories of Abbott park, Ill., as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by Sequoia Pharmaceuticals of Gaithersburg, Md., as a pharmacological enhancer.

In one embodiment of the present invention, a compound of Formulas I or II is used in combination with ritonavir. In one embodiment, the combination is an oral fixed dose combination. In another embodiment, the compound of Formulas I or II is formulated as a long acting parenteral injection and ritonavir is formulated as an oral composition. In one embodiment, is a kit containing the compound of Formulas I or II is formulated as a long acting parenteral injection and ritonavir formulated as an oral composition. In another embodiment, the compound of Formulas I or II is formulated as a long acting parenteral injection and ritonavir is formulated as an injectable composition. In one embodiment, is a kit containing the compound of Formulas I or II is formulated as a long acting parenteral injection and ritonavir formulated as an injectable composition.

In another embodiment of the present invention, a compound of Formulas I or II is used in combination with GS-9350. In one embodiment, the combination is an oral fixed dose combination. In another embodiment, the compound of Formulas I or II is formulated as a long acting parenteral injection and GS-9350 is formulated as an oral composition. In one embodiment, is a kit containing the compound of Formulas I or II is formulated as a long acting parenteral injection and GS-9350 formulated as an oral composition. In another embodiment, the compound of Formulas I or II is formulated as a long acting parenteral injection and GS-9350 is formulated as an injectable composition. In one embodiment, is a kit containing the compound of Formulas I or II is formulated as a long acting parenteral injection and GS-9350 formulated as an injectable composition.

In one embodiment of the present invention, a compound of Formulas I or II is used in combination with SPI-452. In one embodiment, the combination is an oral fixed dose combination. In another embodiment, the compound of Formulas I or II is formulated as a long acting parenteral injection and SPI-452 is formulated as an oral composition. In one embodiment, is a kit containing the compound of Formulas I or II is formulated as a long acting parenteral injection and SPI-452 formulated as an oral composition. In another embodiment, the compound of Formulas I or II is formulated as a long acting parenteral injection and SPI-452 is formulated as an injectable composition. In one embodiment, is a kit containing the compound of Formulas I or II is formulated as a long acting parenteral injection and SPI-452 formulated as an injectable composition.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I or II.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I or II, wherein said virus is an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III, further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I or II, further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In further embodiments, the compound of the present invention, or a pharmaceutically acceptable salt thereof, is chosen from the compounds set forth in Table 1.

TABLE 1

| Compound No. and Example No. | Structure | Chemical Name |
|---|---|---|
| 1 | 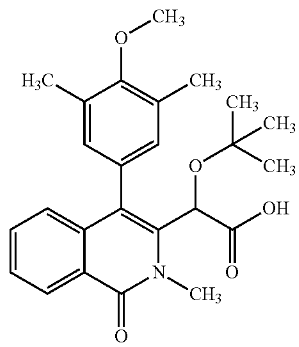 [SMILES: COc1c(C)cc(-c2c(C(OC(C)(C)C)C(=O)O)n(C)c(=O)c3ccccc23)cc1C] | tert-Butoxy-[4-(4-methoxy-3,5-dimethyl-phenyl)-2-methyl-1-oxo-1,2-dihydro-isoquinolin-3-yl]-acetic acid |
| 2 | 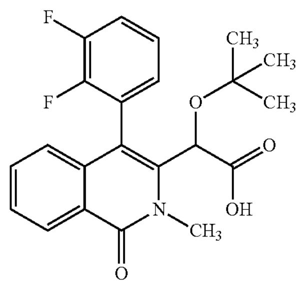 [SMILES: Cn1c(C(OC(C)(C)C)C(=O)O)c(-c2cccc(F)c2F)c2ccccc2c1=O] | tert-Butoxy-[4-(3,4-Difluoro-phenyl)-2-methyl-1-oxo-1,2-dihydro-isoquinolin-3-yl]-acetic acid |
| 3 | 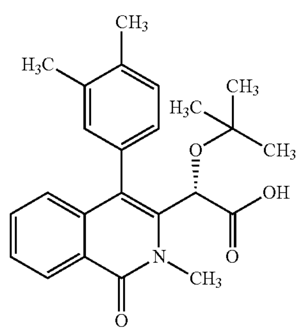 [SMILES: Cc1ccc(-c2c([C@H](OC(C)(C)C)C(=O)O)n(C)c(=O)c3ccccc23)cc1C] | (S)-2-(tert-butoxy)-2-(4-(3,4-dimethylphenyl)-2-methyl-1-oxo-1,2-dihydroisoquinolin-3-yl)acetic acid |
| 4 | 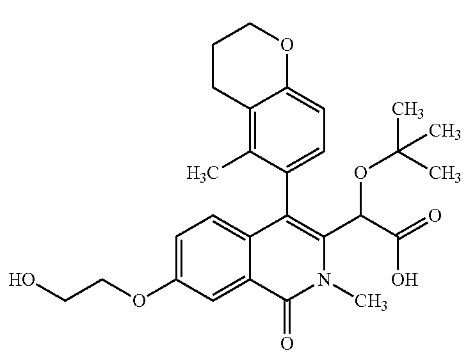 [SMILES: Cc1c(-c2c(C(OC(C)(C)C)C(=O)O)n(C)c(=O)c3cc(OCCO)ccc23)ccc2c1CCCO2] | tert-Butoxy-[7-(2-hydroxy-ethoxy)-2-methyl-4-(5-methyl-chroman-6-yl)-1-oxo-1,2-dihydro-isoquinolin-3-yl]-acetic acid |

TABLE 1-continued

| Compound No. and Example No. | Structure | Chemical Name |
|---|---|---|
| 5 | 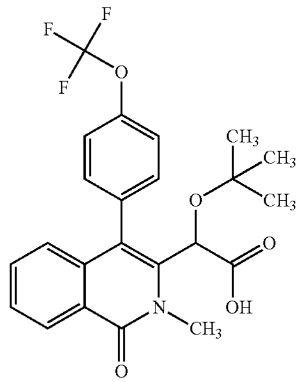 [SMILES: Cn1c(C(OC(C)(C)C)C(=O)O)c(-c2ccc(OC(F)(F)F)cc2)c2ccccc2c1=O] | 2-(tert-butoxy)-2-{2-methyl-1-oxo-4-[4-(trifluoromethoxy)phenyl]-1,2-dihydroisoquinolin-3-yl}acetic acid |
| 6 | 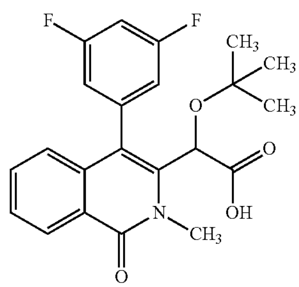 [SMILES: Cn1c(C(OC(C)(C)C)C(=O)O)c(-c2cc(F)cc(F)c2)c2ccccc2c1=O] | 2-(tert-butoxy)-2-[4-(3,5-difluorophenyl)-2-methyl-1-oxo-1,2-dihydroisoquinolin-3-yl]acetic acid |
| 7 | 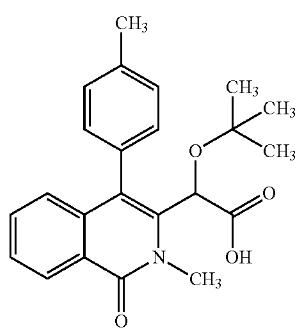 [SMILES: Cc1ccc(-c2c(C(OC(C)(C)C)C(=O)O)n(C)c(=O)c3ccccc23)cc1] | 2-(tert-butoxy)-2-[2-methyl-4-(4-methylphenyl)-1-oxo-1,2-dihydroisoquinolin-3-yl]acetic acid |
| 8 | 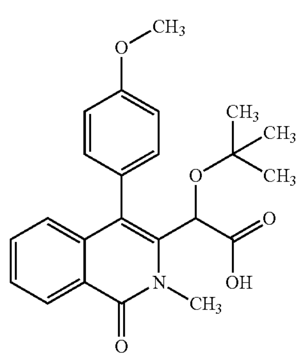 [SMILES: COc1ccc(-c2c(C(OC(C)(C)C)C(=O)O)n(C)c(=O)c3ccccc23)cc1] | 2-(tert-butoxy)-2-[4-(4-methoxyphenyl)-2-methyl-1-oxo-1,2-dihydroisoquinolin-3-yl]acetic acid |

TABLE 1-continued

| Compound No. and Example No. | Structure | Chemical Name |
|---|---|---|
| 9 | 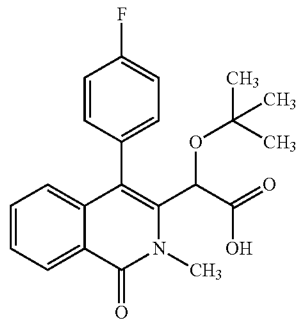 [SMILES: Cn1c(C(OC(C)(C)C)C(=O)O)c(-c2ccc(F)cc2)c2ccccc2c1=O] | 2-(tert-butoxy)-2-[4-(4-fluorophenyl)-2-methyl-1-oxo-1,2-dihydroisoquinolin-3-yl]acetic acid |
| 10 | 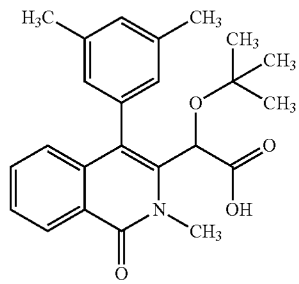 [SMILES: Cc1cc(C)cc(-c2c(C(OC(C)(C)C)C(=O)O)n(C)c(=O)c3ccccc23)c1] | 2-(tert-butoxy)-2-[4-(3,5-dimethylphenyl)-2-methyl-1-oxo-1,2-dihydroisoquinolin-3-yl]acetic acid |
| 11 | 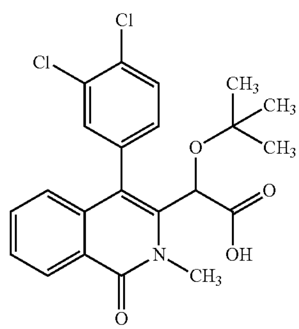 [SMILES: Cn1c(C(OC(C)(C)C)C(=O)O)c(-c2ccc(Cl)c(Cl)c2)c2ccccc2c1=O] | 2-(tert-butoxy)-2-[4-(3,4-dichlorophenyl)-2-methyl-1-oxo-1,2-dihydroisoquinolin-3-yl]acetic acid |
| 12 | 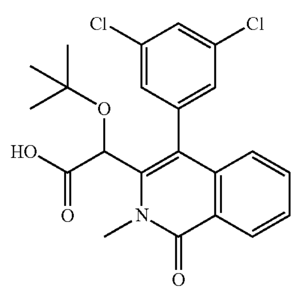 [SMILES: Cn1c(C(OC(C)(C)C)C(=O)O)c(-c2cc(Cl)cc(Cl)c2)c2ccccc2c1=O] | 2-(tert-butoxy)-2-[4-(3,5-dichlorophenyl)-2-methyl-1-oxo-1,2-dihydroisoquinolin-3-yl]acetic acid |
| 13 | 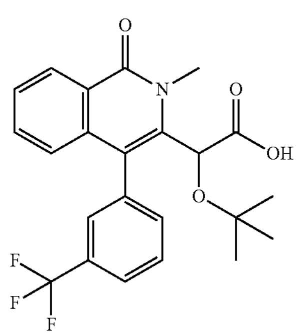 [SMILES: Cn1c(C(OC(C)(C)C)C(=O)O)c(-c2cccc(C(F)(F)F)c2)c2ccccc2c1=O] | 2-(tert-butoxy)-2-{2-methyl-1-oxo-4-[3-(trifluoromethyl)phenyl]-1,2-dihydroisoquinolin-3-yl}acetic acid |

TABLE 1-continued

| Compound No. and Example No. | Structure | Chemical Name |
|---|---|---|
| 14 | 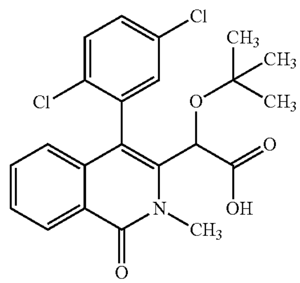 [SMILES: Cn1c(C(OC(C)(C)C)C(=O)O)c(-c2cc(Cl)ccc2Cl)c2ccccc2c1=O] | 2-(tert-butoxy)-2-[4-(2,5-dichlorophenyl)-2-methyl-1-oxo-1,2-dihydroisoquinolin-3-yl]acetic acid |
| 15 | 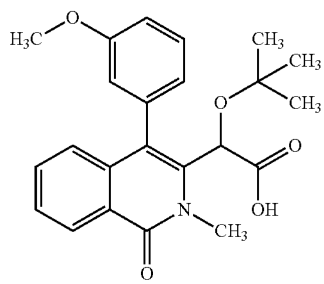 [SMILES: COc1cccc(-c2c(C(OC(C)(C)C)C(=O)O)n(C)c(=O)c3ccccc23)c1] | 2-(tert-butoxy)-2-[4-(3-methoxyphenyl)-2-methyl-1-oxo-1,2-dihydroisoquinolin-3-yl]acetic acid |
| 16 | 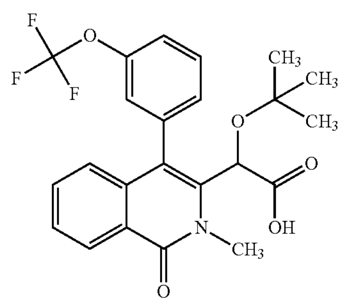 [SMILES: Cn1c(C(OC(C)(C)C)C(=O)O)c(-c2cccc(OC(F)(F)F)c2)c2ccccc2c1=O] | 2-(tert-butoxy)-2-{2-methyl-1-oxo-4-[3-(trifluoromethoxy)phenyl]-1,2-dihydroisoquinolin-3-yl}acetic acid |
| 17 | 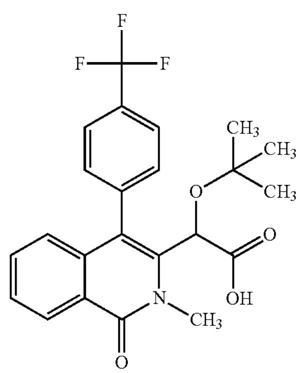 [SMILES: Cn1c(C(OC(C)(C)C)C(=O)O)c(-c2ccc(C(F)(F)F)cc2)c2ccccc2c1=O] | 2-(tert-butoxy)-2-{2-methyl-1-oxo-4-[4-(trifluoromethyl)phenyl]-1,2-dihydroisoquinolin-3-yl}acetic acid |
| 18 | 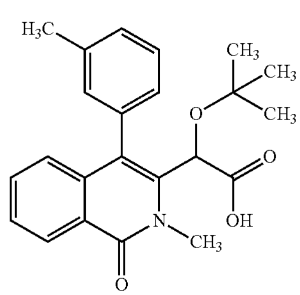 [SMILES: Cc1cccc(-c2c(C(OC(C)(C)C)C(=O)O)n(C)c(=O)c3ccccc23)c1] | 2-(tert-butoxy)-2-[2-methyl-4-(3-methylphenyl)-1-oxo-1,2-dihydroisoquinolin-3-yl]acetic acid |

TABLE 1-continued

| Compound No. and Example No. | Structure | Chemical Name |
|---|---|---|
| 19 | 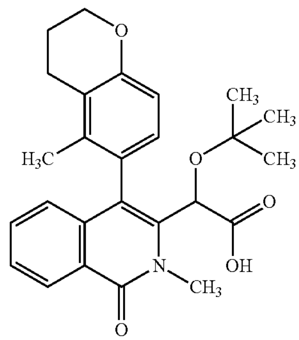 [SMILES: Cc1c(-c2c(C(OC(C)(C)C)C(=O)O)n(C)c(=O)c3ccccc23)ccc2c1CCCO2] | 2-(tert-butoxy)-2-[2-methyl-4-(5-methyl-3,4-dihydro-2H-1-benzopyran-6-yl)-1-oxo-1,2-dihydroisoquinolin-3-yl]acetic acid |
| 20 | 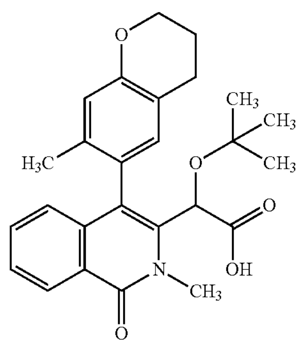 [SMILES: Cc1cc2c(cc1-c1c(C(OC(C)(C)C)C(=O)O)n(C)c(=O)c3ccccc13)CCCO2] | 2-(tert-butoxy)-2-[2-methyl-4-(7-methyl-3,4-dihydro-2H-1-benzopyran-6-yl)-1-oxo-1,2-dihydroisoquinolin-3-yl]acetic acid |
| 21 | 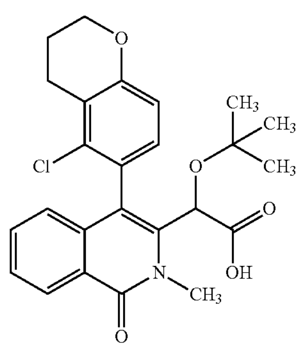 [SMILES: Cn1c(C(OC(C)(C)C)C(=O)O)c(-c2ccc3c(c2Cl)CCCO3)c2ccccc2c1=O] | 2-(tert-butoxy)-2-[4-(5-chloro-3,4-dihydro-2H-1-benzopyran-6-yl)-2-methyl-1-oxo-1,2-dihydroisoquinolin-3-yl]acetic acid |
| 22 | 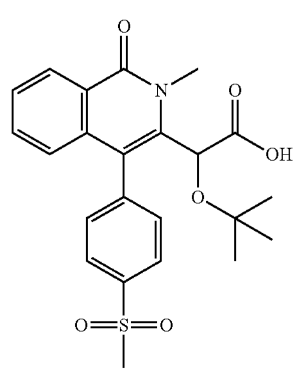 [SMILES: Cn1c(C(OC(C)(C)C)C(=O)O)c(-c2ccc(S(C)(=O)=O)cc2)c2ccccc2c1=O] | 2-(tert-butoxy)-2-[4-(4-methanesulfonylphenyl)-2-methyl-1-oxo-1,2-dihydroisoquinolin-3-yl]acetic acid |

TABLE 1-continued

| Compound No. and Example No. | Structure | Chemical Name |
|---|---|---|
| 23 | 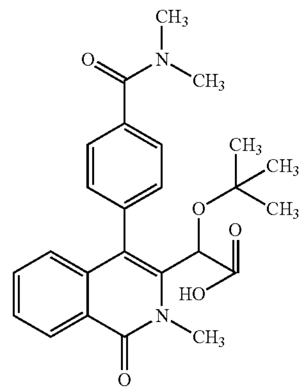 [SMILES: CN(C)C(=O)c1ccc(-c2c(C(OC(C)(C)C)C(=O)O)n(C)c(=O)c3ccccc23)cc1] | 2-(tert-butoxy)-2-{4-[4-(dimethylcarbamoyl)phenyl]-2-methyl-1-oxo-1,2-dihydroisoquinolin-3-yl}acetic acid |
| 24 | 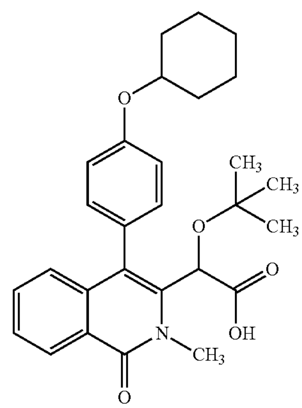 [SMILES: Cn1c(C(OC(C)(C)C)C(=O)O)c(-c2ccc(OC3CCCCC3)cc2)c2ccccc2c1=O] | 2-(tert-butoxy)-2-{4-[4-(cyclohexyloxy)phenyl]-2-methyl-1-oxo-1,2-dihydroisoquinolin-3-yl}acetic acid |
| 25 | 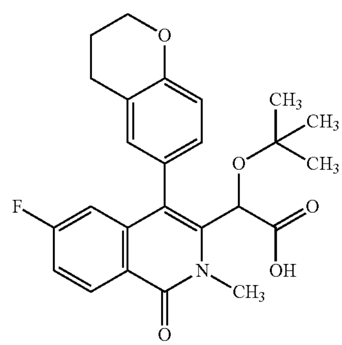 [SMILES: Cn1c(C(OC(C)(C)C)C(=O)O)c(-c2ccc3c(c2)CCCO3)c2cc(F)ccc2c1=O] | 2-(tert-butoxy)-2-[4-(3,4-dihydro-2H-1-benzopyran-6-yl)-6-fluoro-2-methyl-1-oxo-1,2-dihydroisoquinolin-3-yl]acetic acid |
| 26 | 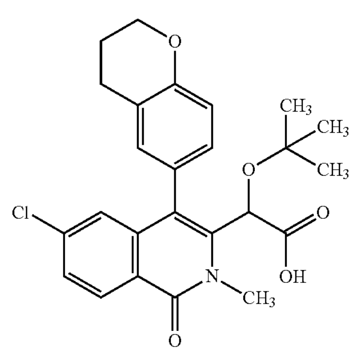 [SMILES: Cn1c(C(OC(C)(C)C)C(=O)O)c(-c2ccc3c(c2)CCCO3)c2cc(Cl)ccc2c1=O] | 2-(tert-butoxy)-2-[6-chloro-4-(3,4-dihydro-2H-1-benzopyran-6-yl)-2-methyl-1-oxo-1,2-dihydroisoquinolin-3-yl]acetic acid |

TABLE 1-continued

| Compound No. and Example No. | Structure | Chemical Name |
|---|---|---|
| 27 | 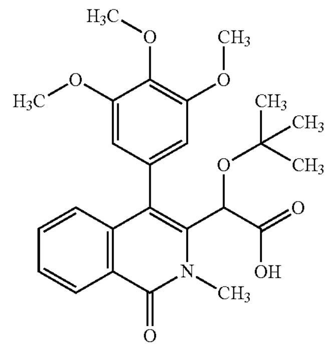 [SMILES: COc1cc(-c2c(C(OC(C)(C)C)C(=O)O)n(C)c(=O)c3ccccc23)cc(OC)c1OC] | 2-(tert-butoxy)-2-[2-methyl-1-oxo-4-(3,4,5-trimethoxyphenyl)-1,2-dihydroisoquinolin-3-yl]acetic acid |
| 28 | 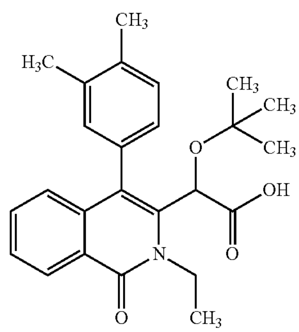 [SMILES: CCn1c(C(OC(C)(C)C)C(=O)O)c(-c2ccc(C)c(C)c2)c2ccccc2c1=O] | 2-(tert-butoxy)-2-[4-(3,4-dimethylphenyl)-2-ethyl-1-oxo-1,2-dihydroisoquinolin-3-yl]acetic acid |
| 29 | 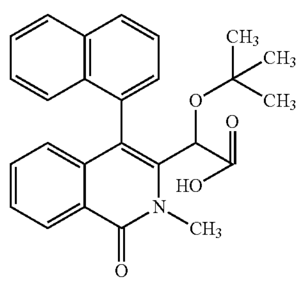 [SMILES: Cn1c(C(OC(C)(C)C)C(=O)O)c(-c2cccc3ccccc23)c2ccccc2c1=O] | 2-(tert-butoxy)-2-[2-methyl-4-(naphthalen-1-yl)-1-oxo-1,2-dihydroisoquinolin-3-yl]acetic acid |
| 30 | 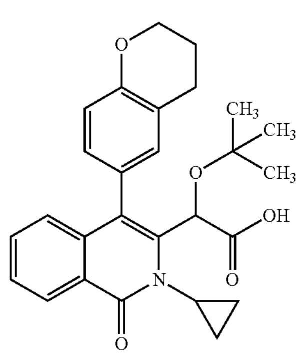 [SMILES: CC(C)(C)OC(C(=O)O)c1c(-c2ccc3c(c2)CCCO3)c2ccccc2c(=O)n1C1CC1] | 2-(tert-butoxy)-2-[2-cyclopropyl-4-(3,4-dihydro-2H-1-benzopyran-6-yl)-1-oxo-1,2-dihydroisoquinolin-3-yl]acetic acid |

TABLE 1-continued

| Compound No. and Example No. | Structure | Chemical Name |
|---|---|---|
| 31 | 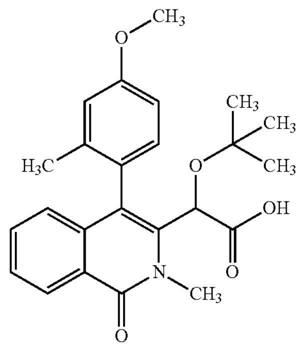 [SMILES: COc1ccc(-c2c(C(OC(C)(C)C)C(=O)O)n(C)c(=O)c3ccccc23)c(C)c1] | 2-(tert-butoxy)-2-[4-(4-methoxy-2-methylphenyl)-2-methyl-1-oxo-1,2-dihydroisoquinolin-3-yl]acetic acid |
| 32 | 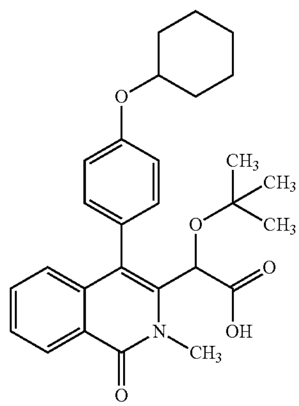 [SMILES: Cn1c(C(OC(C)(C)C)C(=O)O)c(-c2ccc(OC3CCCCC3)cc2)c2ccccc2c1=O] | 2-(tert-butoxy)-2-{4-[4-(cyclohexyloxy)phenyl]-2-methyl-1-oxo-1,2-dihydroisoquinolin-3-yl}acetic acid |
| 33 | 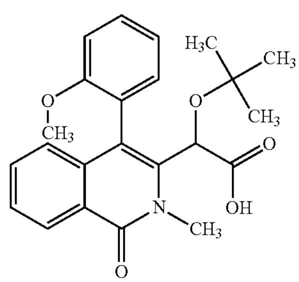 [SMILES: COc1ccccc1-c1c(C(OC(C)(C)C)C(=O)O)n(C)c(=O)c2ccccc12] | 2-(tert-butoxy)-2-[4-(2-methoxyphenyl)-2-methyl-1-oxo-1,2-dihydroisoquinolin-3-yl]acetic acid |
| 34 | 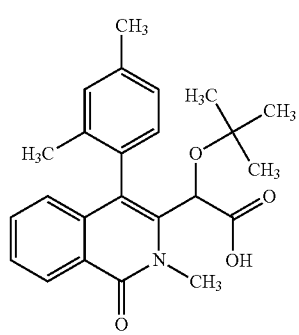 [SMILES: Cc1ccc(-c2c(C(OC(C)(C)C)C(=O)O)n(C)c(=O)c3ccccc23)c(C)c1] | 2-(tert-butoxy)-2-[4-(2,4-dimethylphenyl)-2-methyl-1-oxo-1,2-dihydroisoquinolin-3-yl]acetic acid |

TABLE 1-continued

| Compound No. and Example No. | Structure | Chemical Name |
|---|---|---|
| 35 | 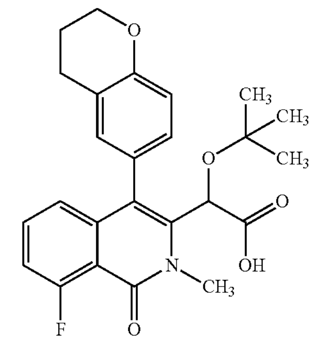 [SMILES: Cn1c(C(OC(C)(C)C)C(=O)O)c(-c2ccc3c(c2)CCCO3)c2cccc(F)c2c1=O] | 2-(tert-butoxy)-2-[4-(3,4-dihydro-2H-1-benzopyran-6-yl)-8-fluoro-2-methyl-1-oxo-1,2-dihydroisoquinolin-3-yl]acetic acid |
| 36 | 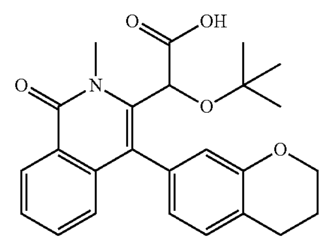 [SMILES: Cn1c(C(OC(C)(C)C)C(=O)O)c(-c2ccc3c(c2)OCCC3)c2ccccc2c1=O] | 2-(tert-butoxy)-2-[4-(3,4-dihydro-2H-1-benzopyran-7-yl)-2-methyl-1-oxo-1,2-dihydroisoquinolin-3-yl]acetic acid |
| 37 | 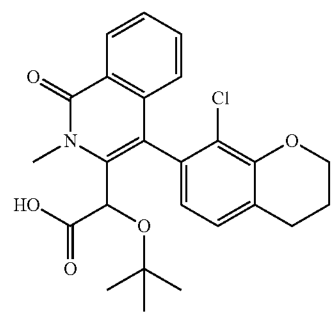 [SMILES: Cn1c(C(OC(C)(C)C)C(=O)O)c(-c2ccc3c(c2Cl)OCCC3)c2ccccc2c1=O] | 2-(tert-butoxy)-2-[4-(8-chloro-3,4-dihydro-2H-1-benzopyran-7-yl)-2-methyl-1-oxo-1,2-dihydroisoquinolin-3-yl]acetic acid |
| 38 | 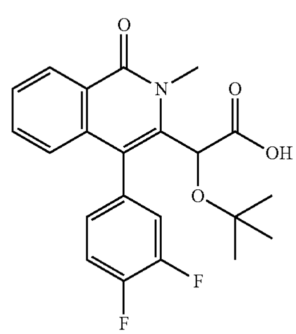 [SMILES: Cn1c(C(OC(C)(C)C)C(=O)O)c(-c2ccc(F)c(F)c2)c2ccccc2c1=O] | 2-(tert-butoxy)-2-[4-(3,4-difluorophenyl)-2-methyl-1-oxo-1,2-dihydroisoquinolin-3-yl]acetic acid |
| 39 | 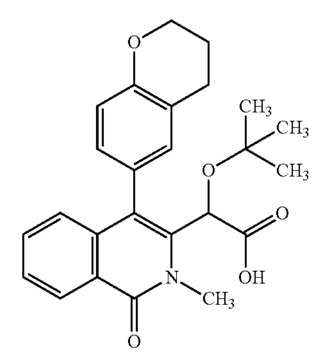 [SMILES: Cn1c(C(OC(C)(C)C)C(=O)O)c(-c2ccc3c(c2)CCCO3)c2ccccc2c1=O] | 2-(tert-butoxy)-2-[4-(3,4-dihydro-2H-1-benzopyran-6-yl)-2-methyl-1-oxo-1,2-dihydroisoquinolin-3-yl]acetic acid |

TABLE 1-continued

| Compound No. and Example No. | Structure | Chemical Name |
|---|---|---|
| 40 | 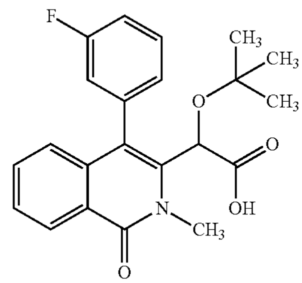 [SMILES: Cn1c(C(OC(C)(C)C)C(=O)O)c(-c2cccc(F)c2)c2ccccc2c1=O] | 2-(tert-butoxy)-2-[4-(3-fluorophenyl)-2-methyl-1-oxo-1,2-dihydroisoquinolin-3-yl]acetic acid |
| 41 | 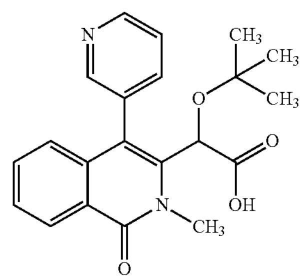 [SMILES: Cn1c(C(OC(C)(C)C)C(=O)O)c(-c2cccnc2)c2ccccc2c1=O] | 2-(tert-butoxy)-2-[2-methyl-1-oxo-4-(pyridin-3-yl)-1,2-dihydroisoquinolin-3-yl]acetic acid |
| 42 | 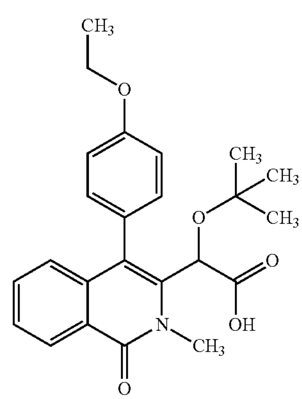 [SMILES: CCOc1ccc(-c2c(C(OC(C)(C)C)C(=O)O)n(C)c(=O)c3ccccc23)cc1] | 2-(tert-butoxy)-2-[4-(4-ethoxyphenyl)-2-methyl-1-oxo-1,2-dihydroisoquinolin-3-yl]acetic acid |

TABLE 1-continued

| Compound No. and Example No. | Structure | Chemical Name |
|---|---|---|
| 43 | 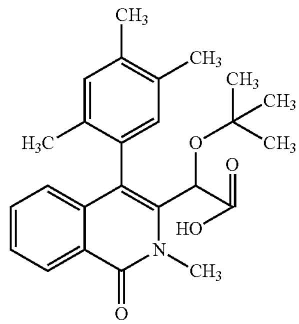 [SMILES: Cc1cc(C)c(-c2c(C(OC(C)(C)C)C(=O)O)n(C)c(=O)c3ccccc23)cc1C] | 2-(tert-butoxy)-2-[2-methyl-1-oxo-4-(2,4,5-trimethylphenyl)-1,2-dihydroisoquinolin-3-yl]acetic acid |
| 44 | 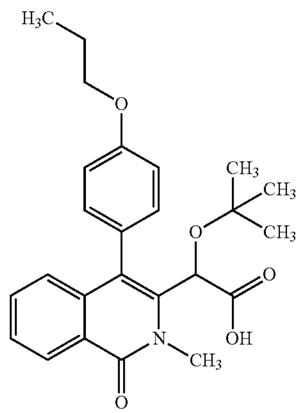 [SMILES: CCCOc1ccc(-c2c(C(OC(C)(C)C)C(=O)O)n(C)c(=O)c3ccccc23)cc1] | 2-(tert-butoxy)-2-[2-methyl-1-oxo-4-(4-propoxyphenyl)-1,2-dihydroisoquinolin-3-yl]acetic acid |
| 45 | 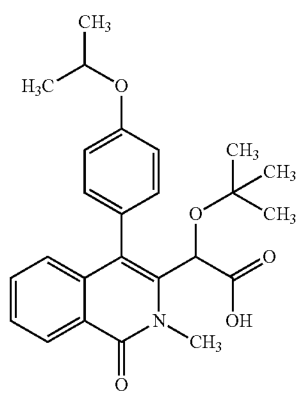 [SMILES: CC(C)Oc1ccc(-c2c(C(OC(C)(C)C)C(=O)O)n(C)c(=O)c3ccccc23)cc1] | 2-(tert-butoxy)-2-{2-methyl-1-oxo-4-[4-(propan-2-yloxy)phenyl]-1,2-dihydroisoquinolin-3-yl}acetic acid |
| 46 | 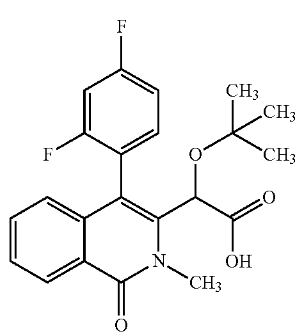 [SMILES: Cn1c(C(OC(C)(C)C)C(=O)O)c(-c2ccc(F)cc2F)c2ccccc2c1=O] | 2-(tert-butoxy)-2-[4-(2,4-difluorophenyl)-2-methyl-1-oxo-1,2-dihydroisoquinolin-3-yl]acetic acid |

TABLE 1-continued

| Compound No. and Example No. | Structure | Chemical Name |
|---|---|---|
| 47 | 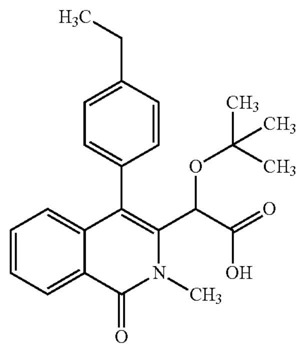 [SMILES: CCc1ccc(-c2c(C(OC(C)(C)C)C(=O)O)n(C)c(=O)c3ccccc23)cc1] | 2-(tert-butoxy)-2-[4-(4-ethylphenyl)-2-methyl-1-oxo-1,2-dihydroisoquinolin-3-yl]acetic acid |
| 48 | 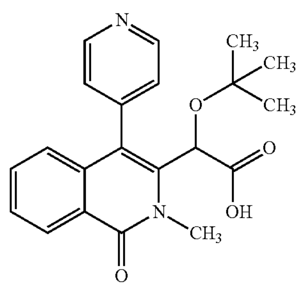 [SMILES: Cn1c(C(OC(C)(C)C)C(=O)O)c(-c2ccncc2)c2ccccc2c1=O] | 2-(tert-butoxy)-2-[2-methyl-1-oxo-4-(pyridin-4-yl)-1,2-dihydroisoquinolin-3-yl]acetic acid |
| 49 | 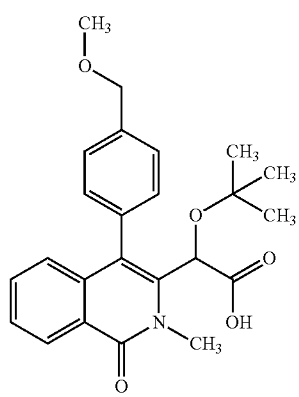 [SMILES: COCc1ccc(-c2c(C(OC(C)(C)C)C(=O)O)n(C)c(=O)c3ccccc23)cc1] | 2-(tert-butoxy)-2-{4-[4-(methoxymethyl)phenyl]-2-methyl-1-oxo-1,2-dihydroisoquinolin-3-yl}acetic acid |
| 50 | 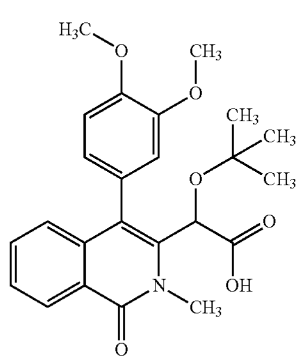 [SMILES: COc1ccc(-c2c(C(OC(C)(C)C)C(=O)O)n(C)c(=O)c3ccccc23)cc1OC] | 2-(tert-butoxy)-2-[4-(3,4-dimethoxyphenyl)-2-methyl-1-oxo-1,2-dihydroisoquinolin-3-yl]acetic acid |

TABLE 1-continued

| Compound No. and Example No. | Structure | Chemical Name |
|---|---|---|
| 51 | 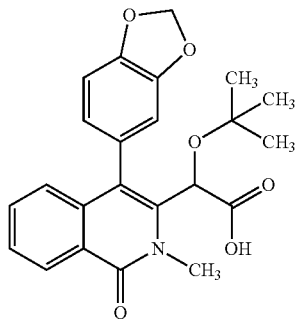 [SMILES: Cn1c(C(OC(C)(C)C)C(=O)O)c(-c2ccc3c(c2)OCO3)c2ccccc2c1=O] | 2-[4-(2H-1,3-benzodioxol-5-yl)-2-methyl-1-oxo-1,2-dihydroisoquinolin-3-yl]-2-(tert-butoxy)acetic acid |
| 52 | 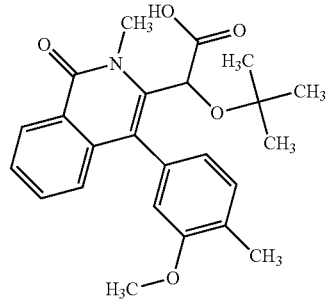 [SMILES: COc1cc(-c2c(C(OC(C)(C)C)C(=O)O)n(C)c(=O)c3ccccc23)ccc1C] | 2-(tert-butoxy)-2-[4-(3-methoxy-4-methylphenyl)-2-methyl-1-oxo-1,2-dihydroisoquinolin-3-yl]acetic acid |
| 53 | 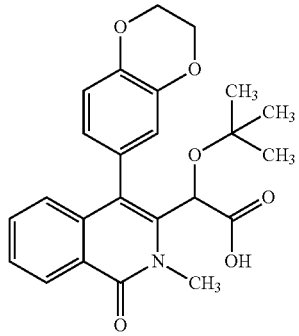 [SMILES: Cn1c(C(OC(C)(C)C)C(=O)O)c(-c2ccc3c(c2)OCCO3)c2ccccc2c1=O] | 2-(tert-butoxy)-2-[4-(2,3-dihydro-1,4-benzodioxin-6-yl)-2-methyl-1-oxo-1,2-dihydroisoquinolin-3-yl]acetic acid |
| 54 | 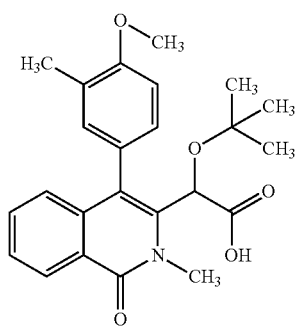 [SMILES: COc1ccc(-c2c(C(OC(C)(C)C)C(=O)O)n(C)c(=O)c3ccccc23)cc1C] | 2-(tert-butoxy)-2-[4-(4-methoxy-3-methylphenyl)-2-methyl-1-oxo-1,2-dihydroisoquinolin-3-yl]acetic acid |

TABLE 1-continued

| Compound No. and Example No. | Structure | Chemical Name |
| --- | --- | --- |
| 55 | 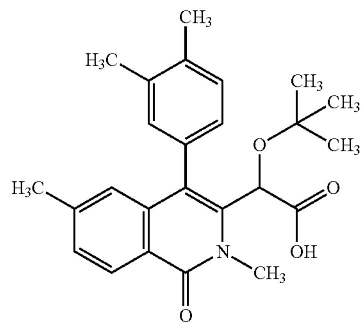 [SMILES: Cc1ccc2c(=O)n(C)c(C(OC(C)(C)C)C(=O)O)c(-c3ccc(C)c(C)c3)c2c1] | 2-(tert-butoxy)-2-[4-(3,4-dimethylphenyl)-2,6-dimethyl-1-oxo-1,2-dihydroisoquinolin-3-yl]acetic acid |
| 56 | 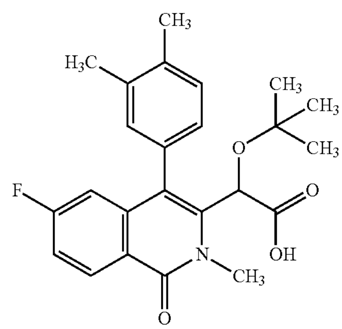 [SMILES: Cc1ccc(-c2c(C(OC(C)(C)C)C(=O)O)n(C)c(=O)c3ccc(F)cc23)cc1C] | 2-(tert-butoxy)-2-[4-(3,4-dimethylphenyl)-6-fluoro-2-methyl-1-oxo-1,2-dihydroisoquinolin-3-yl]acetic acid |
| 57 | 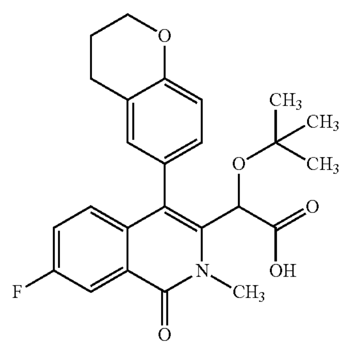 [SMILES: Cn1c(C(OC(C)(C)C)C(=O)O)c(-c2ccc3c(c2)CCCO3)c2ccc(F)cc2c1=O] | 2-(tert-butoxy)-2-[4-(3,4-dihydro-2H-1-benzopyran-6-yl)-7-fluoro-2-methyl-1-oxo-1,2-dihydroisoquinolin-3-yl]acetic acid |
| 58 | 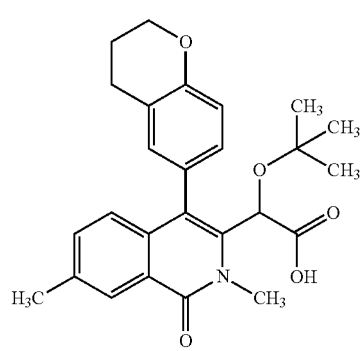 [SMILES: Cc1ccc2c(-c3ccc4c(c3)CCCO4)c(C(OC(C)(C)C)C(=O)O)n(C)c(=O)c2c1] | 2-(tert-butoxy)-2-[4-(3,4-dihydro-2H-1-benzopyran-6-yl)-2,7-dimethyl-1-oxo-1,2-dihydroisoquinolin-3-yl]acetic acid |

TABLE 1-continued

| Compound No. and Example No. | Structure | Chemical Name |
|---|---|---|
| 59 | 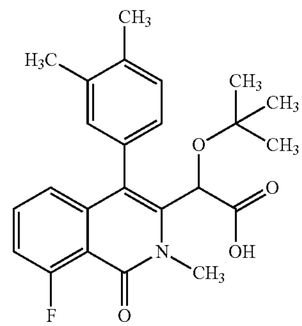 [SMILES: Cc1ccc(-c2c(C(OC(C)(C)C)C(=O)O)n(C)c(=O)c3c(F)cccc23)cc1C] | 2-(tert-butoxy)-2-[4-(3,4-dimethylphenyl)-8-fluoro-2-methyl-1-oxo-1,2-dihydroisoquinolin-3-yl]acetic acid |
| 60 | 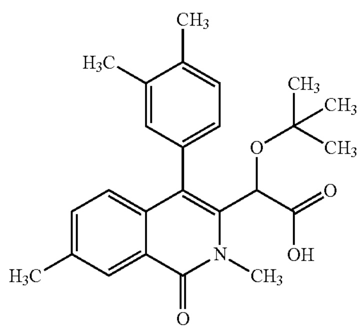 [SMILES: Cc1ccc2c(-c3ccc(C)c(C)c3)c(C(OC(C)(C)C)C(=O)O)n(C)c(=O)c2c1] | 2-(tert-butoxy)-2-[4-(3,4-dimethylphenyl)-2,7-dimethyl-1-oxo-1,2-dihydroisoquinolin-3-yl]acetic acid |
| 61 | 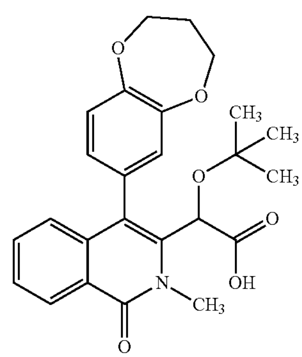 [SMILES: Cn1c(C(OC(C)(C)C)C(=O)O)c(-c2ccc3c(c2)OCCCO3)c2ccccc2c1=O] | 2-(tert-butoxy)-2-[4-(3,4-dihydro-2H-1,5-benzodioxepin-7-yl)-2-methyl-1-oxo-1,2-dihydroisoquinolin-3-yl]acetic acid |
| 62 | 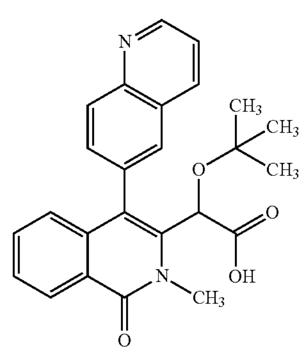 [SMILES: Cn1c(C(OC(C)(C)C)C(=O)O)c(-c2ccc3ncccc3c2)c2ccccc2c1=O] | 2-(tert-butoxy)-2-[2-methyl-1-oxo-4-(quinolin-6-yl)-1,2-dihydroisoquinolin-3-yl]acetic acid |

TABLE 1-continued

| Compound No. and Example No. | Structure | Chemical Name |
|---|---|---|
| 63 | 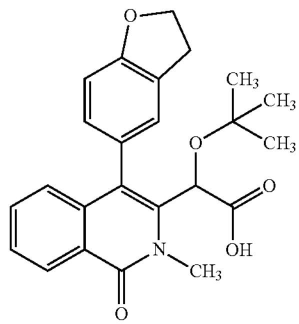 [SMILES: Cn1c(C(OC(C)(C)C)C(=O)O)c(-c2ccc3c(c2)CCO3)c2ccccc2c1=O] | 2-(tert-butoxy)-2-[4-(2,3-dihydro-1-benzofuran-5-yl)-2-methyl-1-oxo-1,2-dihydroisoquinolin-3-yl]acetic acid |
| 64 | 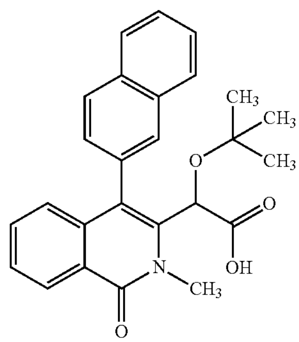 [SMILES: Cn1c(C(OC(C)(C)C)C(=O)O)c(-c2ccc3ccccc3c2)c2ccccc2c1=O] | 2-(tert-butoxy)-2-[2-methyl-4-(naphthalen-2-yl)-1-oxo-1,2-dihydroisoquinolin-3-yl]acetic acid |
| 65 | 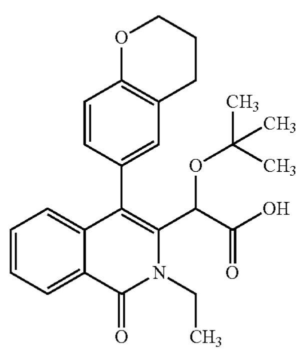 [SMILES: CCn1c(C(OC(C)(C)C)C(=O)O)c(-c2ccc3c(c2)CCCO3)c2ccccc2c1=O] | 2-(tert-butoxy)-2-[4-(3,4-dihydro-2H-1-benzopyran-6-yl)-2-ethyl-1-oxo-1,2-dihydroisoquinolin-3-yl]acetic acid |
| 66 | 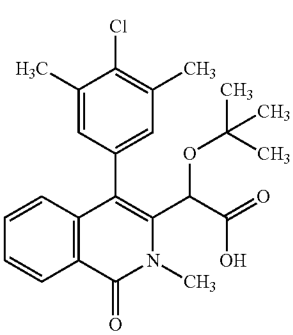 [SMILES: Cc1cc(-c2c(C(OC(C)(C)C)C(=O)O)n(C)c(=O)c3ccccc23)cc(C)c1Cl] | 2-(tert-butoxy)-2-[4-(4-chloro-3,5-dimethylphenyl)-2-methyl-1-oxo-1,2-dihydroisoquinolin-3-yl]acetic acid |

TABLE 1-continued

| Compound No. and Example No. | Structure | Chemical Name |
|---|---|---|
| 67 | 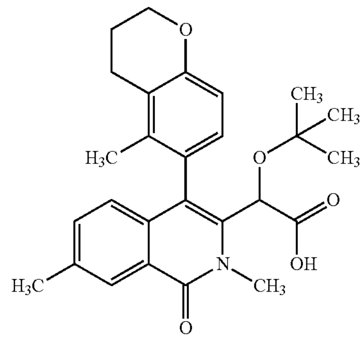 [SMILES: Cc1ccc2c(-c3ccc4c(c3C)CCCO4)c(C(OC(C)(C)C)C(=O)O)n(C)c(=O)c2c1] | 2-(tert-butoxy)-2-[2,7-dimethyl-4-(5-methyl-3,4-dihydro-2H-1-benzopyran-6-yl)-1-oxo-1,2-dihydroisoquinolin-3-yl]acetic acid |
| 68 | 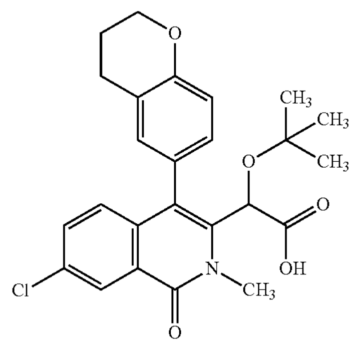 [SMILES: Cn1c(C(OC(C)(C)C)C(=O)O)c(-c2ccc3c(c2)CCCO3)c2ccc(Cl)cc2c1=O] | 2-(tert-butoxy)-2-[7-chloro-4-(3,4-dihydro-2H-1-benzopyran-6-yl)-2-methyl-1-oxo-1,2-dihydroisoquinolin-3-yl]acetic acid |
| 69 | 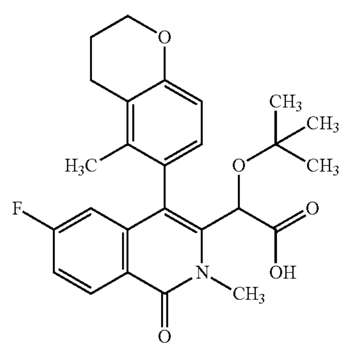 [SMILES: Cc1c(-c2c(C(OC(C)(C)C)C(=O)O)n(C)c(=O)c3ccc(F)cc23)ccc2c1CCCO2] | 2-(tert-butoxy)-2-[6-fluoro-2-methyl-4-(5-methyl-3,4-dihydro-2H-1-benzopyran-6-yl)-1-oxo-1,2-dihydroisoquinolin-3-yl]acetic acid |
| 70 | 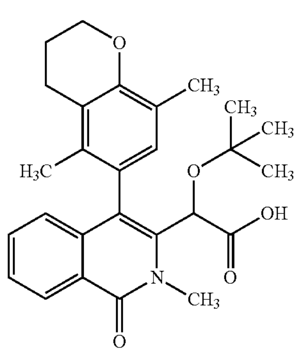 [SMILES: Cc1cc(-c2c(C(OC(C)(C)C)C(=O)O)n(C)c(=O)c3ccccc23)c(C)c2c1OCCC2] | 2-(tert-butoxy)-2-[4-(8-chloro-5-methyl-3,4-dihydro-2H-1-benzopyran-6-yl)-2-methyl-1-oxo-1,2-dihydroisoquinolin-3-yl]acetic acid |

TABLE 1-continued

| Compound No. and Example No. | Structure | Chemical Name |
|---|---|---|
| 71 | 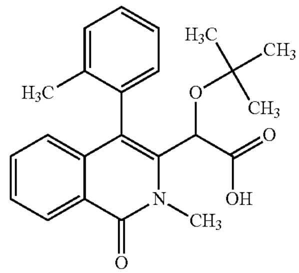 [SMILES: Cc1ccccc1-c1c(C(OC(C)(C)C)C(=O)O)n(C)c(=O)c2ccccc12] | 2-(tert-butoxy)-2-[2-methyl-4-(2-methylphenyl)-1-oxo-1,2-dihydroisoquinolin-3-yl]acetic acid |
| 72 | 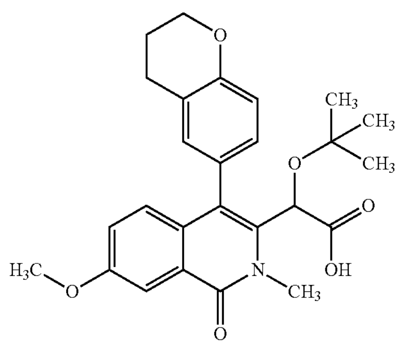 [SMILES: COc1ccc2c(-c3ccc4c(c3)CCCO4)c(C(OC(C)(C)C)C(=O)O)n(C)c(=O)c2c1] | 2-(tert-butoxy)-2-[4-(3,4-dihydro-2H-1-benzopyran-6-yl)-7-methoxy-2-methyl-1-oxo-1,2-dihydroisoquinolin-3-yl]acetic acid |
| 73 | 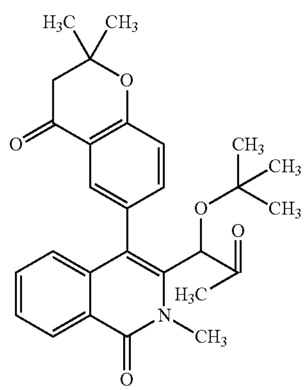 [SMILES: CC(=O)C(OC(C)(C)C)c1c(-c2ccc3c(c2)C(=O)CC(C)(C)O3)c2ccccc2c(=O)n1C] | 2-(tert-butoxy)-2-[4-(2,2-dimethyl-4-oxo-3,4-dihydro-2H-1-benzopyran-6-yl)-2-methyl-1-oxo-1,2-dihydroisoquinolin-3-yl]acetic acid |
| 74 | 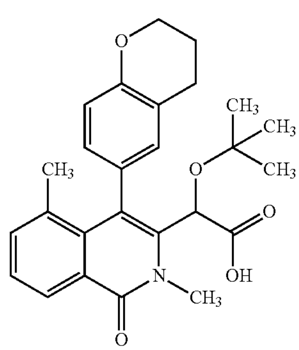 [SMILES: Cc1cccc2c(=O)n(C)c(C(OC(C)(C)C)C(=O)O)c(-c3ccc4c(c3)CCCO4)c12] | 2-(tert-butoxy)-2-[4-(3,4-dihydro-2H-1-benzopyran-6-yl)-2,5-dimethyl-1-oxo-1,2-dihydroisoquinolin-3-yl]acetic acid |

TABLE 1-continued

| Compound No. and Example No. | Structure | Chemical Name |
|---|---|---|
| 75 | 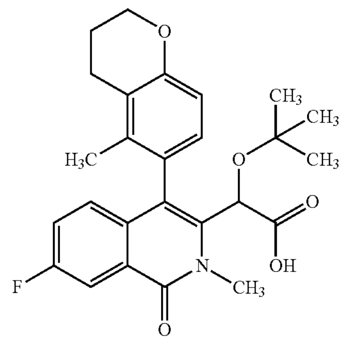 [SMILES: Cc1c(-c2c(C(OC(C)(C)C)C(=O)O)n(C)c(=O)c3cc(F)ccc23)ccc2c1CCCO2] | 2-(tert-butoxy)-2-[7-fluoro-2-methyl-4-(5-methyl-3,4-dihydro-2H-1-benzopyran-6-yl)-1-oxo-1,2-dihydroisoquinolin-3-yl]acetic acid |
| 76 | 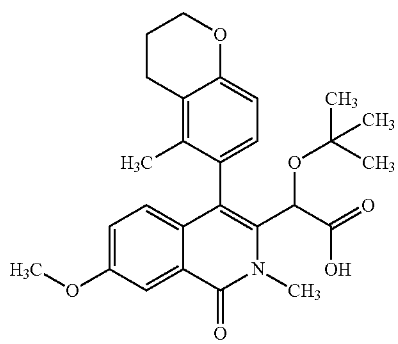 [SMILES: COc1ccc2c(-c3ccc4c(c3C)CCCO4)c(C(OC(C)(C)C)C(=O)O)n(C)c(=O)c2c1] | 2-(tert-butoxy)-2-[7-methoxy-2-methyl-4-(5-methyl-3,4-dihydro-2H-1-benzopyran-6-yl)-1-oxo-1,2-dihydroisoquinolin-3-yl]acetic acid |
| 77 | 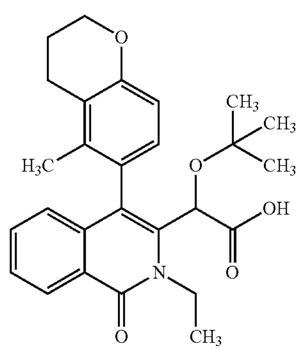 [SMILES: CCn1c(C(OC(C)(C)C)C(=O)O)c(-c2ccc3c(c2C)CCCO3)c2ccccc2c1=O] | 2-(tert-butoxy)-2-[2-ethyl-4-(5-methyl-3,4-dihydro-2H-1-benzopyran-6-yl)-1-oxo-1,2-dihydroisoquinolin-3-yl]acetic acid |
| 78 | 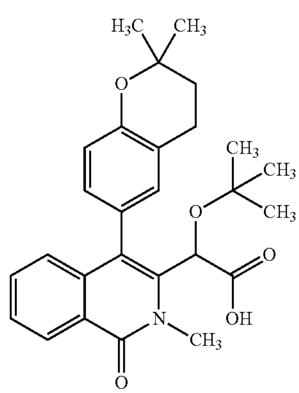 [SMILES: Cn1c(C(OC(C)(C)C)C(=O)O)c(-c2ccc3c(c2)CCC(C)(C)O3)c2ccccc2c1=O] | 2-(tert-butoxy)-2-[4-(2,2-dimethyl-3,4-dihydro-2H-1-benzopyran-6-yl)-2-methyl-1-oxo-1,2-dihydroisoquinolin-3-yl]acetic acid |

TABLE 1-continued

| Compound No. and Example No. | Structure | Chemical Name |
|---|---|---|
| 79 | 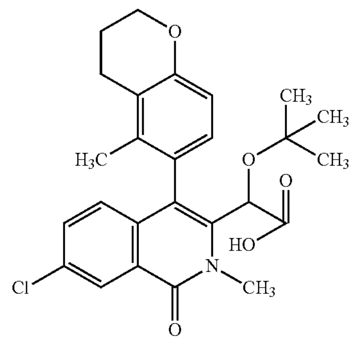 [SMILES: Cc1c(-c2c(C(OC(C)(C)C)C(=O)O)n(C)c(=O)c3cc(Cl)ccc23)ccc2c1CCCO2] | 2-(tert-butoxy)-2-[7-chloro-2-methyl-4-(5-methyl-3,4-dihydro-2H-1-benzopyran-6-yl)-1-oxo-1,2-dihydroisoquinolin-3-yl]acetic acid |
| 80 | 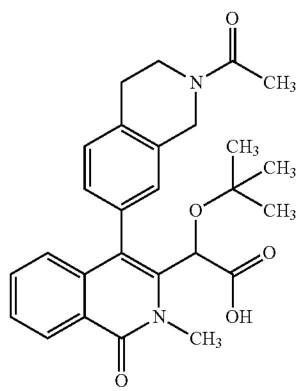 [SMILES: CC(=O)N1CCc2ccc(-c3c(C(OC(C)(C)C)C(=O)O)n(C)c(=O)c4ccccc34)cc2C1] | 2-[4-(2-acetyl-1,2,3,4-tetrahydroisoquinolin-7-yl)-2-methyl-1-oxo-1,2-dihydroisoquinolin-3-yl]-2-(tert-butoxy)acetic acid |
| 81 | 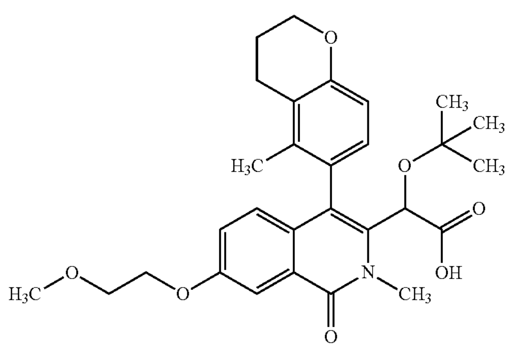 [SMILES: COCCOc1ccc2c(-c3ccc4c(c3C)CCCO4)c(C(OC(C)(C)C)C(=O)O)n(C)c(=O)c2c1] | 2-(tert-butoxy)-2-[7-(2-methoxyethoxy)-2-methyl-4-(5-methyl-3,4-dihydro-2H-1-benzopyran-6-yl)-1-oxo-1,2-dihydroisoquinolin-3-yl]acetic acid |
| 82 | 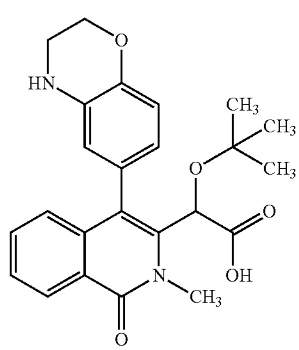 [SMILES: Cn1c(C(OC(C)(C)C)C(=O)O)c(-c2ccc3c(c2)NCCO3)c2ccccc2c1=O] | 2-(tert-butoxy)-2-[4-(3,4-dihydro-2H-1,4-benzoxazin-6-yl)-2-methyl-1-oxo-1,2-dihydroisoquinolin-3-yl]acetic acid |

TABLE 1-continued

| Compound No. and Example No. | Structure | Chemical Name |
|---|---|---|
| 83 | 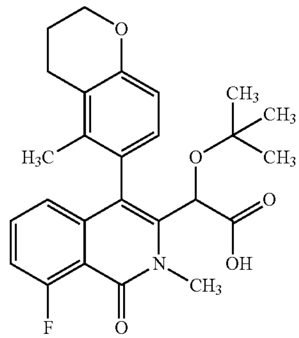 [SMILES: Cc1c(-c2c(C(OC(C)(C)C)C(=O)O)n(C)c(=O)c3c(F)cccc23)ccc2c1CCCO2] | 2-(tert-butoxy)-2-[8-fluoro-2-methyl-4-(5-methyl-3,4-dihydro-2H-1-benzopyran-6-yl)-1-oxo-1,2-dihydroisoquinolin-3-yl]acetic acid |
| 84 | 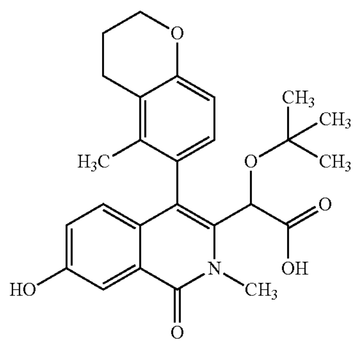 [SMILES: Cc1c(-c2c(C(OC(C)(C)C)C(=O)O)n(C)c(=O)c3cc(O)ccc23)ccc2c1CCCO2] | 2-(tert-butoxy)-2-[7-hydroxy-2-methyl-4-(5-methyl-3,4-dihydro-2H-1-benzopyran-6-yl)-1-oxo-1,2-dihydroisoquinolin-3-yl]acetic acid |
| 85 | 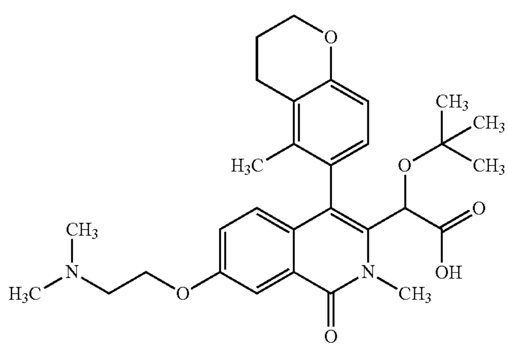 | 2-(tert-butoxy)-2-{7-[2-(dimethylamino)ethoxy]-2-methyl-4-(5-methyl-3,4-dihydro-2H-1-benzopyran-6-yl)-1-oxo-1,2-dihydroisoquinolin-3-yl}acetic acid |
| 86 | 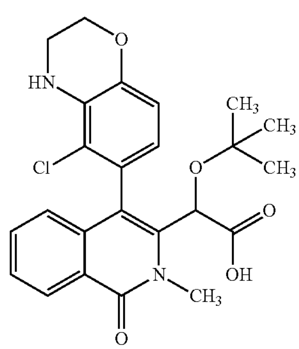 [SMILES: Cn1c(C(OC(C)(C)C)C(=O)O)c(-c2ccc3c(c2Cl)NCCO3)c2ccccc2c1=O] | 2-(tert-butoxy)-2-[4-(5-chloro-3,4-dihydro-2H-1,4-benzoxazin-6-yl)-2-methyl-1-oxo-1,2-dihydroisoquinolin-3-yl]acetic acid |

TABLE 1-continued

| Compound No. and Example No. | Structure | Chemical Name |
|---|---|---|
| 87 | 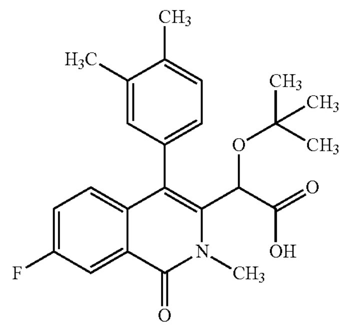 [SMILES: Cc1ccc(-c2c(C(OC(C)(C)C)C(=O)O)n(C)c(=O)c3cc(F)ccc23)cc1C] | 2-(tert-butoxy)-2-[4-(3,4-dimethylphenyl)-7-fluoro-2-methyl-1-oxo-1,2-dihydroisoquinolin-3-yl]acetic acid |
| 88 | 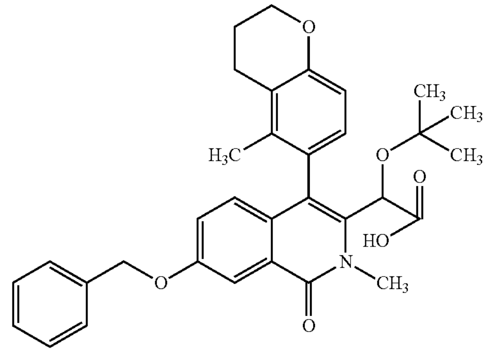 [SMILES: Cc1c(-c2c(C(OC(C)(C)C)C(=O)O)n(C)c(=O)c3cc(OCc4ccccc4)ccc23)ccc2c1CCCO2] | 2-[7-(benzyloxy)-2-methyl-4-(5-methyl-3,4-dihydro-2H-1-benzopyran-6-yl)-1-oxo-1,2-dihydroisoquinolin-3-yl]-2-(tert-butoxy)acetic acid |
| 89 | 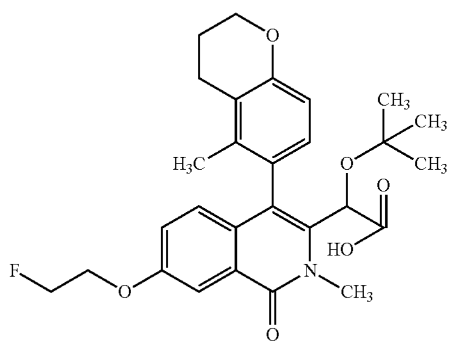 [SMILES: Cc1c(-c2c(C(OC(C)(C)C)C(=O)O)n(C)c(=O)c3cc(OCCF)ccc23)ccc2c1CCCO2] | 2-(tert-butoxy)-2-[7-(2-fluoroethoxy)-2-methyl-4-(5-methyl-3,4-dihydro-2H-1-benzopyran-6-yl)-1-oxo-1,2-dihydroisoquinolin-3-yl]acetic acid |
| 90 | 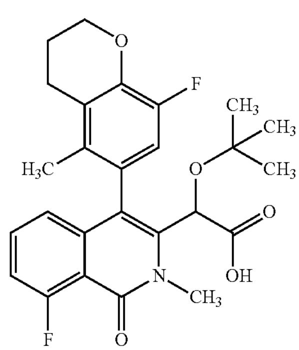 [SMILES: Cc1c(-c2c(C(OC(C)(C)C)C(=O)O)n(C)c(=O)c3c(F)cccc23)cc(F)c2c1CCCO2] | 2-(tert-butoxy)-2-[8-fluoro-4-(8-fluoro-5-methyl-3,4-dihydro-2H-1-benzopyran-6-yl)-2-methyl-1-oxo-1,2-dihydroisoquinolin-3-yl]acetic acid |

TABLE 1-continued

| Compound No. and Example No. | Structure | Chemical Name |
|---|---|---|
| 91 | 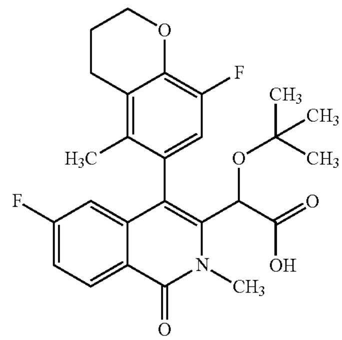 [SMILES: Cc1c(-c2c(C(OC(C)(C)C)C(=O)O)n(C)c(=O)c3ccc(F)cc23)cc(F)c2c1CCCO2] | 2-(tert-butoxy)-2-[6-fluoro-4-(8-fluoro-5-methyl-3,4-dihydro-2H-1-benzopyran-6-yl)-2-methyl-1-oxo-1,2-dihydroisoquinolin-3-yl]acetic acid |
| 92 | 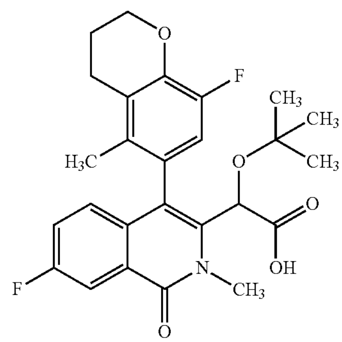 [SMILES: Cc1c(-c2c(C(OC(C)(C)C)C(=O)O)n(C)c(=O)c3cc(F)ccc23)cc(F)c2c1CCCO2] | 2-(tert-butoxy)-2-[7-fluoro-4-(8-fluoro-5-methyl-3,4-dihydro-2H-1-benzopyran-6-yl)-2-methyl-1-oxo-1,2-dihydroisoquinolin-3-yl]acetic acid |
| 93 | 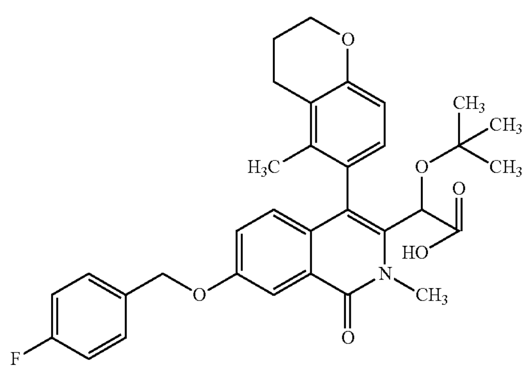 [SMILES: Cc1c(-c2c(C(OC(C)(C)C)C(=O)O)n(C)c(=O)c3cc(OCc4ccc(F)cc4)ccc23)ccc2c1CCCO2] | 2-(tert-butoxy)-2-{7-[(4-fluorophenyl)methoxy]-2-methyl-4-(5-methyl-3,4-dihydro-2H-1-benzopyran-6-yl)-1-oxo-1,2-dihydroisoquinolin-3-yl}acetic acid |
| 94 | 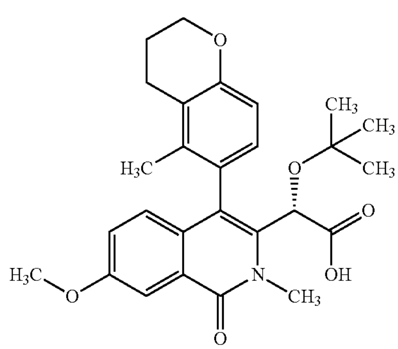 [SMILES: COc1ccc2c(-c3ccc4c(c3C)CCCO4)c([C@H](OC(C)(C)C)C(=O)O)n(C)c(=O)c2c1] | (2S)-2-(tert-butoxy)-2-[7-methoxy-2-methyl-4-(5-methyl-3,4-dihydro-2H-1-benzopyran-6-yl)-1-oxo-1,2-dihydroisoquinolin-3-yl]acetic acid |

TABLE 1-continued

| Compound No. and Example No. | Structure | Chemical Name |
|---|---|---|
| 95 | 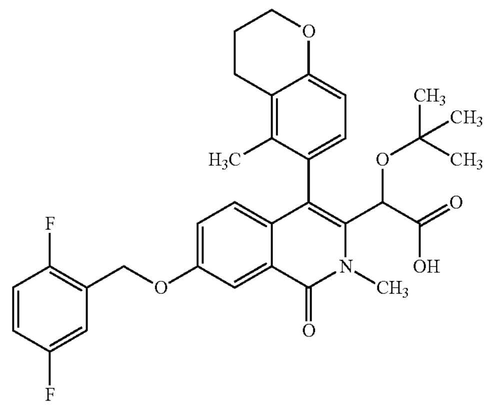 [SMILES: Cc1c(-c2c(C(OC(C)(C)C)C(=O)O)n(C)c(=O)c3cc(OCc4cc(F)ccc4F)ccc23)ccc2c1CCCO2] | 2-(tert-butoxy)-2-{7-[(2,5-difluorophenyl)methoxy]-2-methyl-4-(5-methyl-3,4-dihydro-2H-1-benzopyran-6-yl)-1-oxo-1,2-dihydroisoquinolin-3-yl}acetic acid |
| 96 | 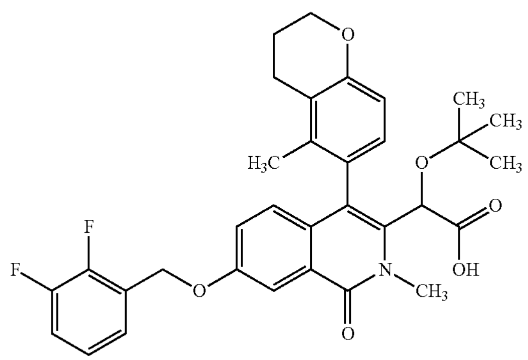 [SMILES: Cc1c(-c2c(C(OC(C)(C)C)C(=O)O)n(C)c(=O)c3cc(OCc4cccc(F)c4F)ccc23)ccc2c1CCCO2] | 2-(tert-butoxy)-2-{7-[(2,3-difluorophenyl)methoxy]-2-methyl-4-(5-methyl-3,4-dihydro-2H-1-benzopyran-6-yl)-1-oxo-1,2-dihydroisoquinolin-3-yl}acetic acid |
| 97 | 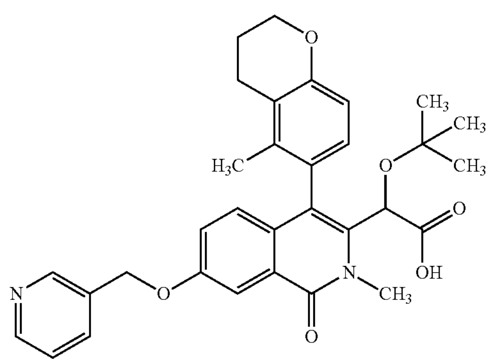 [SMILES: Cc1c(-c2c(C(OC(C)(C)C)C(=O)O)n(C)c(=O)c3cc(OCc4cccnc4)ccc23)ccc2c1CCCO2] | 2-(tert-butoxy)-2-[2-methyl-4-(5-methyl-3,4-dihydro-2H-1-benzopyran-6-yl)-1-oxo-7-(pyridin-3-ylmethoxy)-1,2-dihydroisoquinolin-3-yl]acetic acid |
| 98 | 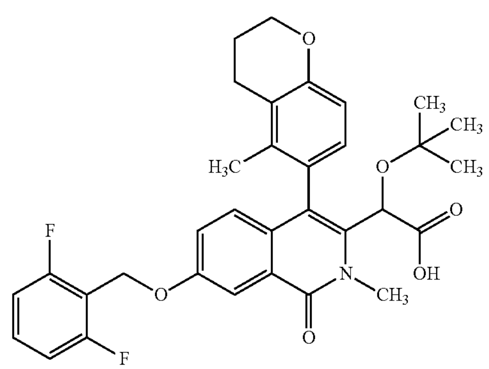 [SMILES: Cc1c(-c2c(C(OC(C)(C)C)C(=O)O)n(C)c(=O)c3cc(OCc4c(F)cccc4F)ccc23)ccc2c1CCCO2] | 2-(tert-butoxy)-2-{7-[(2,6-difluorophenyl)methoxy]-2-methyl-4-(5-methyl-3,4-dihydro-2H-1-benzopyran-6-yl)-1-oxo-1,2-dihydroisoquinolin-3-yl}acetic acid |

TABLE 1-continued

| Compound No. and Example No. | Structure | Chemical Name |
|---|---|---|
| 99 | 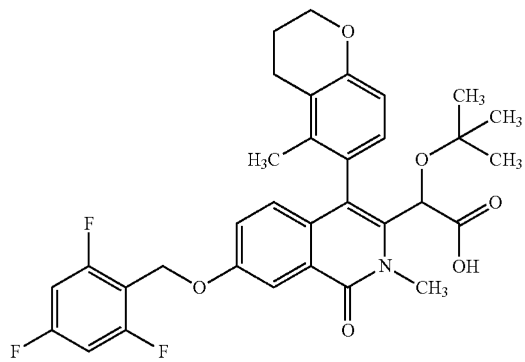 [SMILES: Cc1c(-c2c(C(OC(C)(C)C)C(=O)O)n(C)c(=O)c3cc(OCc4c(F)cc(F)cc4F)ccc23)ccc2c1CCCO2] | 2-(tert-butoxy)-2-[2-methyl-4-(5-methyl-3,4-dihydro-2H-1-benzopyran-6-yl)-1-oxo-7-[(2,4,6-trifluorophenyl)methoxy]-1,2-dihydroisoquinolin-3-yl]acetic acid |
| 100 | 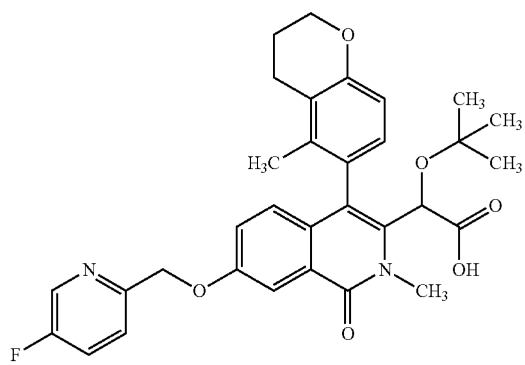 [SMILES: Cc1c(-c2c(C(OC(C)(C)C)C(=O)O)n(C)c(=O)c3cc(OCc4ccc(F)cn4)ccc23)ccc2c1CCCO2] | 2-(tert-butoxy)-2-{7-[(5-fluoropyridin-2-yl)methoxy]-2-methyl-4-(5-methyl-3,4-dihydro-2H-1-benzopyran-6-yl)-1-oxo-1,2-dihydroisoquinolin-3-yl}acetic acid |
| 101 | 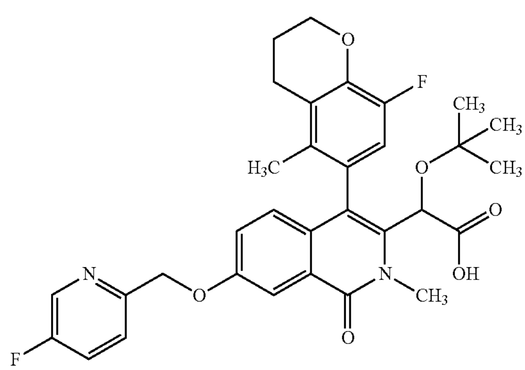 [SMILES: Cc1c(-c2c(C(OC(C)(C)C)C(=O)O)n(C)c(=O)c3cc(OCc4ccc(F)cn4)ccc23)cc(F)c2c1CCCO2] | 2-(tert-butoxy)-2-[4-(8-fluoro-5-methyl-3,4-dihydro-2H-1-benzopyran-6-yl)-7-[(5-fluoropyridin-2-yl)methoxy]-2-methyl-1-oxo-1,2-dihydroisoquinolin-3-yl]acetic acid |
| 102 | 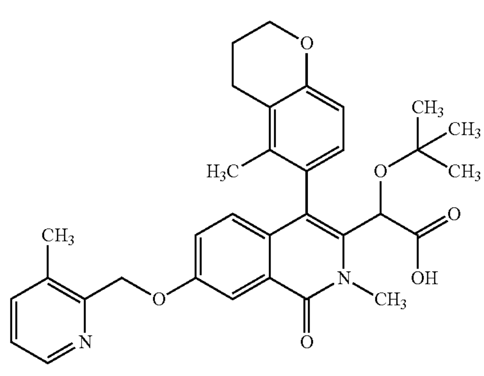 [SMILES: Cc1cccnc1COc1ccc2c(-c3ccc4c(c3C)CCCO4)c(C(OC(C)(C)C)C(=O)O)n(C)c(=O)c2c1] | 2-(tert-butoxy)-2-[2-methyl-4-(5-methyl-3,4-dihydro-2H-1-benzopyran-6-yl)-7-[(3-methylpyridin-2-yl)methoxy]-1-oxo-1,2-dihydroisoquinolin-3-yl]acetic acid |

TABLE 1-continued

| Compound No. and Example No. | Structure | Chemical Name |
|---|---|---|
| 103 | 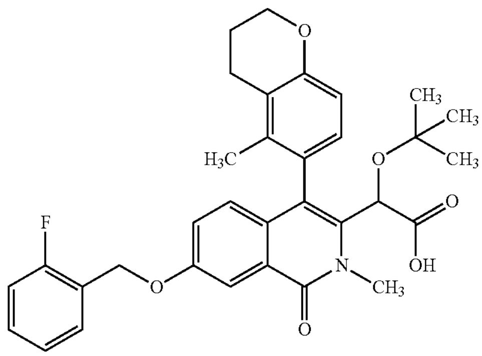 [SMILES: Cc1c(-c2c(C(OC(C)(C)C)C(=O)O)n(C)c(=O)c3cc(OCc4ccccc4F)ccc23)ccc2c1CCCO2] | 2-(tert-butoxy)-2-{7-[(2-fluorophenyl)methoxy]-2-methyl-4-(5-methyl-3,4-dihydro-2H-1-benzopyran-6-yl)-1-oxo-1,2-dihydroisoquinolin-3-yl}acetic acid |
| 104 | 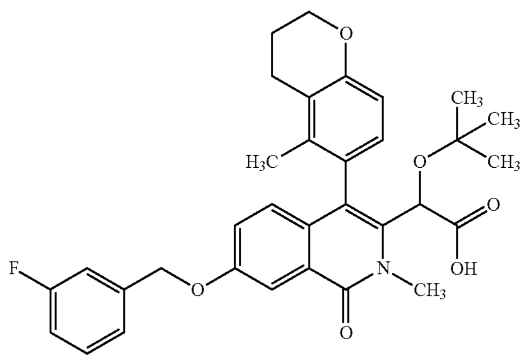 [SMILES: Cc1c(-c2c(C(OC(C)(C)C)C(=O)O)n(C)c(=O)c3cc(OCc4cccc(F)c4)ccc23)ccc2c1CCCO2] | 2-(tert-butoxy)-2-{7-[(3-fluorophenyl)methoxy]-2-methyl-4-(5-methyl-3,4-dihydro-2H-1-benzopyran-6-yl)-1-oxo-1,2-dihydroisoquinolin-3-yl}acetic acid |
| 105 | 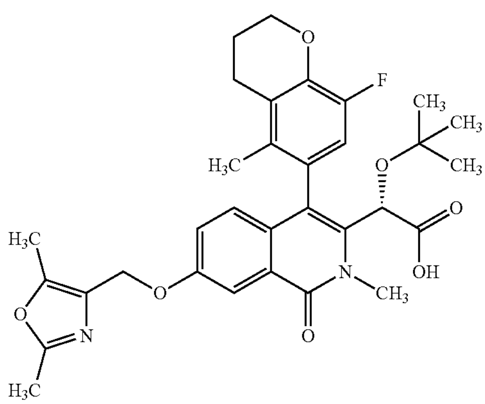 | (2S)-2-(tert-butoxy)-2-{7-[(dimethyl-1,3-oxazol-4-yl)methoxy]-4-(8-fluoro-5-methyl-3,4-dihydro-2H-1-benzopyran-6-yl)-2-methyl-1-oxo-1,2-dihydroisoquinolin-3-yl}acetic acid |
| 106 | 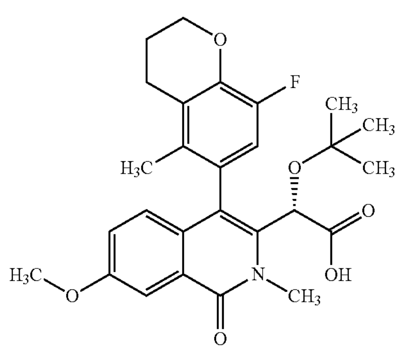 [SMILES: COc1ccc2c(-c3cc(F)c4c(c3C)CCCO4)c([C@H](OC(C)(C)C)C(=O)O)n(C)c(=O)c2c1] | (2S)-2-(tert-butoxy)-2-[4-(8-fluoro-5-methyl-3,4-dihydro-2H-1-benzopyran-6-yl)-7-methoxy-2-methyl-1-oxo-1,2-dihydroisoquinolin-3-yl]acetic acid |

TABLE 1-continued

| Compound No. and Example No. | Structure | Chemical Name |
|---|---|---|
| 107 | 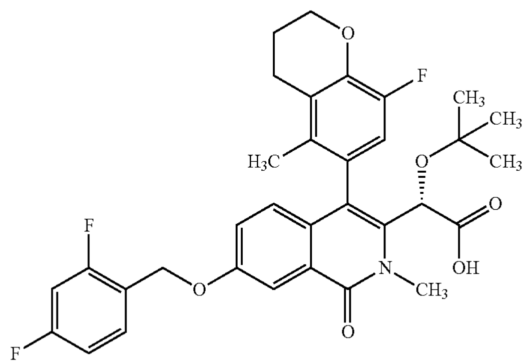 [SMILES: Cc1c(-c2c([C@H](OC(C)(C)C)C(=O)O)n(C)c(=O)c3cc(OCc4ccc(F)cc4F)ccc23)cc(F)c2c1CCCO2] | (2S)-2-(tert-butoxy)-2-{7-[(2,4-difluorophenyl)methoxy]-4-(8-fluoro-5-methyl-3,4-dihydro-2H-1-benzopyran-6-yl)-2-methyl-1-oxo-1,2-dihydroisoquinolin-3-yl}acetic acid |
| 108 | 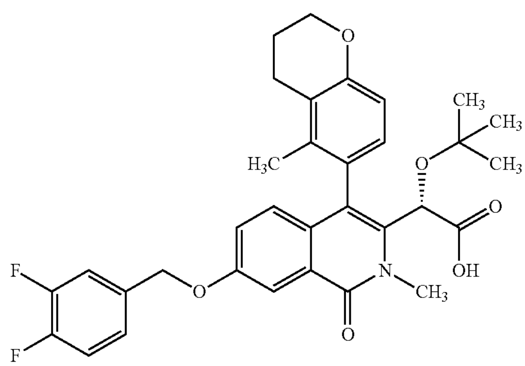 [SMILES: Cc1c(-c2c([C@H](OC(C)(C)C)C(=O)O)n(C)c(=O)c3cc(OCc4ccc(F)c(F)c4)ccc23)ccc2c1CCCO2] | (2S)-2-(tert-butoxy)-2-{7-[(3,4-difluorophenyl)methoxy]-2-methyl-4-(5-methyl-3,4-dihydro-2H-1-benzopyran-6-yl)-1-oxo-1,2-dihydroisoquinolin-3-yl}acetic acid |
| 109 | 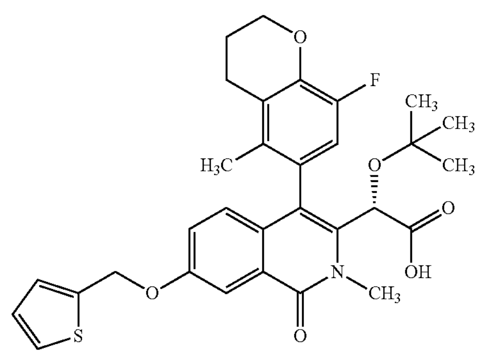 [SMILES: Cc1c(-c2c([C@H](OC(C)(C)C)C(=O)O)n(C)c(=O)c3cc(OCc4cccs4)ccc23)cc(F)c2c1CCCO2] | (2S)-2-(tert-butoxy)-2-[4-(8-fluoro-5-methyl-3,4-dihydro-2H-1-benzopyran-6-yl)-2-methyl-1-oxo-7-(thiophen-2-ylmethoxy)-1,2-dihydroisoquinolin-3-yl]acetic acid |
| 110 | 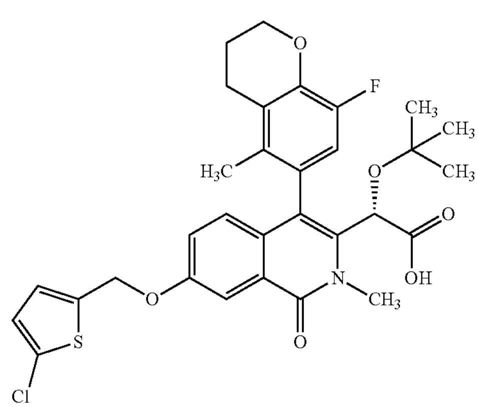 [SMILES: Cc1c(-c2c([C@H](OC(C)(C)C)C(=O)O)n(C)c(=O)c3cc(OCc4ccc(Cl)s4)ccc23)cc(F)c2c1CCCO2] | (2S)-2-(tert-butoxy)-2-{7-[(5-chlorothiophen-2-yl)methoxy]-4-(8-fluoro-5-methyl-3,4-dihydro-2H-1-benzopyran-6-yl)-2-methyl-1-oxo-1,2-dihydroisoquinolin-3-yl}acetic acid |

TABLE 1-continued

| Compound No. and Example No. | Structure | Chemical Name |
|---|---|---|
| 111 | 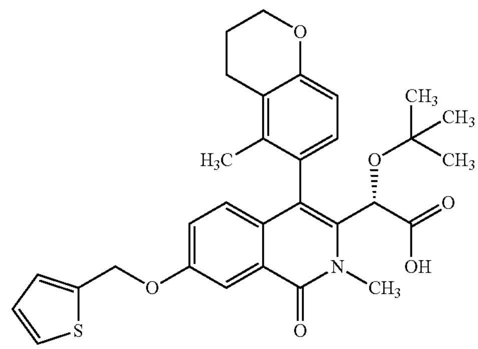 | (2S)-2-(tert-butoxy)-2-[2-methyl-4-(5-methyl-3,4-dihydro-2H-1-benzopyran-6-yl)-1-oxo-7-(thiophen-2-ylmethoxy)-1,2-dihydroisoquinolin-3-yl]acetic acid |
| 112 | 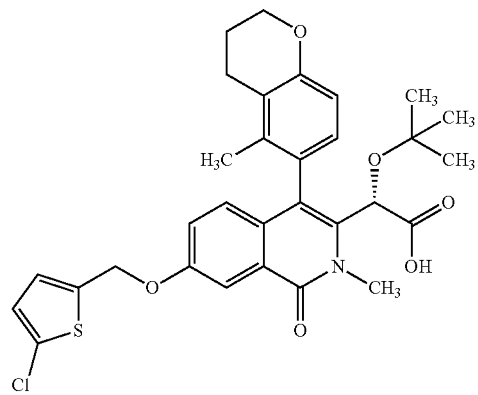 [SMILES: Cc1c(-c2c([C@H](OC(C)(C)C)C(=O)O)n(C)c(=O)c3cc(OCc4ccc(Cl)s4)ccc23)ccc2c1CCCO2] | (2S)-2-(tert-butoxy)-2-{7-[(5-chlorothiophen-2-yl)methoxy]-2-methyl-4-(5-methyl-3,4-dihydro-2H-1-benzopyran-6-yl)-1-oxo-1,2-dihydroisoquinolin-3-yl}acetic acid |
| 113 | 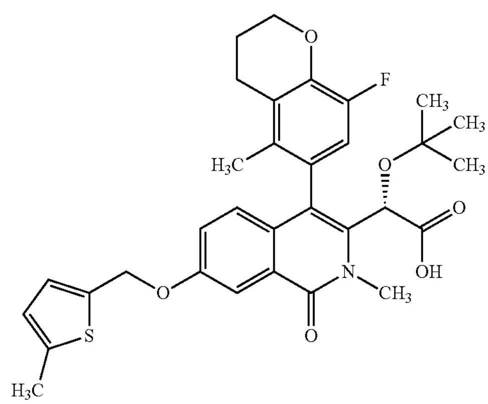 [SMILES: Cc1ccc(COc2ccc3c(-c4cc(F)c5c(c4C)CCCO5)c([C@H](OC(C)(C)C)C(=O)O)n(C)c(=O)c3c2)s1] | (2S)-2-(tert-butoxy)-2-[4-(8-fluoro-5-methyl-3,4-dihydro-2H-1-benzopyran-6-yl)-2-methyl-7-[(5-methylthiophen-2-yl)methoxy]-1-oxo-1,2-dihydroisoquinolin-3-yl]acetic acid |
| 114 | 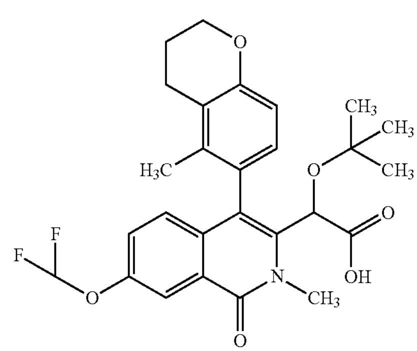 [SMILES: Cc1c(-c2c(C(OC(C)(C)C)C(=O)O)n(C)c(=O)c3cc(OC(F)F)ccc23)ccc2c1CCCO2] | 2-(tert-butoxy)-2-[7-(difluoromethoxy)-2-methyl-4-(5-methyl-3,4-dihydro-2H-1-benzopyran-6-yl)-1-oxo-1,2-dihydroisoquinolin-3-yl]acetic acid |

TABLE 1-continued

| Compound No. and Example No. | Structure | Chemical Name |
|---|---|---|
| 115 | 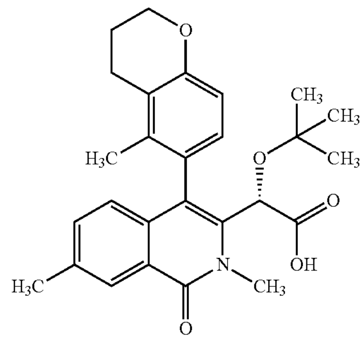 [SMILES: Cc1ccc2c(-c3ccc4c(c3C)CCCO4)c([C@H](OC(C)(C)C)C(=O)O)n(C)c(=O)c2c1] | (2S)-2-(tert-butoxy)-2-[2,7-dimethyl-4-(5-methyl-3,4-dihydro-2H-1-benzopyran-6-yl)-1-oxo-1,2-dihydroisoquinolin-3-yl]acetic acid |
| 116 | 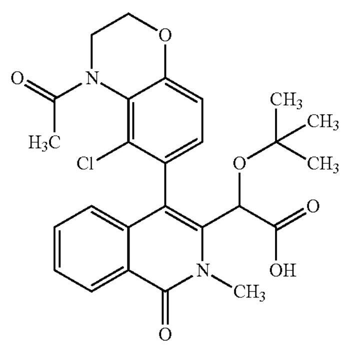 [SMILES: CC(=O)N1CCOc2ccc(-c3c(C(OC(C)(C)C)C(=O)O)n(C)c(=O)c4ccccc34)c(Cl)c21] | 2-[4-(4-acetyl-5-chloro-3,4-dihydro-2H-1,4-benzoxazin-6-yl)-2-methyl-1-oxo-1,2-dihydroisoquinolin-3-yl]-2-(tert-butoxy)acetic acid |
| 117 | 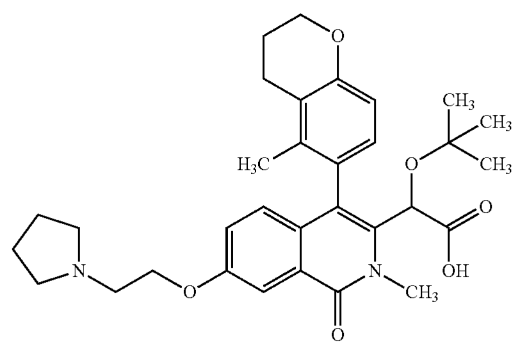 [SMILES: Cc1c(-c2c(C(OC(C)(C)C)C(=O)O)n(C)c(=O)c3cc(OCCN4CCCC4)ccc23)ccc2c1CCCO2] | 2-(tert-butoxy)-2-[2-methyl-4-(5-methyl-3,4-dihydro-2H-1-benzopyran-6-yl)-1-oxo-7-[2-(pyrrolidin-1-yl)ethoxy]-1,2-dihydroisoquinolin-3-yl]acetic acid |
| 118 | 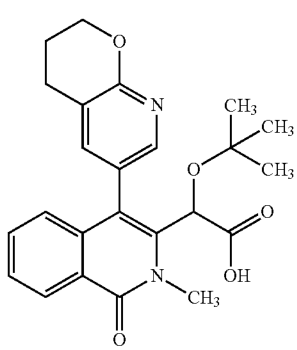 [SMILES: Cn1c(C(OC(C)(C)C)C(=O)O)c(-c2cnc3c(c2)CCCO3)c2ccccc2c1=O] | 2-(tert-butoxy)-2-(2-methyl-1-oxo-4-{2H,3H,4H-pyrano[2,3-b]pyridin-6-yl}-1,2-dihydroisoquinolin-3-yl)acetic acid |

TABLE 1-continued

| Compound No. and Example No. | Structure | Chemical Name |
|---|---|---|
| 119 | 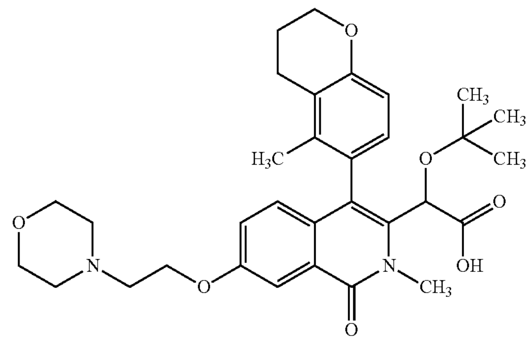 [SMILES: Cc1c(-c2c(C(OC(C)(C)C)C(=O)O)n(C)c(=O)c3cc(OCCN4CCOCC4)ccc23)ccc2c1CCCO2] | 2-(tert-butoxy)-2-[2-methyl-4-(5-methyl-3,4-dihydro-2H-1-benzopyran-6-yl)-7-[2-(morpholin-4-yl)ethoxy]-1-oxo-1,2-dihydroisoquinolin-3-yl]acetic acid |
| 120 | 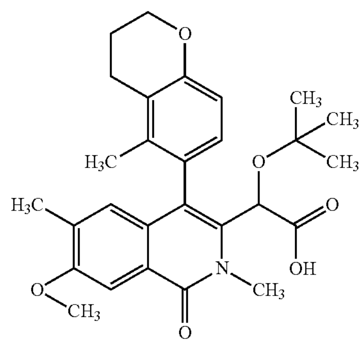 [SMILES: COc1cc2c(=O)n(C)c(C(OC(C)(C)C)C(=O)O)c(-c3ccc4c(c3C)CCCO4)c2cc1C] | 2-(tert-butoxy)-2-[7-methoxy-2,6-dimethyl-4-(5-methyl-3,4-dihydro-2H-1-benzopyran-6-yl)-1-oxo-1,2-dihydroisoquinolin-3-yl]acetic acid |
| 121 | 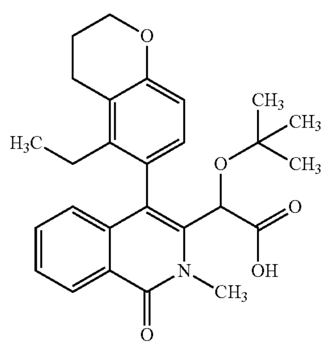 [SMILES: CCc1c(-c2c(C(OC(C)(C)C)C(=O)O)n(C)c(=O)c3ccccc23)ccc2c1CCCO2] | 2-(tert-butoxy)-2-[4-(5-ethyl-3,4-dihydro-2H-1-benzopyran-6-yl)-2-methyl-1-oxo-1,2-dihydroisoquinolin-3-yl]acetic acid |
| 122 | 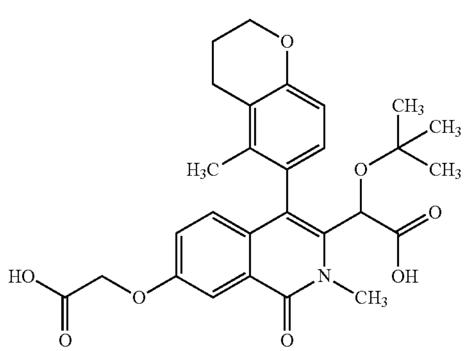 [SMILES: Cc1c(-c2c(C(OC(C)(C)C)C(=O)O)n(C)c(=O)c3cc(OCC(=O)O)ccc23)ccc2c1CCCO2] | 2-({3-[(tert-butoxy)(carboxy)methyl]-2-methyl-4-(5-methyl-3,4-dihydro-2H-1-benzopyran-6-yl)-1-oxo-1,2-dihydroisoquinolin-7-yl}oxy)acetic acid |

TABLE 1-continued

| Compound No. and Example No. | Structure | Chemical Name |
|---|---|---|
| 123 | 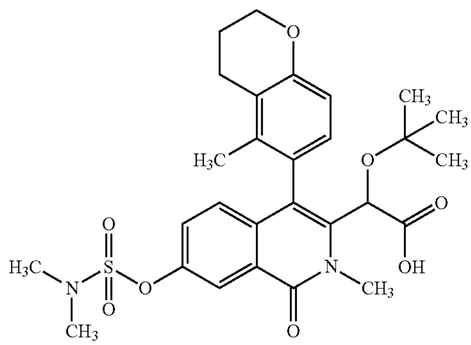 [SMILES: Cc1c(-c2c(C(OC(C)(C)C)C(=O)O)n(C)c(=O)c3cc(OS(=O)(=O)N(C)C)ccc23)ccc2c1CCCO2] | 2-(tert-butoxy)-2-{7-[(dimethylsulfamoyl)oxy]-2-methyl-4-(5-methyl-3,4-dihydro-2H-1-benzopyran-6-yl)-1-oxo-1,2-dihydroisoquinolin-3-yl}acetic acid |
| 124 | 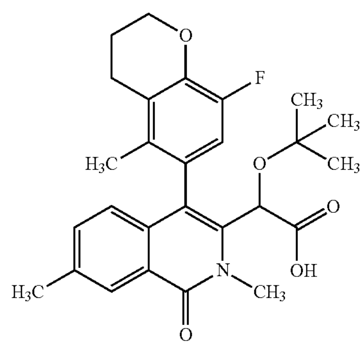 [SMILES: Cc1ccc2c(-c3cc(F)c4c(c3C)CCCO4)c(C(OC(C)(C)C)C(=O)O)n(C)c(=O)c2c1] | 2-(tert-butoxy)-2-[4-(8-fluoro-5-methyl-3,4-dihydro-2H-1-benzopyran-6-yl)-2,7-dimethyl-1-oxo-1,2-dihydroisoquinolin-3-yl]acetic acid |
| 125 | 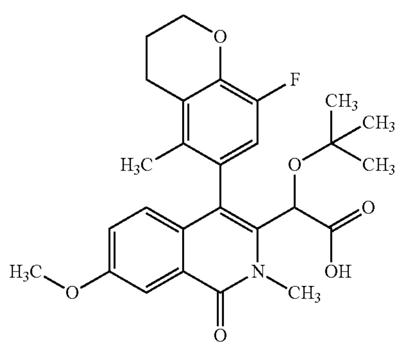 | 2-(tert-butoxy)-2-[4-(8-fluoro-5-methyl-3,4-dihydro-2H-1-benzopyran-6-yl)-7-methoxy-2-methyl-1-oxo-1,2-dihydroisoquinolin-3-yl]acetic acid |
| 126 | 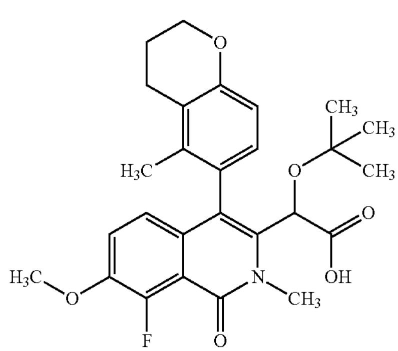 [SMILES: COc1ccc2c(-c3ccc4c(c3C)CCCO4)c(C(OC(C)(C)C)C(=O)O)n(C)c(=O)c2c1F] | 2-(tert-butoxy)-2-[8-fluoro-7-methoxy-2-methyl-4-(5-methyl-3,4-dihydro-2H-1-benzopyran-6-yl)-1-oxo-1,2-dihydroisoquinolin-3-yl]acetic acid |

TABLE 1-continued

| Compound No. and Example No. | Structure | Chemical Name |
|---|---|---|
| 127 | 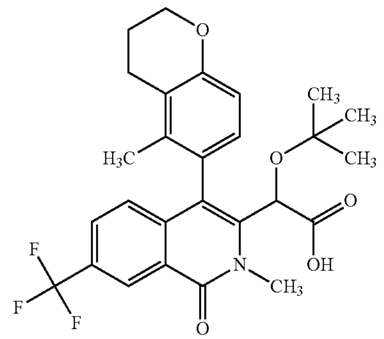 [SMILES: Cc1c(-c2c(C(OC(C)(C)C)C(=O)O)n(C)c(=O)c3cc(C(F)(F)F)ccc23)ccc2c1CCCO2] | 2-(tert-butoxy)-2-[2-methyl-4-(5-methyl-3,4-dihydro-2H-1-benzopyran-6-yl)-1-oxo-7-(trifluoromethyl)-1,2-dihydroisoquinolin-3-yl]acetic acid |
| 128 | 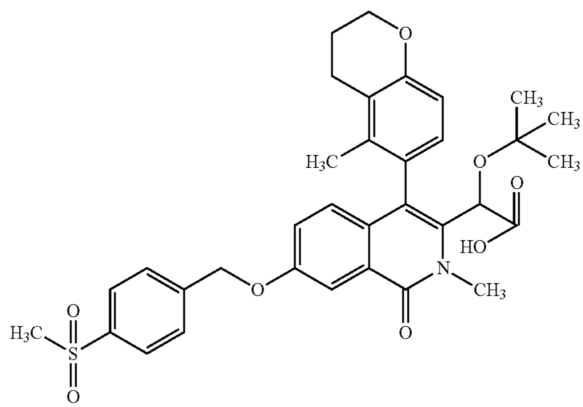 [SMILES: Cc1c(-c2c(C(OC(C)(C)C)C(=O)O)n(C)c(=O)c3cc(OCc4ccc(S(C)(=O)=O)cc4)ccc23)ccc2c1CCCO2] | 2-(tert-butoxy)-2-{7-[(4-methanesulfonylphenyl)-methoxy]-2-methyl-4-(5-methyl-3,4-dihydro-2H-1-benzopyran-6-yl)-1-oxo-1,2-dihydroisoquinolin-3-yl}acetic acid |
| 129 | 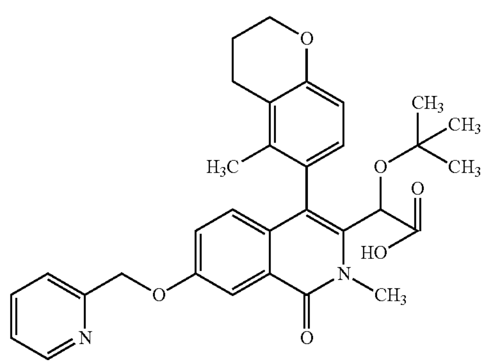 | 2-(tert-butoxy)-2-[2-methyl-4-(5-methyl-3,4-dihydro-2H-1-benzopyran-6-yl)-1-oxo-7-(pyridin-2-ylmethoxy)-1,2-dihydroisoquinolin-3-yl]acetic acid |
| 130 | 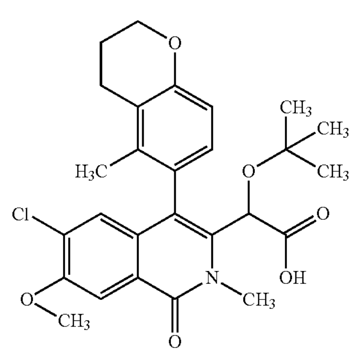 [SMILES: COc1cc2c(=O)n(C)c(C(OC(C)(C)C)C(=O)O)c(-c3ccc4c(c3C)CCCO4)c2cc1Cl] | 2-(tert-butoxy)-2-[6-chloro-7-methoxy-2-methyl-4-(5-methyl-3,4-dihydro-2H-1-benzopyran-6-yl)-1-oxo-1,2-dihydroisoquinolin-3-yl]acetic acid |

TABLE 1-continued

| Compound No. and Example No. | Structure | Chemical Name |
|---|---|---|
| 131 | 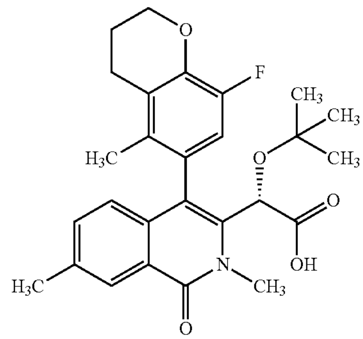 | (2S)-2-(tert-butoxy)-2-[4-(8-fluoro-5-methyl-3,4-dihydro-2H-1-benzopyran-6-yl)-2,7-dimethyl-1-oxo-1,2-dihydroisoquinolin-3-yl]acetic acid |
| 132 | 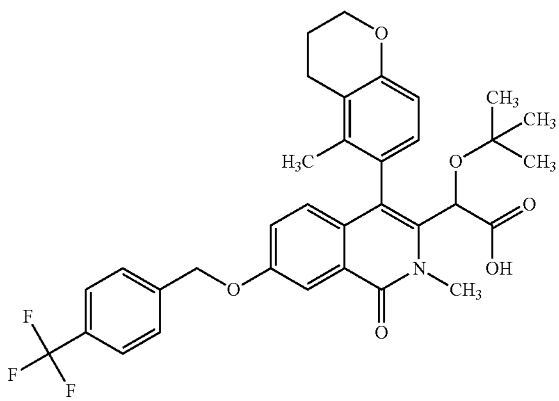 [SMILES: Cc1c(-c2c(C(OC(C)(C)C)C(=O)O)n(C)c(=O)c3cc(OCc4ccc(C(F)(F)F)cc4)ccc23)ccc2c1CCCO2] | 2-(tert-butoxy)-2-[2-methyl-4-(5-methyl-3,4-dihydro-2H-1-benzopyran-6-yl)-1-oxo-7-{[4-(trifluoromethyl)phenyl]methoxy}-1,2-dihydroisoquinolin-3-yl]acetic acid |
| 133 | 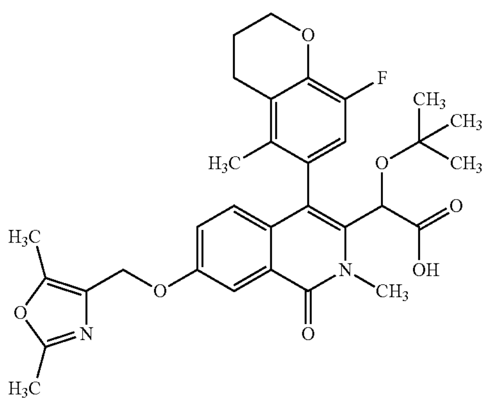 [SMILES: Cc1nc(COc2ccc3c(-c4cc(F)c5c(c4C)CCCO5)c(C(OC(C)(C)C)C(=O)O)n(C)c(=O)c3c2)c(C)o1] | 2-(tert-butoxy)-2-{7-[(dimethyl-1,3-oxazol-4-yl)methoxy]-4-(8-fluoro-5-methyl-3,4-dihydro-2H-1-benzopyran-6-yl)-2-methyl-1-oxo-1,2-dihydroisoquinolin-3-yl}acetic acid |
| 134 | 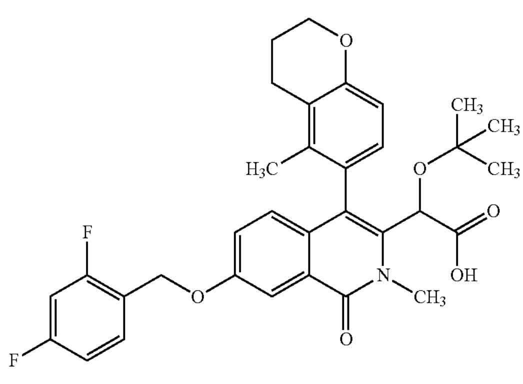 [SMILES: Cc1c(-c2c(C(OC(C)(C)C)C(=O)O)n(C)c(=O)c3cc(OCc4ccc(F)cc4F)ccc23)ccc2c1CCCO2] | 2-(tert-butoxy)-2-{7-[(2,4-difluorophenyl)methoxy]-2-methyl-4-(5-methyl-3,4-dihydro-2H-1-benzopyran-6-yl)-1-oxo-1,2-dihydroisoquinolin-3-yl}acetic acid |

TABLE 1-continued

| Compound No. and Example No. | Structure | Chemical Name |
|---|---|---|
| 135 | 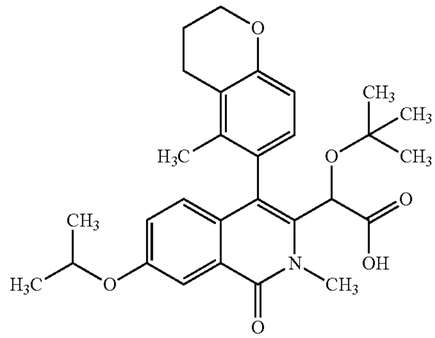 [SMILES: Cc1c(-c2c(C(OC(C)(C)C)C(=O)O)n(C)c(=O)c3cc(OC(C)C)ccc23)ccc2c1CCCO2] | 2-(tert-butoxy)-2-[2-methyl-4-(5-methyl-3,4-dihydro-2H-1-benzopyran-6-yl)-1-oxo-7-(propan-2-yloxy)-1,2-dihydroisoquinolin-3-yl]acetic acid |
| 136 | 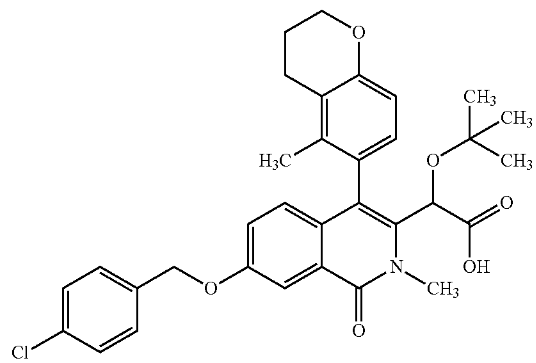 [SMILES: Cc1c(-c2c(C(OC(C)(C)C)C(=O)O)n(C)c(=O)c3cc(OCc4ccc(Cl)cc4)ccc23)ccc2c1CCCO2] | 2-(tert-butoxy)-2-{7-[(4-chlorophenyl)methoxy]-2-methyl-4-(5-methyl-3,4-dihydro-2H-1-benzopyran-6-yl)-1-oxo-1,2-dihydroisoquinolin-3-yl}acetic acid |
| 137 | 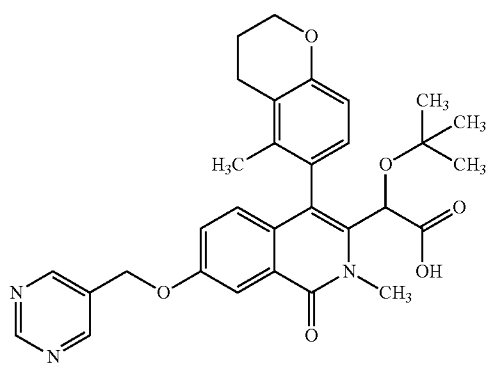 [SMILES: Cc1c(-c2c(C(OC(C)(C)C)C(=O)O)n(C)c(=O)c3cc(OCc4cncnc4)ccc23)ccc2c1CCCO2] | 2-(tert-butoxy)-2-[2-methyl-4-(5-methyl-3,4-dihydro-2H-1-benzopyran-6-yl)-1-oxo-7-(pyrimidin-5-ylmethoxy)-1,2-dihydroisoquinolin-3-yl]acetic acid |
| 138 | 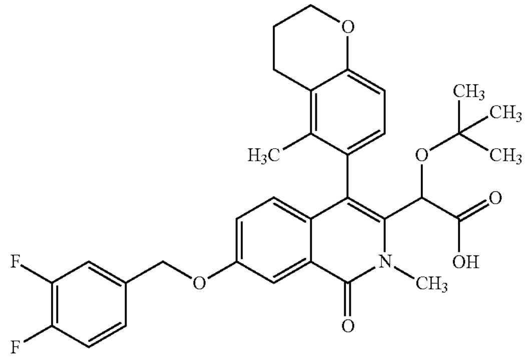 [SMILES: Cc1c(-c2c(C(OC(C)(C)C)C(=O)O)n(C)c(=O)c3cc(OCc4ccc(F)c(F)c4)ccc23)ccc2c1CCCO2] | 2-(tert-butoxy)-2-{7-[(3,4-difluorophenyl)methoxy]-2-methyl-4-(5-methyl-3,4-dihydro-2H-1-benzopyran-6-yl)-1-oxo-1,2-dihydroisoquinolin-3-yl}acetic acid |

TABLE 1-continued

| Compound No. and Example No. | Structure | Chemical Name |
|---|---|---|
| 139 | 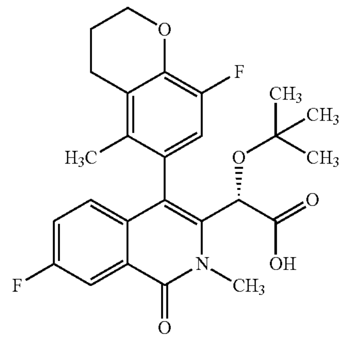 | (2S)-2-(tert-butoxy)-2-[7-fluoro-4-(8-fluoro-5-methyl-3,4-dihydro-2H-1-benzopyran-6-yl)-2-methyl-1-oxo-1,2-dihydroisoquinolin-3-yl]acetic acid |
| 140 | 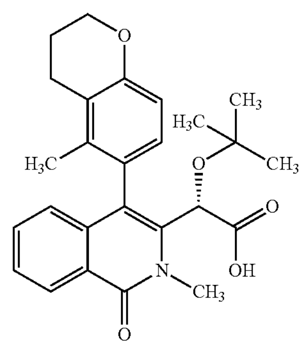 [SMILES: Cc1c(-c2c([C@H](OC(C)(C)C)C(=O)O)n(C)c(=O)c3ccccc23)ccc2c1CCCO2] | (2S)-2-(tert-butoxy)-2-[2-methyl-4-(5-methyl-3,4-dihydro-2H-1-benzopyran-6-yl)-1-oxo-1,2-dihydroisoquinolin-3-yl]acetic acid |
| 141 | 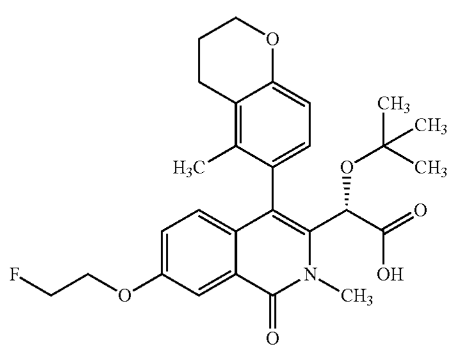 [SMILES: Cc1c(-c2c([C@H](OC(C)(C)C)C(=O)O)n(C)c(=O)c3cc(OCCF)ccc23)ccc2c1CCCO2] | (2S)-2-(tert-butoxy)-2-[7-(2-fluoroethoxy)-2-methyl-4-(5-methyl-3,4-dihydro-2H-1-benzopyran-6-yl)-1-oxo-1,2-dihydroisoquinolin-3-yl]acetic acid |
| 142 | 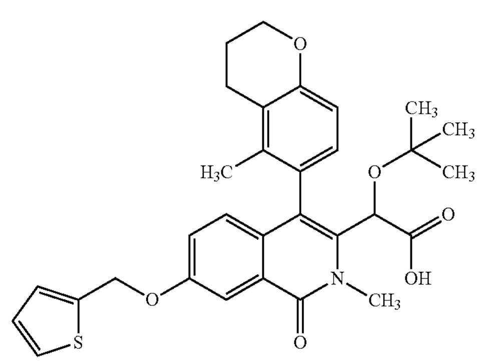 | 2-(tert-butoxy)-2-[2-methyl-4-(5-methyl-3,4-dihydro-2H-1-benzopyran-6-yl)-1-oxo-7-(thiophen-2-ylmethoxy)-1,2-dihydroisoquinolin-3-yl]acetic acid |

TABLE 1-continued

| Compound No. and Example No. | Structure | Chemical Name |
|---|---|---|
| 143 | 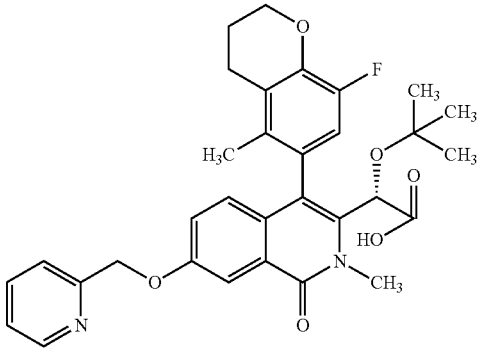 [SMILES: Cc1c(-c2c([C@H](OC(C)(C)C)C(=O)O)n(C)c(=O)c3cc(OCc4ccccn4)ccc23)cc(F)c2c1CCCO2] | (2S)-2-(tert-butoxy)-2-[4-(8-fluoro-5-methyl-3,4-dihydro-2H-1-benzopyran-6-yl)-2-methyl-1-oxo-7-(pyridin-2-ylmethoxy)-1,2-dihydroisoquinolin-3-yl]acetic acid |
| 144 | 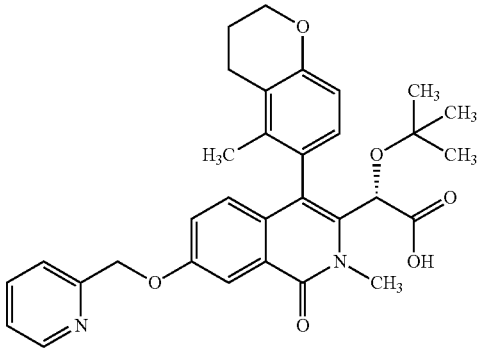 [SMILES: Cc1c(-c2c([C@H](OC(C)(C)C)C(=O)O)n(C)c(=O)c3cc(OCc4ccccn4)ccc23)ccc2c1CCCO2] | (2S)-2-(tert-butoxy)-2-[2-methyl-4-(5-methyl-3,4-dihydro-2H-1-benzopyran-6-yl)-1-oxo-7-(pyridin-2-ylmethoxy)-1,2-dihydroisoquinolin-3-yl]acetic acid |
| 145 | 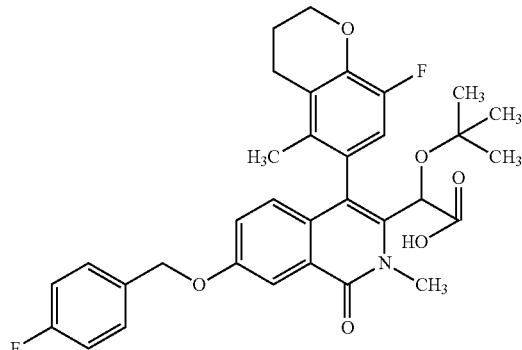 | 2-(tert-butoxy)-2-[4-(8-fluoro-5-methyl-3,4-dihydro-2H-1-benzopyran-6-yl)-7-[(4-fluorophenyl)methoxy]-2-methyl-1-oxo-1,2-dihydroisoquinolin-3-yl]acetic acid |
| 146 | 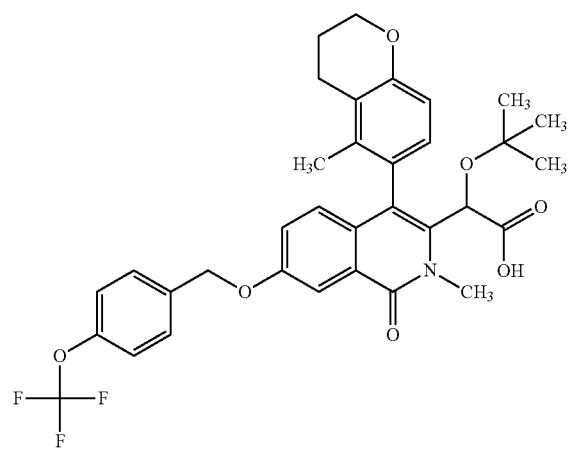 [SMILES: Cc1c(-c2c(C(OC(C)(C)C)C(=O)O)n(C)c(=O)c3cc(OCc4ccc(OC(F)(F)F)cc4)ccc23)ccc2c1CCCO2] | 2-(tert-butoxy)-2-[2-methyl-4-(5-methyl-3,4-dihydro-2H-1-benzopyran-6-yl)-1-oxo-7-{[4-(trifluoromethoxy)phenyl]methoxy}-1,2-dihydroisoquinolin-3-yl]acetic acid |

TABLE 1-continued

| Compound No. and Example No. | Structure | Chemical Name |
|---|---|---|
| 147 | 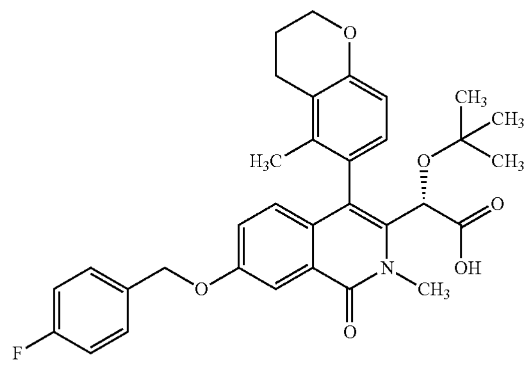 [SMILES: Cc1c(-c2c([C@H](OC(C)(C)C)C(=O)O)n(C)c(=O)c3cc(OCc4ccc(F)cc4)ccc23)ccc2c1CCCO2] | (2S)-2-(tert-butoxy)-2-{7-[(4-fluorophenyl)methoxy]-2-methyl-4-(5-methyl-3,4-dihydro-2H-1-benzopyran-6-yl)-1-oxo-1,2-dihydroisoquinolin-3-yl}acetic acid |
| 148 | 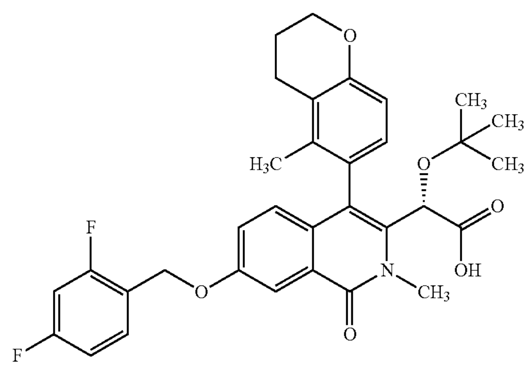 | (2S)-2-(tert-butoxy)-2-{7-[(2,4-difluorophenyl)methoxy]-2-methyl-4-(5-methyl-3,4-dihydro-2H-1-benzopyran-6-yl)-1-oxo-1,2-dihydroisoquinolin-3-yl}acetic acid |
| 149 | 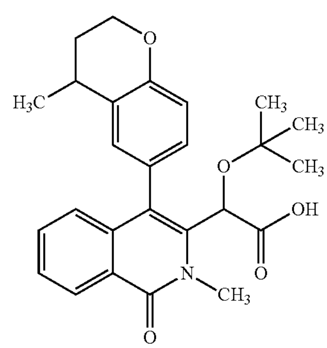 [SMILES: CC1CCOc2ccc(-c3c(C(OC(C)(C)C)C(=O)O)n(C)c(=O)c4ccccc34)cc21] | [(1,1-dimethylethyl)oxy][2-methyl-4-(4-methyl-3,4-dihydro-2H-chromen-6-yl)-1-oxo-1,2-dihydro-3-isoquinolinyl]acetic acid |
| 150 | 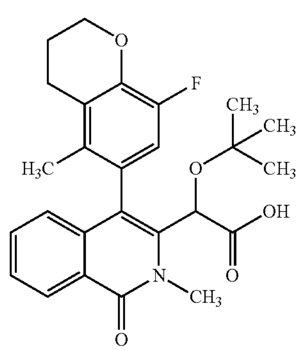 [SMILES: Cc1c(-c2c(C(OC(C)(C)C)C(=O)O)n(C)c(=O)c3ccccc23)cc(F)c2c1CCCO2] | [(1,1-dimethylethyl)oxy][4-(8-fluoro-5-methyl-3,4-dihydro-2H-chromen-6-yl)-2-methyl-1-oxo-1,2-dihydro-3-isoquinolinyl]acetic acid |

TABLE 1-continued

| Compound No. and Example No. | Structure | Chemical Name |
|---|---|---|
| 151 | 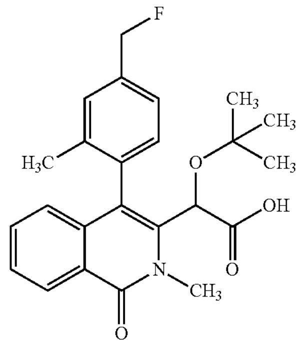 [SMILES: Cc1cc(CF)ccc1-c1c(C(OC(C)(C)C)C(=O)O)n(C)c(=O)c2ccccc12] | [(1,1-dimethylethyl)oxy]{4-[2-fluoro-4-(fluoromethyl)phenyl]-2-methyl-1-oxo-1,2-dihydro-3-isoquinolinyl}acetic acid |
| 152 | 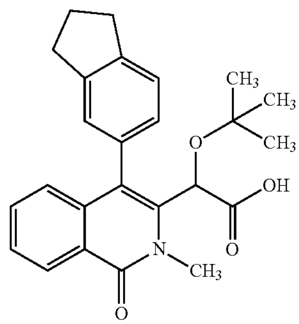 [SMILES: Cn1c(C(OC(C)(C)C)C(=O)O)c(-c2ccc3c(c2)CCC3)c2ccccc2c1=O] | 2-(tert-butoxy)-2-(4-(2,3-dihydro-1H-inden-5-yl)-2-methyl-1-oxo-1,2-dihydroisoquinolin-3-yl)acetic acid |
| 153 | 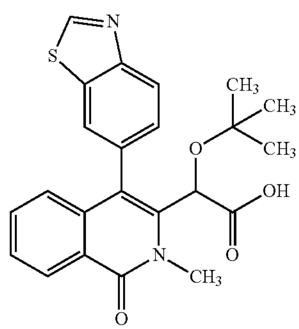 [SMILES: Cn1c(C(OC(C)(C)C)C(=O)O)c(-c2ccc3ncsc3c2)c2ccccc2c1=O] | 2-(4-(benzo[d]thiazol-6-yl)-2-methyl-1-oxo-1,2-dihydroisoquinolin-3-yl)-2-(tert-butoxy)acetic acid |
| 154 | 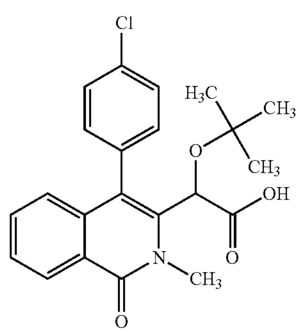 [SMILES: Cn1c(C(OC(C)(C)C)C(=O)O)c(-c2ccc(Cl)cc2)c2ccccc2c1=O] | [4-(4-chlorophenyl)-2-methyl-1-oxo-1,2-dihydro-3-isoquinolinyl][(1,1-dimethylethyl)oxy]acetic acid |
| 155 | 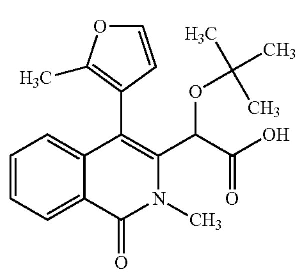 [SMILES: Cc1occc1-c1c(C(OC(C)(C)C)C(=O)O)n(C)c(=O)c2ccccc12] | [(1,1-dimethylethyl)oxy][2-methyl-4-(2-methyl-3-furanyl)-1-oxo-1,2-dihydro-3-isoquinolinyl]acetic |

TABLE 1-continued

| Compound No. and Example No. | Structure | Chemical Name |
|---|---|---|
| 156 | 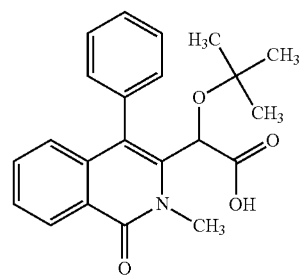 [SMILES: Cn1c(C(OC(C)(C)C)C(=O)O)c(-c2ccccc2)c2ccccc2c1=O] | [(1,1-dimethylethyl)oxy](2-methyl-1-oxo-4-phenyl-1,2-dihydro-3-isoquinolinyl)acetic acid |
| 157 | 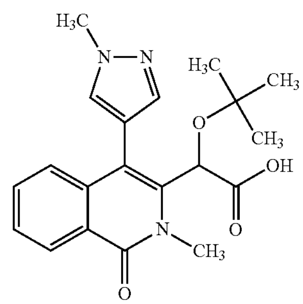 [SMILES: Cn1cc(-c2c(C(OC(C)(C)C)C(=O)O)n(C)c(=O)c3ccccc23)cn1] | [(1,1-dimethylethyl)oxy][2-methyl-4-(1-methyl-1H-pyrazol-4-yl)-1-oxo-1,2-dihydro-3-isoquinolinyl]acetic acid |
| 158 | 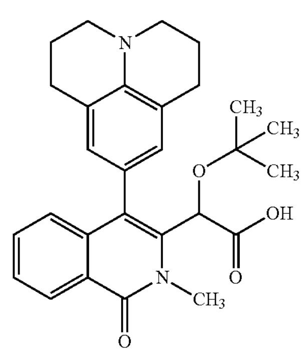 [SMILES: Cn1c(C(OC(C)(C)C)C(=O)O)c(-c2cc3c4c(c2)CCCN4CCC3)c2ccccc2c1=O] | [(1,1-dimethylethyl)oxy][2-methyl-1-oxo-4-(2,3,6,7-tetrahydro-1H,5H-pyrido[3,2,1-ij]quinolin-9-yl)-1,2-dihydro-3-isoquinolinyl]acetic acid |
| 159 | 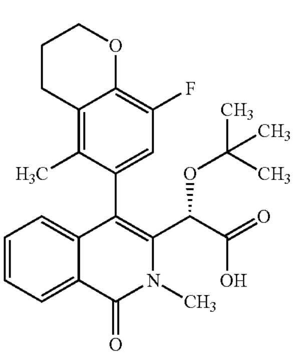 [SMILES: Cc1c(-c2c([C@H](OC(C)(C)C)C(=O)O)n(C)c(=O)c3ccccc23)cc(F)c2c1CCCO2] | (2S)(M)-2-(tert-butoxy)-2-(4-(8-fluoro-5-methylchroman-6-yl)-2-methyl-1-oxo-1,2-dihydroisoquinolin-3-yl)acetic acid |

TABLE 1-continued

| Compound No. and Example No. | Structure | Chemical Name |
|---|---|---|
| 160 | 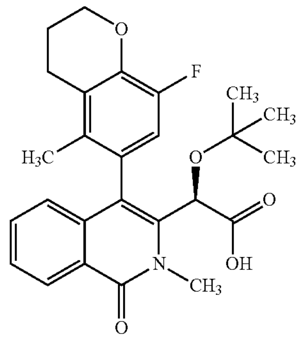 [SMILES: Cc1c(-c2c([C@@H](OC(C)(C)C)C(=O)O)n(C)c(=O)c3ccccc23)cc(F)c2c1CCCO2] | (2R)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]acetic acid |
| 161 | 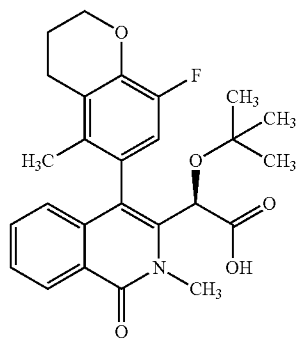 [SMILES: Cc1c(-c2c([C@@H](OC(C)(C)C)C(=O)O)n(C)c(=O)c3ccccc23)cc(F)c2c1CCCO2] | (2R)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]acetic acid |
| 162 | 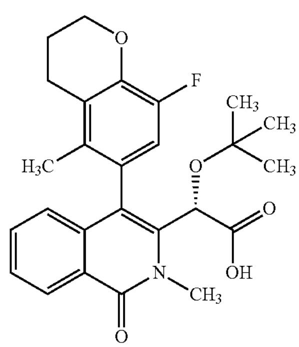 [SMILES: Cc1c(-c2c([C@H](OC(C)(C)C)C(=O)O)n(C)c(=O)c3ccccc23)cc(F)c2c1CCCO2] | (2S)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]acetic acid |
| 163 | 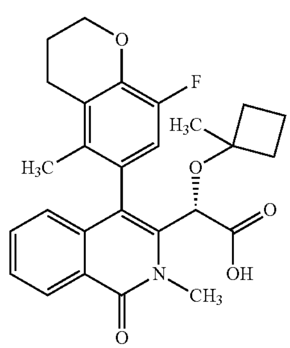 [SMILES: Cc1c(-c2c([C@H](OC3(C)CCC3)C(=O)O)n(C)c(=O)c3ccccc23)cc(F)c2c1CCCO2] | (2S)(M)-2-[4-(8-fluoro-5-methyl-3,4-dihydro-2H-1-benzopyran-6-yl)-2-methyl-1-oxo-1,2-dihydroisoquinolin-3-yl]-2-(1-methylcyclobutoxy)acetic acid |

TABLE 1-continued

| Compound No. and Example No. | Structure | Chemical Name |
|---|---|---|
| 164 | 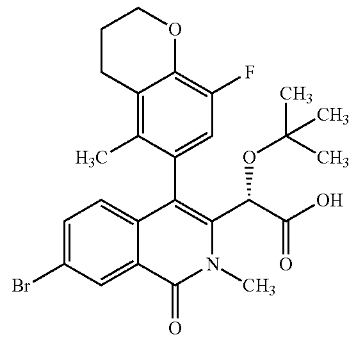 [SMILES: Cc1c(-c2c([C@H](OC(C)(C)C)C(=O)O)n(C)c(=O)c3cc(Br)ccc23)cc(F)c2c1CCCO2] | (2S)(M)-[7-bromo-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid |
| 165 | 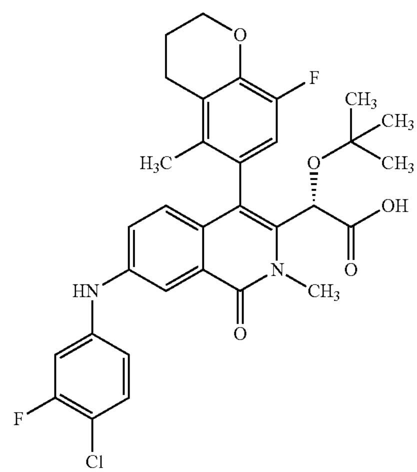 [SMILES: Cc1c(-c2c([C@H](OC(C)(C)C)C(=O)O)n(C)c(=O)c3cc(Nc4ccc(Cl)c(F)c4)ccc23)cc(F)c2c1CCCO2] | (2S)(M)-[7-[(4-chloro-3-fluorophenyl)amino]-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid |
| 166 | 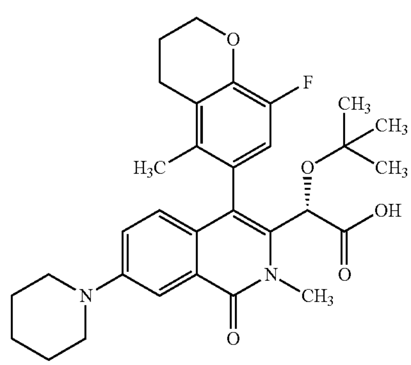 [SMILES: Cc1c(-c2c([C@H](OC(C)(C)C)C(=O)O)n(C)c(=O)c3cc(N4CCCCC4)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-1-oxo-7-(1-piperidinyl)-1,2-dihydro-3-isoquinolinyl]ethanoic acid |
| 167 | 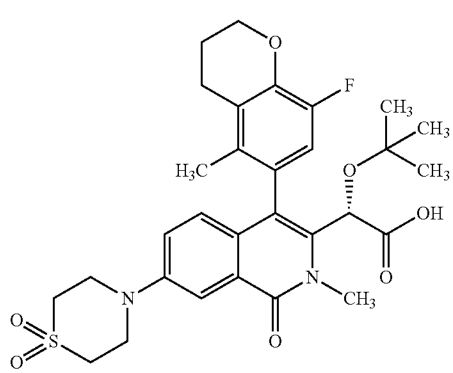 [SMILES: Cc1c(-c2c([C@H](OC(C)(C)C)C(=O)O)n(C)c(=O)c3cc(N4CCS(=O)(=O)CC4)ccc23)cc(F)c2c1CCCO2] | (2S)(M)-[(1,1-dimethylethyl)oxy][7-(1,1-dioxido-4-thiomorpholinyl)-4-(8-fluoro-5-methyl-3,4-dihydro-2H-chromen-6-yl)-2-methyl-1-oxo-1,2-dihydro-3-isoquinolinyl]ethanoic acid |

TABLE 1-continued

| Compound No. and Example No. | Structure | Chemical Name |
|---|---|---|
| 168 | 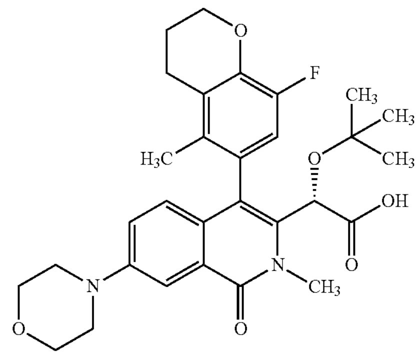 [SMILES: Cc1c(-c2c([C@H](OC(C)(C)C)C(=O)O)n(C)c(=O)c3cc(N4CCOCC4)ccc23)cc(F)c2c1CCCO2] | (S)(M)-2-(tert-butoxy)-2-(4-(8-fluoro-5-methylchroman-6-yl)-2-methyl-7-morpholino-1-oxo-1,2-dihydroisoquinolin-3-yl)acetic acid |
| 169 | 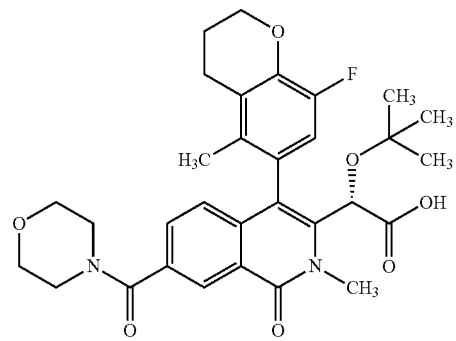 [SMILES: Cc1c(-c2c([C@H](OC(C)(C)C)C(=O)O)n(C)c(=O)c3cc(C(=O)N4CCOCC4)ccc23)cc(F)c2c1CCCO2] | (S)(M)-2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetic acid |
| 170 | 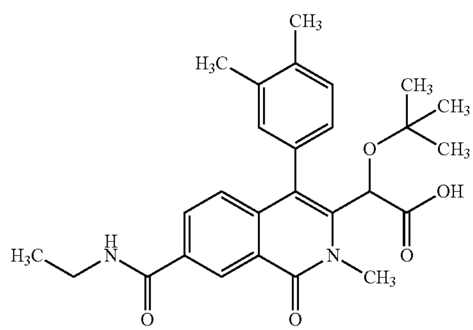 [SMILES: CCNC(=O)c1ccc2c(-c3ccc(C)c(C)c3)c(C(OC(C)(C)C)C(=O)O)n(C)c(=O)c2c1] | [(1,1-dimethylethyl)oxy]{4-(3,4-dimethylphenyl)-7-[(ethylamino)carbonyl]-2-methyl-1-oxo-1,2-dihydro-3-isoquinolinyl}acetic acid |
| 171 | 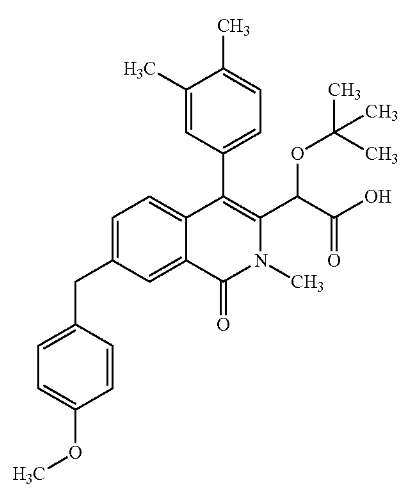 [SMILES: COc1ccc(Cc2ccc3c(-c4ccc(C)c(C)c4)c(C(OC(C)(C)C)C(=O)O)n(C)c(=O)c3c2)cc1] | [(1,1-dimethylethyl)oxy](4-(3,4-dimethylphenyl)-2-methyl-7-{[4-(methyloxy)phenyl]methyl}-1-oxo-1,2-dihydro-3-isoquinolinyl)acetic acid |

TABLE 1-continued

| Compound No. and Example No. | Structure | Chemical Name |
|---|---|---|
| 172 | 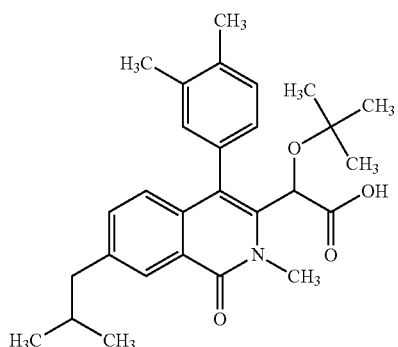 | [(1,1-dimethylethyl)oxy][4-(3,4-dimethylphenyl)-2-methyl-7-(2-methylpropyl)-1-oxo-1,2-dihydro-3-isoquinolinyl]acetic acid |
| 173 | 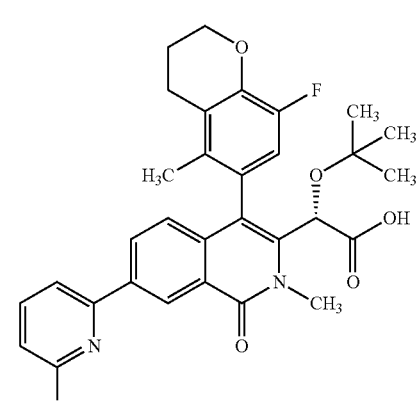 | (2S)(M)-[(1,1-dimethylethyl)oxy][4-(8-fluoro-5-methyl-3,4-dihydro-2H-chromen-6-yl)-2-methyl-7-(6-methyl-2-pyridinyl)-1-oxo-1,2-dihydro-3-isoquinolinyl]ethanoic acid |
| 174 | 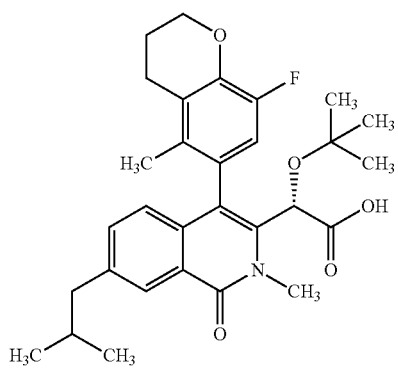 [SMILES: Cc1c(-c2c([C@H](OC(C)(C)C)C(=O)O)n(C)c(=O)c3cc(CC(C)C)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-7-(2-methylpropyl)-1-oxo-1,2-dihydro-3-isoquinolinyl]ethanoic acid |
| 175 | 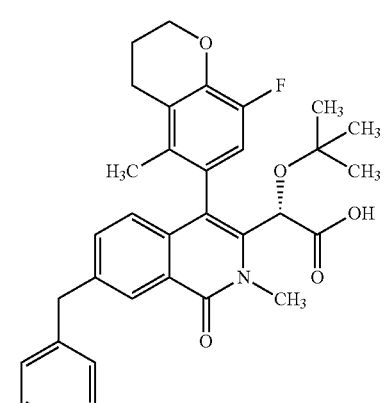 | (2S)(M)-[(1,1-dimethylethyl)oxy][4-(8-fluoro-5-methyl-3,4-dihydro-2H-chromen-6-yl)-2-methyl-1-oxo-7-(phenylmethyl)-1,2-dihydro-3-isoquinolinyl]ethanoic acid |

TABLE 1-continued

| Compound No. and Example No. | Structure | Chemical Name |
|---|---|---|
| 176 | 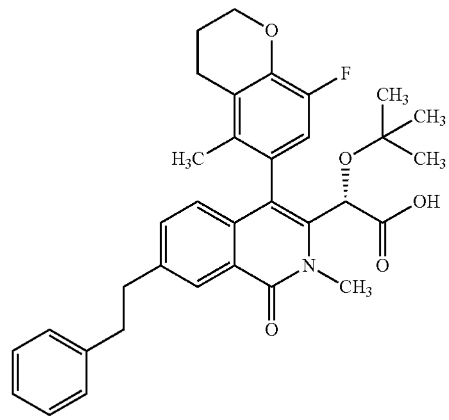 [SMILES: Cc1c(-c2c([C@H](OC(C)(C)C)C(=O)O)n(C)c(=O)c3cc(CCc4ccccc4)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-1-oxo-7-(2-phenylethyl)-1,2-dihydro-3-isoquinolinyl]ethanoic acid |
| 177 | 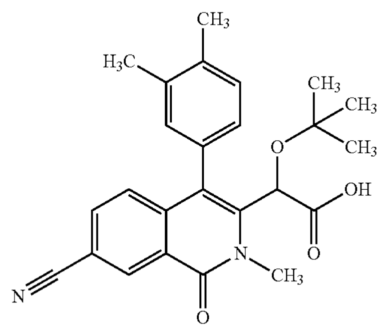 [SMILES: Cc1ccc(-c2c(C(OC(C)(C)C)C(=O)O)n(C)c(=O)c3cc(C#N)ccc23)cc1C] | 7-cyano-4-(3,4-dimethylphenyl)-2-methyl-1-oxo-1,2-dihydro-3-isoquinolinyl][(1,1-dimethylethyl)oxy]acetic acid |
| 178 | 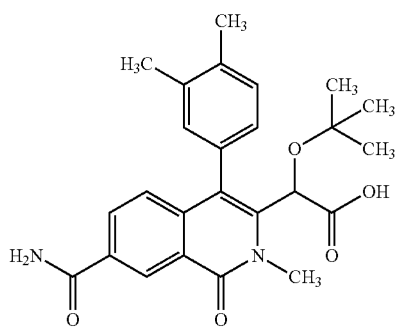 [SMILES: Cc1ccc(-c2c(C(OC(C)(C)C)C(=O)O)n(C)c(=O)c3cc(C(N)=O)ccc23)cc1C] | [7-(aminocarbonyl)-4-(3,4-dimethylphenyl)-2-methyl-1-oxo-1,2-dihydro-3-isoquinolinyl][(1,1-dimethylethyl)oxy]acetic acid |
| 179 | 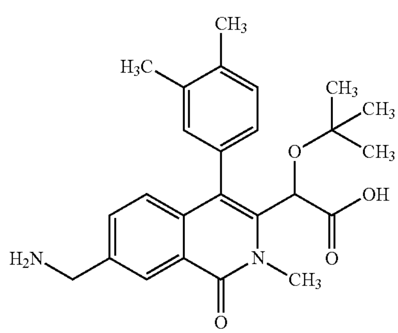 [SMILES: Cc1ccc(-c2c(C(OC(C)(C)C)C(=O)O)n(C)c(=O)c3cc(CN)ccc23)cc1C] | [7-(aminomethyl)-4-(3,4-dimethylphenyl)-2-methyl-1-oxo-1,2-dihydro-3-isoquinolinyl][(1,1-dimethylethyl)oxy]acetic acid-TFA salt |

TABLE 1-continued

| Compound No. and Example No. | Structure | Chemical Name |
|---|---|---|
| 180 | 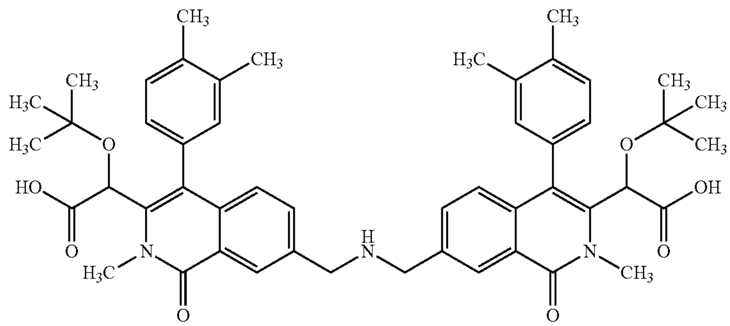 [SMILES: Cc1ccc(-c2c(C(OC(C)(C)C)C(=O)O)n(C)c(=O)c3cc(CNCc4ccc5c(-c6ccc(C)c(C)c6)c(C(OC(C)(C)C)C(=O)O)n(C)c(=O)c5c4)ccc23)cc1C] | 2,2'-(iminobis{methanediyl[4-(3,4-dimethylphenyl)-2-methyl-1-oxo-1,2-dihydroisoquinoline-7,3-diyl]})bis{[(1,1-dimethylethyl)oxy]acetic acid} |
| 181 | 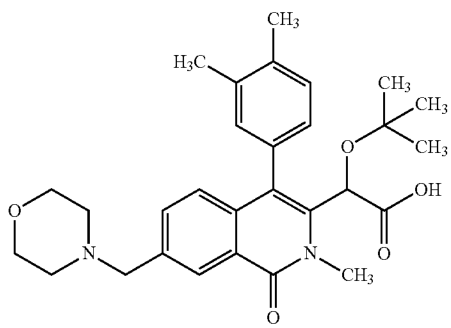 [SMILES: Cc1ccc(-c2c(C(OC(C)(C)C)C(=O)O)n(C)c(=O)c3cc(CN4CCOCC4)ccc23)cc1C] | 2-(tert-butoxy)-2-(4-(3,4-dimethylphenyl)-2-methyl-7-(methylsulfonamidomethyl)-1-oxo-1,2-dihydroisoquinolin-3-yl)acetic acid |
| 182 | 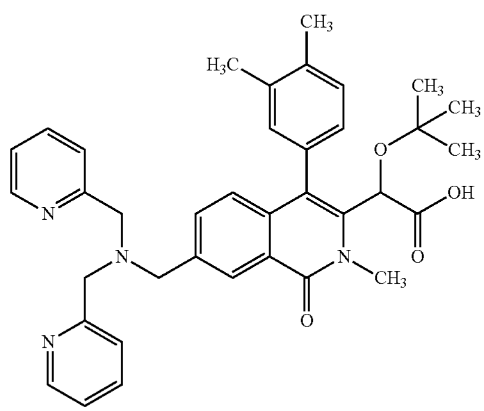 [SMILES: Cc1ccc(-c2c(C(OC(C)(C)C)C(=O)O)n(C)c(=O)c3cc(CN(Cc4ccccn4)Cc4ccccn4)ccc23)cc1C] | 2-(7-((bis(pyridin-2-ylmethyl)amino)methyl)-4-(3,4-dimethylphenyl)-2-methyl-1-oxo-1,2-dihydroisoquinolin-3-yl)-2-(tert-butoxy)acetic acid |
| 183 | 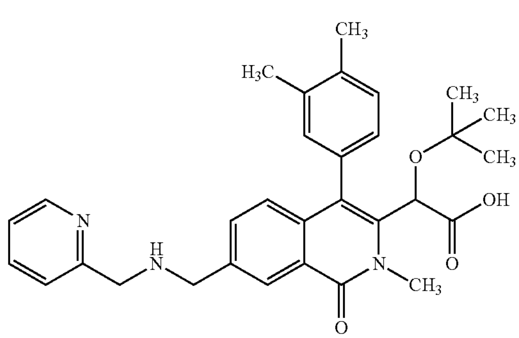 [SMILES: Cc1ccc(-c2c(C(OC(C)(C)C)C(=O)O)n(C)c(=O)c3cc(CNCc4ccccn4)ccc23)cc1C] | 2-(tert-butoxy)-2-(4-(3,4-dimethylphenyl)-2-methyl-1-oxo-7-(((pyridin-2-ylmethyl)amino)methyl)-1,2-dihydroisoquinolin-3-yl)acetic acid |

TABLE 1-continued

| Compound No. and Example No. | Structure | Chemical Name |
|---|---|---|
| 184 | 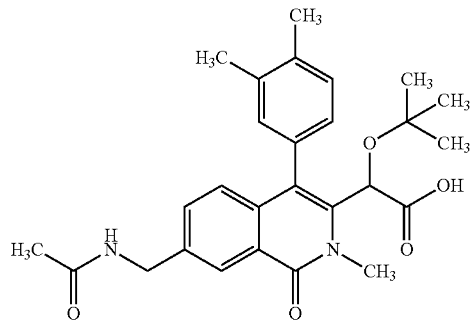 [SMILES: CC(=O)NCc1ccc2c(-c3ccc(C)c(C)c3)c(C(OC(C)(C)C)C(=O)O)n(C)c(=O)c2c1] | 2-(7-(acetamidomethyl)-4-(3,4-dimethylphenyl)-2-methyl-1-oxo-1,2-dihydroisoquinolin-3-yl)-2-(tert-butoxy)acetic acid |
| 185 | 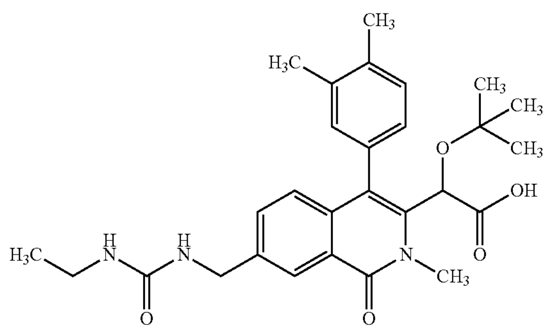 [SMILES: CCNC(=O)NCc1ccc2c(-c3ccc(C)c(C)c3)c(C(OC(C)(C)C)C(=O)O)n(C)c(=O)c2c1] | 2-(tert-butoxy)-2-(4-(3,4-dimethylphenyl)-7-((3-ethylureido)methyl)-2-methyl-1-oxo-1,2-dihydroisoquinolin-3-yl)acetic acid |
| 186 | 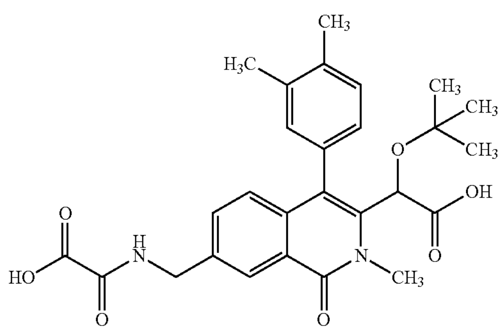 [SMILES: Cc1ccc(-c2c(C(OC(C)(C)C)C(=O)O)n(C)c(=O)c3cc(CNC(=O)C(=O)O)ccc23)cc1C] | 2-(tert-butoxy)-2-(7-((carboxyformamido)methyl)-4-(3,4-dimethylphenyl)-2-methyl-1-oxo-1,2-dihydroisoquinolin-3-yl)acetic acid |
| 187 | 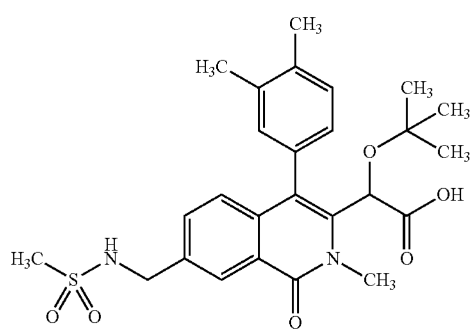 [SMILES: Cc1ccc(-c2c(C(OC(C)(C)C)C(=O)O)n(C)c(=O)c3cc(CNS(C)(=O)=O)ccc23)cc1C] | 2-(tert-butoxy)-2-(4-(3,4-dimethylphenyl)-2-methyl-7-(methylsulfonamidomethyl)-1-oxo-1,2-dihydroisoquinolin-3-yl)acetic acid |

TABLE 1-continued

| Compound No. and Example No. | Structure | Chemical Name |
|---|---|---|
| 188 | 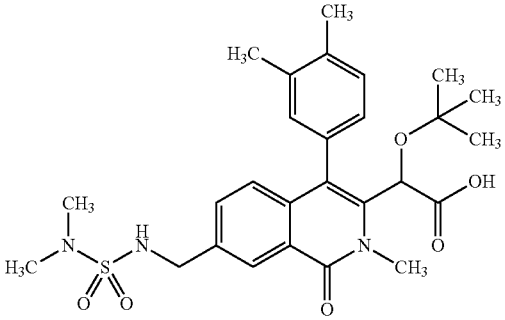 [SMILES: Cc1ccc(-c2c(C(OC(C)(C)C)C(=O)O)n(C)c(=O)c3cc(CNS(=O)(=O)N(C)C)ccc23)cc1C] | 2-(tert-butoxy)-2-(4-(3,4-dimethylphenyl)-7-(((N,N-dimethylsulfamoyl)amino)methyl)-2-methyl-1-oxo-1,2-dihydroisoquinolin-3-yl)acetic acid |
| 189 | 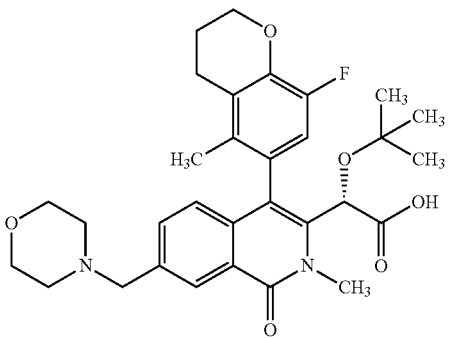 [SMILES: Cc1c(-c2c([C@H](OC(C)(C)C)C(=O)O)n(C)c(=O)c3cc(CN4CCOCC4)ccc23)cc(F)c2c1CCCO2] | (S)(M)-2-(tert-butoxy)-2-(4-(8-fluoro-5-methylchroman-6-yl)-2-methyl-7-(morpholinomethyl)-1-oxo-1,2-dihydroisoquinolin-3-yl)acetic acid |
| 190 | 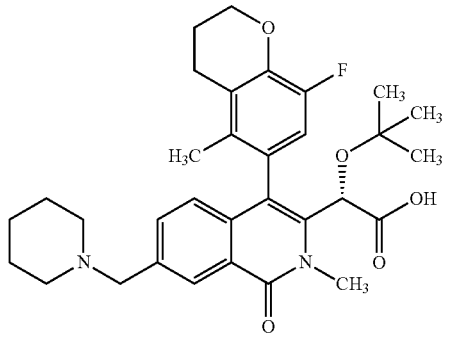 [SMILES: Cc1c(-c2c([C@H](OC(C)(C)C)C(=O)O)n(C)c(=O)c3cc(CN4CCCCC4)ccc23)cc(F)c2c1CCCO2] | (S)(M)-2-(tert-butoxy)-2-(4-(8-fluoro-5-methylchroman-6-yl)-2-methyl-1-oxo-7-(piperidin-1-ylmethyl)-1,2-dihydroisoquinolin-3-yl)acetic acid |
| 191 | 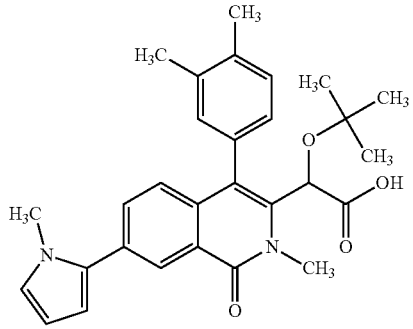 [SMILES: Cc1ccc(-c2c(C(OC(C)(C)C)C(=O)O)n(C)c(=O)c3cc(-c4cccn4C)ccc23)cc1C] | [(1,1-dimethylethyl)oxy][4-(3,4-dimethylphenyl)-2-methyl-7-(1-methyl-1H-pyrrol-2-yl)-1-oxo-1,2-dihydro-3-isoquinolinyl]acetic acid |

TABLE 1-continued

| Compound No. and Example No. | Structure | Chemical Name |
|---|---|---|
| 192 | 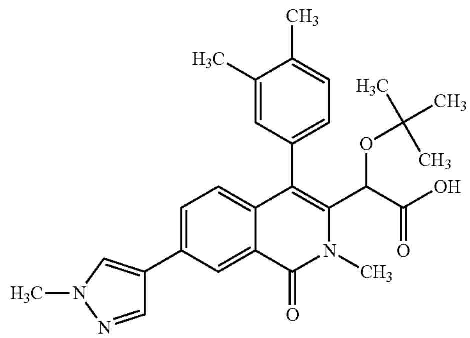 [SMILES: Cc1ccc(-c2c(C(OC(C)(C)C)C(=O)O)n(C)c(=O)c3cc(-c4cnn(C)c4)ccc23)cc1C] | [(1,1-dimethylethyl)oxy][4-(3,4-dimethylphenyl)-2-methyl-7-(1-methyl-1H-pyrazol-4-yl)-1-oxo-1,2-dihydro-3-isoquinolinyl]acetic acid |
| 193 | 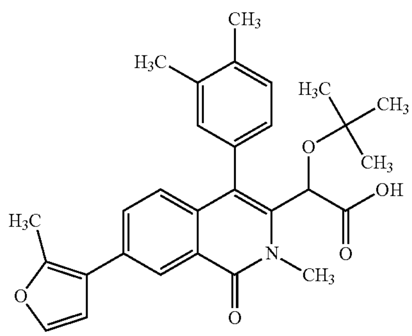 [SMILES: Cc1ccc(-c2c(C(OC(C)(C)C)C(=O)O)n(C)c(=O)c3cc(-c4ccoc4C)ccc23)cc1C] | [(1,1-dimethylethyl)oxy][4-(3,4-dimethylphenyl)-2-methyl-7-(2-methyl-3-furanyl)-1-oxo-1,2-dihydro-3-isoquinolinyl]acetic acid |
| 194 | 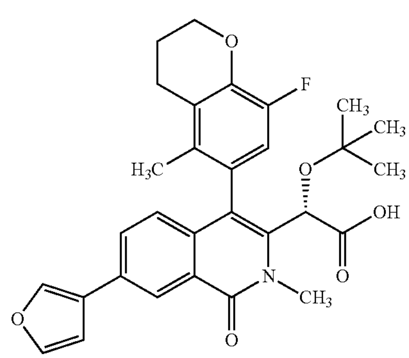 [SMILES: Cc1c(-c2c([C@H](OC(C)(C)C)C(=O)O)n(C)c(=O)c3cc(-c4ccoc4)ccc23)cc(F)c2c1CCCO2] | (2S)(M)-[(1,1-dimethylethyl)oxy][4-(8-fluoro-5-methyl-3,4-dihydro-2H-chromen-6-yl)-7-(3-furanyl)-2-methyl-1-oxo-1,2-dihydro-3-isoquinolinyl]ethanoic acid |
| 195 | 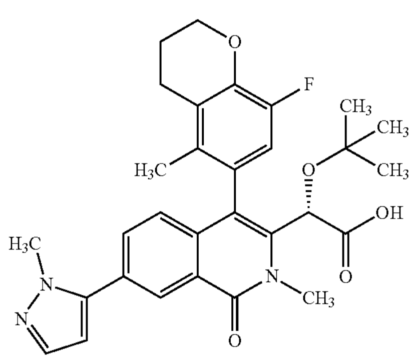 [SMILES: Cc1c(-c2c([C@H](OC(C)(C)C)C(=O)O)n(C)c(=O)c3cc(-c4ccnn4C)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-7-(1-methyl-1H-pyrazol-5-yl)-1-oxo-1,2-dihydro-3-isoquinolinyl]ethanoic acid |

TABLE 1-continued

| Compound No. and Example No. | Structure | Chemical Name |
|---|---|---|
| 196 | 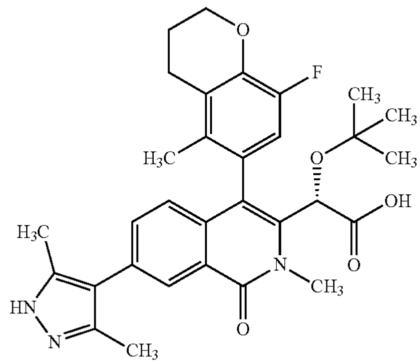 [SMILES: Cc1n[nH]c(C)c1-c1ccc2c(-c3cc(F)c4c(c3C)CCCO4)c([C@H](OC(C)(C)C)C(=O)O)n(C)c(=O)c2c1] | 2S)(M)-[(1,1-dimethylethyl)oxy][7-(3,5-dimethyl-1H-pyrazol-4-yl)-4-(8-fluoro-5-methyl-3,4-dihydro-2H-chromen-6-yl)-2-methyl-1-oxo-1,2-dihydro-3-isoquinolinyl]ethanoic acid |
| 197 | 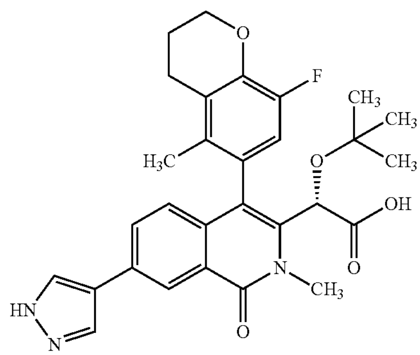 [SMILES: Cc1c(-c2c([C@H](OC(C)(C)C)C(=O)O)n(C)c(=O)c3cc(-c4cn[nH]c4)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-1-oxo-7-(1H-pyrazol-4-yl)-1,2-dihydro-3-isoquinolinyl]ethanoic acid |
| 198 | 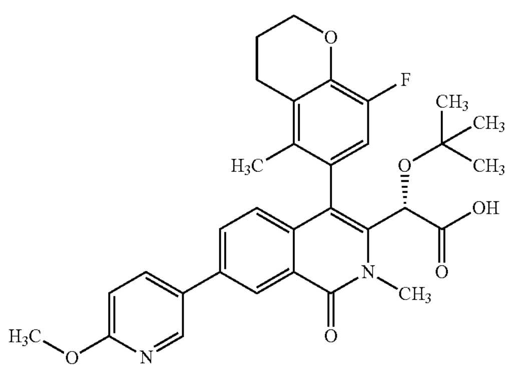 [SMILES: COc1ccc(-c2ccc3c(-c4cc(F)c5c(c4C)CCCO5)c([C@H](OC(C)(C)C)C(=O)O)n(C)c(=O)c3c2)cn1] | (2S)(M)-[(1,1-dimethylethyl)oxy]{4-(8-fluoro-5-methyl-3,4-dihydro-2H-chromen-6-yl)-2-methyl-7-[6-(methyloxy)-3-pyridinyl]-1-oxo-1,2-dihydro-3-isoquinolinyl}ethanoic acid |
| 199 | 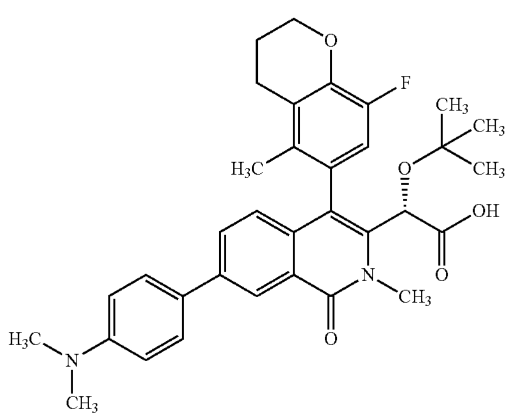 [SMILES: Cc1c(-c2c([C@H](OC(C)(C)C)C(=O)O)n(C)c(=O)c3cc(-c4ccc(N(C)C)cc4)ccc23)cc(F)c2c1CCCO2] | (2S)(M)-[7-[4-(dimethylamino)phenyl]-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid |

TABLE 1-continued

| Compound No. and Example No. | Structure | Chemical Name |
|---|---|---|
| 200 | 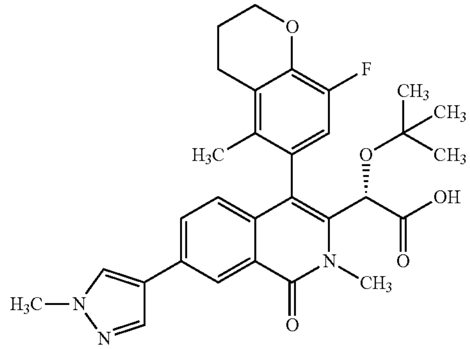 [SMILES: Cc1c(-c2c([C@H](OC(C)(C)C)C(=O)O)n(C)c(=O)c3cc(-c4cnn(C)c4)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-7-(1-methyl-1H-pyrazol-4-yl)-1-oxo-1,2-dihydro-3-isoquinolinyl]ethanoic acid |
| 201 | 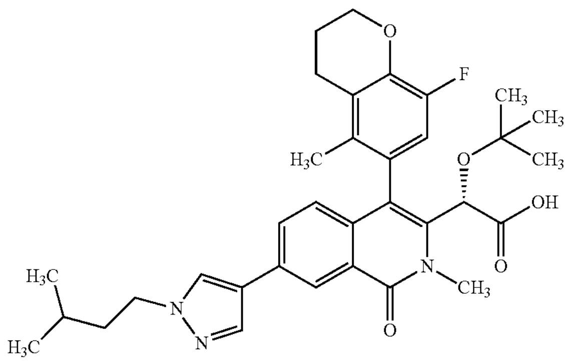 [SMILES: Cc1c(-c2c([C@H](OC(C)(C)C)C(=O)O)n(C)c(=O)c3cc(-c4cnn(CCC(C)C)c4)ccc23)cc(F)c2c1CCCO2] | (2S)(M)-[(1,1-dimethylethyl)oxy]{4-(8-fluoro-5-methyl-3,4-dihydro-2H-chromen-6-yl)-2-methyl-7-[1-(3-methylbutyl)-1H-pyrazol-4-yl]-1-oxo-1,2-dihydro-3-isoquinolinyl}ethanoic acid |
| 202 | 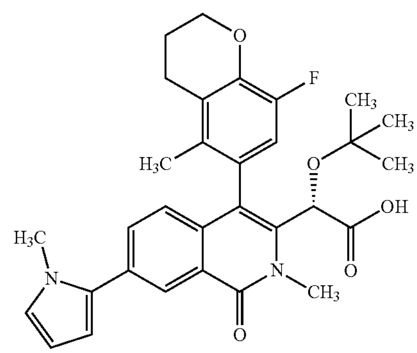 | (S)(M)-[(1,1-dimethylethyl)oxy][4-(8-fluoro-5-methyl-3,4-dihydro-2H-chromen-6-yl)-2-methyl-7-(1-methyl-1H-pyrrol-2-yl)-1-oxo-1,2-dihydro-3-isoquinolinyl]ethanoic acid |
| 203 | 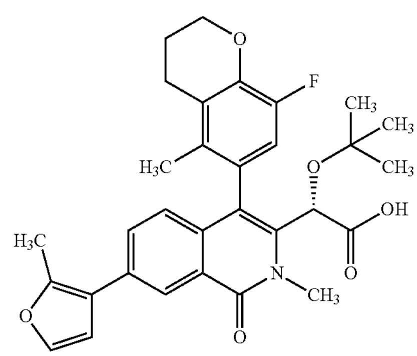 [SMILES: Cc1occc1-c1ccc2c(-c3cc(F)c4c(c3C)CCCO4)c([C@H](OC(C)(C)C)C(=O)O)n(C)c(=O)c2c1] | (2S)(M)-[(1,1-dimethylethyl)oxy][4-(8-fluoro-5-methyl-3,4-dihydro-2H-chromen-6-yl)-2-methyl-7-(2-methyl-3-furanyl)-1-oxo-1,2-dihydro-3-isoquinolinyl]ethanoic acid |

TABLE 1-continued

| Compound No. and Example No. | Structure | Chemical Name |
|---|---|---|
| 204 | 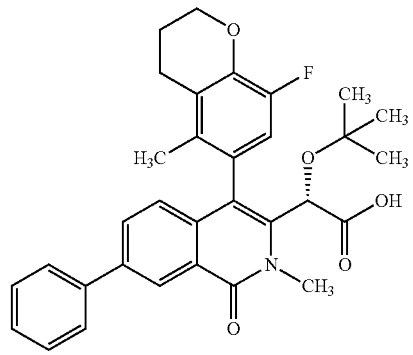 [SMILES: Cc1c(-c2c([C@H](OC(C)(C)C)C(=O)O)n(C)c(=O)c3cc(-c4ccccc4)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-1-oxo-7-phenyl-1,2-dihydro-3-isoquinolinyl]ethanoic acid |
| 205 | 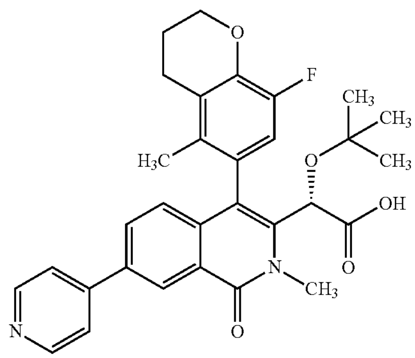 [SMILES: Cc1c(-c2c([C@H](OC(C)(C)C)C(=O)O)n(C)c(=O)c3cc(-c4ccncc4)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-1-oxo-7-(4-pyridinyl)-1,2-dihydro-3-isoquinolinyl]ethanoic acid |
| 206 | 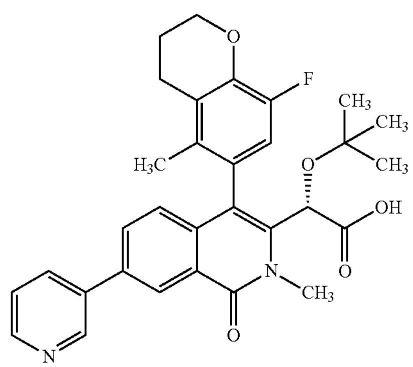 [SMILES: Cc1c(-c2c([C@H](OC(C)(C)C)C(=O)O)n(C)c(=O)c3cc(-c4cccnc4)ccc23)cc(F)c2c1CCCO2] | (2S)(M)-[(1,1-dimethylethyl)oxy][4-(8-fluoro-5-methyl-3,4-dihydro-2H-chromen-6-yl)-2-methyl-1-oxo-7-(3-pyridinyl)-1,2-dihydro-3-isoquinolinyl]ethanoic acid |
| 207 | 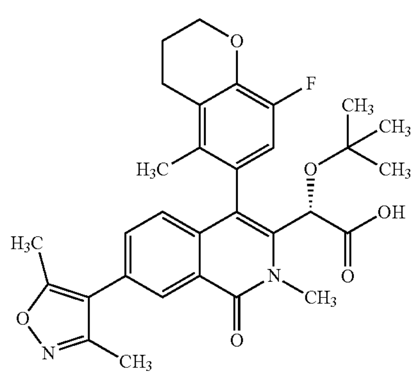 [SMILES: Cc1noc(C)c1-c1ccc2c(-c3cc(F)c4c(c3C)CCCO4)c([C@H](OC(C)(C)C)C(=O)O)n(C)c(=O)c2c1] | (2S)(M)-[(1,1-dimethylethyl)oxy][7-(3,5-dimethyl-4-isoxazolyl)-4-(8-fluoro-5-methyl-3,4-dihydro-2H-chromen-6-yl)-2-methyl-1-oxo-1,2-dihydro-3-isoquinolinyl]ethanoic acid |

TABLE 1-continued

| Compound No. and Example No. | Structure | Chemical Name |
|---|---|---|
| 208 | 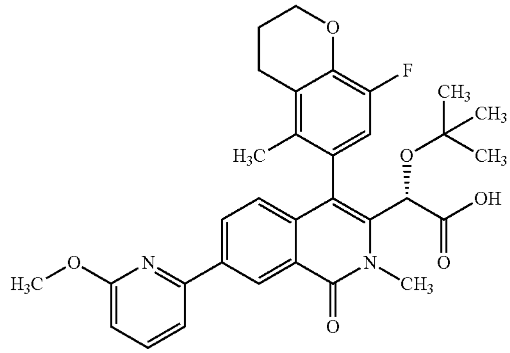 [SMILES: COc1cccc(-c2ccc3c(-c4cc(F)c5c(c4C)CCCO5)c([C@H](OC(C)(C)C)C(=O)O)n(C)c(=O)c3c2)n1] | (2S)(M)-[(1,1-dimethylethyl)oxy]{4-(8-fluoro-5-methyl-3,4-dihydro-2H-chromen-6-yl)-2-methyl-7-[6-(methyloxy)-2-pyridinyl]-1-oxo-1,2-dihydro-3-isoquinolinyl}ethanoic acid |
| 209 | 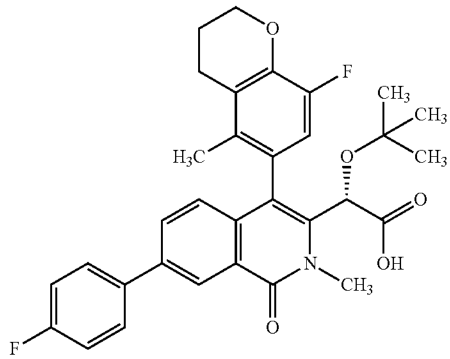 [SMILES: Cc1c(-c2c([C@H](OC(C)(C)C)C(=O)O)n(C)c(=O)c3cc(-c4ccc(F)cc4)ccc23)cc(F)c2c1CCCO2] | (S)(M)-2-(tert-butoxy)-2-(4-(8-fluoro-5-methylchroman-6-yl)-7-(4-fluorophenyl)-2-methyl-1-oxo-1,2-dihydroisoquinolin-3-yl)acetic acid |
| 210 | 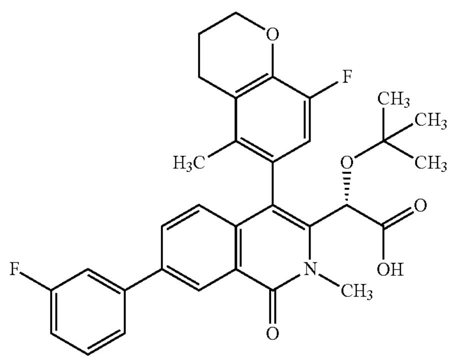 [SMILES: Cc1c(-c2c([C@H](OC(C)(C)C)C(=O)O)n(C)c(=O)c3cc(-c4cccc(F)c4)ccc23)cc(F)c2c1CCCO2] | (S)(M)-2-(tert-butoxy)-2-(4-(8-fluoro-5-methylchroman-6-yl)-7-(3-fluorophenyl)-2-methyl-1-oxo-1,2-dihydroisoquinolin-3-yl)acetic acid |
| 211 | 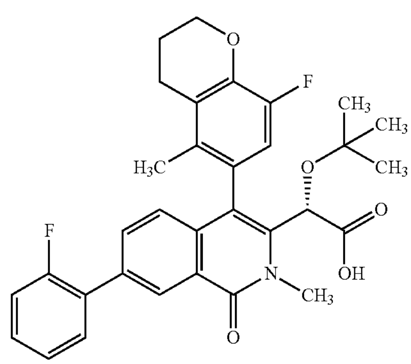 [SMILES: Cc1c(-c2c([C@H](OC(C)(C)C)C(=O)O)n(C)c(=O)c3cc(-c4ccccc4F)ccc23)cc(F)c2c1CCCO2] | (S)(M)-2-(tert-butoxy)-2-(4-(8-fluoro-5-methylchroman-6-yl)-7-(2-fluorophenyl)-2-methyl-1-oxo-1,2-dihydroisoquinolin-3-yl)acetic acid |

TABLE 1-continued

| Compound No. and Example No. | Structure | Chemical Name |
|---|---|---|
| 212 | 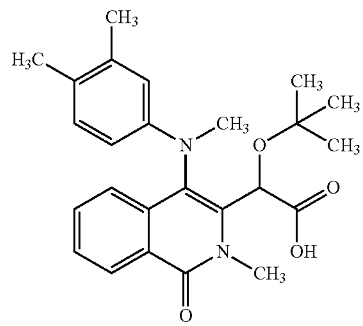 [SMILES: Cc1ccc(N(C)c2c(C(OC(C)(C)C)C(=O)O)n(C)c(=O)c3ccccc23)cc1C] | 2-(tert-Butoxy)-2-(4-((3,4-dimethylphenyl)(methyl)-amino)-2-methyl-1-oxo-1,2-dihydroisoquinolin-3-yl)acetic acid |
| 213 | 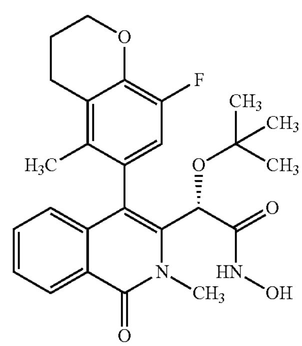 [SMILES: Cc1c(-c2c([C@H](OC(C)(C)C)C(=O)NO)n(C)c(=O)c3ccccc23)cc(F)c2c1CCCO2] | (S)(M)-2-(tert-butoxy)-2-(4-(8-fluoro-5-methylchroman-6-yl)-2-methyl-1-oxo-1,2-dihydroisoquinolin-3-yl)-N-hydroxyacetamide |
| 214 | 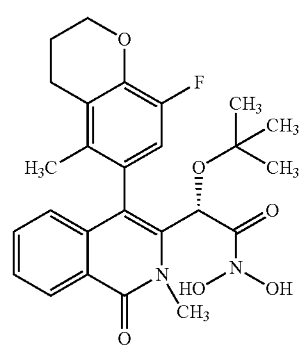 [SMILES: Cc1c(-c2c([C@H](OC(C)(C)C)C(=O)N(O)O)n(C)c(=O)c3ccccc23)cc(F)c2c1CCCO2] | (S)(M)-2-(tert-butoxy)-2-(4-(8-fluoro-5-methylchroman-6-yl)-2-methyl-1-oxo-1,2-dihydroisoquinolin-3-yl)-N-hydroxy-N-methylacetamide |
| 215 | 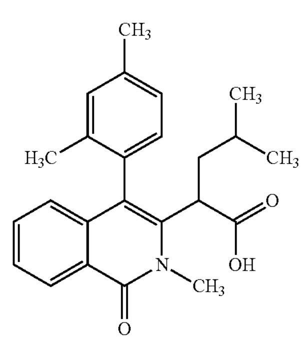 [SMILES: Cc1ccc(-c2c(C(CC(C)C)C(=O)O)n(C)c(=O)c3ccccc23)c(C)c1] | (2S)(M)-2-[(1,1-dimethylethyl)oxy]-2-[4-(8-fluoro-5-methyl-3,4-dihydro-2H-chromen-6-yl)-2-methyl-1-oxo-1,2-dihydro-3-isoquinolinyl]-N-(methylsulfonyl)ethanamide |

TABLE 1-continued

| Compound No. and Example No. | Structure | Chemical Name |
|---|---|---|
| 216 | 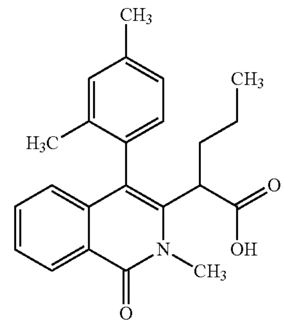 [SMILES: CCCC(C(=O)O)c1c(-c2ccc(C)cc2C)c2ccccc2c(=O)n1C] | 2-[4-(2,4-dimethylphenyl)-2-methyl-1-oxo-1,2-dihydro-3-isoquinolinyl]pentanoic acid |
| 217 | 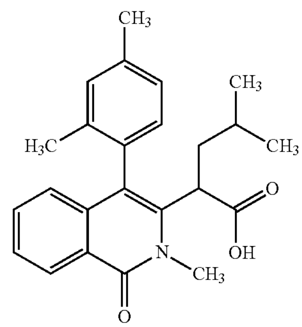 [SMILES: Cc1ccc(-c2c(C(CC(C)C)C(=O)O)n(C)c(=O)c3ccccc23)c(C)c1] | 2-[4-(2,4-dimethylphenyl)-2-methyl-1-oxo-1,2-dihydro-3-isoquinolinyl]-4-methylpentanoic acid |
| 218 | 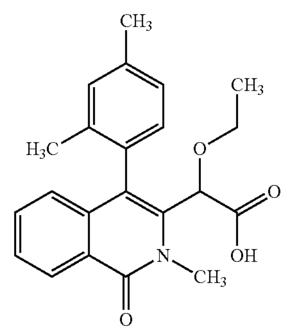 [SMILES: CCOC(C(=O)O)c1c(-c2ccc(C)cc2C)c2ccccc2c(=O)n1C] | Methyl [4-(2,4-dimethylphenyl)-2-methyl-1-oxo-1,2-dihydro-3-isoquinolinyl](ethyloxy)-acetate |
| 219 | 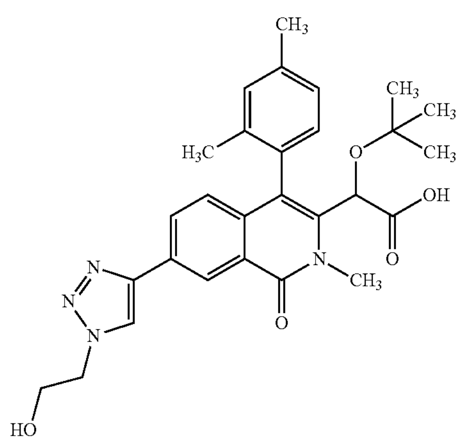 [SMILES: Cc1ccc(-c2c(C(OC(C)(C)C)C(=O)O)n(C)c(=O)c3cc(-c4cn(CCO)nn4)ccc23)c(C)c1] | [(1,1-dimethylethyl)oxy]{4-(2,4-dimethylphenyl)-7-[1-(2-hydroxyethyl)-1H-1,2,3-triazol-4-yl]-2-methyl-1-oxo-1,2-dihydro-3-isoquinolinyl}acetic acid. |

The compounds of Table 1 can be synthesized according to the Synthetic Methods, General Schemes, and the Examples described below.

In certain embodiments, the compound(s) of the present invention, or a pharmaceutically acceptable salt thereof, is chosen from the compounds set forth in Table 1.

Synthetic Methods

The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Ernka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=aqueous
μL=microliters
μM=micromolar
NMR=nuclear magnetic resonance
boc=tert-butoxycarbonyl
br=broad
Cbz=benzyloxycarbonyl
d=doublet
δ=chemical shift
° C.=degrees celcius
DCM=dichloromethane
dd=doublet of doublets
DMEM=Dulbeco's Modified Eagle's Medium
DMF=N,N-dimethylformamide
DMSO=dimethylsulfoxide
EtOAc=ethyl acetate
g=gram
h or hr=hours
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
m=multiplet
M=molar
$M+H^+$=parent mass spectrum peak plus $H^+$
mg=milligram
min=minutes
mL=milliliter
mM=millimolar
mmol=millimole
MS=mass spectrum
nm=nanomolar
ppm=parts per million q.s.=sufficient amount
s=singlet
RT=room temperature
sat.=saturated
t=triplet
TFA=trifluoroacetic acid Schemes and Experimental Procedures The following schemes and procedures illustrate how compounds of the present invention can be prepared. The specific solvents and reaction conditions referred to are also illustrative and are not intended to be limiting. Compounds not described are either commercially available or are readily prepared by one skilled in the art using available starting materials. The Examples disclosed herein are for illustrative purposes only and are not intended to limit the scope of the invention.

Scheme 1: General Route 1

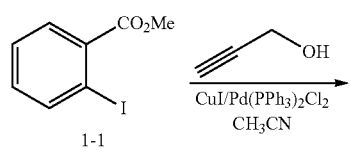
1-1

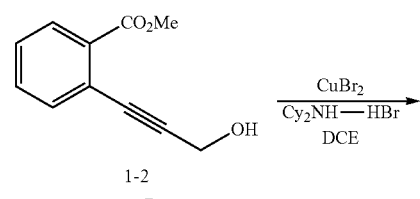
1-2

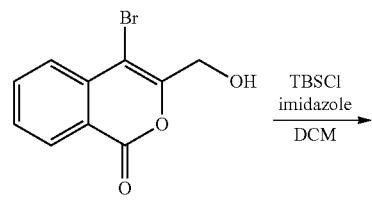
1-3

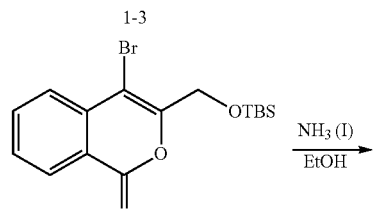
1-4

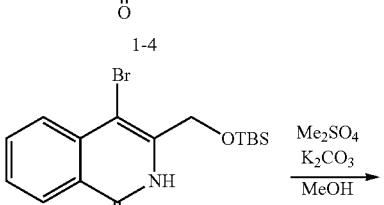
1-5

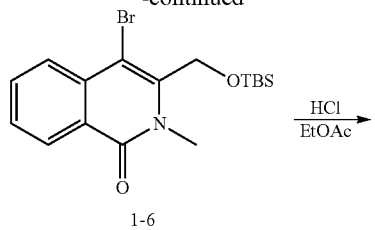
1-6

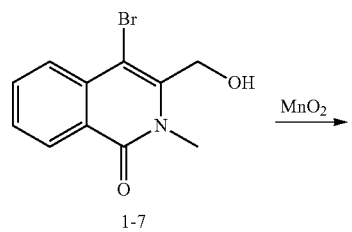
1-7

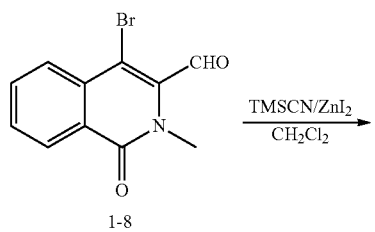
1-8

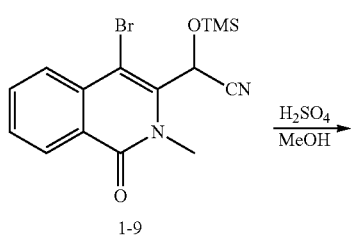
1-9

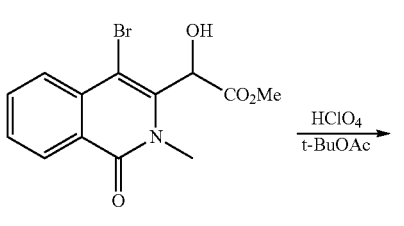
1-10

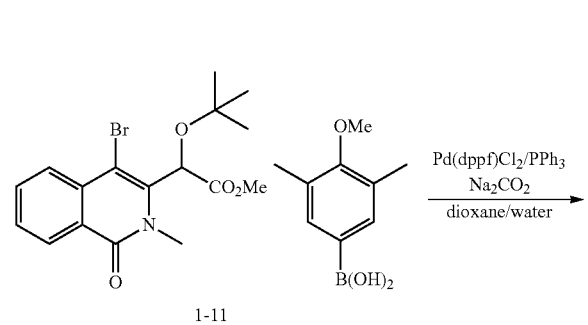
1-11

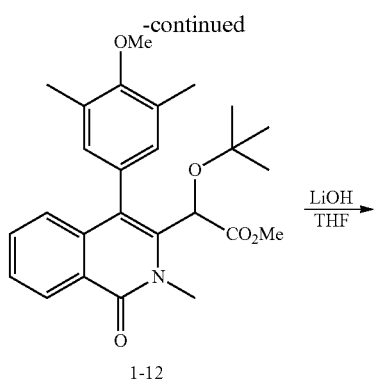

1-12

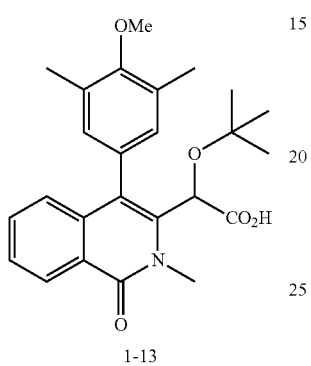

1-13

Example 1

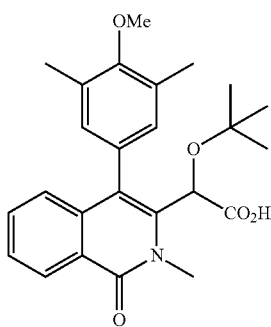 [SMILES: COc1c(C)cc(-c2c(C(OC(C)(C)C)C(=O)O)n(C)c(=O)c3ccccc23)cc1C]

Tert-Butoxy-[4-(4-methoxy-3,5-dimethyl-phenyl)-2-methyl-1-oxo-1,2-dihydro-isoquinolin-3-yl]-acetic acid Step A Preparation of 2-(3-Hydroxy-prop-1-ynyl)-benzoic acid methyl ester

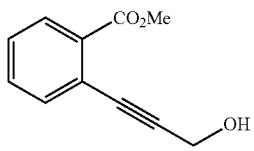 [SMILES: COC(=O)c1ccccc1C#CCO]

To a suspension of compound 1 (88.0 g, 335.9 mmol), compound 2 (28.3 g, 503.8 mmol), copper iodide (1.2 g, 6.7 mmol), Pd(PPh$_3$)Cl2 (7.0 g, 10.0 mmol) and Et$_3$N (triethylamine) (68.0 g, 671.8 mmol) in acetonitrile (1 L) was bubbled N$_2$ for 20 min. The resultant mixture was stirred at reflux under N$_2$ for 3 hr. The reaction mixture was filtered and the filtrate was concentrated to dryness. The residue was purified by chromatography to afford title product. (m=58.8 g, yield=92.0%). $^1$HNMR: (400 MHz, d6-DMSO) δ 2.48 (t, J=6.2 Hz, 1H), 3.88 (s, 3 H), 4.52 (d, J=5.6 Hz, 2 H), 7.32 (t, J=7.6 Hz, 1H), 7.41 (t, J=7.6 Hz, 1H), 7.51 (d, J=7.6 Hz, 1H), 7.90 (d, J=7.2 Hz, 1H).

Step B

4-Bromo-3-hydroxymethyl-isochromen-1-one

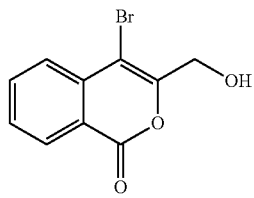 [SMILES: O=c1oc(CO)c(Br)c2ccccc12]

To a suspension of compound 3 (78.0 g, 410.1 mmol) and copper bromide (137.4 g, 615.1 mmol) in 1,2-dichloro-ethane (1 L), was added dicyclohexyl-amine hydrochloride (10.7 g, 41.0 mmol). The resultant mixture was stirred at reflux under N$_2$ for 2 hours. The reaction mixture was filtered, and the cake was washed with dichloromethane (3*200 ml). The combined organic phases were concentrated to dryness and the residue was purified by chromatography column on silica gel to afford title product as a pale yellow solid. (m=31.5 g, yield=30%). LCMS (10-80 AB_2MIN-E.M): Rt=0.802, purity=56%, M+1=254.9.

Step C

4-Bromo-3-(tert-butyl-dimethyl-silanyloxymethyl)-isochromen-1-one

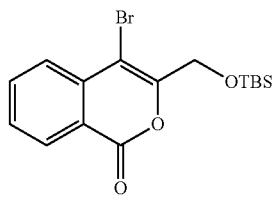 [SMILES: CC(C)(C)[Si](C)(C)OCc1oc(=O)c2ccccc2c1Br]

Compound 4 (5.0 g, 0.2 mmol), TBSCl (15.0 g, 1.0 mmol) and imidazole (6.8 g, 1.0 mol) were suspended in DCM (50 ml). The mixture was stirred at room temperature for 2 hours. The reaction mixture was washed with water, brine, dried over sodium sulfate and concentrated to dryness. The residue was purified by chromatography column on silica gel to afford title product. (m=7.4 g, yield=100%).

Step D

4-Bromo-3-(tert-butyl-dimethyl-silanyloxymethyl)-2Hisoquinolin-1-one

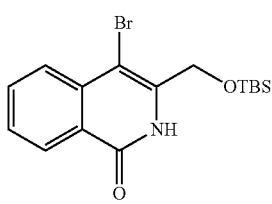 [SMILES: CC(C)(C)[Si](C)(C)OCc1[nH]c(=O)c2ccccc2c1Br]

Compound 5 (7.4 g, 20.0 mmol) was dissolved in 4N NH$_3$/EtOH (50 ml). The mixture was stirred at room temperature for 30 min. The reaction mixture was concentrated and the residue was dissolved in 4N HCl/EA (20 ml). The solution was stirred at room temperature for 10 min, quenched by adding sodium bicarbonate and washed by water, brine, dried over sodium sulfate and concentrated to dryness. The residue was purified by chromatography column on silica gel to afford title product. (m=5.0 g, yield=67.8%). $^1$HNMR: (400 MHz, d6-DMSO) δ 0.00 (s, 6 H), 0.77 (s, 9 H), 4.60 (s, 2H), 7.45 (t, J=8.4 Hz, 1H), 7.70 (m, 2H), 7.09 (t, J=8.4 Hz, 1H), 11.25 (br, 1H).

Step E

4-Bromo-3-(tert-butyl-dimethyl-silanyloxymethyl)-2-methyl-2H-isoquinolin-1-one

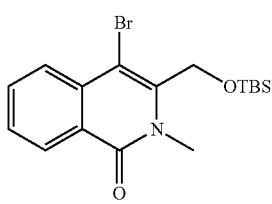 [SMILES: Cn1c(CO[Si](C)(C)C(C)(C)C)c(Br)c2ccccc2c1=O]

To a suspension of compound 6 (3.8 g, 10.3 mmol) and potassium carbonate (2.1 g, 15.6 mmol) in methanol (50 ml) was added sulfuric acid dimethyl ester (6.3 g, 50.0 mmol). The resultant mixture was stirred at 60° C. for 4 hrs. The reaction mixture was filtered, the filtrate was concentrated and the residue was treated with acetic acid ethyl ester (200 mL), washed by water (3*200 mL), brine, dried over sodium sulfate and concentrated. The residue was purified by chromatography column on silica gel to afford title product. (m=2.5 g, yield=65%). $^1$HNMR: (400 MHz, d6-DMSO) δ 0.12 (s, 6 H), 0.86 (s, 9 H), 3.69 (s, 3H), 5.05 (s, 2 H), 7.59 (t, J=7.6 Hz, 1H), 7.81 (t, J=7.2 Hz, 1H), 7.91 (d, J=8.0 Hz, 1H), 8.25 (d, J=8.0 Hz, 1H).

Step F

4-Bromo-3-hydroxymethyl-2-methyl-2H-isoquinolin-1-one

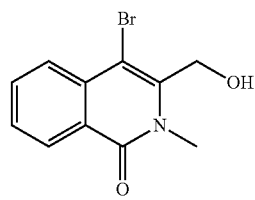

Compound 7 (2.5 g, 6.5 mmol) was dissolved in 4N HCl/EA (15 ml) and the resultant mixture was stirred at room temperature for 0.5 hour. The reaction mixture was adjusted pH to 8.0 by adding 2N aq sodium bicarbonate. The organic phase was separated, washed by water, brine, dried over sodium sulfate and concentrated to dryness. The residue was used for the next step directly. (m=1.5 g, yield=88.2%).

Step G

4-Bromo-2-methyl-1-oxo-1,2-dihydro-isoquinoline-3-carbaldehyde

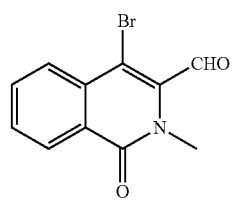

To a solution of compound 8 (800.0 mg, 3.0 mmol) in dichloromethane (10 ml), was added manganese dioxide (2.6 g, 30.0 mmol). The resultant mixture was stirred at 70° C. under N$_2$ for 2 h. The reaction mixture was filtered, and the filtrate was concentrated to dryness to afford title product which was used for the next step directly. (m=600.0 mg, yield=75%).

Step H (4-Bromo-2-methyl-1-oxo-1,2-dihydro-isoquinolin-3-yl)-trimethyl silanyloxy-acetonitrile

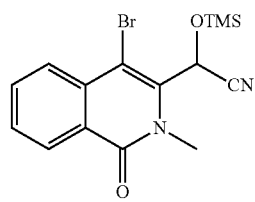

To a suspension of compound 9 (600.0 mg, 2.25 mmol) and zinc diiodide (1.4 g, 4.5 mmol) in dichloromethane (10 ml), was added trimethylsilanyl cyanide (2.2 g, 22.5 mmol). The resultant mixture was stirred at room temperature overnight. The reaction mixture was filtered, and the filtrate was washed with water (3*50 ml), brine, dried over sodium sulfate and concentrated to dryness. The residue was used for the next step directly without other purification. (m=500.0 mg, yield=68.2%).

Step I (4-Bromo-2-methyl-1-oxo-1,2-dihydro-isoquinolin-3-yl-hydroxy-acetic acid methyl ester

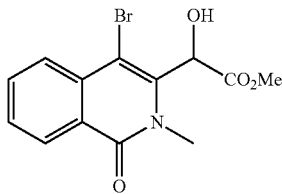 [SMILES: COC(=O)C(O)c1c(Br)c2ccccc2c(=O)n1C]

To a mixture of concentrated sulfuric acid (0.2 ml) and methanol (0.6 ml) was added compound 10 (40.0 mg, 0.1 mmol). The resultant mixture was stirred at reflux under $N_2$ for 2 h. The reaction mixture was diluted with acetic acid ethyl ester (5 ml) washed by water (3*5 ml), sat'd $NaHCO_3$ (3*10 ml), brine, dried over sodium sulfate and concentrated to dryness to afford crude product. (m=28.0 g, yield=78.3%).

Step J (4-Bromo-2-methyl-1-oxo-1,2-dihydro-isoquinolin-3-yl)-tert-but oxy-acetic acid methyl ester

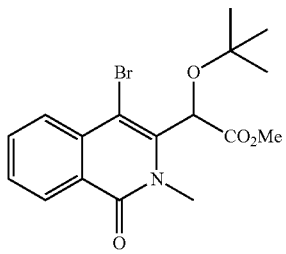 [SMILES: COC(=O)C(OC(C)(C)C)c1c(Br)c2ccccc2c(=O)n1C]

To a solution of compound 11 (28.0 mg, 0.08 mmol) in acetic acid tert-butyl ester (0.2 ml) was added perchloric acid (25.8 mg, 0.26 mmol). The resultant mixture was stirred at room temperature for 10 minute. The reaction mixture was diluted with acetic acid ethyl ester (5 ml) and was adjusted pH to 6 by adding 1N aq $NaHCO_3$. The organic phase was separated and washed by brined, dried over sodium sulfate and concentrated to dryness. The residue was purified by pre-TLC to afford title product. (m=18.0 mg, yield=55.4%). $^1$HNMR: (400 MHz, d6-DMSO) δ 1.28 (s, 9 H), 3.66 (s, 3 H), 3.75 (s, 3H), 6.12 (s, 1 H), 7.53 (t, J=8.4 Hz, 1H), 7.71 (t, J=8.4 Hz, 1H), 7.99 (d, J=8.4 Hz, 1H), 8.44 (d, J=8.0 Hz, 1H).

Step K tert-Butoxy-[4-(4-methoxy-3,5-dimethyl-phenyl)-2-methyl-1-oxo-1,2-dihydro-isoquinolin-3-yl]-acetic acid methyl ester

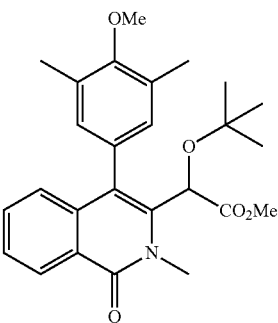 [SMILES: COC(=O)C(OC(C)(C)C)c1c(-c2cc(C)c(OC)c(C)c2)c2ccccc2c(=O)n1C]

To a solution of (4-Bromo-2-methyl-1-oxo-1,2-dihydro-isoquinolin-3-yl)-tert-butoxy-acetic acid methyl ester (120 mg, 0.3 mmol) in 5 ml of dioxane/$H_2O$ (5:1) was added 4-methoxy-3,5-trimethylphenylboronic acid (66 mg, 0.36 mmol), $PPh_3$ (48 mg, 0.18 mmol) and $Na_2CO_3$ (96 mg, 0.9 mmol), then Pd(dppf)$Cl_2$ (48 g, 0.06 mmol). Then the resultant mixture was stirred at 90° C. under $N_2$ overnight. LCMS showed SM was consumed, the reaction mixture was cooled to RT, removed the solvent, the residue was purified by column chromatography on silica gel eluted with (PE:EA=10:1) to afford title product. (m=130 mg, yield=81%).

LCMS: (10-80 AB__2MIN-E.M): Rt=1.352, purity=98%, M+1=438.

Step L tert-Butoxy-[4-(4-methoxy-3,5-dimethyl-phenyl)-2-methyl-1-oxo-1,2-dihydro-isoquinolin-3-yl]-acetic acid

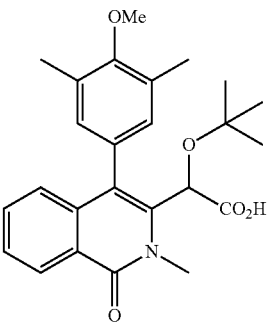 [SMILES: COc1c(C)cc(-c2c(C(OC(C)(C)C)C(=O)O)n(C)c(=O)c3ccccc23)cc1C]

To a solution of tert-Butoxy-[4-(4-methoxy-3,5-dimethyl-phenyl)-2-methyl-1-oxo-1,2-dihydro-isoquinolin-3-yl]-acetic acid methyl ester (130 mg, 0.3 mmol) in THF (3.0 ml) was added an aqueous LiOH (1N, 1.22 ml). The mixture was stirred at 60° C. overnight. LCMS showed SM was consumed, cooled to RT, removed the solvent, added water, extracted with EA to remove impurity, the aqueous layer was adjusted to pH=6 with 1N HCl, extracted with EA, the organic layer was washed with water and brine, dried over Na₂SO₄, filtered, concentrated to dryness, gave the desired product. (m=73 mg, Yield: 58%): ¹HNMR: (400 MHz, d6-DMSO) δ 1.03 (s, 9H), 2.31 (s, 6H), 3.64 (s, 3H), 3.79 (s, 3H), 5.29 (s, 3H), 6.94 (s, 1H), 7.13 (d, J=8.0 Hz, 1H), 7.24 (s, 1H), 7.49 (m, 2H), 8.46 (d, J=8.0 Hz, 1H). LCMS: (10-80 AB__2MIN-E.M): Rt=1.258, purity=96.0%, M+1=424.
Scheme 2: General Route 2
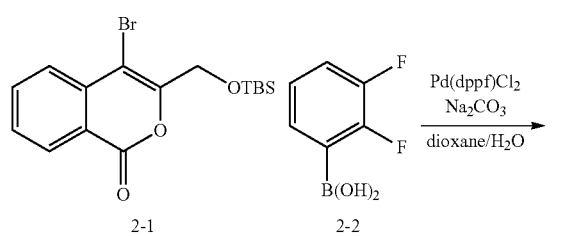
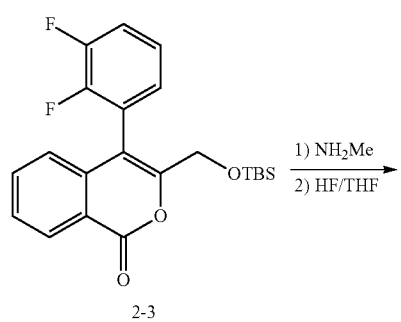
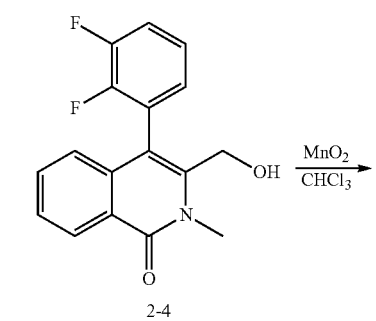
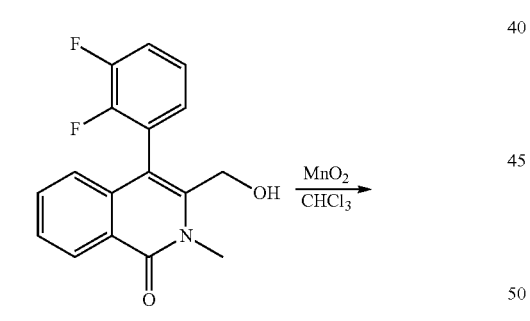
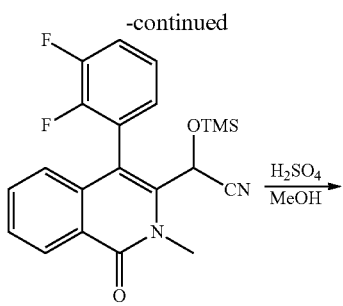
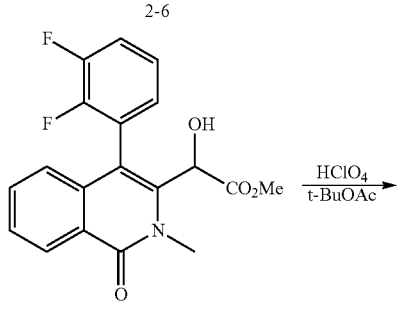
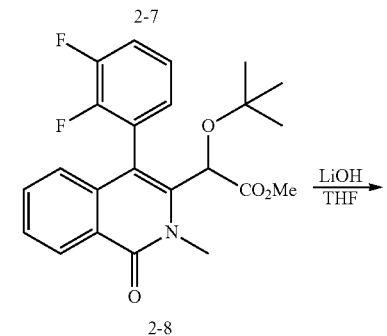
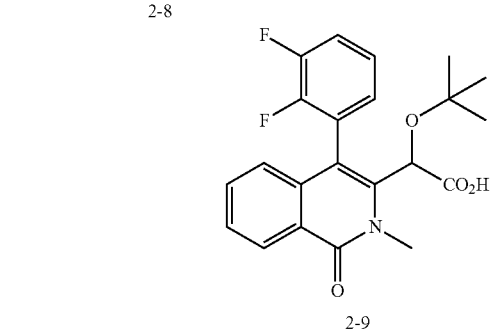
Example 2
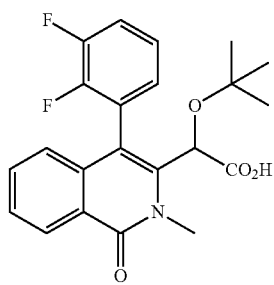 [SMILES: Cn1c(C(OC(C)(C)C)C(=O)O)c(-c2cccc(F)c2F)c2ccccc2c1=O]

tert-Butoxy-[4-(3,4-Difluoro-phenyl)-2-methyl-1-oxo-1,2-dihydro-isoquinolin-3-yl]-acetic acid Step A 3-(tert-Butyl-dimethyl-silanyloxymethyl)-4-(2,3-difluoro-phenyl)-isochromen-1-one

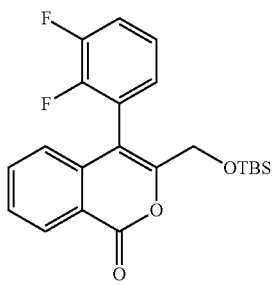 [SMILES: CC(C)(C)[Si](C)(C)OCc1oc(=O)c2ccccc2c1-c1cccc(F)c1F]

To a solution of 4-Bromo-3-(tert-butyl-dimethyl-silanyloxymethyl)-isochromen-1-one (1.3 g, 3.53 mmol) in 15 ml of dioxane/H$_2$O (5:1) was added 3,4-Difluorophenylboronic acid (0.83 g, 5.3 mmol) and Na$_2$CO$_3$ (0.75 g, 7.06 mmol), then Pd(dppf)Cl$_2$ (0.26 g, 0.35 mmol). Then the resultant mixture was stirred for 2 hours at 90° C. under N$_2$. TLC showed SM was consumed, the reaction mixture was cooled to RT, removed the solvent, the residue was purified by column chromatography on silica gel eluted with (PE:EA=50:1) to afford title product. (m=1.3 g, yield=85%). $^1$HNMR: (400 MHz, CDCl$_3$) δ 0.00 (s, 6 H), 0.83 (s, 9 H), 4.30 (tt, J=12 Hz, 2H), 7.00 (d, J=8.4 Hz, 1H), 7.11 (t, J=6.0 Hz, 1H), 7.20 (m, 1H), 7.31 (tt, J=6.8 Hz, 1H), 7.54 (t, J=6.8 Hz, 1H), 7.64 (t, J=6.8 Hz, 1H), 8.36 (d, J=8.0 Hz, 1H).

Step B 4-(2,3-Difluoro-phenyl)-3-hydroxymethyl-2-methyl-2H-isoquinolin-1-one

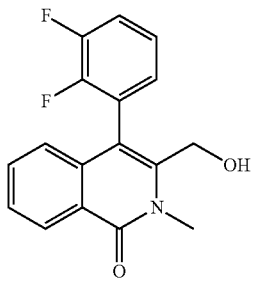 [SMILES: Cn1c(CO)c(-c2cccc(F)c2F)c2ccccc2c1=O]

3-(tert-Butyl-dimethyl-silanyloxymethyl)-4-(3,4-Difluoro-phenyl)-isochromen-1-one (720 mg, 1.79 mmol) was dissolved in 4N NH$_3$/EtOH (10 ml). The mixture was stirred at 60° C. for 1 h. TLC showed SM was consumed, the reaction mixture was cooled to RT, then concentrated to dryness and the residue was dissolved in THF (10 ml), added a aqueous solution of HF (50%, 10 ml), the solution was stirred at RT for 2 h, TLC showed the reaction was completed, quenched by adding 2N NaOH to pH=7~8, extracted with EA, and washed with water and brine, dried over sodium sulfate and concentrated to dryness and gave the desired product. (m=0.5 g, yield=92.7%). $^1$HNMR: (400 MHz, CDCl$_3$) δ 3.79 (s, 3H), 4.44 (m, 2H), 6.93 (d, J=8.0 Hz, 1H), 6.98 (m, 1H), 7.16 (m, 1H), 7.25 (dd, J$_1$=6.4 Hz, J$_2$=12.0 Hz, 1H), 7.45 (m, 2H), 8.44 (d, J=6.8 Hz, 1H).

Step C 4-(3,4-Difluoro-phenyl)-2-methyl-1-oxo-1,2-dihydro-isoquinoline-3-carbaldehyde

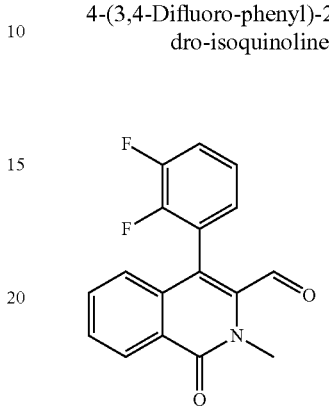

To a solution of 4-(3,4-Difluoro-phenyl)-3-hydroxymethyl-2-methyl-2H-isoquinolin-1-one (500 mg, 1.66 mmol) in CHCl$_3$ (10 ml) was added MnO$_2$ (1.87 g, 21.6 mmol). The reaction mixture was stirred at 70° C. overnight under N$_2$. TLC showed SM was consumed, cooled to RT, the reaction mixture was filtered, and the filtrate was concentrated to dryness to afford title product which was used for the next step directly. (m=460.0 mg, yield=92.6%.) $^1$HNMR: (400 MHz, d6-DMSO) δ 3.89 (s, 3H), 7.09 (t, J=6.0 Hz, 1H), 7.15 (d, J=6.8 Hz, 1H), 7.24 (m, 1H), 7.36 (dd, J$_1$=9.6 Hz, J$_2$=15.6 Hz, 1H), 7.55 (m, 2H), 8.55 (d, J=8.0 Hz, 1H), 9.61 (s, 1H).

Step D

[4-(3,4-Difluoro-phenyl)-2-methyl-1-oxo-1,2-dihydro-isoquinolin-3-yl]-trimethylsilanyloxy-acetonitrile

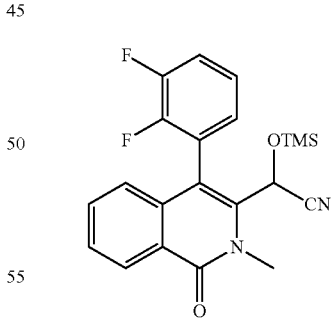

To a suspension of 4-(3,4-Difluoro-phenyl)-2-methyl-1-oxo-1,-dihydro-isoquinoline-3-carbaldehyde (460 mg, 1.53 mmol) and zinc iodide (0.98 g, 3.06 mmol) in CH$_2$Cl$_2$ (10 ml) was added TMSCN (1.52 g, 15.3 mmol). The reaction mixture was stirred at room temperature overnight. TLC showed SM was consumed, the reaction mixture was filtered, and the filtrate was washed with water (3*50 ml), then brine, dried over Na$_2$SO$_4$ and concentrated to dryness. The residue was used for the next step directly without other purification.

(m=0.6 g, yield=98%). LCMS: (10-80 AB_2MIN-E.M): Rt=1.338~1.351, purity=86%, M+1=399.

Step E

[4-(3,4-Difluoro-phenyl)-2-methyl-1-oxo-1,2-dihydro-isoquinolin-3-yl]-hydroxy-acetic acid methyl ester

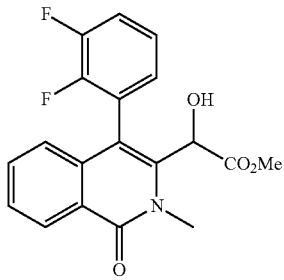 [SMILES: COC(=O)C(O)c1c(-c2cccc(F)c2F)c2ccccc2c(=O)n1C]

To a mixture of conc. $H_2SO_4$ (2.5 ml) and methanol (7.5 ml) was added [4-(3,4-Difluoro-phenyl)-2-methyl-1-oxo-1,2-dihydro-isoquinolin-3-y]-trimethylsilanyloxy-acetonitrile (580 mg, 1.45 mmol), after addition, the resultant mixture was stirred at reflux overnight under $N_2$. TLC showed SM was consumed, diluted with EA, adjusted with saturated $NaHCO_3$ to pH=8~9, extracted with EA, the organic layers was dried over $Na_2SO_4$ and concentrated to dryness to afford crude product. (m=430 mg, yield=79%). LCMS: (10-80 AB_2MIN-E.M): Rt=1.021, purity=64%, M+1=360.

Step F tert-Butoxy-[4-(3,4-Difluoro-phenyl)-2-methyl-1-oxo-1,2-dihydro-isoquinolin-3-yl]-acetic acid methyl ester

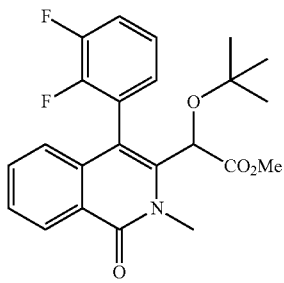 [SMILES: COC(=O)C(OC(C)(C)C)c1c(-c2cccc(F)c2F)c2ccccc2c(=O)n1C]

To a solution of [4-(3,4-Difluoro-phenyl)-2-methyl-1-oxo-1,2-dihydro-isoquinolin-3-yl]-hydroxy-acetic acid methyl ester (114 mg, 0.31 mmol) in t-BuOAc (10 ml) was added $HClO_4$ (0.17 ml, 1.11 mmol). The reaction mixture was stirred at RT overnight. TLC showed most SM consumed, ended the reaction, added ice-water, adjusted to pH=6 by adding 1N aq $NaHCO_3$, extracted with EA, washed with water and brine, dried over $Na_2SO_4$ and concentrated to dryness. The residue was purified by pre-TLC to afford title product. (m=57 mg, yield=43.2%).

LCMS: (10-80 AB_2MIN-E.M): Rt=1.271~1.298~1.314, purity-93.0%, M+1=416.

Step G tert-Butoxy-[4-(3,4-Difluoro-phenyl)-2-methyl-1-oxo-1,2-dihydro-isoquinolin-3-yl]-acetic acid

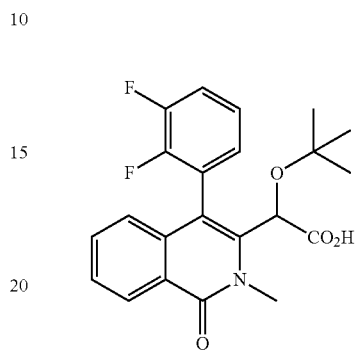

To a solution of tert-Butoxy-[4-(3,4-Difluoro-phenyl)-2-methyl-1-oxo-1,2-dihydro-isoquinolin-3-yl]-acetic acid methyl ester (72 mg, 0.15 mmol) in THF (2.0 ml) was added an aqueous LiOH (1 N, 0.69 ml). The mixture was stirred at 60° C. overnight. LCMS showed SM was consumed, cooled to RT, removed the solvent, added water, extracted with EA to remove impurity, the aqueous layer was adjusted to pH=6 with 1N HCl, extracted with EA, the organic layer was washed with water and brine, dried over $Na_2SO_4$, filtered, concentrated to dryness, gave the desired product. (m=46 mg, Yield: 66%). $^1$HNMR: (400 MHz, d6-DMSO) δ 0.91 (s, 5H), 1.00 (s, 4H), 3.56 (s, 1.67H), 3.63 (s, 1.33H), 4.93 (s, 1H), 6.84 (d, J=8.0 Hz, 0.5H), 6.99 (d, J=8.0 Hz, 0.5H), 7.15 (s, 0.5H), 7.30 (m, 1H), 7.44 (m, 0.5H), 7.60 (m, 3H), 8.28 (d, J=8.0 Hz, 1H).

LCMS: (10-80 AB_2MIN-E.M): Rt=1.177~1.201, purity=99.0%, M+1=402.

Scheme 3: General Route Synthesis of Chiral Groups within R4 Substituent

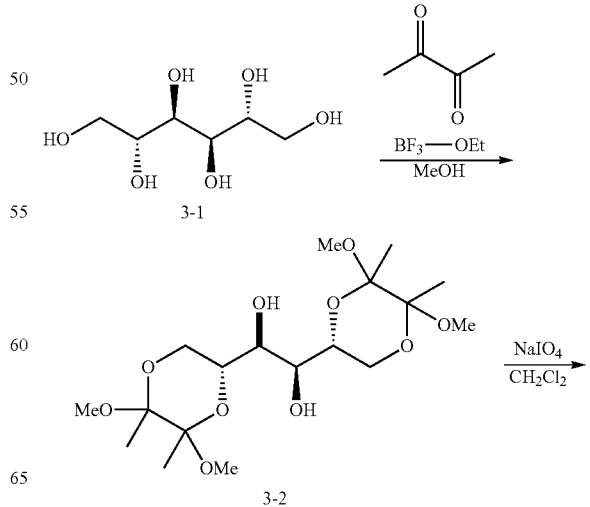

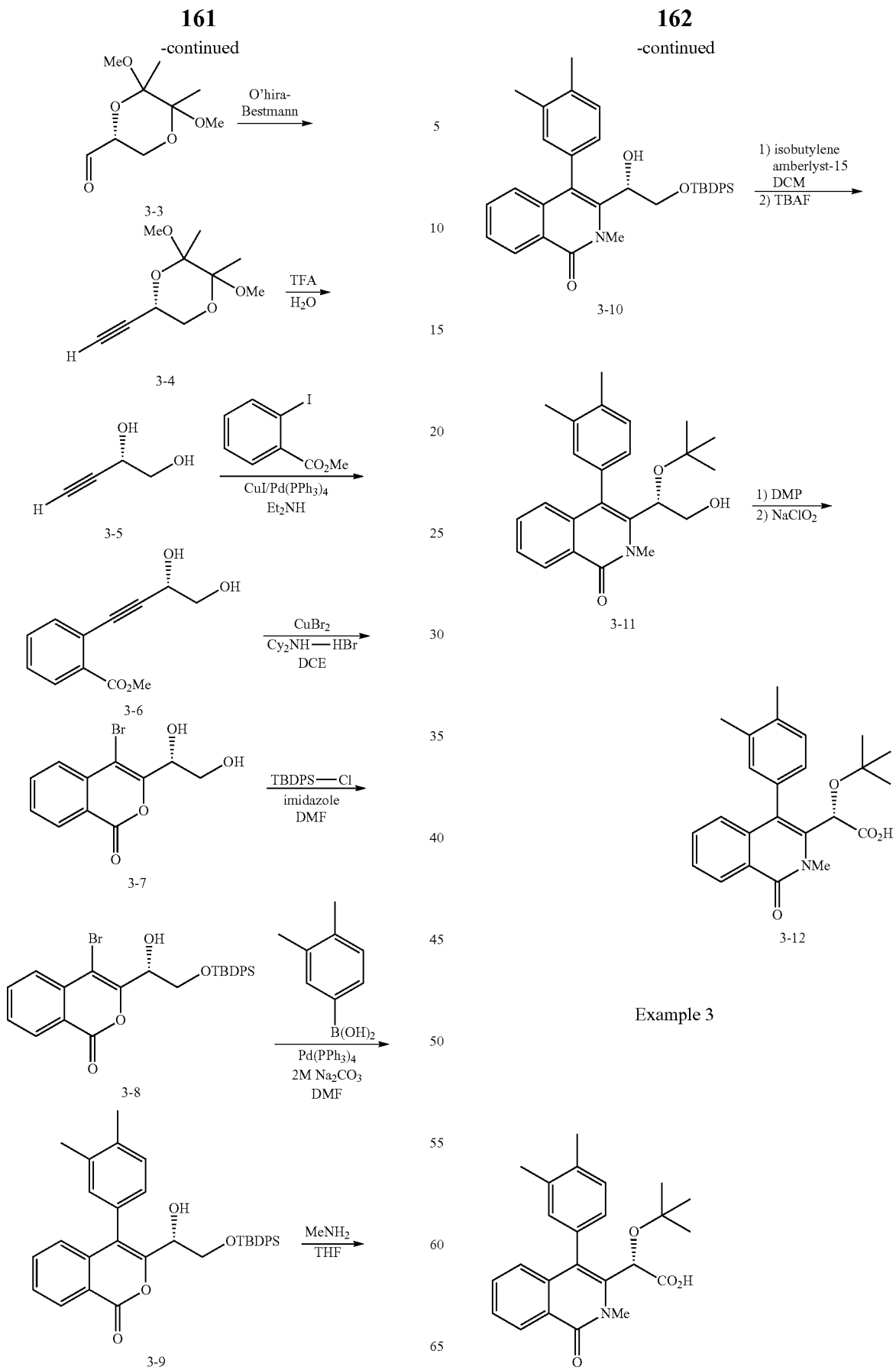
Example 3

163

(S)-2-(tert-butoxy)-2-(4-(3,4-dimethylphenyl)-2-methyl-1-oxo-1,2-dihydroisoquinolin-3-yl)acetic acid Step A (S)-methyl 2-(3,4-dihydroxybut-1-yn-1-yl)benzoate

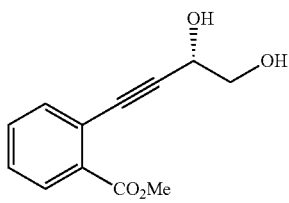 [SMILES: COC(=O)c1ccccc1C#C[C@H](O)CO]

A solution of methyl 2-iodobenzoate (2.312 ml, 15.26 mmol), (2S)-3-butyne-1,2-diol (1.380 g, 16.03 mmol), and Et$_3$N (10.64 ml, 76 mmol) in Acetonitrile (25.2 ml) was degassed with N2 for 10 min and treated with CuI (0.581 g, 3.05 mmol) and Pd(PPh$_3$)$_4$ (0.264 g, 0.229 mmol) and the reaction mixture was heated to 80° C. After 20 min, the reaction mixture was cooled to ambient temperature. The reaction mixture was diluted with EtOAc and washed with saturated aqueous NH$_4$Cl, water and brine. The organic phase was dried (Na$_2$SO$_4$), filtered and concentrated in vacuo. The residue was purified by silica gel chromatography (ethyl acetate-hexanes 0-100%) to afford the title compound (2.88 g, 13.08 mmol, 86% yield) as a beige solid: Rt=0.54 min, ES+ MS: 221 (M+1).

Step B (R)-4-bromo-3-(1,2-dihydroxyethyl)-1H-isochromen-1-one

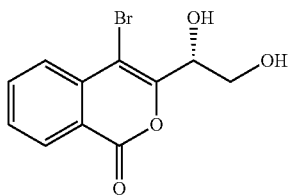 [SMILES: O=c1oc([C@H](O)CO)c(Br)c2ccccc12]

A suspension of methyl 2-[(3S)-3,4-dihydroxy-1-butyn-1-yl]benzoate (500 mg, 2.270 mmol) in 1,2-Dichloroethane (DCE) (22 mL) was treated with dicyclohexylamine HBr (59.5 mg, 0.227 mmol) and then copper (II) bromide (1014 mg, 4.54 mmol) and stirred at 80° C. After 1.5 h, the reaction mixture was diluted with EtOAc, filtered through Celite and concentrated in vacuo. The residue was purified by silica gel chromatography (ethyl acetate-hexanes 0-70%) to afford the title compound (200 mg, 0.702 mmol, 31% yield) as brown solid: Rt=0.46 min,

ES+ MS: 286 (M+1).

164

Step C (R)-4-bromo-3-(2-((tert-butyldiphenylsilyl)oxy)-1-hydroxyethyl)-1H-isochromen-1-one

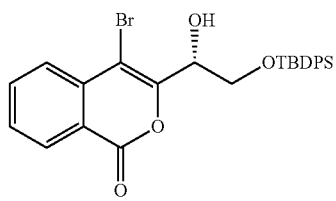

A solution of 4-bromo-3-[(1R)-1,2-dihydroxyethyl]-1H-2-benzopyran-1-one (145 mg, 0.509 mmol) and imidazole (51.9 mg, 0.763 mmol) in N,N-Dimethylformamide (DMF) (2.4 mL) was treated with tert-butyldiphenylchlorosilane (159 µl, 0.610 mmol). After 20 min, the reaction mixture was poured into water and extracted with EtOAc. The organic phase was dried with Na$_2$SO$_4$, filtered and concentrated. The residue was purified by silica gel chromatography (ethyl acetate-hexanes 0-50%) to afford the title compound (169 mg, 0.323 mmol, 64% yield) as a white foam: Rt=1.24 min, ES+ MS: 546 (M+23).

Step D (R)-3-(2-((tert-butyldiphenylsilyl)oxy)-1-hydroxyethyl)-4-(3,4-dimethylphenyl)-1H-isochromen-1-one

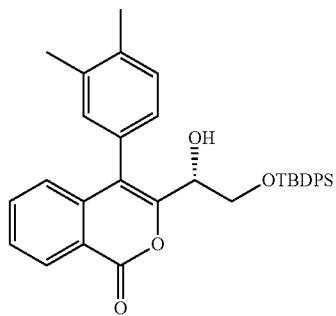

A solution of 4-bromo-3-((1R)-2-{[(1,1-dimethylethyl)(diphenyl)silyl]oxy}-1-hydroxyethyl)-1H-2-benzopyran-1-one (142 mg, 0.271 mmol) and 3,4-dimethylphenylboronic acid (61.0 mg, 0.407 mmol) in N,N-Dimethylformamide (DMF) (2.5 mL) was degassed with N$_2$ for 10 min. The reaction mixture was treated with 2M Na$_2$CO$_3$ (149 µl, 0.298 mmol) and Pd(PPh$_3$)$_4$ (16 mg, 0.014 mmol) and irradiated in the microwave for 20 min at 120° C. The reaction mixture was diluted with EtOAc, and washed with saturated aqueous NH$_4$Cl, brine, dried (Na$_2$SO$_4$), filtered and concentrated. The residue was purified by silica gel chromatography (ethyl acetate-hexanes 0-30%) to afford the title compound (92 mg, 0.168 mmol, 62% yield) as a white solid: Rt=1.31, 1.33 (atropisomers), ES+ MS: 571 (M+23).

Step E (S)-3-(2-((tert-butyldiphenylsilyl)oxy)-1-hydroxyethyl)-4-(3,4-dimethylphenyl)-2-methylisoquinolin-1(2H)-one

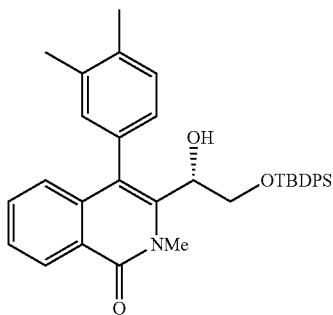

A solution of 3-((1R)-2-{[(1,1-dimethylethyl)(diphenyl)silyl]oxy}-1-hydroxyethyl)-4-(3,4-dimethylphenyl)-1H-2-benzopyran-1-one (92 mg, 0.168 mmol) was dissolved in 2M methyl amine in THF (1.3 mL, 2.51 mmol) was heated to 80° C. After 18 h, the reaction mixture was concentrated in vacuo and treated with 4M HCl in dixoane (2 mL). The reaction stirred for 20 min and poured into 1M aqueous NaOH and extracted with EtOAc. The organic layer was dried ($Na_2SO_4$), filtered and concentrated. The residue was purified by silica gel chromatography (ethyl acetate-hexanes 0-50%) to afford the title compound (13 mg, 0.023 mmol, 14% yield) as a colorless film: Rt=1.28, ES+ MS: 562 (M+1).

Step F (S)-3-(1-(tert-butoxy)-2-hydroxyethyl)-4-(3,4-dimethylphenyl)-2-methylisoquinolin-1(2H)-one

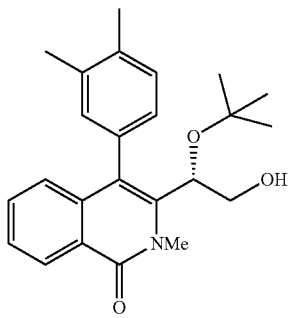 [SMILES: Cc1ccc(-c2c([C@@H](CO)OC(C)(C)C)n(C)c(=O)c3ccccc23)cc1C]

A −78° C. suspension of 3-((1S)-2-{[(1,1-dimethylethyl)(diphenyl)silyl]oxy}-1-hydroxyethyl)-4-(3,4-dimethylphenyl)-2-methyl-1(2H)-isoquinolinone (12 mg, 0.021 mmol) and amberlyst 15 resin (6 mg, 0.036 mmol) in Dichloromethane (DCM) (290 µl) was treated with isobutylene until the volume approximately doubled. The reaction mixture was sealed and allowed to warm to ambient temperature. After 48 h, the reaction mixture was cooled to −78° C. and then opened to the atmosphere. The reaction mixture was filtered through a short pad of silica and rinsed with EtOAc. The filtrate was concentrated in vacuo. The residue was dissolved in Tetrahydrofuran (THF) (290 µl) and treated with 1.0 M TBAF in THF (145 µl, 0.145 mmol). After 2 h, the reaction mixture was filtered through a short pad of silica gel and washed with EtOAc. The filtrate was concentrated in vacuo and purified by reverse phase hplc to afford the title compound (6 mg, 0.016 mmol, 43.6% yield) as a white solid: Rt=1.02, ES+ MS: 380 (M+1).

Step G (S)-2-(tert-butoxy)-2-(4-(3,4-dimethylphenyl)-2-methyl-1-oxo-1,2-dihydroisoquinolin-3-yl)acetic acid

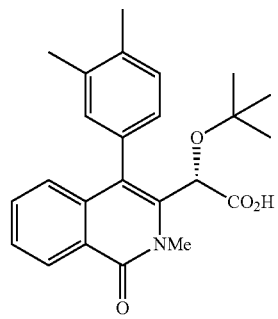 [SMILES: Cc1ccc(-c2c([C@H](OC(C)(C)C)C(=O)O)n(C)c(=O)c3ccccc23)cc1C]

A solution of 3-{(1S)-1-[(1,1-dimethylethyl)oxy]-2-hydroxyethyl}-4-(3,4-dimethylphenyl)-2-methyl-1(2H)-isoquinolinone (4 mg, 10.54 µmol) in DMSO is treated with DMP (13 mg, 0.032 mmol). After 18 h, the reaction mixture was filtered through a pad of silica gel and washed with 1:1 EtOAc-hexanes. The filtrate was concentrated, dissolved in EtOAc and washed with $H_2O$ (3×), brine, dried ($Na_2SO_4$), filtered and concentrated. The residue was then dissolved in tert-Butanol (51.5 µl) and Tetrahydrofuran (THF) (51 µl) and treated with 2,3-dimethyl-2-butene (3 µl, 0.02 mmol) and a solution of $NaClO_2$ (1.787 mg, 0.016 mmol) and NaH2PO4 (1.2 mg, 10.5 µmol) in water (100 uL). The crude reaction mixture was diluted with water and extracted with EtOAc (3×). The combined organics were washed with brine, dried ($Na_2SO_4$), filtered and concentrated. The residue was dissolved in DMF (250 uL) and purified by Gilson to afford the title compound: Rt=0.95, 0.97 (atropisomers), ES+ MS: 394 (M+1). The chirality of the above compound was established by comparison to authentic material of (R)- and (S)-(tert-butoxy)-2-(4-(3,4-dimethylphenyl)-2-methyl-1-oxo-1,2-dihydroisoquinolin-3-yl)acetic acid using a Chiral SFC 20% MeOH/80% $CO_2$; 4.6×250 mm IC column; Rt (R)=1 min; (S)=7.22 min.

Scheme 4: General Experimental Procedure of $R^7$ Alkoxyl Analogs

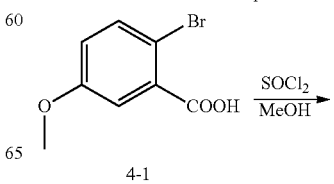

4-1

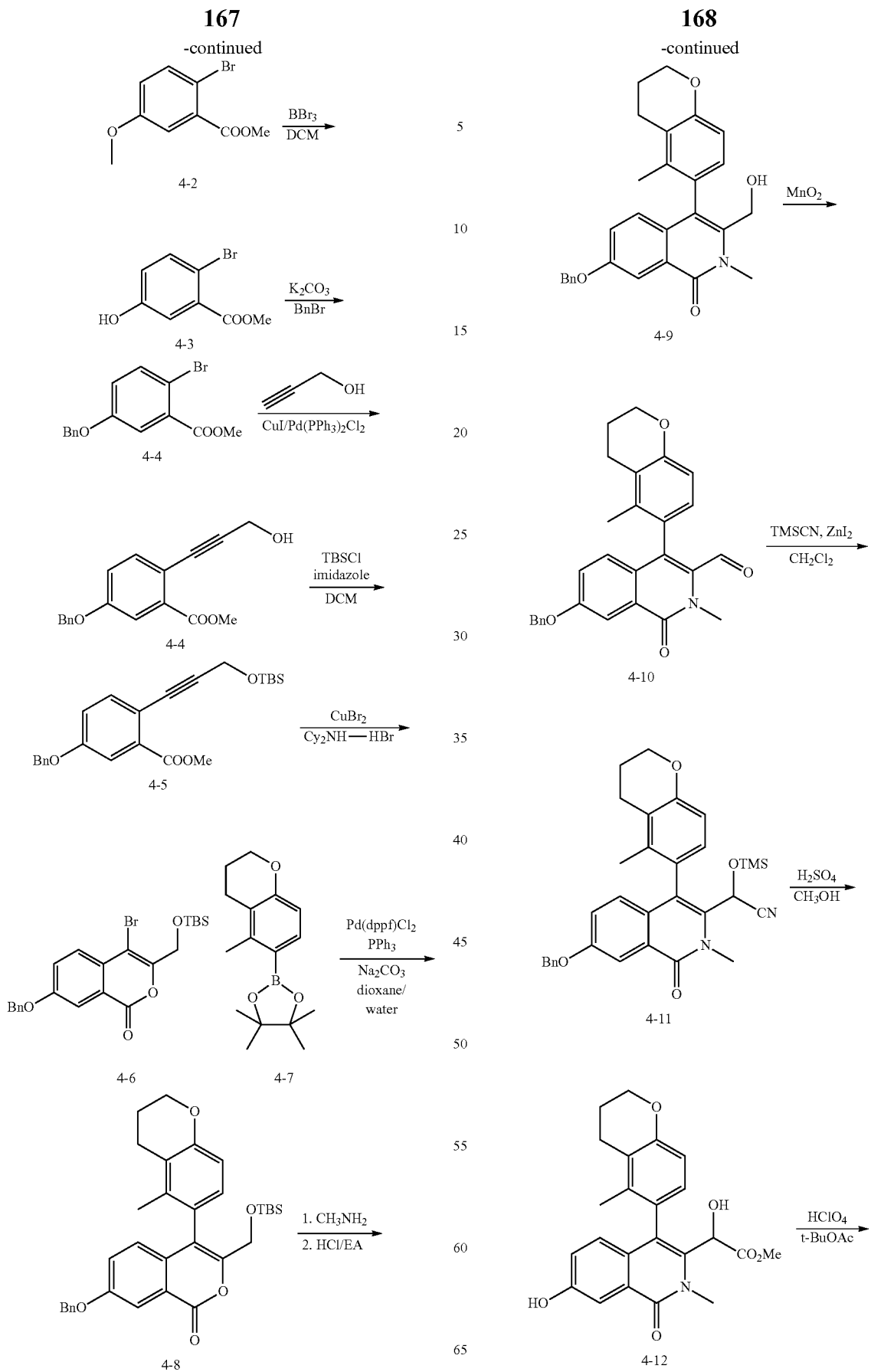

169
-continued

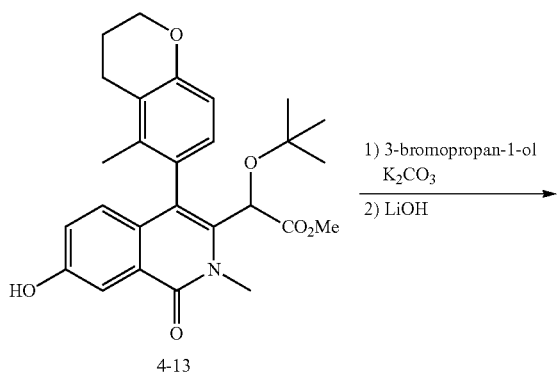

4-13

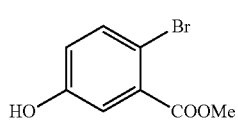

4-14

Example 4

[structure at bottom left of page 169]

170 tert-Butoxy-[7-(2-hydroxy-ethoxy)-2-methyl-4-(5-meth-4-(5-methyl-chroman-6-yl)-1-oxo-1,2-dihydro-isoquinolin-3-yl]-acetic acid Step A Preparation of methyl 2-bromo-5-methoxybenzoate

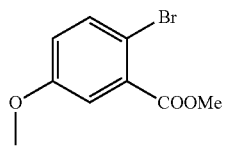

To a solution of 2-bromo-5-methoxybenzoic acid (150 g, 649 mmol) in Methanol (1500 mL) stirred under nitrogen at 0° C. was added sulfurous dichloride (69.4 mL, 974 mmol) dropwise during 30 min. The reaction mixture was stirred at 65° C. for 12 hr. The solvents were evaporated off, then water (750 mL) and EtOAc (750 mL) was poured into the residue. The mixture was partitiononed. The aqueous layer was extracted with EtOAc (250 mL*3). Combined organic phase was washed with water (200 mL*2), dried over anhydrous $Na_2SO_4$ and concentrated to give 150 g (90%) of the title compound.

Step B

2-Bromo-5-hydroxy-benzoic acid methyl ester

To a solution of compound methyl 2-bromo-5-methoxy-benzoate (100 g, 410 mmol) in DCM (2000 mL) was added and $BBr_3$ (1N, 150 mL) at −78° C. under $N_2$ The mixture was stirred at 0° C. under $N_2$ for 24 hr. The reaction was quenched with MeOH (500 mL), concentrated to dryness, diluted with $H_2O$ (50 mL), and extracted with ethyl acetate (800 mL*3), The organic phase was washed with saturated sodium bicarbonate solution 50 mL, dried over $Na_2SO_4$. After concentration, the crude product was purified by silica gel chromatography eluted with PE:EA=1:1 to give title product (80 g, 85% yield) as yellow oil. LCMS (10-80 AB_2MIN.M): Rt=0.820, purity=85%, M+1=231.

Step C

5-Benzyloxy-2-bromo-benzoic acid methyl ester

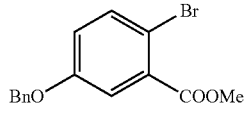 [SMILES: COC(=O)c1cc(OCc2ccccc2)ccc1Br]

To a solution of 2-Bromo-5-hydroxy-benzoic acid methyl ester (80 g, 347 mmol) and $K_2CO_3$ (71.9 g, 520 mmol) in DMF (800 mL) was added BnBr (500 g, 416.2 mmol) at RT. The mixture was stirred at RT under $N_2$ for 5 hr. The reaction mixture was diluted with $H_2O$ (500 mL) and extracted with ethyl acetate (100 mL*3). The organic phase was washed with saturated sodium bicarbonate solution 500 mL, dried over $Na_2SO_4$. After concentration, the crude product was purified by silica gel chromatography eluted with PE:EA=4:1 to give title product (100 g, 90% yield) as an off-white solid.

Step D

5-Benzyloxy-2-(3-hydroxy-prop-1-ynyl)-benzoic acid methyl ester

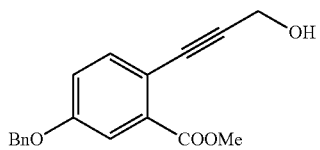 [SMILES: COC(=O)c1cc(OCc2ccccc2)ccc1C#CCO]

To a solution of 5-Benzyloxy-2-bromo-benzoic acid methyl ester (120 g, 374 mmol) and prop-2-yn-1-ol (41.9 g, 747 mmol) in triethylamine (1 L), copper(I) iodide (0.712 g, 3.74 mmol) and bis(triphenylphosphine)palladium(II) chloride (26.2 g, 37.4 mmol) at RT under $N_2$. The mixture was heated at 50° C. reflux under $N_2$ for 12 hr. The reaction was cooled to room temperature, concentrated to dryness, diluted with $H_2O$ (50 mL) and extracted with ethyl acetate (500 mL*3). The organic phase was washed with saturated sodium bicarbonate solution 500 mL, dried over $Na_2SO_4$. After concentration, the crude product was purified by silica gel chromatography eluted with PE:EA=10:1~4:1 to give title product (80 g, 72%) as yellow oil.

LCMS (10-80 AB_2MIN.M): Rt=1.124, purity=53%, M+1=279.

Step E

5-Benzyloxy-2-[3-(tert-butyl-dimethyl-silanyloxy)-prop-1-ynyl]-benzoic acid methyl ester

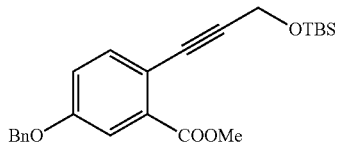 [SMILES: COC(=O)c1cc(OCc2ccccc2)ccc1C#CCO[Si](C)(C)C(C)(C)C]

To a solution of 5-Benzyloxy-2-(3-hydroxy-prop-1-ynyl)-benzoic acid methyl ester (80 g, 270 mmol) in DCM (1.5 L) was added imidazole (36.8 g, 540 mmol) and TBSCl (61 g, 405 mmol). The mixture was stirred at room temperature for 3 hours. The reaction mixture was washed with water, brine, dried over $Na_2SO_4$ and concentrated to dryness. The residue was purified by chromatography column on silica gel to afford title product (90 g, 81%).

LCMS (10-80 AB_2MIN.M): Rt=1.499, purity=73%, M+1=411.

Step F

7-Benzyloxy-4-bromo-3-(tert-butyl-dimethyl-silanyloxymethyl)-isochromen-1-one

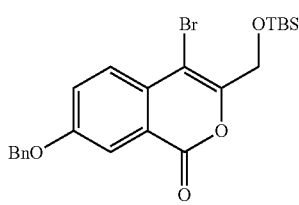 [SMILES: CC(C)(C)[Si](C)(C)OCc1oc(=O)c2cc(OCc3ccccc3)ccc2c1Br]

To a suspension of 5-Benzyloxy-2-[3-(tert-butyl-dimethyl-silanyloxy)-prop-1-ynyl]-benzoic acid methyl ester (90 g, 219 mmol) and copper bromide (58.8 g, 263 mmol) in 1,2-dichloro-ethane (1 L), was added dicyclohexylamine hydrobromide (5.75 g, 21.92 mmol). The resultant mixture was stirred at reflux under $N_2$. After 2 h, the reaction mixture was cooled to ambient temperature, and partitioned between dichloromethane and water. The organic layer was dried ($MgSO_4$), filtered and concentrated in vacuo. The residue was purified by chromatography column on silica gel to afford title product (40 g, 38.4%) as a pale yellow solid.

LCMS (10-80 AB_2MIN.M): Rt=1.617, purity=80%, M+1=475.

Step G

7-Benzyloxy-3-(tert-butyl-dimethyl-silanyloxymethyl)-4-(5-methyl-chroman-6-yl)-isochromen-1-one

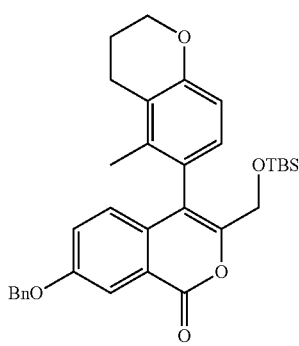 [SMILES: Cc1c(-c2c(CO[Si](C)(C)C(C)(C)C)oc(=O)c3cc(OCc4ccccc4)ccc23)ccc2c1CCCO2]

To a solution of 7-Benzyloxy-4-bromo-3-(tert-butyl-dimethyl-silanyloxymethyl)-isochromen-1-one (30 g, 63.1 mmol) and 4,4,5,5-tetramethyl-2-(5-methylchroman-6-yl)-1,3,2-dioxaborolane (51.9 g, 89 mmol) in 1,4-dioxane/$H_2O$ (400/100 mL) was added Pd(dppf)Cl$_2$ (4.62 g, 6.31 mmol), Na$_2$CO$_3$ (20 g, 189 mmol), and PPh$_3$ (4.96 g, 18.93 mmol). The resultant mixture was stirred at refluxing under $N_2$. After 12 h, the reaction mixture was cooled to ambient temperature and partitioned between dichloromethane and water. The organic layer was washed with brine, dried (MgSO$_4$), filtered and concentrated in vacuo. The residue was purified by chromatography column on silica gel to afford title product as a pale solid (5.0 g). LCMS (10-80 AB_2MIN.M): Rt=1.541, purity=93.3%, M+1=542.

Step H

7-Benzyloxy-3-hydroxymethyl-2-methyl-4-(5-methyl-chroman-6-yl)-2H-isoquinolin-1-one

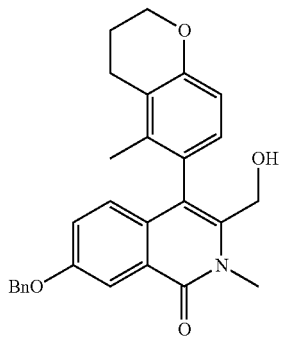 [SMILES: Cc1c(-c2c(CO)n(C)c(=O)c3cc(OCc4ccccc4)ccc23)ccc2c1CCCO2]

The mixture of 7-Benzyloxy-3-(tert-butyl-dimethyl-silanyloxymethyl)-4-(5-methyl-chroman-6-yl)-isochromen-1-one (5.0 g, 9.21 mmol) and CH$_3$NH$_2$/EtOH (10 mL) was stirred at 80° C. for 1 hour. The solvent was removed in vacuo and the resulting mixture was acidified by HCl-EA solution to pH 1-2. The mixture was diluted with water and extracted with EA (3*100 mL) and dried over sodium sulfate and concentrated to dryness. The residue was purified by chromatography column on silica gel to afford title product (3.5 g, 86%).

LCMS (10-80 AB_2MIN.M): Rt=1.278, purity=77%, M+1=442.

Step I

7-Benzyloxy-2-methyl-4-(5-methyl-chroman-6-yl)-1-oxo-1,2-dihydro-isoquinoline-3-carbaldehyde

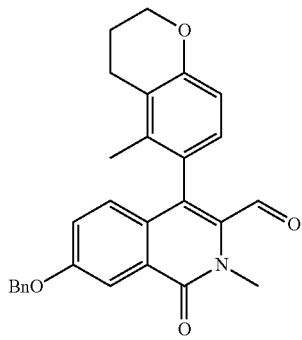 [SMILES: Cc1c(-c2c(C=O)n(C)c(=O)c3cc(OCc4ccccc4)ccc23)ccc2c1CCCO2]

To a solution of 7-Benzyloxy-3-hydroxymethyl-2-methyl-4-(5-methyl-chroman-6-yl)-2H-isoquinolin-1-one (3.5 g, 7.93 mmol) in dichloromethane (100 ml) was added manganese dioxide (6.89 g, 79.3 mmol). The resultant mixture was stirred at 70° C. under N$_2$ for 2 h. The reaction mixture was filtered and concentrated to dryness to afford the title product (3.0 g, 86%).

LCMS (10-80 AB_2MIN.M): Rt=1.338 purity=89%, M+1=440.

Step J

[7-Benzyloxy-2-methyl-4-(5-methyl-chroman-6-yl)-1-oxo-1,2-dihydro-isoquinolin-3-yl]-trimethylsilanyloxy-acetonitrile

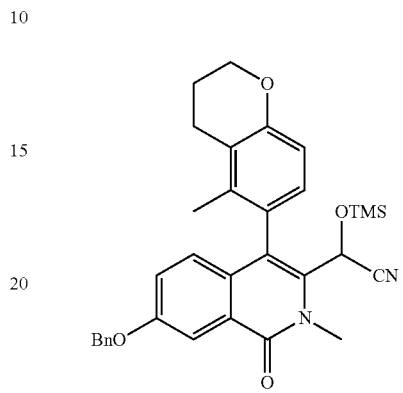

To a suspension of 7-Benzyloxy-2-methyl-4-(5-methyl-chroman-6-yl)-1-oxo-1,2-dihydro-isoquinoline-3-carbaldehyde (3.0 g, 6.83 mmol) and zinc diiodide (4.36 g, 13.65 mmol) in dichloromethane (60 ml), was added trimethylsilanyl cyanide (6.77 g, 68.3 mmol). The resultant mixture was stirred at room temperature for 45 min. The reaction mixture was diluted with water (50 ml) and extracted with DCM, dried over sodium sulfate and concentrated to dryness. The residue was used for the next step directly without other purification (2.5 g, 68%).

LCMS (10-80 AB_2MIN.M): Rt=1.465, purity=93.5%, M+1=539.

Step K

Hydroxyl-[7-hydroxy-2-methyl-4-(5-methyl-chroman-6-yl)-1-oxo-1,2-dihydro-isoquinolin-3-yl]-acetic acid methyl ester

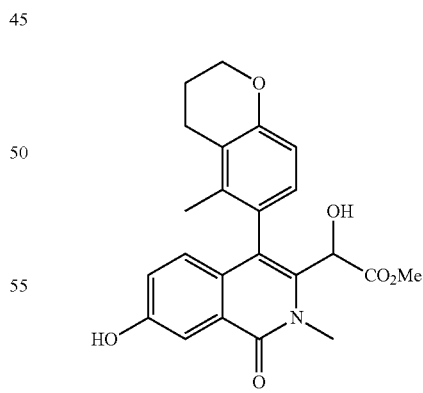

To a solution of [7-Benzyloxy-2-methyl-4-(5-methyl-chroman-6-yl)-1-oxo-1,2-dihydro-isoquinolin-3-yl]-trimethylsilanyloxy-acetonitrile (2.5 g, 4.64 mmol) in H$_2$SO$_4$/CH$_3$OH (30 mL, V/V=1:3). The resulting mixture was heated to 80° C. under N$_2$ for 12 h. The reaction mixture was poured into ice water and extracted with DCM (50 mL*3), dried over sodium sulfate and concentrated to dryness. The mixture was purified by chromatography column on silica gel to afford the title product (0.6 g, 32%). LCMS (10-80 AB_2MIN.M): Rt=0.993, purity=75%, M+1=410.

Step L tert-Butoxy-[7-hydroxy-2-methyl-4-(5-methyl-chroman-6-yl)-1-oxo-1,2-dihydro-isoquinolin-3-yl]-acetic acid methyl ester; compound with methane

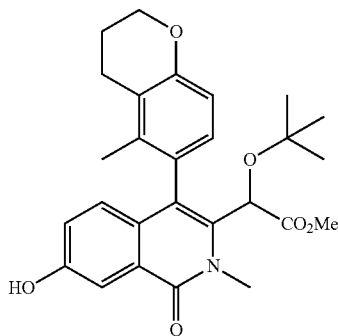 [SMILES: COC(=O)C(OC(C)(C)C)c1c(-c2ccc3c(c2C)CCCO3)c2ccc(O)cc2c(=O)n1C]

To a solution of Hydroxyl-[7-hydroxy-2-methyl-4-(5-methyl-chroman-6-yl)-1-oxo-1,2-dihydro-isoquinolin-3-yl]-acetic acid methyl ester (600 mg, 1.465 mmol) in t-BuOAc (10 ml) was added HClO$_4$ (512 mg, 5.12 mmol). The resultant mixture was stirred at RT under N$_2$ for 2 h. The reaction mixture was diluted with water and extracted with EA (50 mL*3), dried over sodium sulfate and concentrated to dryness. The mixture was purified by chromatography column on silica gel to afford the title product (300 mg, 44%). LCMS (10-80 AB_2MIN.M): Rt=1.308, purity=96%, M+1=466.

Step M tert-Butoxy-[7-(2-hydroxy-ethoxy)-2-methyl-4-(5-methyl-chroman-6-yl)-1-oxo-1,2-dihydro-isoquinolin-3-yl]-acetic acid methyl ester

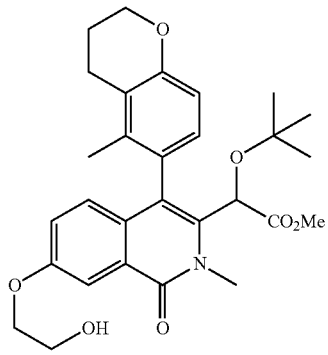 [SMILES: COC(=O)C(OC(C)(C)C)c1c(-c2ccc3c(c2C)CCCO3)c2ccc(OCCO)cc2c(=O)n1C]

To a solution of tert-Butoxy-[7-hydroxy-2-methyl-4-(5-methyl-chroman-6-yl)-1-oxo-1,2-dihydro-isoquinolin-3-yl]-acetic acid methyl ester (50 mg, 0.17 mmol) in DMF (1 ml) was added K$_2$CO$_3$ (44.5 mg, 0.322 mmol) and 3-bromopropan-1-ol (40.3 mg, 0.322 mmol) at RT. The resultant mixture was stirred at 70° C. for 3 hr. The reaction mixture was diluted with water and extracted with EA (10 mL*3), dried over sodium sulfate and concentrated to dryness. The mixture was purified by Pre-TLC to afford the title product (30 mg, 55%). LCMS (10-80 AB_2MIN.M): Rt=1.223, purity=93.7%, M+1=510.

Step N tert-Butoxy-[7-(2-hydroxy-ethoxy)-2-methyl-4-(5-methyl-chroman-6-yl)-1-oxo-1,2-dihydro-isoquinolin-3-yl]-acetic acid

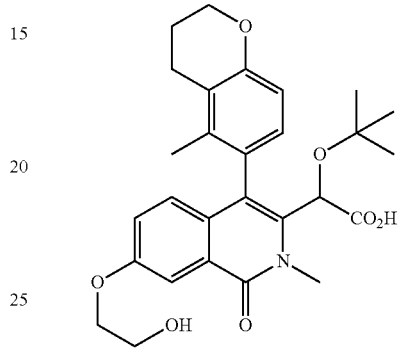

To a solution of tert-Butoxy-[7-(2-hydroxy-ethoxy)-2-methyl-4-(5-methyl-chroman-6-yl)-1-oxo-1,2-dihydro-isoquinolin-3-yl]-acetic acid methyl ester (30 mg, 0.059 mmol) in THF (3 ml), was added 1N LiOH (3 mL). The resultant mixture was stirred at 70° C. overnight. The solvent was removed in vacuo; the reaction mixture was acidified by 1N HCl solution to pH 5-6. The white solid was filtered to afford the title product (9 mg, 30.8%). LCMS (10-80 AB_2MIN.M): Rt=1.190, purity=97.3%, M+1=496.

The compounds in Table 2 were prepared in a manner similar to the examples shown above.

TABLE 2

| Example No. | Retention time, LCMS | MS(M + H)+ |
| --- | --- | --- |
| 5 | 1.46 | 449.43 |
| 6 | 1.19 | 401.41 |
| 7 | 1.25 | 379.46 |
| 8 | 1.19 | 395.46 |
| 9 | 1.14 | 383.42 |
| 10 | 1.22 | 393.49 |
| 11 | 1.29, 1.32 | 434.32 |
| 12 | 1.32 | 434.32 |
| 13 | 1.25, 1.28 | 433.43 |
| 14 | 120-1.22 | 434.32 |
| 15 | 1.17, 1.20 | 395.46 |
| 16 | 1.21, 1.23 | 449.43 |
| 17 | 1.21 | 433.43 |
| 18 | 1.23 | 379.46 |
| 19 | 1.23, 1.25 | 435.52 |
| 20 | 1.25 | 435.52 |
| 21 | 1.23 | 455.94 |
| 22 | 1.17 | 443.52 |
| 23 | 1.02 | 436.51 |
| 24 | 1.37 | 463.58 |
| 25 | 1.25, 1.26 | 439.49 |
| 26 | 1.22 | 455.94 |
| 27 | 1.15 | 455.51 |
| 28 | 1.31 | 407.51 |
| 29 | 1.28 | 415.49 |
| 30 | 1.2 | 447.54 |
| 31 | 1.14 | 409.49 |

TABLE 2-continued

| Example No. | Retention time, LCMS | MS(M + H)+ |
|---|---|---|
| 32 | 1.28 | 457.53 |
| 33 | 1.13, 1.17 | 395.46 |
| 34 | 1.3 | 393.49 |
| 35 | 1.13 | 439.49 |
| 36 | 1.2 | 421.5 |
| 37 | 1.25 | 455.94 |
| 38 | 1.19 | 401.41 |
| 39 | 1.22 | 421.5 |
| 40 | 1.19 | 383.42 |
| 41 | 1.04 | 366.42 |
| 42 | 1.23 | 409.49 |
| 43 | 1.25 | 407.51 |
| 44 | 1.27, 1.29 | 423.51 |
| 45 | 1.27 | 423.51 |
| 46 | 1.18, 1.19 | 401.41 |
| 47 | 1.29 | 393.49 |
| 48 | 1.04 | 366.42 |
| 49 | 1.15 | 409.49 |
| 50 | 1.10, 1.14 | 425.49 |
| 51 | 1.14, 1.16 | 409.44 |
| 52 | 1.22, 1.26 | 409.49 |
| 53 | 1.13, 1.16 | 423.47 |
| 54 | 1.21, 1.24 | 409.49 |
| 55 | 1.21 | 407.51 |
| 56 | 1.29 | 411.48 |
| 57 | 1.17 | 439.49 |
| 58 | 1.18 | 435.52 |
| 59 | 1.24 | 411.48 |
| 60 | 1.3 | 407.51 |
| 61 | 1.15, 1.18 | 437.5 |
| 62 | 0.89 | 416.48 |
| 63 | 1.15, 1.17 | 407.47 |
| 64 | 1.23 | 415.49 |
| 65 | 1.23 | 435.52 |
| 66 | 1.39 | 427.93 |
| 67 | 1.2 | 449.55 |
| 68 | 1.3 | 455.94 |
| 69 | 1.17, 1.19 | 453.52 |
| 70 | 1.27, 1.31 | 469.97 |
| 71 | 1.21 | 379.46 |
| 72 | 1.21 | 451.52 |
| 73 | 1.17, 1.22 | 463.54 |
| 74 | 1.15 | 435.52 |
| 75 | 1.26 | 453.52 |
| 76 | 1.26 | 465.55 |
| 77 | 1.28 | 449.55 |
| 78 | 1.3 | 449.55 |
| 79 | 1.3 | 469.97 |
| 80 | 1.02, 1.11 | 462.55 |
| 81 | 1.23 | 509.6 |
| 82 | 1.03, 1.13 | 422.49 |
| 83 | 1.2 | 453.52 |
| 84 | 1.22 | 451.52 |
| 85 | 0.14 | 522.65 |
| 86 | 1.09, 1.12, 1.15 | 457.15 |
| 87 | 1.29 | 412.18 |
| 88 | 5.89 | 542.23 |
| 89 | 5.14, 5.16 | 498.29 |
| 90 | 1.23 | 472.19 |
| 91 | 5.13, 5.15 | 472.29 |
| 92 | 1.19, 1.23 | 472.29 |
| 93 | 1.39, 1.42 | 560.24 |
| 94 | 1.21 | 466.34 |
| 95 | 5.95, 5.98 | 578.39 |
| 96 | 5.95, 5.97 | 579.39 |
| 97 | 4.36, 4.43 | 543.38 |
| 98 | 5.81, 5.86 | 578.37 |
| 99 | 5.93, 5.98 | 596.39 |
| 100 | 5.32, 5.37 | 561.39 |
| 101 | 1.24 | 579.38 |
| 102 | 4.45, 4.59 | 557.41 |
| 103 | 5.86, 5.91 | 560.38 |
| 104 | 5.92, 5.97 | 560.4 |
| 105 | 1.2 | 579.39 |
| 106 | 1.19 | 484.36 |
| 107 | 1.4 | 596.37 |
| 108 | 1.45 | 578.38 |
| 109 | 1.35 | 566.36 |
| 110 | 1.46 | 600.32 |
| 111 | 1.39 | 548.36 |
| 112 | 1.51 | 582.33 |
| 113 | 1.42 | 580.39 |
| 114 | 1.34, 1.36 | 502.31 |
| 115 | 1.29 | 450.34 |
| 116 | 1.01 | 499.28 |
| 117 | 0.91 | 549.39 |
| 118 | 0.91, 0.98 | 423.3 |
| 119 | 0.89 | 565.39 |
| 120 | 1.35, 1.37 | 480.34 |
| 121 | 5.42, 5.44 | 450.34 |
| 122 | 1.11 | 510.3 |
| 123 | 5.38, 5.44 | 559.33 |
| 124 | 1.37 | 468.32 |
| 125 | 1.32 | 484.33 |
| 126 | 4.95, 4.99 | 484.29 |
| 127 | 1.38, 1.41 | 504.29 |
| 128 | 1.24 | 620.29 |
| 129 | 1.14, 1.15 | 543.32 |
| 130 | 5.40, 5.47 | 500.25 |
| 131 | 1.23 | 468.35 |
| 132 | 6.20, 6.25 | 610.31 |
| 133 | 1.2 | 579.4 |
| 134 | 5.90, 5.95 | 578.31 |
| 135 | 5.58, 5.64 | 494.4 |
| 136 | 6.15, 6.20 | 576.27 |
| 137 | 4.74, 4.78 | 544.32 |
| 138 | 5.98 | 578.3 |
| 139 | | |
| 140 | | |
| 141 | | |
| 142 | | |
| 143 | 1.11 | 561.31 |
| 144 | 1.14 | 543.33 |
| 145 | 1.38 | 578.32 |
| 146 | 6.27, 6.32 | 626.35 |
| 147 | 1.43 | 560.38 |
| 148 | 1.43 | 578.37 |
| 149 | 1.24 | 436.35 |
| 150 | 1.2 | 454.31 |
| 151 | 4.65, 4.70 | 416.28 |
| 152 | 1.32 | 406.3 |
| 153 | 1.00 | 423.23 |
| 154 | 1.2 | 400.18 |
| 155 | 1.1 | 370.27 |
| 156 | 1.13 | 366.25 |
| 157 | 0.88 | 370.28 |
| 158 | 1.42 | 461.36 |

Scheme 5: General Route B for Synthesis of Chiral Groups within R[4] Substituent
As a general synthetic approach, the P or M isomer may be prepared for any compounds of the invention using the specific chemistry shown below for the single isomer (2S)(M)-2-(tert-butoxy)-2-[4-(8-fluoro-5-methyl-3,4-dihydro-2H-1-benzopyran-6-yl)-2-methyl-1-oxo-1,2-dihydroisoquinolin-3-yl]-acetic acid.
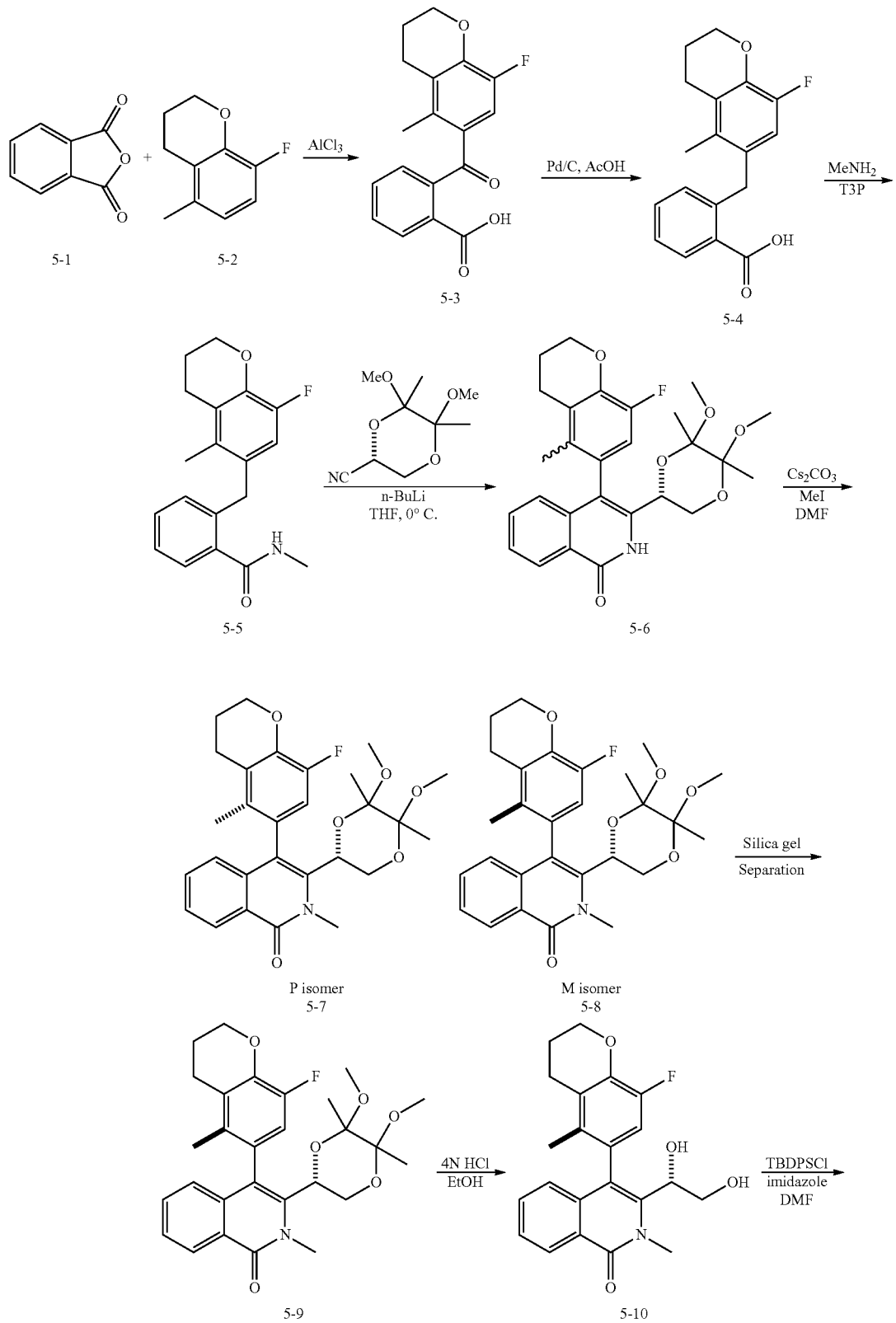

181
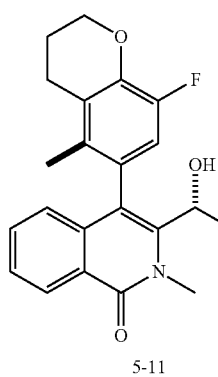
5-11
t-butyl acetate
HClO₄
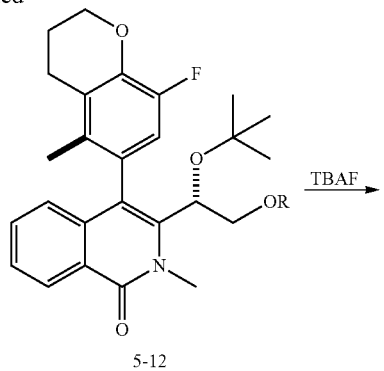
5-12
TBAF
182
-continued
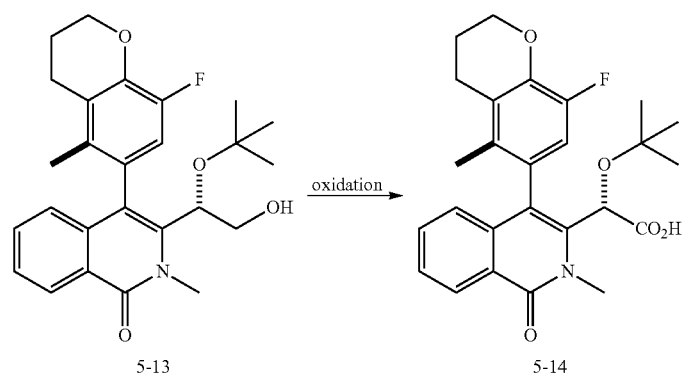
5-13 → 5-14 (oxidation)
Example 159
(2S)(M)-2-(tert-butoxy)-2-(4-(8-fluoro-5-methyl-chroman-6-yl)-2-methyl-1-oxo-1,2-dihydroisoquinolin-3-yl)acetic acid
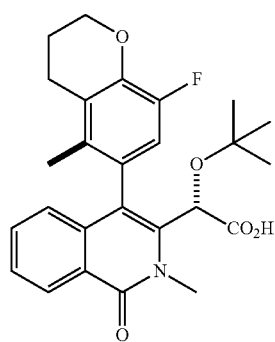
Step A
2-(8-fluoro-5-methylchroman-6-carbonyl)benzoic acid
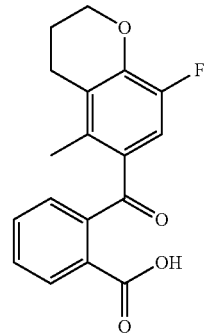 [SMILES: Cc1c(C(=O)c2ccccc2C(=O)O)cc(F)c2c1CCCO2]

An ice cold mixture of 8-fluoro-5-methylchroman (0.955 g, 5.75 mmol) in 1,2-Dichloroethane (DCE) (10 mL) was treated with aluminum chloride (1.532 g, 11.49 mmol) followed by isobenzofuran-1,3-dione (0.809 g, 5.46 mmol). The mixture was allowed to warm to ambient temperature and stirred for 90 minutes. Water was then added and the mixture was extracted with ethyl acetate. The extracts were washed with brine, dried over sodium sulfate, filtered and concentrated to give the title compound as an off-white solid: $^1$H NMR (400 MHz, DMSO-$d_6$) δ ppm 1.92-2.05 (m, 2 H), 2.34 (s, 3 H), 2.62-2.79 (m, 2 H), 4.15-4.30 (m, 2 H), 6.68 (d, J=11.73 Hz, 1 H), 7.40 (d, J=7.43 Hz, 1 H), 7.51-7.76 (m, 2 H), 7.88 (d, J=7.43 Hz, 1 H), 13.15 (br. s., 1 H); LC/MS (m/z) ES$^+$=315 (M+1).

Step B 2-((8-fluoro-5-methylchroman-6-yl)methyl)benzoic acid

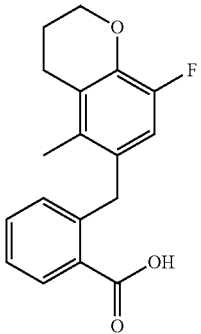 [SMILES: Cc1c(Cc2ccccc2C(=O)O)cc(F)c2c1CCCO2]

A mixture of 2-(8-fluoro-5-methylchroman-6-carbonyl) benzoic acid (673 mg, 2.141 mmol) in acetic Acid (15 mL) was treated with Pd/C (60.0 mg) and the mixture was stirred under 50 psi of hydrogen at 65° C. until the reaction was judged complete by LCMS. The mixture was filtered over Celite and the filtrate was concentrated to give the title compound as a white solid: $^1$H NMR (400 MHz, DMSO-$d_6$) δ ppm 1.80-2.05 (m, 5 H), 2.63 (t, J=6.44 Hz, 2 H), 3.95-4.15 (m, 2 H), 4.24 (s, 2 H), 6.57 (d, J=12.29 Hz, 1 H), 6.95 (d, J=7.61 Hz, 1 H), 7.21-7.34 (m, 1 H), 7.42 (td, J=7.56, 1.27 Hz, 1 H), 7.81 (dd, J=7.71, 1.07 Hz, 1 H), 12.92 (br. s., 1H); LC/MS (m/z) ES$^+$=301 (M+1).

Step C 2-((8-fluoro-5-methylchroman-6-yl)methyl)-N-methylbenzamide

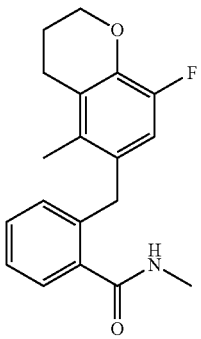 [SMILES: CNC(=O)c1ccccc1Cc1cc(F)c2c(c1C)CCCO2]

A solution of 2-((8-fluoro-5-methylchroman-6-yl)methyl) benzoic was dissolved in DMF (2.5 mL) and treated with Methyl amine in ethanol (237 μl, 1.906 mmol) and T3P (295 μl, 0.496 mmol). After 2 h, the solids were filtered off and washed with EtOAc to afford title compound (43 mg) as a white solid: $^1$H NMR (400 MHz, DMSO-$d_6$) δ=8.22 (d, 1 H), 7.34-7.17 (m, 3 H), 6.85 (d, J=7.6 Hz, 1 H), 6.79 (d, J=8.2 Hz, 1 H), 6.52 (d, J=8.2 Hz, 1 H), 4.07-3.97 (m, 4 H), 2.73 (d, J=4.5 Hz, 3 H), 2.59 (t, J=6.5 Hz, 2 H), 2.00-1.87 (m, 5 H); LC/MS (m/z) ES$^+$=296 (M+1).

Step D 3-((2S)-5,6-dimethoxy-5,6-dimethyl-1,4-dioxan-2-yl)-4-(8-fluoro-5-methylchroman-6-yl)isoquinolin-1(2H)-one

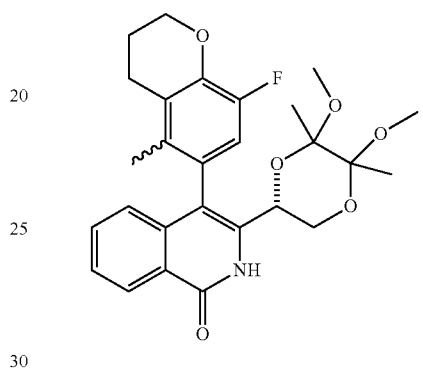

An ice cooled suspension of 2-((8-fluoro-5-methylchroman-6-yl)methyl)-N-methylbenzamide (300 mg, 0.957 mmol) in THF (5 mL) was treated with 2.5M nBuLi in hexanes (804 μl, 2.010 mmol). Upon addition of the n-BuLi, the reaction became homogeneous and dark red in color. After 10 min, a solution of (2S)-5,6-dimethoxy-5,6-dimethyl-1,4-dioxane-2-carbonitrile (289 mg, 1.436 mmol) in THF (0.5 mL) was added and the colorless solution was maintained at 0° C. for 5 min. The reaction was quenched with sat. aq. NH4Cl and extracted with EtOAc. The combined organics were washed with brine, dried (Na$_2$SO$_4$), filtered and concentrated. The residue was purified by ISCO (0-10% MeOH-DCM) to afford the title compound (408 mg, 0.844 mmol, 88% yield) as a 1:1 mixture of diastereomers as a pale yellow foam. LC/MS (m/z) ES$^+$=484 (M+1). Rt=2.17, 2.20.

Step E 3-((2S)(M)-5,6-dimethoxy-5,6-dimethyl-1,4-dioxan-2-yl)-4-(8-fluoro-5-methylchroman-6-yl)-2-methyl-isoquinolin-1(2H)-one

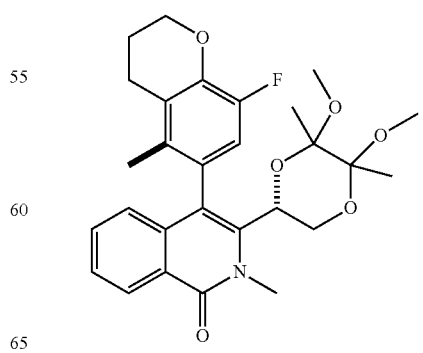

A solution of 3-((2S)-5,6-dimethoxy-5,6-dimethyl-1,4-dioxan-2-yl)-4-(8-fluoro-5-methylchroman-6-yl)isoquinolin-1(2H)-one (408 mg, 0.844 mmol) in N,N-Dimethylformamide (DMF) (5568 µl) was treated with Cs₂CO₃ (504 mg, 0.928 mmol). After 5 min, the reaction mixture was quenched with sat. aq. NH4Cl and extracted with EtOAc. The combined organics were washed with brine, dried (MgSO₄), filtered and concentrated. The residue was purified by ISCO (0-50% EtOAc-hexanes) to afford 3-((2S)(M)-5,6-dimethoxy-5,6-dimethyl-1,4-dioxan-2-yl)-4-(8-fluoro-5-methylchroman-6-yl)-2-methylisoquinolin-1(2H)-one (240 mg, 0.48 mmol, 57% yield).

P Isomer: 120 mg as a White Solid:

1H NMR (400 MHz, CHLOROFORM-d) δ=8.49 (d, 1 H), 7.52-7.43 (m, 2 H), 6.87-6.79 (m, 1 H), 6.64 (d, J=10.9 Hz, 1 H), 4.94 (dd, J=4.5, 12.1 Hz, 1 H), 4.31 (dd, J=3.3, 6.6 Hz, 2 H), 4.10 (t, J=11.8 Hz, 1 H), 4.02 (s, 3 H), 3.43 (dd, J=4.5, 11.5 Hz, 1 H), 3.32 (s, 3 H), 3.06 (s, 3 H), 2.73 (s, 2 H), 2.23-2.07 (m, 2 H), 1.89 (s, 3 H), 1.29 (d, J=7.4 Hz, 6 H); LC/MS (m/z) ES⁺=498 (M+1).

M Isomer: 120 mg as a White Solid:

¹H NMR (400 MHz, CHLOROFORM-d) δ=8.49 (d, J=8.0 Hz, 1 H), 7.55-7.43 (m, 2 H), 6.83 (d, J=10.2 Hz, 2 H), 5.14 (dd, J=4.2, 12.0 Hz, 1 H), 4.32 (d, J=3.3 Hz, 2 H), 4.21-4.11 (m, 1 H), 4.04 (s, 3 H), 3.33 (s, 4 H), 3.20 (s, 3 H), 2.70 (t, J=6.4 Hz, 2 H), 2.18 (br. s., 2 H), 1.75 (s, 3 H), 1.32 (d, J=12.7 Hz, 6 H); LC/MS (m/z) ES⁺=498 (M+1).

Step F (2S)(M)-3-(1,2-dihydroxyethyl)-4-(8-fluoro-5-methylchroman-6-yl)-2-methylisoquinolin-1(2H)-one

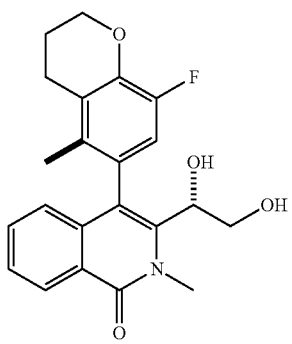

A solution of 3-((2S)-5,6-dimethoxy-5,6-dimethyl-1,4-dioxan-2-yl)-4-(8-fluoro-5-methylchroman-6-yl)-2-methyl-isoquinolin-1(2H)-one (120 mg, 0.241 mmol) in ethanol (2171 µl) was treated with 2N HCl (241 µl, 0.965 mmol) and irradiated in the microwave for 20 min at 120° C. The reaction mixture was poured into sat. aq. NaHCO₃ (pH of aq was ~8) and extracted with EtOAc. The combined organics were washed with brine, dried (Na₂SO₄), filtered and concentrated to afford (2S)(M)-3-(1,2-dihydroxyethyl)-4-(8-fluoro-5-methylchroman-6-yl)-2-methylisoquinolin-1(2H)-one (90 mg, 0.235 mmol, 97% yield) as a white solid: R_f=0.71, ES+ MS: 384 (M+1).

Step G (2S)(M)-3-(2-((tert-butyldiphenylsilyl)oxy)-1-hydroxyethyl)-4-(8-fluoro-5-methylchroman-6-yl)-2-methylisoquinolin-1(2H)-one

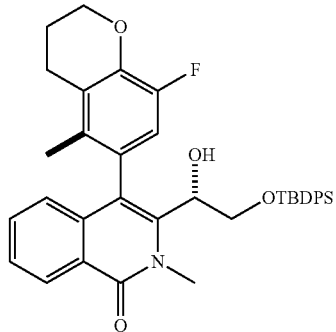

A solution of (2S)(M)-3-(1,2-dihydroxyethyl)-4-(8-fluoro-5-methylchroman-6-yl)-2-methylisoquinolin-1(2H)-one (90 mg, 0.235 mmol) in N,N-Dimethylformamide (DMF) (1107 µl) was treated with imidazole (19.18 mg, 0.282 mmol) and tbdpscl (67.1 µl, 0.258 mmol). After 2 h, the reaction mixture was poured into sat. aq. NH₄Cl and extracted with EtOAc. The combined organics were washed with brine, dried (MgSO₄), filtered and concentrated. The residue was purified by ISCO (0-50% EtOAc-hexanes) to afford (2S)(M)-3-(2-((tert-butyldiphenylsilyl)oxy)-1-hydroxyethyl)-4-(8-fluoro-5-methylchroman-6-yl)-2-methylisoquinolin-1(2H)-one (92 mg, 0.148 mmol, 63.0% yield) as a white foam: ¹H NMR (400 MHz, CHLOROFORM-d) δ=8.49-8.40 (m, 1 H), 7.61-7.55 (m, 2 H), 7.54-7.41 (m, 6 H), 7.38 (dd, J=7.4, 12.3 Hz, 4 H), 6.85-6.76 (m, 2 H), 5.08-4.92 (m, 1 H), 4.30 (t, J=5.2 Hz, 2 H), 4.02 (t, J=10.2 Hz, 1 H), 3.75 (s, 3 H), 3.60 (dd, J=4.3, 10.6 Hz, 1 H), 2.72 (d, J=2.7 Hz, 1 H), 2.57 (s, 2 H), 2.13 (d, J=4.9 Hz, 2 H), 1.02 (s, 9 H); LC/MS (m/z) ES⁺=622 (M+1).

Step H (2S)(M)-3-(1-(tert-butoxy)-2-((tert-butyldiphenysily)oxy)ethyl)-4-(8-fluoro-5-methylchroman-6-yl)-2-methylisoquinolin-1(2H)-one

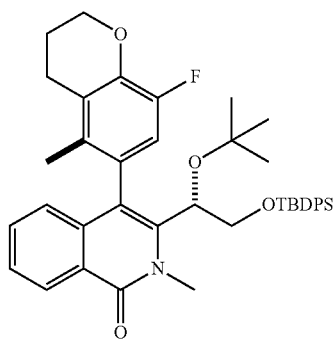

A solution of (S)-3-(2-((tert-butyldiphenylsilyl)oxy)-1-hydroxyethyl)-4-(8-fluoro-5-methylchroman-6-yl)-2-methylisoquinolin-1(2H)-one (92 mg, 0.148 mmol) in tert-butyl acetate (1994 μl, 14.80 mmol) was treated with 2 drops of 70% perchloric acid. After 18 h, the reaction mixture was poured into sat. aq. NaHCO$_3$ and extracted with EtOAc. The combined organics were washed with brine, dried (MgSO$_4$), filtered and concentrated. The residue was purified by ISCO (0-30% EtOAc-hexanes) to afford (S)-3-(1-(tert-butoxy)-2-((tert-butyldiphenylsilyl)oxy)ethyl)-4-(8-fluoro-5-methylchroman-6-yl)-2-methylisoquinolin-1(2H)-one (49 mg, 0.072 mmol, 48.9% yield) as a white foam: $^1$H NMR (400 MHz, CHLOROFORM-d) δ=8.45 (dd, J=1.5, 7.7 Hz, 1 H), 7.70-7.63 (m, 2 H), 7.63-7.56 (m, 2 H), 7.41 (none, 8 H), 6.89 (d, J=11.3 Hz, 1 H), 6.85-6.78 (m, 1 H), 4.83 (dd, J=2.0, 7.4 Hz, 1 H), 4.30 (t, J=5.2 Hz, 2 H), 3.88 (dd, J=7.5, 10.6 Hz, 1 H), 3.82 (s, 3 H), 3.58 (dd, J=2.0, 10.7 Hz, 1 H), 2.73-2.52 (m, 2 H), 2.20-2.07 (m, 2 H), 1.64 (s, 3 H), 1.16 (s, 9 H), 0.98 (s, 9 H); LC/MS (m/z) ES$^+$=678 (M+1).

Step I (2S)(M)-3-(1-(tert-butoxy)-2-hydroxyethyl)-4-(8-fluoro-5-methylchroman-6-yl)-2-methylisoquinolin-1(2H)-one

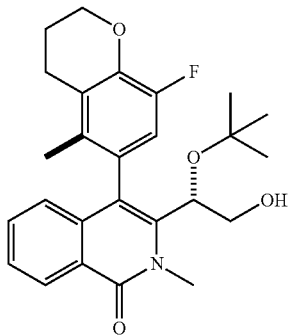

1.0M TBAF in THF (723 μl, 0.723 mmol) was added to (S)-3-(1-(tert-butoxy)-2-((tert-butyldiphenylsilyl)oxy)ethyl)-4-(8-fluoro-5-methylchroman-6-yl)-2-methylisoquinolin-1(2H)-one (49 mg, 0.072 mmol). After 1 h, the reaction mixture was concentrated in vacuo, dissovled in a minimal amount of DCM (~700 uL) and purified by ISCO (0-100% EtOAc-hexanes) to afford (2S)(M)-3-(1-(tert-butoxy)-2-hydroxyethyl)-4-(8-fluoro-5-methylchroman-6-yl)-2-methylisoquinolin-1(2H)-one (31 mg, 0.071 mmol, 98% yield) as a white solid: $^1$H NMR (400 MHz, CHLOROFORM-d) δ=8.49 (dd, 1 H), 7.49 (ddd, J=1.9, 4.8, 7.2 Hz, 2 H), 6.88 (d, J=11.3 Hz, 1 H), 6.78 (dd, J=1.5, 7.5 Hz, 1 H), 4.78 (dd, J=4.2, 10.1 Hz, 1 H), 4.33 (t, J=5.2 Hz, 2 H), 3.92 (s, 3 H), 3.87-3.77 (m, 1 H), 3.46 (td, J=4.3, 11.2 Hz, 1 H), 2.73 (q, J=6.6 Hz, 2 H), 2.26-2.10 (m, 3 H), 1.82 (s, 3 H), 1.19 (s, 9 H); LC/MS (m/z) ES$^+$=440 (M+1).

Step J (2S)(M)-2-(tert-butoxy)-2-(4-(8-fluoro-5-methylchroman-6-yl)-2-methyl-1-oxo-1,2-dihydroisoquinolin-3-yl)acetic acid

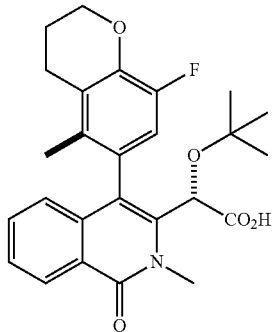

An ice cooled suspension of (2S)(M)-3-(1-(tert-butoxy)-2-hydroxyethyl)-4-(8-fluoro-5-methylchroman-6-yl)-2-methylisoquinolin-1(2H)-one (31 mg, 0.071 mmol) and NaHCO$_3$ (5.92 mg, 0.071 mmol) in Dichloromethane (DCM) (646 μl) was treated with DMP (44.9 mg, 0.106 mmol) and warmed to ambient temperature. After 45 min, the reaction mixture was poured into sat. aq. NaHCO$_3$ and extracted with DCM. The combined extracts were washed with brine, dried (Na$_2$SO$_4$), filtered and concentrated. The residue (42 mg white foam) was dissolved in t-BuOH (0.7 mL) and treated with 2-Me-2-Butene (59.8 μl, 0.564 mmol) and a solution of NaH$_2$PO$_4$ (25.4 mg, 0.212 mmol) and NaClO$_2$ (23.92 mg, 0.212 mmol) in water (120 uL). After 20 min, the reaction mixture was diluted with H$_2$O and extracted with EtOAc. The combined organics were washed with brine, dried (Na$_2$SO$_4$), filtered and concentrated. The residue was Gilson to afford (2S)(M)-2-(tert-butoxy)-2-(4-(8-fluoro-5-methylchroman-6-yl)-2-methyl-1-oxo-1,2-dihydroisoquinolin-3-yl)acetic acid (12 mg, 0.026 mmol, 37.5% yield) as a white solid: $^1$H NMR (400 MHz, DMSO-d$_6$) δ=13.35-13.22 (m, 1 H), 8.33-8.26 (m, 1 H), 7.66-7.58 (m, 1 H), 7.54 (d, J=7.0 Hz, 1 H), 6.89 (d, J=11.5 Hz, 1 H), 6.77 (d, J=8.0 Hz, 1 H), 4.97 (s, 1 H), 4.23 (t, J=5.0 Hz, 2 H), 3.62 (s, 3 H), 2.70 (t, J=5.7 Hz, 2 H), 2.09-1.99 (m, 2 H), 1.81 (s, 3 H), 1.09 (s, 9 H); LC/MS (m/z) ES$^+$=454 (M+1).

Example 163

(2S)(M)-2-[4-(8-fluoro-5-methyl-3,4-dihydro-2H-1-benzopyran-6-yl)-2-methyl-1-oxo-1,2-dihydroisoquinolin-3-yl]-2-(1-methylcyclobutoxy)acetic acid

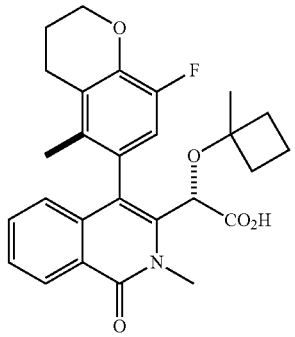

The title compound was made in a manner similar to Example 159 except using methylenecyclobutane in Step H. $^{1}$H NMR (400 MHz, CHLOROFORM-d) δ=8.55-8.46 (m, 1 H), 7.58-7.46 (m, 2 H), 6.92-6.84 (m, 1 H), 6.79 (d, J=11.1 Hz, 1 H), 4.31 (t, J=5.0 Hz, 2 H), 3.74 (s, 3 H), 2.73 (d, J=3.1 Hz, 2 H), 2.16 (br. s., 4 H), 1.92 (s, 5 H), 1.78-1.65 (m, 1 H), 1.65-1.52 (m, 1 H), 1.29 (s, 3 H); LC/MS (m/z) ES$^{+}$=466 (M+1).

Scheme 6: General Route for Synthesis of Examples with a R$^{7}$ = Nitrogen Bearing Substituent using Palladium Chemistry

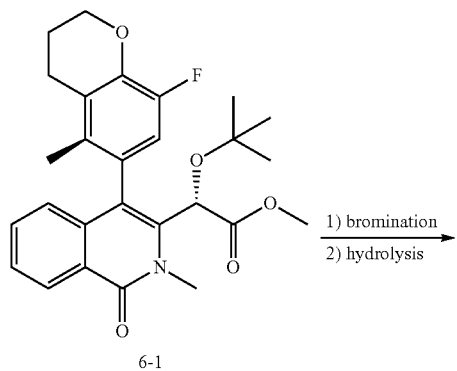

6-1

1) bromination
2) hydrolysis

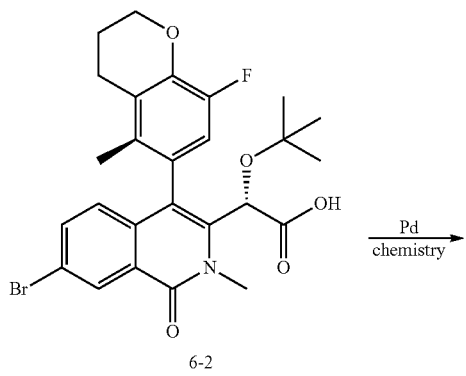

6-2

Pd chemistry

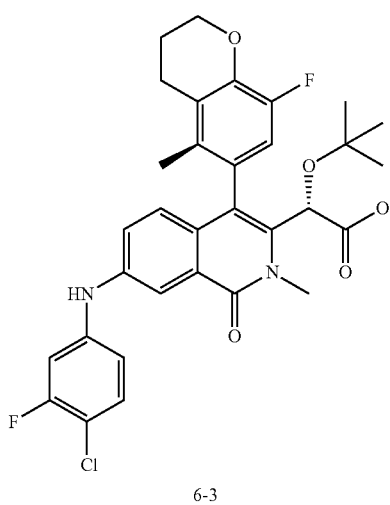

6-3

Example 165

(2S)(M)-[7-[(4-chloro-3-fluorophenyl)amino]-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid

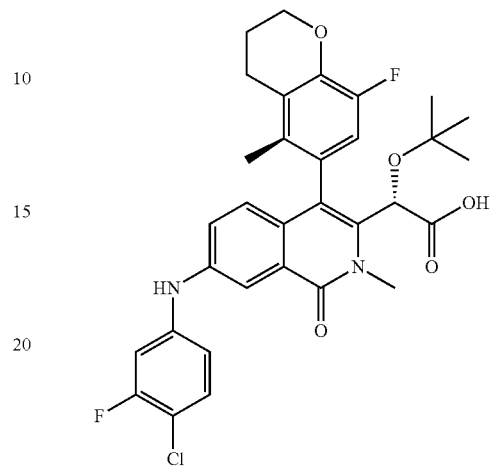

Step A

Methyl (2S)(M)-[7-bromo-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoate

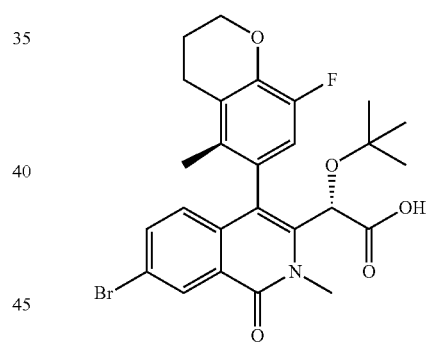

An ice cold mixture of (S)(M)-methyl 2-(tert-butoxy)-2-(4-(8-fluoro-5-methylchroman-6-yl)-2-methyl-1-oxo-1,2-dihydroisoquinolin-3-yl)acetate (528 mg, 1.129 mmol) in N,N-Dimethylformamide (DMF) (8.0 mL) was treated slowly with a solution of bromine (0.116 mL, 2.259 mmol) in Dichloromethane (DCM) (0.4 mL) to give an orange solution. The ice bath was removed and the mixture, which was excluded from light by wrapping the reaction vessel with aluminum foil, was allowed to stir at ambient temperature overnight. The mixture was cooled to 0° C., quenched with saturated sodium bicarbonate and then extracted with ethyl acetate. The extracts were washed with water, followed by brine, dried over sodium sulfate, filtered and then concentrated. The residue was purified on silica gel (0-50% ethyl acetate/hexanes gradient) to afford the title compound as a white foam (480 mg, 78%). $^{1}$H NMR (400 MHz, CHLOROFORM-d) δ=8.63 (d, J=2.0 Hz, 1 H), 7.57 (dd, J=2.0, 8.6 Hz, 1 H), 6.81 (d, J=10.9 Hz, 1 H), 6.70 (d, J=8.6 Hz, 1 H), 5.11 (s, 1 H), 4.32 (t, J=5.1 Hz, 2 H), 3.74 (s, 3 H), 3.68 (s, 3 H), 2.74 (t, J=6.4 Hz, 2 H), 2.27-2.08 (m, 2 H), 1.83 (s, 3 H), 1.22-1.09 (s, 9 H); LC/MS (m/z) ES+=546 (M+1).

Step B (2S)(M)-[7-bromo-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid

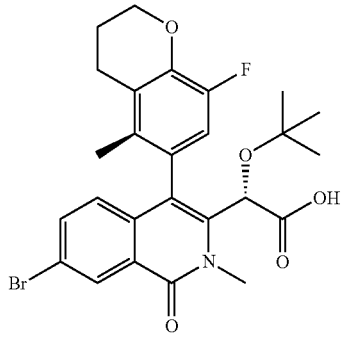

A mixture of (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate (15.00 mg, 0.027 mmol) in tetrahydrofuran (THF) (0.5 mL), methanol (0.5 mL) and water (0.2 mL) was treated with lithium hydroxide (25.00 mg, 1.044 mmol) and heated to 60° C. for 2 hours. The mixture was concentrated, partitioned between 1N hydrochloric acid and ethyl acetate and the layers were separated. The organic phase was washed with brine, dried over sodium sulfate, filtered and concentrated. The residue was purified by reverse phase chromatography to afford the title compound as a white solid (14 mg, 94%). $^1$H NMR (400 MHz, CHLOROFORM-d) δ=8.64 (d, J=2.0 Hz, 1 H), 7.60 (dd, J=2.1, 8.6 Hz, 1 H), 6.83 (d, J=11.1 Hz, 1 H), 6.74 (d, J=8.8 Hz, 1 H), 5.20 (s, 1 H), 4.31 (m, 2 H), 3.71 (s, 3 H), 2.82-2.65 (m, 2 H), 2.22-2.06 (m, 2 H), 1.93 (s, 3 H), 1.23 (s, 9 H); LC/MS (m/z) ES+=532 (M+1).

Step C (2S)(M)-[7-[(4-chloro-3-fluorophenyl)amino]-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid

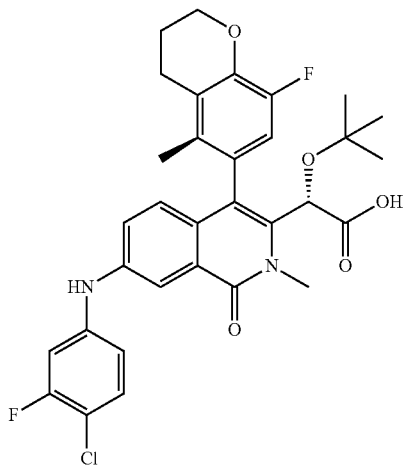

A degassed mixture of (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate (22.00 mg, 0.040 mmol), 4-chloro-3-fluoroaniline (11.72 mg, 0.081 mmol) and sodium tert-butoxide (11.61 mg, 0.121 mmol) in 1,4-Dioxane (1.0 mL) was treated with Pd$_2$(dba)$_3$ (2.084 mg, 2.013 μmol) and 2-dicyclohexylphosphino-2'-(N,N-dimethyl-amino)biphenyl (3.17 mg, 8.05 μmol) and then irradiated in the microwave at 100° C. for 10 minutes. The mixture was diluted with ethyl acetate and washed with saturated sodium bicarbonate, followed by brine. The organic phase was dried over sodium sulfate, filtered and concentrated. The crude residue in methanol (1.0 mL), tetrahydrofuran (THF) (1.0 mL) and water (0.2 mL) was treated with lithium hydroxide (19.28 mg, 0.805 mmol) and then heated at 65° C. for 4 hours. The mixture was concentrated, water was added and the mixture was adjusted to pH 3 with 1N hydrochloric acid. The mixture was extracted with ethyl acetate and the extracts were washed with brine, dried over sodium sulfate, filtered and concentrated. The residue was purified by reverse phase chromatography to afford the title compound as a tan solid (11.8 mg, 49%). $^1$H NMR (400 MHz, CHLOROFORM-d) δ=8.10 (m, 1 H), 7.32-7.17 (m, 2 H), 6.93 (m, 1 H), 6.89-6.74 (m, 3 H), 5.18 (s, 1 H), 4.31 (m, 2 H), 3.71 (s, 3 H), 2.78-2.67 (m, 2 H), 2.15 (m, 2 H), 1.96 (s, 3 H), 1.23 (s, 9 H); LC/MS (m/z) ES+=598 (M+1).

Example 166

(2S)(M)-[(1,1-dimethylethyl)oxy][4-(8-fluoro-5-methyl-3,4-dihydro-2H-chromen-6-yl)-2-methyl-1-oxo-7-(1-piperidinyl)-1,2-dihydro-3-isoquinolinyl]ethanoic acid

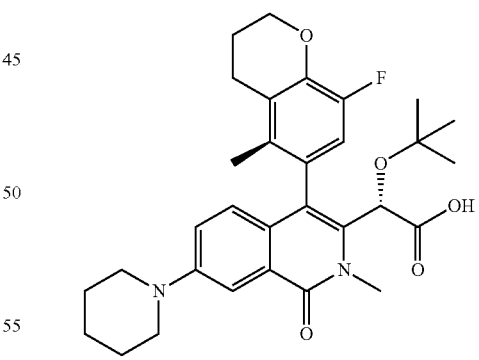

The title compound was prepared in two steps in a manner similar to that described in Example 165 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and piperidine and was isolated as a yellow solid (11.0 mg, 42%) after reverse phase chromatography. $^1$H NMR (400 MHz, CHLOROFORM-d) δ=8.43 (m, 1 H), 7.84 (m, 1 H), 6.97 (m, 1 H), 6.80 (m, 1 H), 5.21 (s, 1 H), 4.31 (t, J=5.0 Hz, 2 H), 3.73 (s, 3 H), 3.53 (m, 4 H), 2.71 (m, 2 H), 2.23-2.11 (m, 2 H), 2.05 (m, 4 H), 1.88 (s, 3 H), 1.75 (m, 2 H), 1.21 (s, 9 H); LC/MS (m/z) ES⁺=537 (M+1).

Example 167

(2S)(M)-[(1,1-dimethylethyl)oxy][7-(1,1-dioxido-4-thiomorpholinyl)-4-(8-fluoro-5-methyl-3,4-dihydro-2H-chromen-6-yl)-2-methyl-1-oxo-1,2-dihydro-3-isoquinolinyl]ethanoic acid

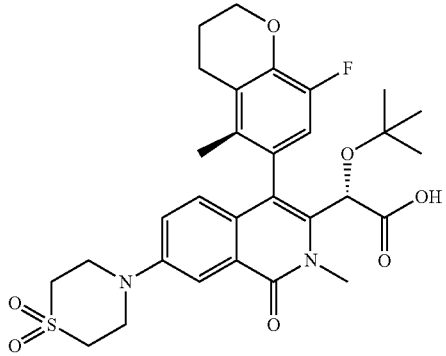

The title compound was prepared in two steps in a manner similar to that described in example 165 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and thiomorpholine 1,1-dioxide and was isolated as a colorless residue (1.6 mg, 6%) after reverse phase chromatography. ¹H NMR (400 MHz, CHLOROFORM-d) δ=7.91 (m, 1 H), 7.12 (m, 1 H), 6.89-6.76 (m, 2 H), 5.17 (s, 1 H), 4.36-4.26 (m, 2 H), 4.08-3.93 (m, 4 H), 3.71 (s, 3 H), 3.17-3.05 (m, 4 H), 2.78-2.61 (m, 2 H), 2.15 (m, 2 H), 1.96 (s, 3 H), 1.22 (s, 9 H); LC/MS (m/z) ES⁺=587 (M+1).

Example 168

(S)(M)-2-(tert-butoxy)-2-(4-(8-fluoro-5-methylchroman-6-yl)-2-methyl-7-morpholino-1-oxo-1,2-dihydroisoquinolin-3-yl)acetic acid

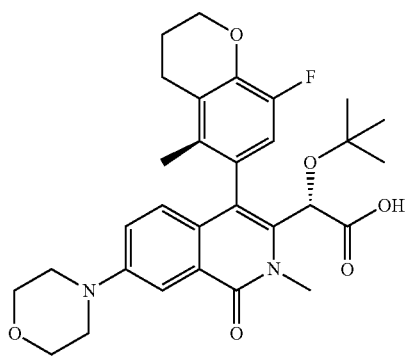

The title compound was prepared in two steps in a manner similar to that described in example 165 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and morpholine and was isolated as a tan solid (9.1 mg, 49%) after reverse phase chromatography. ¹H NMR (400 MHz, CHLOROFORM-d) d=7.89 (d, J=2.7 Hz, 1 H), 7.20 (dd, J=2.7, 9.0 Hz, 1 H), 6.89-6.76 (m, 2 H), 5.18 (s, 1 H), 4.31 (m, 2 H), 3.95-3.84 (m, 4 H), 3.73 (s, 3 H), 3.35-3.26 (m, 4 H), 2.72 (m, 2 H), 2.15 (m, 2 H), 1.93 (s, 3 H), 1.21 (s, 9 H); LC/MS (m/z) ES⁺=539 (M+1).

Scheme 7: General Route A for Synthesis of Examples with a R⁷ = Amide Bearing Substituent using Palladium Chemistry

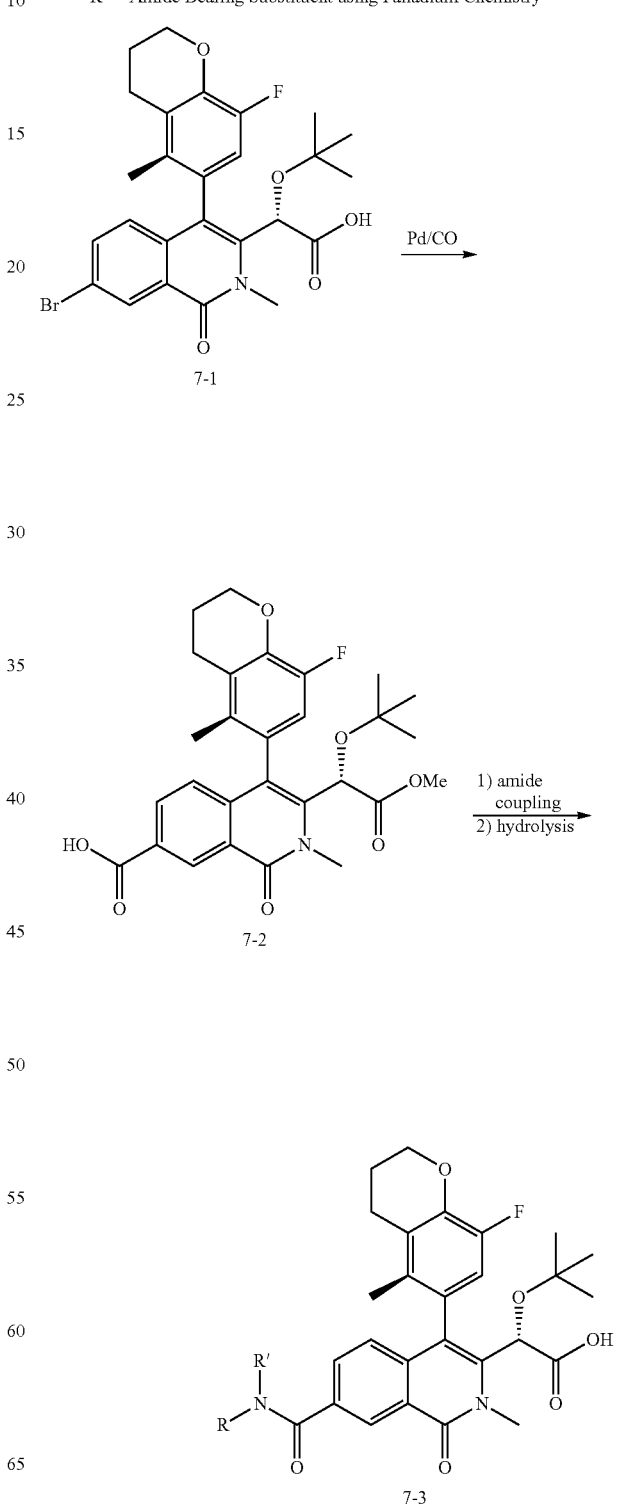

Example 169

(S)(M)-2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetic acid

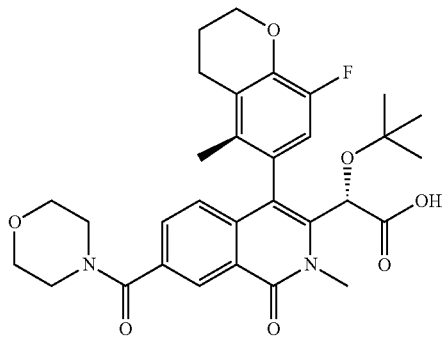

Step A (S)(M)-3-(1-(tert-butoxy)-2-methoxy-2-oxoethyl)-4-(8-fluoro-5-methylchroman-6-yl)-2-methyl-1-oxo-1,2-dihydroisoquinoline-7-carboxylic acid

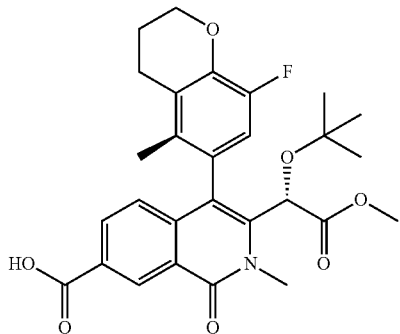

A mixture of (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate (38.5 mg, 0.070 mmol), dimethylamine (2M in THF) (176 µl, 0.352 mmol), and Hunig's base (24.61 µl, 0.141 mmol) in N,N-Dimethylformamide (DMF) (504 µl) and water (500 µl) was degassed with CO for 2 min, treated with Pd(OAc)$_2$ (1.5 mg, 7.05 µmol) and 1,3-bis(diphenylphosphino)propane (2.9 mg, 7.05 µmol). The reaction was degassed with CO for 3 min, placed under vacuum, filled and purged with CO 3×, and then stirred under 50 psi CO at 80° C. After 18 h, the reaction mixture was diluted with ethyl acetate and the organic layer washed with water, brine, dried (Na$_2$SO$_4$), filtered and concentrated. The residue was purified by reverse phase chromatography (10-100% MeCN/H2O-0.2% NH4OH) to afford (S)(M)-3-(1-(tert-butoxy)-2-methoxy-2-oxoethyl)-4-(8-fluoro-5-methyl-chroman-6-yl)-2-methyl-1-oxo-1,2-dihydroisoquinoline-7-carboxylic acid (11.6 mg, 0.023 mmol, 32.2% yield) as a colorless oil. LCMS (m/z) ES$^+$=512(M+1).

Step B (S)(M)-Methyl 2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetate

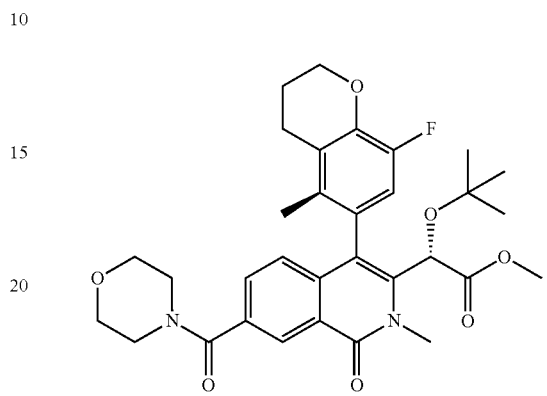

A solution of (S)(M)-3-(1-(tert-butoxy)-2-methoxy-2-oxoethyl)-4-(8-fluoro-5-methylchroman-6-yl)-2-methyl-1-oxo-1,2-dihydroisoquinoline-7-carboxylic acid (11 mg, 0.022 mmol) in ethyl acetate (398 µl) was treated with morpholine (7.49 µl, 0.086 mmol), Et$_3$N (8.99 µl, 0.065 mmol), and T3P (15.36 µl, 0.026 mmol). After stirring for 2.5 hours at rt, the reaction was concentrated and purified by reverse phase HPLC (10-100% MeCN/H$_2$O-0.2% NH$_4$OH) to afford (S)(M)-methyl 2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetate (7 mg, 0.012 mmol, 56.1% yield) as a white solid. LCMS (m/z) ES$^+$=581 (M+1).

Step C (S)(M)-2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetic acid

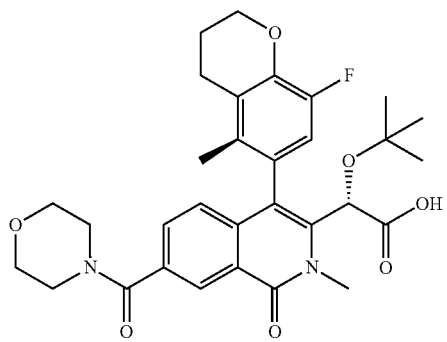

(S)(M)-methyl 2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetate was hydrolyzed in a manner similar to that described in Example 165 step C to afford (S)(M)-2-(tert-butoxy)-2-(4-(8-fluoro-5-methylchroman-6-yl)-2-methyl-7-(morpholine-4-carbonyl)-1-oxo-1,2-dihydroisoquinolin-3-yl)acetic acid (2.8 mg, 4.45 µmol, 39.7% yield) as a white solid. $^1$H NMR (400 MHz, CHLOROFORM-d) δ ppm 8.41 (d, J=1.7 Hz, 1 H), 7.59 (dd, J=1.8, 8.4 Hz, 1 H), 6.95 (d, J=8.5 Hz, 1 H), 6.79 (d, J=11.4 Hz, 1 H), 4.96 (s, 1 H), 4.25 (dd, J=4.6, 5.7 Hz, 2 H), 3.84 (s, 3 H), 3.84-3.58 (m, 6 H), 3.59-3.43 (m, 2 H), 2.85-2.65 (m, 2 H), 2.20-2.05 (m, 2 H), 1.99 (s, 3 H), 1.15 (s, 9 H); LCMS (m/z) ES$^+$=567 (M+1).

Scheme 8: General Route B for Synthesis of Examples with a R$^7$ = Amide Bearing Substituent using Palladium Chemistry

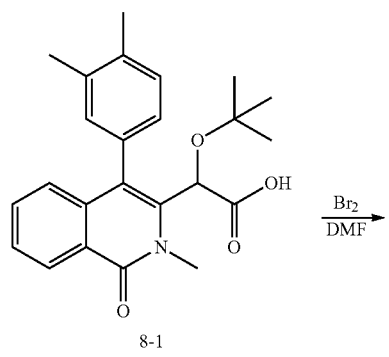

8-1

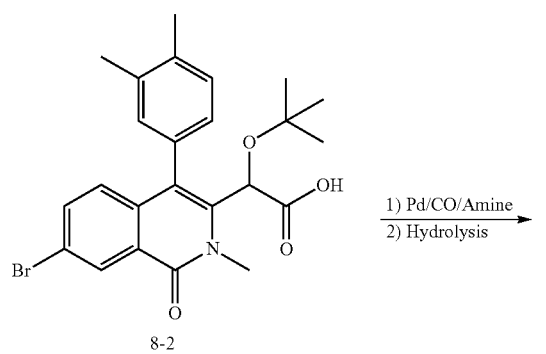

8-2

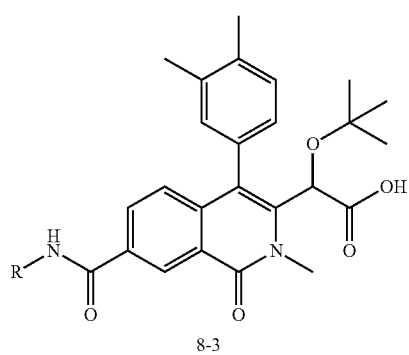

8-3

Example 170

[(1,1-dimethylethyl)oxy]{4-(3,4-dimethylphenyl)-7-[(ethylamino)carbonyl]-2-methyl-1-oxo-1,2-dihydro-3-isoquinolinyl}acetic acid

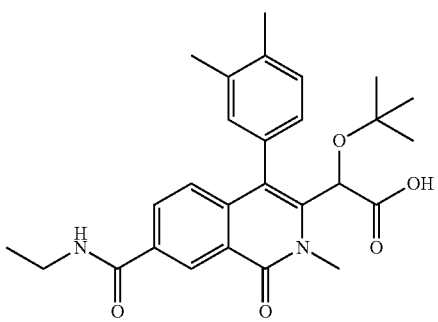 [SMILES: CCNC(=O)c1ccc2c(-c3ccc(C)c(C)c3)c(C(OC(C)(C)C)C(=O)O)n(C)c(=O)c2c1]

Step A methyl [7-bromo-4-(3,4-dimethylphenyl)-2-methyl-1-oxo-1,2-dihydro-3-isoquinolinyl][(1,1-dimethylethyl)oxy]acetate

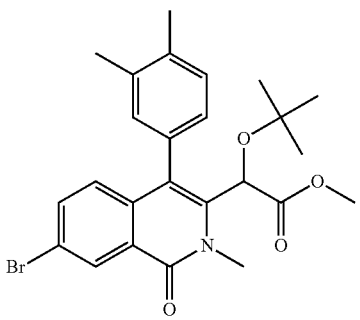 [SMILES: COC(=O)C(OC(C)(C)C)c1c(-c2ccc(C)c(C)c2)c2ccc(Br)cc2c(=O)n1C]

An ice cold mixture of methyl 2-(tert-butoxy)-2-(4-(3,4-dimethylphenyl)-2-methyl-1-oxo-1,2-dihydroisoquinolin-3-yl)acetate (187 mg, 0.459 mmol) in N,N-Dimethylformamide (DMF) (2.0 mL) was treated with a solution of bromine (0.071 mL, 1.377 mmol) in dichloromethane (DCM) (2.0 mL). The ice bath was removed and the mixture, which was excluded from light by wrapping the reaction vessel with aluminum foil, was allowed to stir at ambient temperature overnight. The mixture was quenched by adding saturated sodium bicarbonate and then extracted with ethyl acetate. The extracts were washed with water, then brine, dried over sodium sulfate, filtered and concentrated. The residue was purified on silica gel to afford the title compound as a thick colorless oil (123 mg, 55%) that solidified upon standing. $^1$H NMR (400 MHz, CHLOROFORM-d) δ=8.63 (d, J=2.1 Hz, 1 H), 7.56 (ddd, J=2.2, 6.0, 8.6 Hz, 1 H), 7.31-7.22 (m, 1 H), 7.20-6.88 (m, 3 H), 5.20 (s, 1 H), 3.83-3.74 (m, 3 H), 3.69 (m, 3 H), 2.37 (s, 3 H), 2.31 (s, 3 H), 1.01 (m, 9 H); LC/MS (m/z) ES+=486 (M+1).

Step B

Methyl [(1,1-dimethylethyl)oxy]{4-(3,4-dimethylphenyl)-7-[(ethylamino)carbonyl]-2-methyl-1-oxo-1,2-dihydro-3-isoquinolinyl}acetate

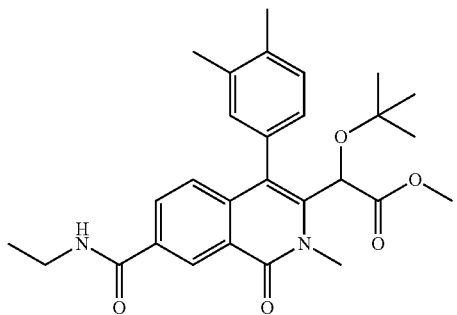 [SMILES: CCNC(=O)c1ccc2c(-c3ccc(C)c(C)c3)c(C(OC(C)(C)C)C(=O)OC)n(C)c(=O)c2c1]

A mixture of methyl [7-bromo-4-(3,4-dimethylphenyl)-2-methyl-1-oxo-1,2-dihydro-3-isoquinolinyl][(1,1-dimethylethyl)oxy]acetate (33 mg, 0.068 mmol), ethylamine HCl (11.06 mg, 0.136 mmol), and Hunig's base (47.4 µl, 0.271 mmol) in N,N-Dimethylformamide (DMF) (631 µl) was degassed with $N_2$ for 8 min, and then treated with $Pd(OAc)_2$ (1.5 mg, 6.78 µmol) and 1,3-bis(diphenylphosphino)propane (2.80 mg, 6.78 µmol). The reaction was placed under vacuum, filled and purged with N2 3×, followed by CO 3×. The reaction was stirred at 50 psi (CO) at 80° C. overnight. Additional DMF (1 mL), ethylamine HCl (11.06 mg, 0.136 mmol), and Hunig's base (47.4 µl, 0.271 mmol) were added, the reaction was degassed with N2 for 5 min, treated with $Pd(OAc)_2$ (1.523 mg, 6.78 µmol) and 1,3-bis(diphenylphosphino)propane (2.80 mg, 6.78 µmol), filled and purged with N2 3×, CO 3×, and stirred at 80° C. under 50 psi of CO for 5 hours. The mixture was filtered, extracted with EtOAc, washed with water, brine, dried with $Na_2SO_4$, filtered, and concentrated. The residue was purified by column chromatography (0-100% EtOAc/Hexane, followed with 0-20% MeOH/DCM) to afford methyl [(1,1-dimethylethyl)oxy]{4-(3,4-dimethylphenyl)-7-[(ethylamino)carbonyl]-2-methyl-1-oxo-1,2-dihydro-3-isoquinolinyl}acetate (9.3 mg, 0.019 mmol, 28.6% yield); LC/MS (m/z) ES+=479 (M+1).

Step C

[(1,1-dimethylethyl)oxy]{4-(3,4-dimethylphenyl)-7-[(ethylamino)carbonyl]-2-methyl-1-oxo-1,2-dihydro-3-isoquinolinyl}acetic acid Methyl [(1,1-dimethylethyl)oxy]{4-(3,4-dimethylphenyl)-7-[(ethylamino)carbonyl]-2-methyl-1-oxo-1,2-dihydro-3-isoquinolinyl}acetate was hydrolyzed in a manner similar to that described in Example 165 Step C to give [(1,1-dimethylethyl)oxy]{4-(3,4-dimethylphenyl)-7-[(ethylamino)carbonyl]-2-methyl-1-oxo-1,2-dihydro-3-isoquinolinyl}acetic acid (3.8 mg, 8.18 µmol, 48.9% yield) as a white solid: $^1$NMR (400 MHz, CHLOROFORM-d) δ ppm 8.76 (s, 1 H), 8.12 (t, J=6.9 Hz, 1 H), 7.43-7.28 (m, 2 H), 7.25-7.14 (m, 1 H), 7.12-6.97 (m, 1 H), 6.55 (br. s., 1 H), 5.38 (s, 1 H), 3.71 (s, 3 H), 3.61-3.44 (m, 2 H), 2.37 (s, 3 H), 2.32 (s, 3 H), 1.28 (t, J=7.3 Hz, 3 H), 1.12-1.01 (m, 9 H); LCMS (m/z) ES+=465 (M+1).

Scheme 9: General Route for Synthesis of Examples with a $R^7$ = Alkyl, Benzyl and Aromatic Bearing Substituents using Palladium Chemistry

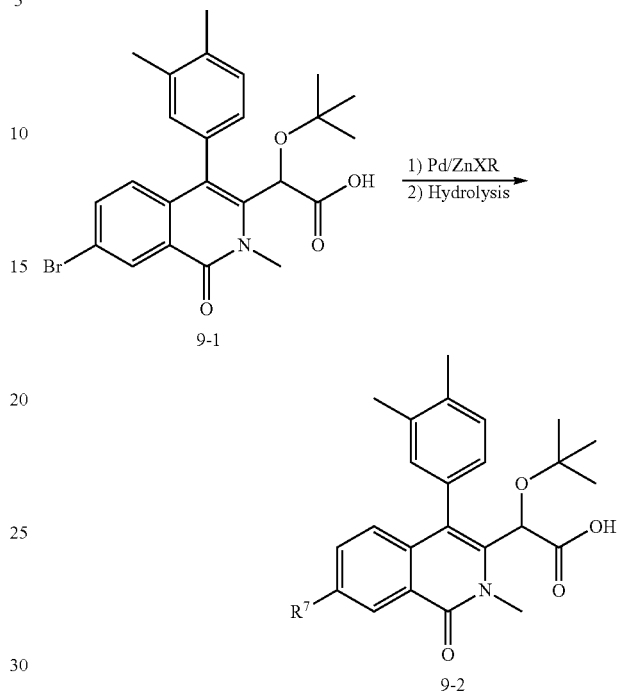

Example 171

[(1,1-dimethylethyl)oxy](4-(3,4-dimethylphenyl)-2-methyl-7-{[4-(methyloxy)phenyl]methyl}-1-oxo-1,2-dihydro-3-isoquinolinyl)acetic acid

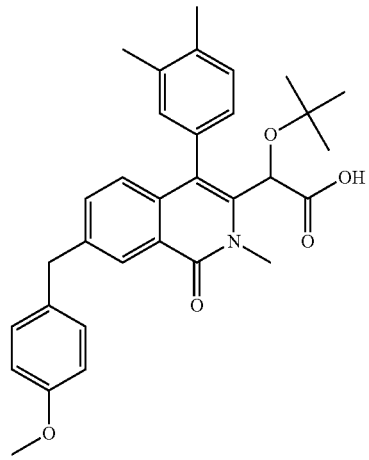 [SMILES: COc1ccc(Cc2ccc3c(-c4ccc(C)c(C)c4)c(C(OC(C)(C)C)C(=O)O)n(C)c(=O)c3c2)cc1]

A mixture of methyl [7-bromo-4-(3,4-dimethylphenyl)-2-methyl-1-oxo-1,2-dihydro-3-isoquinolinyl][(1,1-dimethylethyl)oxy]acetate (34.0 mg, 0.070 mmol) and (4-methoxybenzyl)zinc(II) bromide (0.280 mL, 0.140 mmol) in N,N-Dimethylformamide (DMF) (1.2 mL) was degassed with nitrogen for 5 minutes. $Pd(PPh_3)_4$ (8.08 mg, 6.99 µmol) was added and the mixture was irradiated in the microwave at 120° C. for 20 minutes. The mixture was diluted with ethyl acetate, washed with water, followed by brine, dried over sodium sulfate, filtered and then concentrated to give a dark residue. The crude residue was treated with 2M lithium hydroxide (0.140 mL, 0.280 mmol) in Tetrahydrofuran (THF) (0.8 mL) and Methanol (0.8 mL) and then stirred at 70° C. for 30 minutes. Additional 2 M lithium hydroxide (0.200 mL, 0.400 mmol) was added and the mixture was stirred at 70° C. for 2 additional hours. The mixture was concentrated and the residue was purified by reverse phase chromatography to afford the title compound as a white solid (11 mg, 31%). $^1$H NMR (400 MHz, CHLOROFORM-d) δ=8.39-8.30 (m, 1 H), 7.41-7.29 (m, 2 H), 7.29-7.18 (m, 1 H), 7.17-7.09 (m, 2 H), 7.09-6.96 (m, 2 H), 6.81 (dd, J=2.0, 8.6 Hz, 2 H), 5.34 (s, 1 H), 4.04 (s, 2 H), 3.77 (s, 3 H), 3.68 (s, 3 H), 2.35 (m, 3 H), 2.30 (m, 3 H), 1.06 (m, 9 H); LC/MS (m/z) ES$^+$=514 (M+1).

Example 172

[(1,1-dimethylethyl)oxy][4-(3,4-dimethylphenyl)-2-methyl-7-(2-methylpropyl)-1-oxo-1,2-dihydro-3-isoquinolinyl]acetic acid

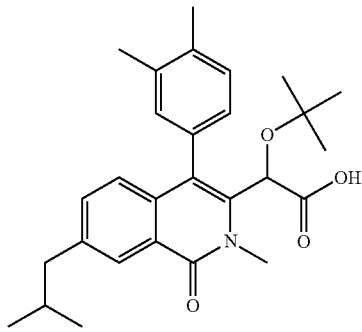 [SMILES: Cc1ccc(-c2c(C(OC(C)(C)C)C(=O)O)n(C)c(=O)c3cc(CC(C)C)ccc23)cc1C]

The title compound was prepared in two steps in a manner similar to that described in Example 171 from methyl 2-(7-bromo-4-(3,4-dimethylphenyl)-2-methyl-1-oxo-1,2-dihydroisoquinolin-3-yl)-2-(tert-butoxy)acetate and isobutylzinc (II) bromide and was isolated as a white solid (11.7 mg, 37%) after reverse phase chromatography: $^1$H NMR (400 MHz, CHLOROFORM-d) δ=8.27 (s, 1 H), 7.42-7.22 (m, 3 H), 7.16-7.00 (m, 2 H), 5.35 (m, 1 H), 3.70 (s, 3 H), 2.61 (m, 2 H), 2.36 (m, 3 H), 2.32 (m, 3 H), 2.00-1.85 (m, 1 H), 1.07 (m, 9 H), 0.96-0.85 (m, 6 H); LC/MS (m/z) ES$^+$=450 (M+1).

Example 173

(2S)(M)-[(1,1-dimethylethyl)oxy][4-(8-fluoro-5-methyl-3,4-dihydro-2H-chromen-6-yl)-2-methyl-7-(6-methyl-2-pyridinyl)-1-oxo-1,2-dihydro-3-isoquinolinyl]ethanoic acid

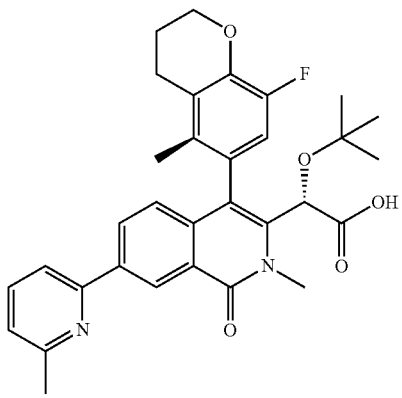

A mixture of (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate (22.00 mg, 0.040 mmol) and (3-methylpyridin-2-yl)zinc(II) bromide in N,N-Dimethylformamide (DMF) (1.2 mL) was treated with Pd(PPh$_3$)$_4$ (4.65 mg, 4.03 μmol) and then irradiated in the microwave at 120° C. for 20 minutes. The mixture was diluted with ethyl acetate and washed with saturated sodium bicarbonate, then brine. The organic phase was dried over sodium sulfate, filtered and concentrated. The crude residue, in methanol (0.75 mL), tetrahydrofuran (THF) (0.75 mL) and water (0.2 mL), was treated with lithium hydroxide (9.64 mg, 0.403 mmol) and heated to 60° C. for 40 minutes. Additional lithium hydroxide (9.64 mg, 0.403 mmol) was added and heating was continued at 60° C. for 5 additional hours. The mixture was concentrated, partitioned between ethyl acetate and 1N hydrochloric acid, and then extracted with ethyl acetate. The extracts were washed with brine, dried over sodium sulfate, filtered and concentrated. The residue was purified by reverse phase chromatography to afford the desired product as a slightly impure pale yellow solid (12.4 mg, 47%) as the trifluoroacetate salt. $^1$H NMR (400 MHz, CHLOROFORM-d) δ=8.80 (s, 1 H), 8.66 (s, 1 H), 8.21 (m), 7.84-7.55 (m, 1 H), 7.55-7.40 (m, 2 H), 7.08 (m, 1 H), 6.86 (m, 1 H), 5.22 (s, 1 H), 4.36-4.22 (m, 2 H), 3.73 (s, 3 H), 2.72 (s, 2 H), 2.55 (s, 3 H), 2.24-2.05 (m, 2 H), 1.88 (s, 3 H), 1.22 (s, 9 H); LC/MS (m/z) ES$^+$=545 (M+1).

Example 174

(2S)(M)-[(1,1-dimethylethyl)oxy][4-(8-fluoro-5-methyl-3,4-dihydro-2H-chromen-6-yl)-2-methyl-7-(2-methylpropyl)-1-oxo-1,2-dihydro-3-isoquinolinyl]ethanoic acid

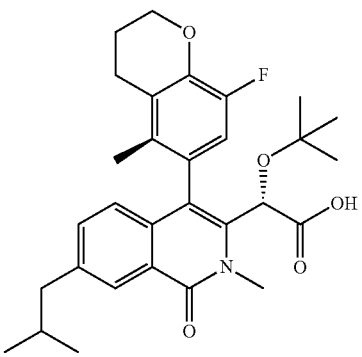

The title compound was prepared in two steps in a manner similar to that described in Example 173 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and isobutylzinc bromide, except that the intermediate Negishi product was purified by reverse phase chromatography before the ester hydrolysis step. Following the hydrolysis step, the title compound was isolated a white solid (11.2 mg, 58%) after reverse phase chromatography. $^1$H NMR (400 MHz, CHLOROFORM-d) d=8.27 (d, J=1.6 Hz, 1 H), 7.31 (dd, J=1.9, 8.3 Hz, 1 H), 6.85 (m, 1 H), 6.77 (d, J=8.4 Hz, 1 H), 5.20 (s, 1 H), 4.31 (m, 2 H), 3.72 (s, 3 H), 2.78-2.67 (m, 2 H), 2.60 (d, J=7.2 Hz, 2 H), 2.24-2.08 (m, 2 H), 1.99-1.84 (m, 4 H), 1.22 (s, 9 H), 0.91 (d, J=6.6 Hz, 6 H); LC/MS (m/z) ES⁺=510 (M+1).

Example 175

(2S)(M)-[(1,1-dimethylethyl)oxy][4-(8-fluoro-5-methyl-3,4-dihydro-2H-chromen-6-yl)-2-methyl-1-oxo-7-(phenylmethyl)-1,2-dihydro-3-isoquinolinyl] ethanoic acid

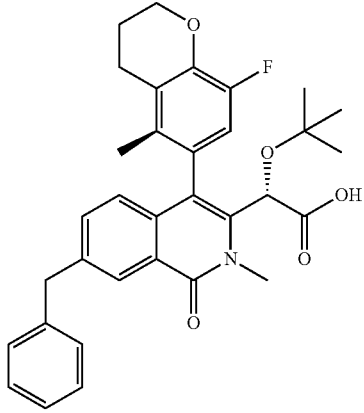

The title compound was prepared in two steps in a manner similar to that described in Example 173 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and benzylzinc bromide, except that the intermediate Negishi product was purified by reverse phase chromatography before the ester hydrolysis step. Following the hydrolysis step, the title compound was isolated a white solid (11.1 mg, 52%) after reverse phase chromatography. ¹H NMR (400 MHz, CHLOROFORM-d) δ=8.37 (d, J=1.4 Hz, 1 H), 7.33 (dd, J=1.8, 8.4 Hz, 1 H), 7.30-7.24 (m, 2 H), 7.22-7.16 (m, 3 H), 6.82 (m, 1 H), 6.77 (d, J=8.4 Hz, 1 H), 5.20 (s, 1 H), 4.30 (m, 2 H), 4.10 (s, 2 H), 3.71 (s, 3 H), 2.71 (m, 2 H), 2.22-2.04 (m, 2 H), 1.93 (s, 3 H), 1.22 (s, 9 H); LC/MS (m/z) ES⁺=544 (M+1).

Example 176

(2S)(M)-[(1,1-dimethylethyl)oxy][4-(8-fluoro-5-methyl-3,4-dihydro-2H-chromen-6-yl)-2-methyl-1-oxo-7-(2-phenylethyl)-1,2-dihydro-3-isoquinolinyl] ethanoic acid

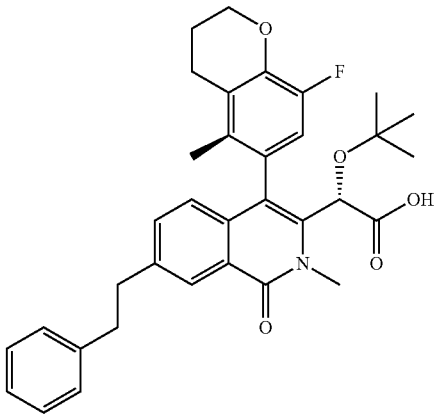

The title compound was prepared in two steps in a manner similar to that described in Example 173 from (S)-methyl 2-(7-bromo-4-(8-fluoro-5-methylchroman-6-yl)-2-methyl-1-oxo-1,2-dihydroisoquinolin-3-yl)-2-(tert-butoxy)acetate and phenethylzinc bromide, except that the intermediate Negishi product was purified by reverse phase chromatography before the ester hydrolysis step. Following the hydrolysis step, the title compound was isolated a white solid (9.2 mg, 45%) after reverse phase chromatography. ¹H NMR (400 MHz, CHLOROFORM-d) δ=8.37 (m, 1 H), 7.37-7.25 (m, 3 H), 7.21 (m, 3 H), 6.84 (m, 1 H), 6.77 (d, J=8.4 Hz, 1 H), 5.21 (s, 1 H), 4.35-4.24 (m, 2 H), 3.75-3.67 (m, 3 H), 3.11-3.01 (m, 2 H), 3.01-2.92 (m, 2 H), 2.82-2.62 (m, 2 H), 2.23-2.06 (m, 2 H), 1.94 (s, 3 H), 1.27-1.17 (m, 9 H); LC/MS (m/z) ES⁺=558 (M+1).

Scheme 10: General Route for Synthesis of Examples with a R⁷ = Nitrile, Primary Amide, and Methyl Amine Bearing Substituents using Palladium Chemistry

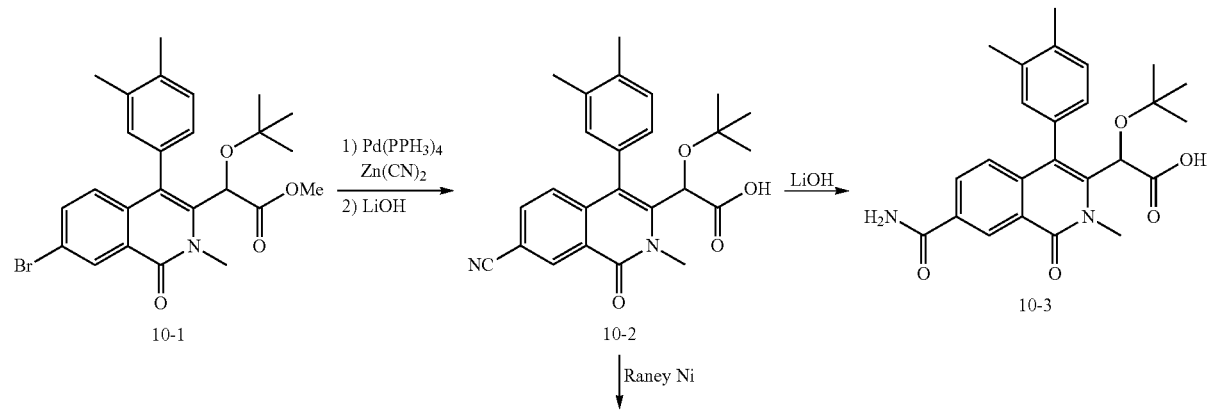

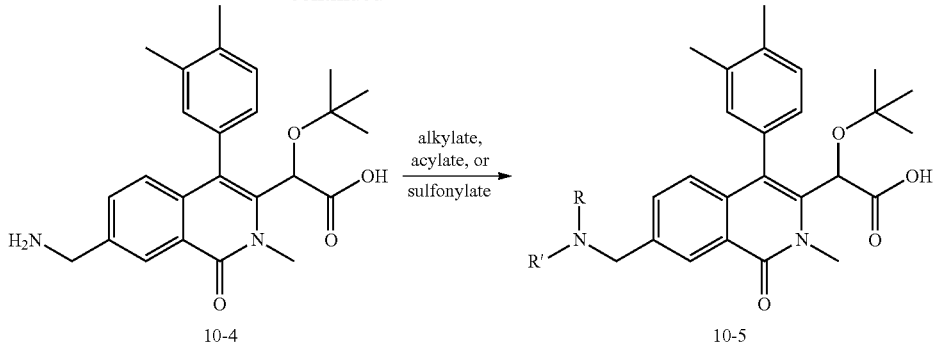

10-4 → 10-5 (alkylate, acylate, or sulfonylate)

Example 177

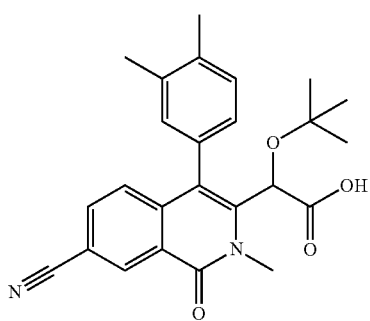 [SMILES: Cc1ccc(-c2c(C(OC(C)(C)C)C(=O)O)n(C)c(=O)c3cc(C#N)ccc23)cc1C]

7-cyano-4-(3,4-dimethylphenyl)-2-methyl-1-oxo-1,2-dihydro-3-isoquinolinyl]][(1,1-dimethylethyl)oxy]acetic acid

Step A

Methyl [7-cyano-4-(3,4-dimethylphenyl)-2-methyl-1-oxo-1,2-dihydro-3-isoquinolinyl]][(1,1-dimethylethyl)oxy]acetate

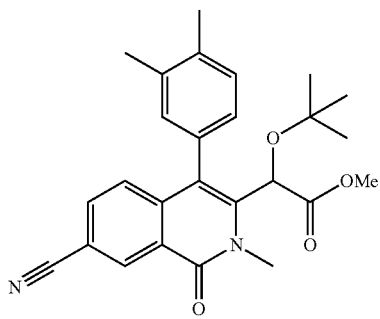 [SMILES: COC(=O)C(OC(C)(C)C)c1c(-c2ccc(C)c(C)c2)c2ccc(C#N)cc2c(=O)n1C]

A mixture of methyl [7-bromo-4-(3,4-dimethylphenyl)-2-methyl-1-oxo-1,2-dihydro-3-isoquinolinyl]][(1,1-dimethylethyl)oxy]acetate (160 mg, 0.329 mmol) and Zn(CN)$_2$ (38.6 mg, 0.329 mmol) in N,N-Dimethylformamide (DMF) (3289 µl) was degassed with N$_2$ for 5 min, treated with Pd(Ph$_3$P)$_4$ (38.0 mg, 0.033 mmol), and irradiated in microwave at 120° C. for 30 min. The mixture was diluted with water, extracted with EtOAc, washed with water, brine, dried with Na$_2$SO$_4$, filtered, and concentrated. the residue was purified by column chromatography (SiO2, 0-60% EtOAc/Hexane) to afford methyl [7-cyano-4-(3,4-dimethylphenyl)-2-methyl-1-oxo-1,2-dihydro-3-isoquinolinyl]][(1,1-dimethylethyl)oxy]acetate (116.8 mg, 0.270 mmol, 82% yield) as colorless oil that slowly became a white solid: $^1$H NMR (400 MHz, CHLOROFORM-d) δ ppm 8.85-8.76 (m, 1 H), 7.65 (ddd, J=1.9, 6.1, 8.3 Hz, 1 H), 7.30-7.24 (m, 1 H), 7.23-7.09 (m, 2 H), 7.07-6.96 (m, 1 H), 5.22 (s, 1 H), 3.80 (s, 1.5 H), 3.78 (s, 1.5 H), 3.70 (s, 1.5 H), 3.69 (s, 1.5 ; H), 2.37 (s, 3 H), 2.32 (s, 3 H), 1.02 (s, 4.5 H), 1.01 (s, 4.5 H); LCMS (m/z) ES$^+$=433 (M+1).

Step B

[7-cyano-4-(3,4-dimethylphenyl)-2-methyl-1-oxo-1,2-dihydro-3-isoquinolinyl]][(1,1-dimethylethyl)oxy]acetic acid

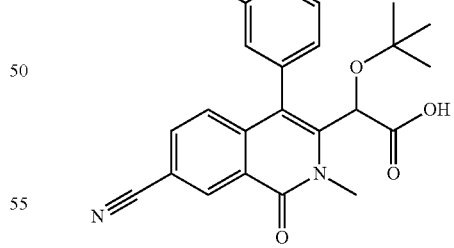

Methyl [7-cyano-4-(3,4-dimethylphenyl)-2-methyl-1-oxo-1,2-dihydro-3-isoquinolinyl]][(1,1-dimethylethyl)oxy]acetate was hydrolyzed in a manner similar to that described in Example 165 Step C to afford [7-cyano-4-(3,4-dimethylphenyl)-2-methyl-1-oxo-1,2-dihydro-3-isoquinolinyl]][(1,1-dimethylethyl)oxy]acetic acid (6.2 mg, 0.015 mmol, 37.7% yield) as white solid: $^1$H NMR (400 MHz, CHLOROFORM-d) δ ppm 8.80 (s, 1 H), 7.68 (ddd, J=1.7, 6.7, 8.4 Hz, 1 H), 7.39-7.28 (m, 2 H), 7.23 (dd, J=8.5, 13.3 Hz, 1 H), 7.07-6.97

(m, 1 H), 5.35 (s, 1 H), 3.71 (s, 3 H), 2.37 (s, 3 H), 2.35-2.30 (m, 3 H), 1.08 (s, 4.5 H), 1.07 (s, 4.5 H); LCMS (m/z) ES$^+$=419 (M+1).

Example 178

[7-(aminocarbonyl)-4-(3,4-dimethylphenyl)-2-methyl-1-oxo-1,2-dihydro-3-isoquinolinyl][(1,1-dimethylethyl)oxy]acetic acid

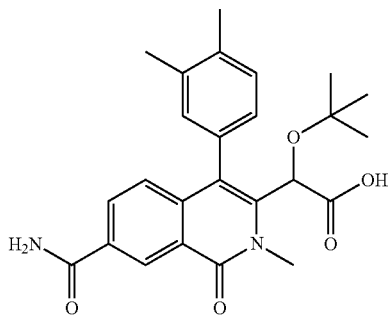 [SMILES: Cc1ccc(-c2c(C(OC(C)(C)C)C(=O)O)n(C)c(=O)c3cc(C(N)=O)ccc23)cc1C]

A solution of methyl [7-cyano-4-(3,4-dimethylphenyl)-2-methyl-1-oxo-1,2-dihydro-3-isoquinolinyl][(1,1-dimethylethyl)oxy]acetate (17 mg, 0.039 mmol) in tetrahydrofuran (THF) (0.600 mL) and methanol (0.6 mL) was treated with LiOH (0.118 mL, 0.236 mmol) and stirred at 50° C. for 2 hours. Additional LiOH (300 uL) was added and the reaction was stirred at 50° C. for 4 h, and then cooled to rt overnight. The mixture was concentrated and purified with reverse phase chromatography (20-100% MeCN/H2O-0.1% TFA, 12 min) to afford [7-(aminocarbonyl)-4-(3,4-dimethylphenyl)-2-methyl-1-oxo-1,2-dihydro-3-isoquinolinyl][(1,1-dimethylethyl)oxy]acetic acid (9.6 mg, 0.022 mmol, 56.0% yield) as white solid: $^1$H NMR (400 MHz, CHLOROFORM-d) δ ppm 9.02 (s, 1 H), 8.22-8.10 (m, 1 H), 7.39-7.28 (m, 4 H), 7.25-7.15 (m, 1 H), 7.09-6.99 (m, 1 H), 5.39 (d, J=1.2 Hz, 1 H), 3.76 (s, 3 H), 2.38 (s, 3 H), 2.33 (s, 3 H), 1.08 (s, 4.5 H), 1.06 (s, 4.5 H); LCMS (m/z) ES$^+$=437 (M+1).

Example 179

[7-(aminomethyl)-4-(3,4-dimethylphenyl)-2-methyl-1-oxo-1,2-dihydro-3-isoquinolinyl][(1,1-dimethylethyl)oxy]acetic acid-TFA salt

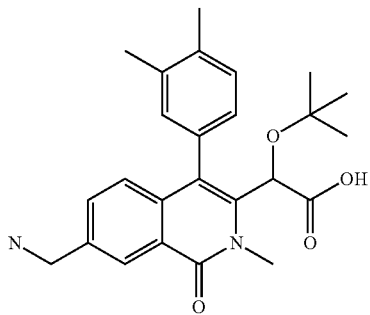 [SMILES: Cc1ccc(-c2c(C(OC(C)(C)C)C(=O)O)n(C)c(=O)c3cc(CN)ccc23)cc1C]

A solution of methyl [7-cyano-4-(3,4-dimethylphenyl)-2-methyl-1-oxo-1,2-dihydro-3-isoquinolinyl][(1,1-dimethylethyl)oxy]acetate (30 mg, 0.069 mmol) in Ethanol (3.5 mL), saturated with ammonia gas, was treated with Raney 2800 Nickel (0.5 mL, 0.069 mmol), purged and filled with N$_2$ 3×, H$_2$ 3×, and stirred under H$_2$ at 40 psi overnight. The mixture was filtered through Celite, washed with MeOH, and concentrated. The residue was purified by column chromatography (0-20% MeOH/DCM) to afford methyl [7-(aminomethyl)-4-(3,4-dimethylphenyl)-2-methyl-1-oxo-1,2-dihydro-3-isoquinolinyl][(1,1-dimethylethyl)oxy]acetate (23.7 mg, 0.054 mmol, 78% yield) as a colorless oil. The methyl ester was hydrolyzed in a manner similar to that described in Example 165 Step C and purified by reverse phase HPLC to afford [7-(aminomethyl)-4-(3,4-dimethylphenyl)-2-methyl-1-oxo-1,2-dihydro-3-isoquinolinyl][(1,1-dimethylethyl)oxy]acetic acid-TFA salt (18.8 mg, 0.033 mmol, 76% yield) as off white solid: $^1$H NMR (400 MHz, METHANOL-d$_4$) δ ppm 8.42 (s, 1 H), 7.61 (d, J=8.4 Hz, 1 H), 7.36-7.15 (m, 3 H), 7.11-6.99 (m, 1 H), 5.23 (s, 1 H), 4.23 (s, 2 H), 3.70 (s, 3 H), 2.36 (s, 3 H), 2.31 (s, 3 H), 0.98 (s, 9 H); LCMS (m/z) ES$^+$=423 (M+1).

Example 180

2,2'-(iminobis{methanediyl[4-(3,4-dimethylphenyl)-2-methyl-1-oxo-1,2-dihydroisoquinoline-7,3-diyl]})bis{[(1,1-dimethylethyl)oxy]acetic acid}

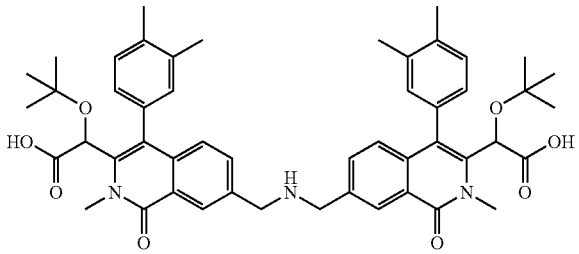 [SMILES: Cc1ccc(-c2c(C(OC(C)(C)C)C(=O)O)n(C)c(=O)c3cc(CNCc4ccc5c(-c6ccc(C)c(C)c6)c(C(OC(C)(C)C)C(=O)O)n(C)c(=O)c5c4)ccc23)cc1C]

A solution of methyl [7-cyano-4-(3,4-dimethylphenyl)-2-methyl-1-oxo-1,2-dihydro-3-isoquinolinyl][(1,1-dimethylethyl)oxy]acetate (53 mg, 0.123 mmol) in methanol (817 µl) and tetrahydrofuran (THF) (408 µl) was treated with 10% Pd/C (13.04 mg, 0.012 mmol), purged and filled with N2 3×, H2 3×, and then stirred at 50 psi at rt overnight. The reaction was filtered through celite, washed with MeOH and EtOAc, and concentrated. The residue was purified by column chromatography (0-100% EtOAc/Hexane, then 0-20% MeOH/DCM) to afford dimethyl 2,2'-(7,7'-(azanediylbis(methylene))bis(4-(3,4-dimethylphenyl)-2-methyl-1-oxo-1,2-dihydroisoquinoline-7,3-diyl))bis(2-(tert-butoxy)acetate) (16.3 mg, 0.019 mmol, 15.54% yield) as clear oil. The bis-methyl ester was hydrolyzed in a manner similar to that described in Example 165 Step C and purified by reverse phase HPLC to afford 2,2'-(iminobis{methanediyl[4-(3,4-dimethylphenyl)-2-methyl-1-oxo-1,2-dihydroisoquinoline-7,3-diyl]})bis{[(1,1-dimethylethyl)oxy]acetic acid}(18.3 mg, 0.018 mmol, 98% yield) as an off-white solid: $^1$H NMR (400 MHz, METHANOL-d$_4$) δ ppm 8.51 (s, 2 H), 7.73-7.64 (m, 2 H), 7.40-7.17 (m, 6 H), 7.16-7.01 (m, 2 H), 5.27 (s, 2 H), 4.43 (s, 4 H), 3.73 (d, J=1.7 Hz, 6 H), 2.39 (s, 6 H), 2.34 (s, 6 H), 1.01 (s, 18 H); LCMS (m/z) ES$^+$=828 (M+1).

Example 181

2-(tert-butoxy)-2-(4-(3,4-dimethylphenyl)-2-methyl-7-(methylsulfonamidomethyl)-1-oxo-1,2-dihydroisoquinolin-3-yl)acetic acid

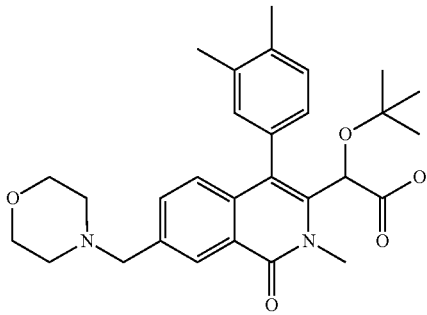 [SMILES: Cc1ccc(-c2c(C(OC(C)(C)C)C(=O)O)n(C)c(=O)c3cc(CN4CCOCC4)ccc23)cc1C]

A solution of methyl 2-(7-(aminomethyl)-4-(3,4-dimethylphenyl)-2-methyl-1-oxo-1,2-dihydroisoquinolin-3-yl)-2-(tert-butoxy)acetate (17 mg, 0.039 mmol) in toluene (750 μl) was treated with DIEA (13.60 μl, 0.078 mmol) and 1-bromo-2-(2-bromoethoxy)ethane (5.87 μl, 0.047 mmol). The mixture was stirred at 90° C. for 6 hours. Additional DIEA (13.60 μl, 0.078 mmol) and 1-bromo-2-(2-bromoethoxy)ethane (5.87 μl, 0.047 mmol) were added, the reaction was stirred at 90° C. overnight. The reaction was cooled to rt, diluted with EtOAc, washed with water, brine, dried with $Na_2SO_4$, filtered, and concentrated. The residue was purified by column chromatography (0-10% MeOH/DCM) to afford methyl 2-(tert-butoxy)-2-(4-(3,4-dimethylphenyl)-2-methyl-7-(morpholinomethyl)-1-oxo-1,2-dihydroisoquinolin-3-yl)acetate (15.6 mg, 0.031 mmol, 79% yield). The methyl ester was hydrolyzed in a manner similar to that described in Example 165 Step C and purified by reverse phase HPLC to afford 2-(tert-butoxy)-2-(4-(3,4-dimethyl phenyl)-2-methyl-7-(methylsulfonamidomethyl)-1-oxo-1,2-dihydroisoquinolin-3-yl)acetic acid (14 mg, 0.027 mmol, 88% yield) as a white solid. $^1$H NMR (400 MHz, CHLOROFORM-d) δ ppm 8.42 (s, 1 H), 7.71-7.61 (m, 1 H), 7.24-7.33 (m, 1 H), 7.26-7.17 (m, 2 H), 7.07-6.96 (m, 1 H), 5.35 (s, 1 H), 4.40-4.22 (m, 2 H), 4.03-3.81 (m, 4 H), 3.71 (s, 3 H), 3.59-3.37 (m, 2 H), 2.92 (br. s., 2 H), 2.37 (s, 3 H), 2.32 (s, 1.5 H), 2.29 (s, 1.5 H). 1.06 (s, 4.5 H), 1.05 (s, 4.5 H); LCMS (m/z) ES$^+$=493 (M+1).

Example 182

2-(7-((bis(pyridin-2-ylmethyl)amino)methyl)-4-(3,4-dimethylphenyl)-2-methyl-1-oxo-1,2-dihydroisoquinolin-3-yl)-2-(tert-butoxy)acetic acid

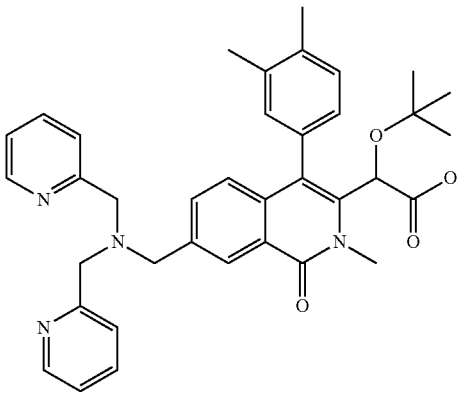 [SMILES: Cc1ccc(-c2c(C(OC(C)(C)C)C(=O)O)n(C)c(=O)c3cc(CN(Cc4ccccn4)Cc4ccccn4)ccc23)cc1C]

Example 183

2-(tert-butoxy)-2-(4-(3,4-dimethylphenyl)-2-methyl-1-oxo-7-(((pyridin-2-ylmethyl)amino)methyl)-1,2-dihydroisoquinolin-3-yl)acetic acid

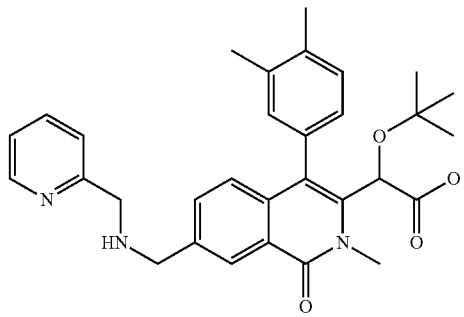 [SMILES: Cc1ccc(-c2c(C(OC(C)(C)C)C(=O)O)n(C)c(=O)c3cc(CNCc4ccccn4)ccc23)cc1C]

An ice cold solution of methyl 2-(7-(aminomethyl)-4-(3,4-dimethylphenyl)-2-methyl-1-oxo-1,2-dihydroisoquinolin-3-yl)-2-(tert-butoxy)acetate (25 mg, 0.057 mmol) in 1,2-Dichloroethane (DCE) (1 mL) was treated with picolinaldehyde (0.016 mL, 0.172 mmol) and acetic acid (6.56 μL, 0.115 mmol). The mixture was stirred at 00° C. for 10 min, warmed to rt for 30 min, treated with sodium triacetoxyborohydride (24.27 mg, 0.115 mmol), and stirred overnight. The reaction was quenched with sat. NaHCO$_3$, extracted with EtOAc 2×, washed with sat. NaHCO$_3$, brine, dried with Na$_2$SO$_4$, filtered, and concentrated. Purification with column chromatography (0-20% MeOH/DCM) gave 31.5 mg clear oil as mixture of 2-(7-((bis(pyridin-2-ylmethyl)amino)methyl)-4-(3,4-dimethylphenyl)-2-methyl-1-oxo-1,2-dihydroisoquinolin-3-yl)-2-(tert-butoxy)acetic acid and 2-(tert-butoxy)-2-(4-(3,4-dimethylphenyl)-2-methyl-1-oxo-7-(((pyridin-2-ylmethyl)amino)methyl)-1,2-dihydroisoquinolin-3-yl)acetic acid. The mixture was hydrolyzed in a manner similar to that described in Example 165 Step C and purified by reverse phase HPLC to afford: 2-(7-((bis(pyridin-2-ylmethyl)amino)methyl)-4-(3,4-dimethylphenyl)-2-methyl-1-oxo-1,2-dihydroisoquinolin-3-yl)-2-(tert-butoxy)acetic acid, Trifluoroacetic acid salt (28.8 mg, 0.038 mmol, 66.5% yield) as white solid. $^1$H NMR (400 MHz, CHLOROFORM-d) δ ppm 8.83 (d, J=4.9 Hz, 2 H), 8.27 (d, J=1.4 Hz, 1 H), 8.21-8.11 (m, 2 H), 7.92 (d, J=7.9 Hz, 2 H), 7.62 (t, J=6.7 Hz, 2 H), 7.59-7.49 (m, 1 H), 7.32-7.23 (m, 2 H), 7.13-6.93 (m, 2 H), 5.36 (s, 1 H), 4.27 (s, 4 H), 3.94 (s, 2 H), 3.67 (s, 3 H), 2.37 (s, 3 H), 2.32 (s, 3 H), 1.06 (s, 4.5 H), 1.05 (s, 4.5 H); LCMS (m/z) ES$^+$=605 (M+1) and 2-(tert-butoxy)-2-(4-(3,4-dimethylphenyl)-2-methyl-1-oxo-7-(((pyridin-2-ylmethyl)amino)methyl)-1,2-dihydroisoquinolin-3-yl)acetic acid, trifluoroacetic acid salt (5.4 mg, 7.74 μmol, 13.52% yield) as white solid. $^1$H NMR (400 MHz, CHLOROFORM-d) δ ppm 8.60 (d, J=4.8 Hz, 1 H), 8.49 (br. s., 1 H), 7.97 (t, J=7.7 Hz, 1 H), 7.91-8.01 (m, 1 H), 7.73-7.65 (m, 1 H), 7.65-7.57 (m, 1 H), 7.56-7.46 (m, 1 H), 7.33-7.23 (m, 2 H), 7.23-7.16 (m, 1 H), 7.09-6.96 (m, 1 H), 5.35 (s, 1 H), 4.47 (d, J=2.1 Hz, 2 H), 4.42 (s, 2 H), 3.66 (d, J=2.8 Hz, 3 H), 2.37 (s, 3 H), 2.31 (d, J=8.0 Hz, 3 H), 1.05 (d, J=6.1 Hz, 9 H). LCMS (m/z) ES$^+$=514 (M+1).

Example 184

2-(7-(acetamidomethyl)-4-(3,4-dimethylphenyl)-2-methyl-1-oxo-1,2-dihydroisoquinolin-3-yl)-2-(tert-butoxy)acetic acid

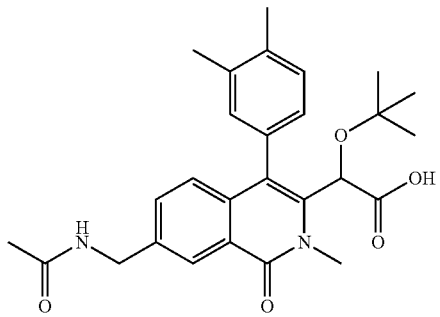 [SMILES: CC(=O)NCc1ccc2c(-c3ccc(C)c(C)c3)c(C(OC(C)(C)C)C(=O)O)n(C)c(=O)c2c1]

An ice cold solution of methyl 2-(7-(aminomethyl)-4-(3,4-dimethylphenyl)-2-methyl-1-oxo-1,2-dihydroisoquinolin-3-yl)-2-(tert-butoxy)acetate (25 mg, 0.057 mmol) in dichloromethane (DCM) (549 µl) was treated with Et₃N (15.96 µl, 0.115 mmol) and acetic anhydride (8.11 µl, 0.086 mmol), and then stirred for 3 hours. The mixture was quenched with sat. NaHCO₃, extracted with DCM, washed with brine, dried with Na₂SO₄, filtered, and concentrated. The residue was hydrolyzed in a manner similar to that described in Example 165 Step C and purified by reverse phase HPLC to afford 2-(7-(acetamidomethyl)-4-(3,4-dimethylphenyl)-2-methyl-1-oxo-1,2-dihydroisoquinolin-3-yl)-2-(tert-butoxy)acetic acid (21.6 mg, 0.045 mmol, 85% yield) as an off-white solid: ¹H NMR (400 MHz, CHLOROFORM-d) δ ppm, 8.37 (s, 1 H), 7.47 (t, J=7.3 Hz, 1 H), 7.39-7.29 (m, 1 H), 7.24 (d, J=7.2 Hz, 1 H), 7.13 (dd, J=8.4, 12.6 Hz, 1 H), 7.09-6.98 (m, 1 H), 6.11 (br. s., 1 H), 5.34 (s, 1 H), 4.63-4.45 (m, 2 H), 3.69 (s, 3 H), 2.36 (s, 3 H), 2.31 (s, 3 H), 2.05 (s, 3 H), 1.10-0.96 (m, 9 H); LCMS (m/z) ES+=465 (M+1).

Example 185

2-(tert-butoxy)-2-(4-(3,4-dimethylphenyl)-7-((3-ethylureido)methyl)-2-methyl-1-oxo-1,2-dihydroisoquinolin-3-yl)acetic acid

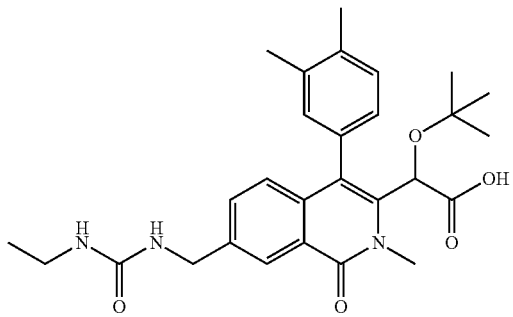 [SMILES: CCNC(=O)NCc1ccc2c(-c3ccc(C)c(C)c3)c(C(OC(C)(C)C)C(=O)O)n(C)c(=O)c2c1]

A solution of methyl 2-(7-(aminomethyl)-4-(3,4-dimethylphenyl)-2-methyl-1-oxo-1,2-dihydroisoquinolin-3-yl)-2-(tert-butoxy)acetate (17 mg, 0.039 mmol) in Toluene (750 µl) was treated with ethyl isocyanate (9.25 µl, 0.117 mmol) and stirred at 70° C. for 2 hours. The reaction was cooled to rt, concentrated, and purified with column chromatography (0-10% MeOH/DCM) to afford methyl 2-(tert-butoxy)-2-(4-(3,4-dimethylphenyl)-7-((3-ethylureido)methyl)-2-methyl-1-oxo-1,2-dihydroisoquinolin-3-yl)acetate (11.8 mg, 0.023 mmol, 59.7% yield). The methyl ester was then hydrolyzed in a manner similar to that described in Example 165 Step C and purified by reverse phase HPLC to afford 2-(tert-butoxy)-2-(4-(3,4-dimethylphenyl)-7-((3-ethylureido)methyl)-2-methyl-1-oxo-1,2-dihydroisoquinolin-3-yl)acetic acid (9.1 mg, 0.018 mmol, 86% yield) as a white solid: ¹H NMR (400 MHz, CHLOROFORM-d) δ ppm 8.35 (s, 1 H), 7.56-7.42 (m, 1 H), 7.37-7.28 (m, 1 H), 7.25-7.20 (m, 1 H), 7.12 (dd, J=8.5, 11.0 Hz, 1 H), 7.08-6.97 (m, 1 H), 5.32 (d, J=3.1 Hz, 1 H), 4.46 (s, 2 H), 3.69 (s, 3 H), 3.18 (q, J=7.1 Hz, 2 H), 2.36 (s, 3 H), 2.30 (d, J=9.4 Hz, 3 H), 1.13 (t, J=7.2 Hz, 3 H), 1.04 (d, J=5.1 Hz, 9 H); LCMS (m/z) ES⁺=494 (M+1).

Example 186

2-(tert-butoxy)-2-(7-((carboxyformamido)methyl)-4-(3,4-dimethylphenyl)-2-methyl-1-oxo-1,2-dihydroisoquinolin-3-yl)acetic acid

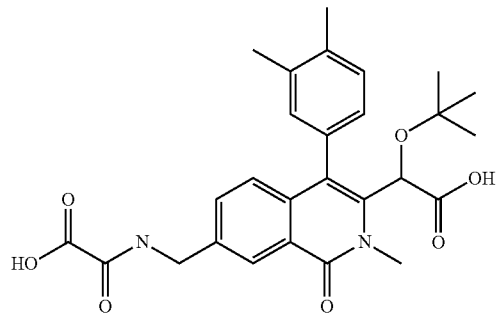 [SMILES: Cc1ccc(-c2c(C(OC(C)(C)C)C(=O)O)n(C)c(=O)c3cc(CNC(=O)C(=O)O)ccc23)cc1C]

An ice cold solution of methyl 2-(7-(aminomethyl)-4-(3,4-dimethylphenyl)-2-methyl-1-oxo-1,2-dihydroisoquinolin-3-yl)-2-(tert-butoxy)acetate (25 mg, 0.057 mmol) in tetrahydrofuran (THF) (1.000 mL) was treated with DIEA (0.015 mL, 0.086 mmol) and methyl 2-chloro-2-oxoacetate (6.35 µL, 0.069 mmol). After stirring for 40 min, the reaction was quenched with sat. NaHCO₃, extracted with EtOAc, washed with sat. NaHCO₃, Brine, dried with Na₂SO₄, filtered, and concentrated. The residue was hydrolyzed in a manner similar to that described in Example 165 Step C and purified by reverse phase HPLC to afford 2-(tert-butoxy)-2-(7-((carboxyformamido)methyl)-4-(3,4-dimethylphenyl)-2-methyl-1-oxo-1,2-dihydroisoquinolin-3-yl)acetic acid (13.7 mg, 0.026 mmol, 61.2% yield) as a white solid: ¹H NMR (400 MHz, METHANOL-d₄) δ ppm 8.32 (s, 1 H), 7.61-7.49 (m, 1 H), 7.36-7.22 (m, 2 H), 7.04-7.14 (m, 2 H), 5.26 (s, 1 H), 4.59 (s, 2 H), 3.75-3.68 (m, 3 H), 2.39 (s, 3 H), 2.34 (s, 3 H), 1.04-0.96 (m, 9 H); LCMS (m/z) ES⁺=495 (M+1).

Example 187

2-(tert-butoxy)-2-(4-(3,4-dimethylphenyl)-2-methyl-7-(methylsulfonamidomethyl)-1-oxo-1,2-dihydroisoquinolin-3-yl)acetic acid

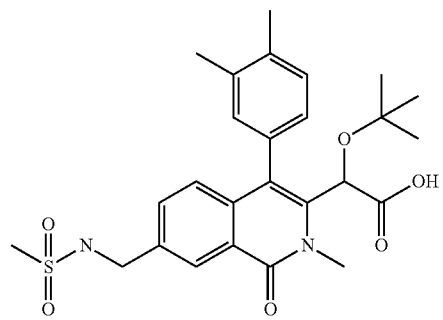 [SMILES: Cc1ccc(-c2c(C(OC(C)(C)C)C(=O)O)n(C)c(=O)c3cc(CNS(C)(=O)=O)ccc23)cc1C]

An ice cold solution of methyl 2-(7-(aminomethyl)-4-(3,4-dimethylphenyl)-2-methyl-1-oxo-1,2-dihydroisoquinolin-3-yl)-2-(tert-butoxy)acetate (17 mg, 0.039 mmol) in dichloromethane (DCM) (750 µl) was treated with Et₃N (8.14 µl, 0.058 mmol) and MsCl (3.64 µl, 0.047 mmol), stirred for 1 hour, and then warmed to rt for 1 hour. Additional Et₃N (8 uL) and MsCl (4 uL) were added at 00° C., the reaction was stirred at rt for 1 hour, and then concentrated. The residue was purified by column chromatography (0-10% MeOH/DCM) to afford methyl 2-(tert-butoxy)-2-(4-(3,4-dimethylphenyl)-2-methyl-7-(methylsulfonamidomethyl)-1-oxo-1,2-dihydroisoquinolin-3-yl)acetate (17 mg, 0.033 mmol, 85% yield) as yellow solid. The methyl ester was hydrolyzed in a manner similar to that described in Example 165 Step C and purified by reverse phase HPLC to afford 2-(tert-butoxy)-2-(4-(3,4-dimethylphenyl)-2-methyl-7-(methylsulfonamidomethyl)-1-oxo-1,2-dihydroisoquinolin-3-yl)acetic acid (14 mg, 0.027 mmol, 88% yield) as a white solid. ¹H NMR (400 MHz, CHLOROFORM-d) δ ppm 8.44 (s, 1 H), 7.59-7.50 (m, 1 H), 7.40-7.29 (m, 1 H), 7.29-7.24 (m, 1 H), 7.17 (dd, J=8.4, 12.5 Hz, 1 H), 7.08-6.99 (m, 1 H), 5.35 (s, 1 H), 5.15-5.03 (m, 1 H), 4.44 (d, J=5.7 Hz, 2 H), 3.67 (s, 3 H), 2.97-2.89 (m, 3 H), 2.37 (s, 3 H), 2.32 (s, 3 H), 1.09-1.02 (m, 9 H); LCMS (m/z) ES⁺=501 (M+1).

Example 188

2-(tert-butoxy)-2-(4-(3,4-dimethylphenyl)-7-(((N,N-dimethylsulfamoyl)amino)methyl)-2-methyl-1-oxo-1,2-dihydroisoquinolin-3-yl)acetic acid

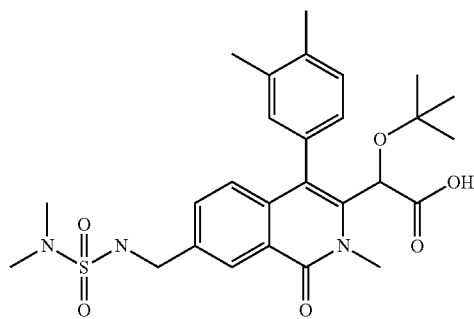 [SMILES: Cc1ccc(-c2c(C(OC(C)(C)C)C(=O)O)n(C)c(=O)c3cc(CNS(=O)(=O)N(C)C)ccc23)cc1C]

An ice cold solution of methyl 2-(7-(aminomethyl)-4-(3,4-dimethylphenyl)-2-methyl-1-oxo-1,2-dihydroisoquinolin-3-yl)-2-(tert-butoxy)acetate (25 mg, 0.057 mmol) in dichloromethane (DCM) (1 mL) was treated with Et₃N (0.012 mL, 0.086 mmol) and dimethylsulfamoyl chloride (7.33 µL, 0.069 mmol), stirred for 15 min, and then warmed to rt for 1 hour. Additional Et₃N (25 uL) and dimethylsulfamoyl chloride (15 uL) were added, the reaction was stirred at rt overnight. The reaction was concentrated and purified by column chromatography (0-10% MeOH/DCM) to afford methyl 2-(tert-butoxy)-2-(4-(3,4-dimethylphenyl)-7-(((N,N-dimethylsulfamoyl)amino)methyl)-2-methyl-1-oxo-1,2-dihydroisoquinolin-3-yl)acetate (22.6 mg, 0.042 mmol, 72.6% yield) as clear oil. The methyl ester was hydrolyzed in a manner similar to that described in Example 165 Step C and purified by reverse phase HPLC to afford 2-(tert-butoxy)-2-(4-(3,4-dimethylphenyl)-7-(((N,N-dimethylsulfamoyl)amino)methyl)-2-methyl-1-oxo-1,2-dihydroisoquinolin-3-yl)acetic acid (18.4 mg, 0.034 mmol, 82% yield) as white solid. ¹H NMR (400 MHz, CHLOROFORM-d) δ ppm 8.42 (s, 1 H), 7.54 (td, J=1.9, 8.2 Hz, 1 H), 7.41-7.30 (m, 1 H), 7.30-7.23 (m, 1 H), 7.16 (dd, J=8.4, 12.9 Hz, 1 H), 7.09-6.99 (m, 1 H), 5.35 (s, 1 H), 4.53 (br. s., 1 H), 4.36 (br. s., 2 H), 3.69 (d, J=1.0 Hz, 3 H), 2.81 (s, 3 H), 2.80 (s, 3 H), 2.36 (s, 3 H), 2.32 (s, 3 H), 1.07 (s, 4.5 H), 1.06 (s, 4.5 H); LCMS (m/z) ES⁺=530 (M+1).

Example 189

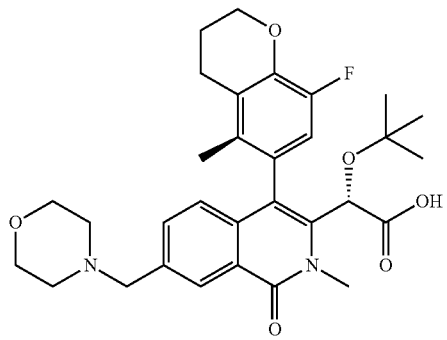

(S)(M)-2-(tert-butoxy)-2-(4-(8-fluoro-5-methylchroman-6-yl)-2-methyl-7-(morpholinomethyl)-1-oxo-1,2-dihydroisoquinolin-3-yl)acetic acid Step A (S)(M)-methyl 2-(tert-butoxy)-2-(7-cyano-4-(8-fluoro-5-methylchroman-6-yl)-2-methyl-1-oxo-1,2-dihydroisoquinolin-3-yl)acetate

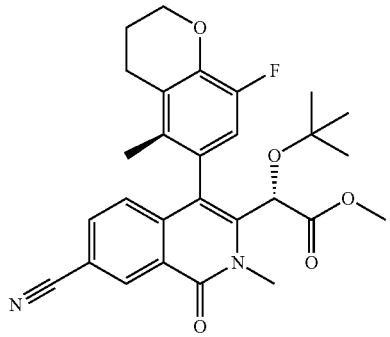

A mixture of (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate (100 mg, 0.183 mmol) and Zn(CN)₂ (21.49 mg, 0.183 mmol) in N,N-dimethylformamide (DMF) (1830 µl) was degassed with N₂ for 5 min, treated with Pd(Ph₃P)₄ (21.15 mg, 0.018 mmol), and irradiated in microwave at 120° C. for 30 min. The mixture was diluted with water, extracted with EtOAc, washed with water, brine, dried with Na₂SO₄, filtered, and concentrated. Purification with column chromatography (SiO2, 0-60% EtOAc/Hexane) afforded (S)(M)-methyl 2-(tert-butoxy)-2-(7-cyano-4-(8-fluoro-5-methylchroman-6-yl)-2-methyl-1-oxo-1,2-dihydroisoquinolin-3-yl)acetate (75.8 mg, 0.154 mmol, 84% yield) as white solid. ¹H NMR (400 MHz, CHLOROFORM-d) δ=8.80 (d, J=1.7 Hz, 1 H), 7.65 (dd, J=1.9, 8.5 Hz, 1 H), 6.91 (d, J=8.5 Hz, 1 H), 6.80 (d, J=11.0 Hz, 1 H), 5.14 (s, 1 H), 4.32 (dd, J=4.6, 5.6 Hz, 2 H), 3.74 (s, 3 H), 3.69 (s, 3 H), 2.73 (t, J=6.5 Hz, 2 H), 2.23-2.11 (m, 2 H), 1.82 (s, 3 H), 1.16 (s, 9 H); LCMS (m/z) ES⁺=493 (M+1).

Step B (S)(M)-Methyl 2-(7-(aminomethyl)-4-(8-fluoro-5-methylchroman-6-yl)-2-methyl-1-oxo-1,2-dihydroisoquinolin-3-yl)-2-(tert-butoxy)acetate, hydrochloride

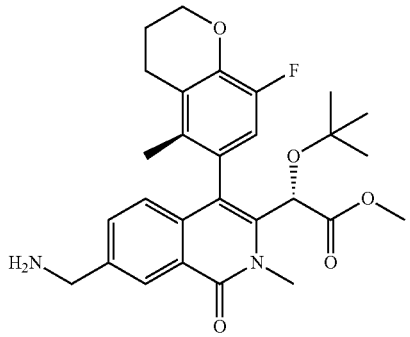

A solution of (S)(M)-methyl 2-(tert-butoxy)-2-(7-cyano-4-(8-fluoro-5-methylchroman-6-yl)-2-methyl-1-oxo-1,2-dihydroisoquinolin-3-yl)acetate (38 mg, 0.077 mmol) in methanol (990 µl) and tetrahydrofuran (THF) (330 µl) was treated with HCl (4M in dioxane) (23.15 µl, 0.093 mmol) and Pd/C (8.21 mg, 7.72 µmol), purged and filled with N₂ 3×, H₂ 3×, and stirred under 50 psi H₂ at rt overnight. The mixture was filtered through Celite, washed with MeOH and EtOAc, and concentrated to afford crude (S)(M)-methyl 2-(7-(aminomethyl)-4-(8-fluoro-5-methylchroman-6-yl)-2-methyl-1-oxo-1,2-dihydroisoquinolin-3-yl)-2-(tert-butoxy)acetate, hydrochloride (37.8 mg, 0.071 mmol, 92% yield) as off white solid. ¹H NMR (400 MHz, METHANOL-d₄) δ ppm 8.47 (s, 1 H), 7.67 (d, J=8.3 Hz, 1 H), 6.98 (d, J=8.4 Hz, 1 H), 6.80 (d, J=11.1 Hz, 1 H), 5.22 (s, 1 H), 4.32-4.20 (m, 4 H), 3.75 (s, 3 H), 3.71 (s, 3 H), 2.79 (q, J=5.6 Hz, 2 H), 2.20-2.06 (m, 2 H), 1.86 (s, 3 H), 1.17 (s, 9 H). LCMS (m/z) ES⁺=497 (M+1).

Step C (S(M))-methyl 2-(tert-butoxy)-2-(4-(8-fluoro-5-methylchroman-6-yl)-2-methyl-7-(morpholinomethyl)-1-oxo-1,2-dihydroisoquinolin-3-yl)acetate

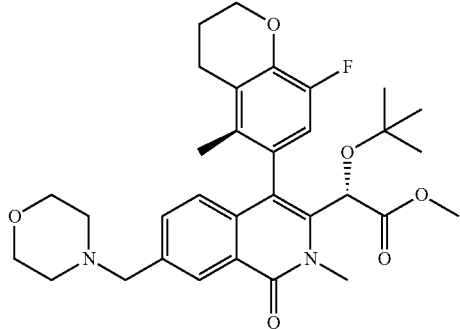

A solution of (S)(M)-methyl 2-(7-(aminomethyl)-4-(8-fluoro-5-methylchroman-6-yl)-2-methyl-1-oxo-1,2-dihydroisoquinolin-3-yl)-2-(tert-butoxy)acetate, hydrochloride (18 mg, 0.034 mmol) in N,N-Dimethylformamide (DMF) (308 µl) was treated with DIEA (23.59 µl, 0.135 mmol) and 1-bromo-2-(2-bromoethoxy)ethane (6.37 µl, 0.051 mmol). The reaction was stirred at 90° C. for 4 hours. The reaction was cooled to rt, diluted with water, extracted with EtOAc (2×), washed with water, brine, dried with Na₂SO₄, filtered, and concentrated to give 20.6 mg yellow oil. Purified with reverse phase HPLC (10-90% MeCN/H2O-0.1% TFA) to give (S)(M)-methyl 2-(tert-butoxy)-2-(4-(8-fluoro-5-methylchroman-6-yl)-2-methyl-7-(morpholinomethyl)-1-oxo-1,2-dihydroisoquinolin-3-yl)acetate (13.6 mg, 0.024 mmol, 71.1% yield). LCMS (m/z) ES⁺=567 (M+1).

Step D (S)(M)-2-(tert-butoxy)-2-(4-(8-fluoro-5-methylchroman-6-yl)-2-methyl-7-(morpholinomethy)-1-oxo-1,2-dihydroisoquinolin-3-yl)acetic acid (S)(M)-methyl 2-(tert-butoxy)-2-(4-(8-fluoro-5-methylchroman-6-yl)-2-methyl-7-(morpholinomethyl)-1-oxo-1,2-dihydroisoquinolin-3-yl)acetate (13 mg, 0.023 mmol) was hydrolyzed in a manner similar to that described in Example 165 Step C to afford the title compound (8.1 mg, 0.013 mmol, 57.5% yield) as off white solid: ¹H NMR (400 MHz, CHLOROFORM-d) δ ppm 8.38 (s, 1 H), 7.50 (dd, J=1.7, 8.4 Hz, 1 H), 6.87-6.74 (m, 2 H), 5.14 (s, 1 H), 4.35-4.23 (m, 2 H), 3.80-3.61 (m, 9 H), 2.70 (t, J=6.3 Hz, 2 H), 2.52 (br. s., 4 H), 2.21-2.07 (m, 2 H), 1.90 (s, 3 H), 1.19 (s, 9 H); LCMS (m/z) ES⁺=553 (M+1).

Example 190

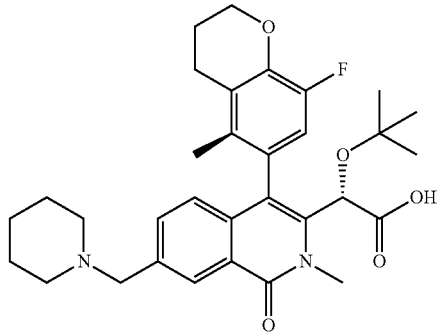

(S)(M)-2-(tert-butoxy)-2-(4-(8-fluoro-5-methylchroman-6-yl)-2-methyl-1-oxo-7-(piperidin-1-ylmethyl)-1,2-dihydroisoquinolin-3-yl)acetic acid, Trifluoroacetic acid salt The title compound was prepared in a manner similar to that described in Example 189 from (S)(M)-methyl 2-(7-(aminomethyl)-4-(8-fluoro-5-methylchroman-6-yl)-2-methyl-1-oxo-1,2-dihydroisoquinolin-3-yl)-2-(tert-butoxy)acetate, hydrochloride and 1,5-dibromopentane. The hydrolysis of the ester and subsequent purification afforded (S)(M)-2-(tert-butoxy)-2-(4-(8-fluoro-5-methylchroman-6-yl)-2-methyl-1-oxo-7-(piperidin-1-ylmethyl)-1,2-dihydroisoquinolin-3-yl)acetic acid—TFA salt as white solid. ¹H NMR (400 MHz, CHLOROFORM-d) δ ppm 11.71 (br. s., 1 H), 8.35 (s, 1 H), 7.62 (dd, J=1.4, 8.4 Hz, 1 H), 6.87 (d, J=8.5 Hz, 1 H), 6.77 (d, J=11.0 Hz, 1 H), 5.17 (s, 1 H), 4.39-4.29 (m, 2 H), 4.29-4.14 (m, 2 H), 3.77 (s, 3 H), 3.67-3.35 (m, 2 H), 2.83-2.50 (m, 4 H), 2.24-2.09 (m, 2 H), 2.00-1.72 (m, 9 H), 1.19 (s, 9 H LCMS (m/z) ES⁺=551 (M+1).

Scheme 11: General Route for Synthesis of Examples with a R⁷ = Aromatic Bearing Substituents using Palladium Chemistry and Boronic Acids

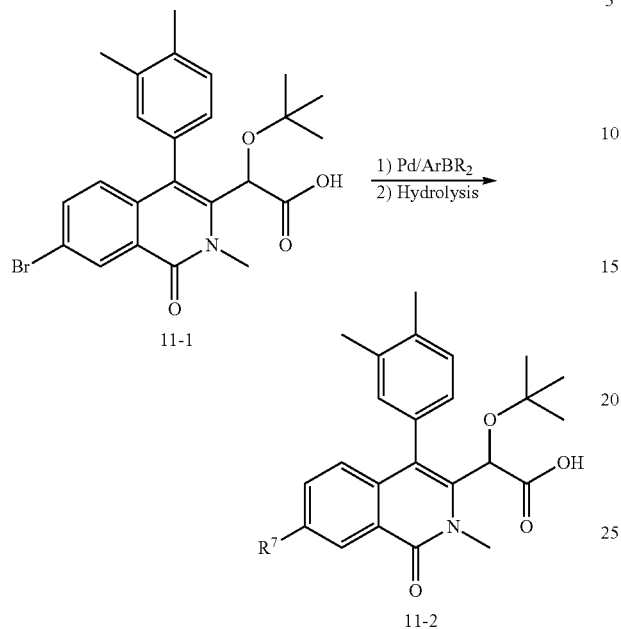

Example 191

[(1,1'-dimethylethyl)oxy][4-(3,4-dimethylphenyl)-2-methyl-7-(1-methyl-1H-pyrrol-2-yl)-1-oxo-1,2-dihydro-3-isoquinolinyl]acetic acid

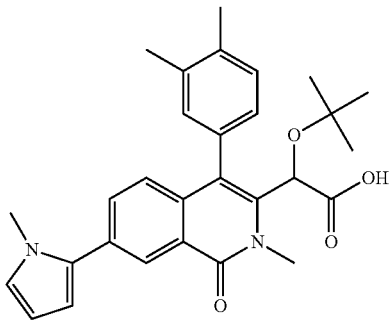 [SMILES: Cc1ccc(-c2c(C(OC(C)(C)C)C(=O)O)n(C)c(=O)c3cc(-c4cccn4C)ccc23)cc1C]

A mixture of methyl [7-bromo-4-(3,4-dimethylphenyl)-2-methyl-1-oxo-1,2-dihydro-3-isoquinolinyl][(1,1-dimethylethyl)oxy]acetate (28.0 mg, 0.058 mmol), 1-methyl-2-(4,4,5,5-tetramethyl-1,3,2-dioxaborolan-2-yl)-1H-pyrrole (35.8 mg, 0.173 mmol) and sodium carbonate (0.086 mL, 0.173 mmol) in N,N-dimethylformamide (DMF) (1.2 mL) was degassed with nitrogen for 5 minutes. Pd(PPh₃)₄ (6.65 mg, 5.76 μmol) was added and the mixture was irradiated in the microwave at 120° C. for 20 minutes. The mixture was diluted with ethyl acetate and then washed consecutively with saturated sodium bicarbonate, water, and brine. The organic phase was dried over sodium sulfate, filtered and concentrated to a dark residue. The crude residue was treated with lithium hydroxide (0.115 mL, 0.230 mmol) in tetrahydrofuran (THF) (0.4 mL) and methanol (0.4 mL) and the mixture was stirred for 2 hours at 50° C. and then overnight at ambient temperature. The mixture was concentrated and then purified by reverse phase chromatography to afford the title compound as a pale yellow solid (13 mg, 48%): ¹H NMR (400 MHz, CHLOROFORM-d) δ=8.52 (s, 1 H), 7.60 (td, J=2.0, 7.8 Hz, 1 H), 7.41 (s, 1 H), 7.32-7.24 (m, 1 H), 7.24-7.03 (m, 2 H), 6.77 (s, 1 H), 6.34 (m, 1 H), 6.26-6.12 (m, 1 H), 5.37 (s, 1 H), 3.76 (d, J=2.1 Hz, 3 H), 3.71 (d, J=1.4 Hz, 3 H), 2.37 (d, J=1.0 Hz, 3 H), 2.34 (d, J=4.1 Hz, 3 H), 1.09 (d, J=4.7 Hz, 9 H); LC/MS (m/z) ES⁺=473 (M+1).

Example 192

[(1,1-dimethylethyl)oxy][4-(3,4-dimethylphenyl)-2-methyl-7-(1-methyl-1H-pyrazol-4-yl)-1-oxo-1,2-dihydro-3-isoquinolinyl]acetic acid

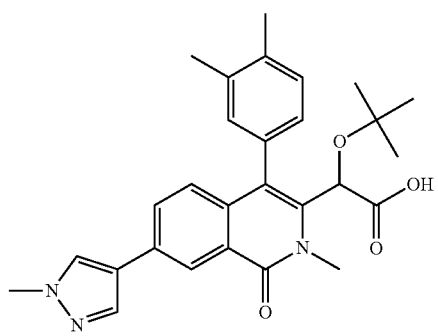 [SMILES: Cc1ccc(-c2c(C(OC(C)(C)C)C(=O)O)n(C)c(=O)c3cc(-c4cnn(C)c4)ccc23)cc1C]

The title compound was prepared in two steps in a manner similar to that described in Example 191 from methyl [7-bromo-4-(3,4-dimethylphenyl)-2-methyl-1-oxo-1,2-dihydro-3-isoquinolinyl][(1,1-dimethylethyl)oxy]acetate and 1-methyl-4-(4,4,5,5-tetramethyl-1,3,2-dioxaborolan-2-yl)-1H-pyrazole and was isolated as a pale yellow solid (20 mg, 57%) after reverse phase chromatography as the trifluoroacetate salt: ¹H NMR (400 MHz, CHLOROFORM-d) δ=8.59 (s, 1 H), 7.91 (s, 1 H), 7.82 (s, 1 H), 7.70-7.53 (m, 1 H), 7.45-7.31 (m, 1 H), 7.32-7.22 (m, 1 H), 7.17 (dd, J=8.5, 12.4 Hz, 1 H), 7.12-7.03 (m, 1 H), 5.36 (d, J=1.0 Hz, 1 H), 4.00 (s, 3 H), 3.73 (s, 3 H), 2.38 (s, 3 H), 2.33 (d, J=2.5 Hz, 3 H), 1.07 (d, 9 H); LC/MS (m/z) ES⁺=474 (M+1).

Example 193

[(1,1-dimethylethyl)oxy][4-(3,4-dimethylphenyl)-2-methyl-7-(2-methyl-3-furanyl)-1-oxo-1,2-dihydro-3-isoquinolinyl]acetic acid

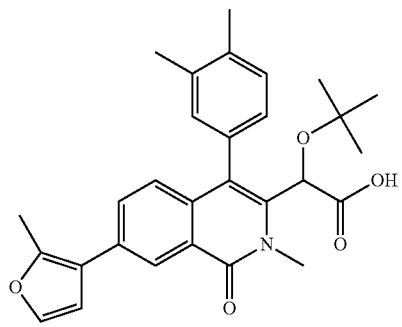 [SMILES: Cc1ccc(-c2c(C(OC(C)(C)C)C(=O)O)n(C)c(=O)c3cc(-c4ccoc4C)ccc23)cc1C]

The title compound was prepared in two steps in a manner similar to that described in Example 191 from methyl [7-bromo-4-(3,4-dimethylphenyl)-2-methyl-1-oxo-1,2-dihydro-3-isoquinolinyl][(1,1-dimethylethyl)oxy]acetate and 4,4,5,5-tetramethyl-2-(2-methyl-3-furanyl)-1,3,2-diox aborolane and was isolated as a pale yellow solid (10 mg, 49%) after reverse phase chromatography: ¹H NMR (400 MHz, CHLOROFORM-d) δ=8.58-8.46 (m, 1 H), 7.62-7.53 (m, 1 H), 7.46-7.33 (m, 2 H), 7.32-7.24 (m, 1 H), 7.24-7.05 (m, 2 H), 6.62 (t, J=1.9 Hz, 1 H), 5.37 (s, 1 H), 3.71 (d, J=1.2 Hz, 3 H), 2.51 (d, J=2.3 Hz, 3 H), 2.37 (d, J=1.2 Hz, 3 H), 2.33 (d, J=2.0 Hz, 3 H), 1.09 (d, J=4.5 Hz, 9 H); LC/MS (m/z) ES⁺=474 (M+1).

Example 194

(2S)(M)-[(1,1-dimethylethyl)oxy][4-(8-fluoro-5-methyl-3,4-dihydro-2H-chromen-6-yl)-7-(3-furanyl)-2-methyl-1-oxo-1,2-dihydro-3-isoquinolinyl]ethanoic acid

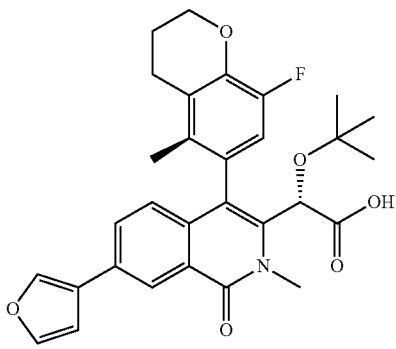

A mixture of (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate (19.30 mg, 0.035 mmol), furan-3-ylboronic acid (17.56 mg, 0.141 mmol) and sodium carbonate (0.053 mL, 0.106 mmol) in N,N-dimethylformamide (DMF) (1.0 mL) was degassed with nitrogen for 5 minutes. Pd(PPh₃)₄ (4.08 mg, 3.53 μmol) was added and the mixture was irradiated in the microwave at 120° C. for 20 minutes. The mixture was diluted with ethyl acetate, then washed with water and brine. The organic phase was dried over sodium sulfate, filtered and concentrated to afford a dark residue. The crude residue was treated with 2 M lithium hydroxide (0.088 mL, 0.177 mmol) in methanol (1.0 mL) and tetrahydrofuran (THF) (1.0 mL) at 70° C. for 6 hours monitoring the reaction progress by LCMS. Additional 2 M lithium hydroxide (0.088 mL, 0.177 mmol) was added and heating at 70° C. was continued for 2 hours. Additional lithium hydroxide (16.92 mg, 0.706 mmol) and water (0.200 mL) were added and heating at 70° C. was continued for one hour. The mixture was concentrated and then purified by reverse phase chromatography to afford the title compound as a yellow solid (8.7 mg, 47%): ¹H NMR (400 MHz, CHLOROFORM-d) δ=8.60 (m, 1 H), 7.85 (s, 1 H), 7.64 (m, 1 H), 7.51 (m, 1 H), 6.90-6.81 (m, 3 H), 5.22 (s, 1 H), 4.36-4.24 (m, 2 H), 3.74 (s, 3 H), 2.79-2.65 (m, 2 H), 2.16 (m, 2 H), 1.95 (s, 3 H), 1.24 (s, 9 H); LC/MS (m/z) ES⁺=520 (M+1).

Example 195

(2S)(M)-[(1,1-dimethylethyl)oxy][4-(8-fluoro-5-methyl-3,4-dihydro-2H-chromen-6-yl)-2-methyl-7-(1-methyl-1H-pyrazol-5-yl)-1-oxo-1,2-dihydro-3-isoquinolinyl]ethanoic acid

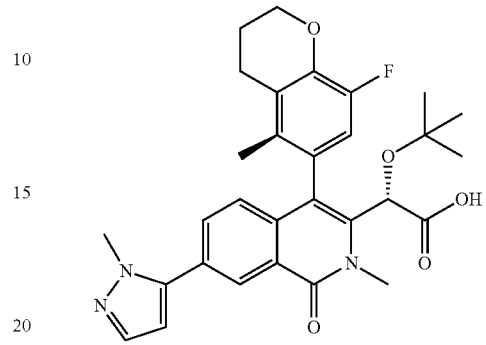

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 1-methyl-5-(4,4,5,5-tetramethyl-1,3,2-dioxaborolan-2-yl)-1H-pyrazole and was isolated as an off-white solid (13.8 mg, 60%) after reverse phase chromatography: ¹H NMR (400 MHz, CHLOROFORM-d) δ=8.57 (m, 1 H), 7.63-7.52 (m, 2 H), 6.97 (m, 1 H), 6.87 (m, 1 H), 6.41 (d, J=2.0 Hz, 1 H), 5.24 (s, 1 H), 4.32 (m, 2 H), 3.97 (s, 3 H), 3.76 (s, 3 H), 2.80-2.68 (m, 2 H), 2.17 (m, 2 H), 1.97 (s, 3 H), 1.24 (s, 9 H); LC/MS (m/z) ES⁺=534 (M+1).

Example 196

(2S)(M)-[(1,1-dimethylethyl)oxy][7-(3,5-dimethyl-1H-pyrazol-4-yl)-4-(8-fluoro-5-methyl-3,4-dihydro-2H-chromen-6-yl)-2-methyl-1-oxo-1,2-dihydro-3-isoquinolinyl]ethanoic acid

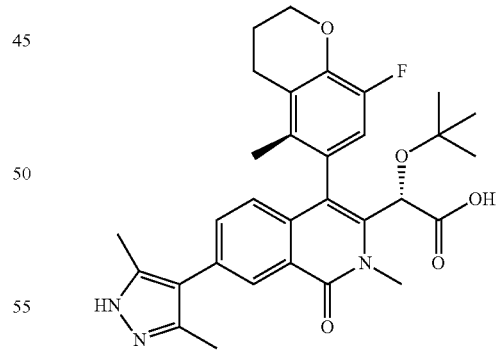

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 3,5-dimethyl-4-(4,4,5,5-tetramethyl-1,3,2-dioxaborolan-2-yl)-1H-pyrazole and was isolated as an off-white solid (9.6 mg, 43%) after reverse phase chromatography as the trifluoroacetate salt: ¹H NMR (400 MHz, CHLOROFORM-d) δ=8.41 (m, 1 H), 7.40 (m, 1 H), 6.99 (m, 1 H), 6.87 (m, 1 H), 5.24 (s, 1 H), 4.33 (m, 2 H), 3.77 (s, 3 H), 2.85-2.63 (m, 3 H), 2.42 (s, 6 H), 2.17 (d, J=2.1 Hz, 2 H), 1.97 (s, 3 H), 1.23 (s, 9 H); LC/MS (m/z) ES$^+$=548 (M+1).

Example 197

(2S)(M)-[(1,1-dimethylethyl)oxy][4-(8-fluoro-5-methyl-3,4-dihydro-2H-chromen-6-yl)-2-methyl-1-oxo-7-(1H-pyrazol-4-yl)-1,2-dihydro-3-isoquinolinyl]ethanoic acid

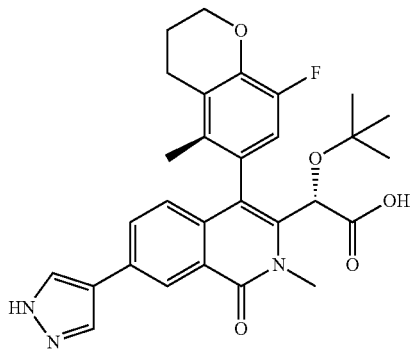

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 4-(4,4,5,5-tetramethyl-1,3,2-dioxaborolan-2-yl)-1H-pyrazole and was isolated as an off-white residue (9 mg, 49%) after reverse phase chromatography. $^1$H NMR (400 MHz, CHLOROFORM-d) δ=8.65 (s, 1 H), 8.05 (m, 2 H), 7.67 (m, 1 H), 6.97-6.78 (m, 2 H), 5.23 (s, 1 H), 4.33 (t, J=5.1 Hz, 2 H), 3.77 (s, 3 H), 2.74 (m, 2 H), 2.22-2.10 (m, 2 H), 1.95 (s, 3 H), 1.24 (s, 9 H); LC/MS (m/z) ES$^+$=520 (M+1).

Example 198

(2S)(M)-[(1,1-dimethylethyl)oxy]{4-(8-fluoro-5-methyl-3,4-dihydro-2H-chromen-6-yl)-2-methyl-7-[6-(methyloxy)-3-pyridinyl]-1-oxo-1,2-dihydro-3-isoquinolinyl}ethanoic acid

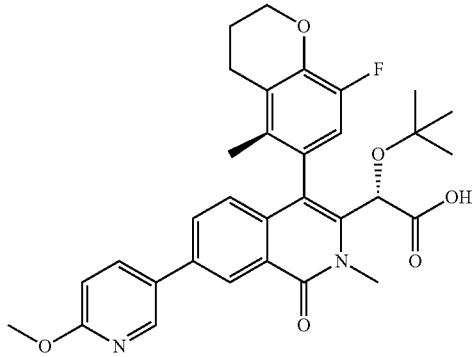

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 2-methoxy-5-(4,4,5,5-tetramethyl-1,3,2-dioxaborolan-2-yl)pyridine, except that the intermediate Suzuki product was purified by reverse phase chromatography before the ester hydrolysis step. Following hydrolysis, the title compound was isolated as a white solid (11.7 mg, 37%) after reverse phase chromatography: $^1$H NMR (400 MHz, CHLOROFORM-d) δ=8.67 (d, J=1.8 Hz, 1 H), 8.51 (d, J=2.1 Hz, 1 H), 7.97 (dd, J=2.5, 8.6 Hz, 1 H), 7.72 (dd, J=2.0, 8.4 Hz, 1 H), 6.96 (d, J=8.6 Hz, 1 H), 6.93-6.78 (m, 2 H), 5.24 (s, 1 H), 4.39-4.26 (m, 2 H), 4.01 (s, 3 H), 3.76 (s, 3 H), 2.79-2.66 (m, 2 H), 2.22-2.10 (m, 2 H), 1.94 (s, 3 H), 1.24 (s, 9 H); LC/MS (m/z) ES$^+$=561 (M+1).

Example 199

(2S)(M)-[7-[4-(dimethylamino)phenyl]-4-(8-fluoro-5-methyl-3,4-dihydro-2H-chromen-6-yl)-2-methyl-1-oxo-1,2-dihydro-3-isoquinolinyl][(1,1-dimethylethyl)oxy]ethanoic acid

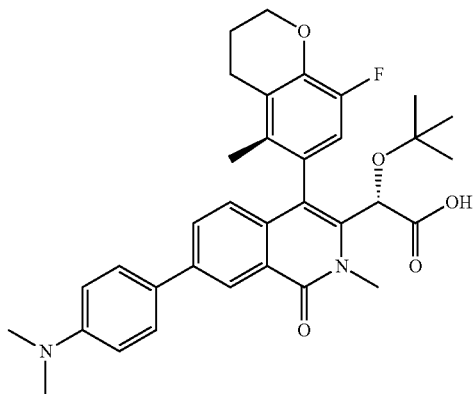

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and N,N-dimethyl-4-(4,4,5,5-tetramethyl-1,3,2-dioxaborolan-2-yl)aniline and was isolated as a yellow-brown solid (3.5 mg, 17%) after reverse phase chromatography: $^1$H NMR (400 MHz, CHLOROFORM-d) δ=8.69 (m, 1 H), 7.74 (m, 1 H), 7.62 (m, 2 H), 6.88 (m, 2 H), 6.82 (m, 2 H), 5.21 (s, 1 H), 4.31 (m, 2 H), 3.73 (s, 3 H), 3.01 (s, 6 H), 2.73 (br. s., 2 H), 2.29-1.64 (m, 5 H), 1.23 (s, 9 H); LC/MS (m/z) ES$^+$=573 (M+1).

Example 200

(2S)(M)-[(1,1-dimethylethyl)oxy][4-(8-fluoro-5-methyl-3,4-dihydro-2H-chromen-6-yl)-2-methyl-7-(1-methyl-1H-pyrazol-4-yl)-1-oxo-1,2-dihydro-3-isoquinolinyl]ethanoic acid

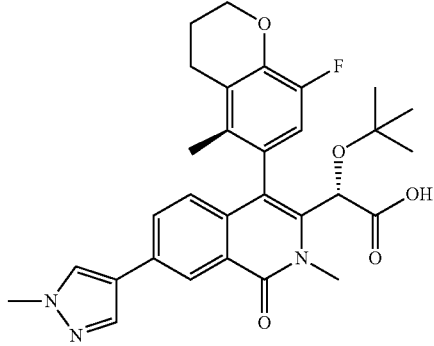

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and (1-methyl-1H-pyrazol-4-yl)boronic acid and was isolated as a white solid (10 mg, 41%) after reverse phase chromatography: ¹H NMR (400 MHz, CHLOROFORM-d) δ=8.57 (d, J=1.6 Hz, 1 H), 7.88 (s, 1 H), 7.78 (s, 1 H), 7.63 (m, 1 H), 6.92-6.80 (m, 2 H), 5.21 (s, 1 H), 4.37-4.27 (m, 2 H), 3.98 (s, 3 H), 3.74 (s, 3 H), 2.79-2.66 (m, 2 H), 2.23-2.11 (m, 2 H), 1.95 (s, 3 H), 1.23 (s, 9 H); LC/MS (m/z) ES⁺=534 (M+1).

Example 201

(2S)(M)-[(1,1-dimethylethyl)oxy]{4-(8-fluoro-5-methyl-3,4-dihydro-2H-chromen-6-yl)-2-methyl-7-[1-(3-methylbutyl)-1H-pyrazol-4-yl]-1-oxo-1,2-dihydro-3-isoquinolinyl}ethanoic acid

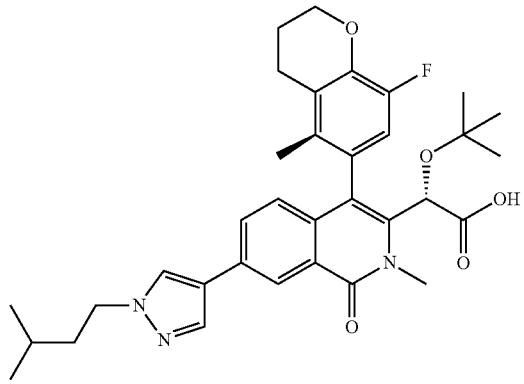

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 1-isopentyl-4-(4,4,5,5-tetramethyl-1,3,2-dioxaborolan-2-yl)-1H-pyrazole and was isolated as a white solid (15.9 mg, 59%) after reverse phase chromatography: ¹H NMR (400 MHz, CHLOROFORM-d) δ=8.59 (m, 1H), 7.91 (s, 1 H), 7.84 (s, 1 H), 7.65 (m, 1 H), 6.93-6.80 (m, 2 H), 5.22 (s, 1 H), 4.38-4.29 (m, 2 H), 4.23 (t, J=7.4 Hz, 2 H), 3.76 (s, 3 H), 2.80-2.67 (m, 2 H), 2.23-2.11 (m, 2 H), 1.94 (s, 3 H), 1.82 (m, 2 H), 1.61 (m, 1 H), 1.23 (s, 9 H), 0.97 (d, J=6.6 Hz, 6 H); LC/MS (m/z) ES⁺=590 (M+1).

Example 202

(S)(M)-[(1,1-dimethylethyl)oxy][4-(8-fluoro-5-methyl-3,4-dihydro-2H-chromen-6-yl)-2-methyl-7-(1-methyl-1H-pyrrol-2-yl)-1-oxo-1,2-dihydro-3-isoquinolinyl]ethanoic acid

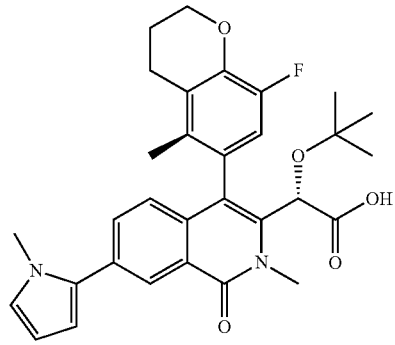

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 1-methyl-2-(4,4,5,5-tetramethyl-1,3,2-dioxaborolan-2-yl)-1H-pyrrole and was isolated as a yellow solid (9.7 mg, 48%) after reverse phase chromatography: ¹H NMR (400 MHz, CHLOROFORM-d) δ=8.52 (m, 1 H), 7.60 (m, 1 H), 6.93-6.82 (m, 2 H), 6.81-6.73 (m, 1 H), 6.34 (m, 1 H), 6.27-6.17 (m, 1 H), 5.23 (s, 1 H), 4.32 (t, J=5.0 Hz, 2 H), 3.75 (m, 6 H), 2.74 (m, 2 H), 2.21-2.10 (m, 2 H), 1.97 (s, 3 H), 1.24 (s, 9 H); LC/MS (m/z) ES⁺=533 (M+1).

Example 203

(2S)(M)-[(1,1-dimethylethyl)oxy][4-(8-fluoro-5-methyl-3,4-dihydro-2H-chromen-6-yl)-2-methyl-7-(2-methyl-3-furanyl)-1-oxo-1,2-dihydro-3-isoquinolinyl]ethanoic acid

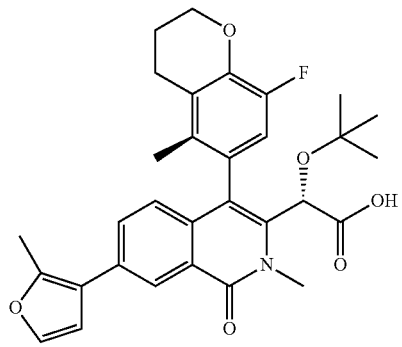

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 4,4,5,5-tetramethyl-2-(2-methylfuran-3-yl)-1,3,2-dioxaborolane and was isolated as a white solid (7.5 mg, 39%) after reverse phase chromatography. ¹H NMR (400 MHz, CHLOROFORM-d) δ=8.52 (d, J=1.8 Hz, 1 H), 7.58 (m, 1 H), 7.36 (d, J=1.8 Hz, 1 H), 6.97-6.80 (m, 2 H), 6.61 (m, 1 H), 5.23 (s, 1 H), 4.32 (m, 2 H), 3.75 (s, 3 H), 2.78-2.63 (m, 2 H), 2.51 (s, 3 H), 2.16 (m, 2 H), 1.96 (s, 3 H), 1.24 (s, 9 H); LC/MS (m/z) ES⁺=534 (M+1).

Example 204

(2S)(M)-[(1,1-dimethylethyl)oxy][4-(8-fluoro-5-methyl-3,4-dihydro-2H-chromen-6-yl)-2-methyl-1-oxo-7-phenyl-1,2-dihydro-3-isoquinolinyl]ethanoic acid

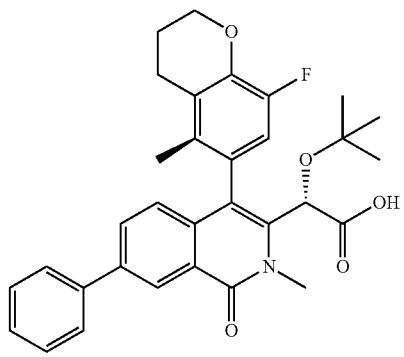

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and phenylboronic acid and was isolated as a white solid (14.3 mg, 76%) after reverse phase chromatography: $^1$H NMR (400 MHz, CHLOROFORM-d) δ=8.74 (d, J=1.8 Hz, 1 H), 7.77 (dd, J=2.0, 8.4 Hz, 1 H), 7.73-7.64 (m, 2 H), 7.52-7.43 (m, 2 H), 7.42-7.34 (m, 1 H), 6.94 (m, 1 H), 6.88 (m, 1 H), 5.23 (s, 1 H), 4.36-4.27 (m, 2 H), 3.76 (s, 3 H), 2.72 (m, 2 H), 2.21-2.10 (m, 2 H), 1.93 (s, 3 H), 1.23 (s, 9 H); LC/MS (m/z) ES$^+$=530 (M+1).

Example 205

(2S)(M)-[(1,1-dimethylethyl)oxy][4-(8-fluoro-5-methyl-3,4-dihydro-2H-chromen-6-yl)-2-methyl-1-oxo-7-(4-pyridinyl)-1,2-dihydro-3-isoquinolinyl]ethanoic acid

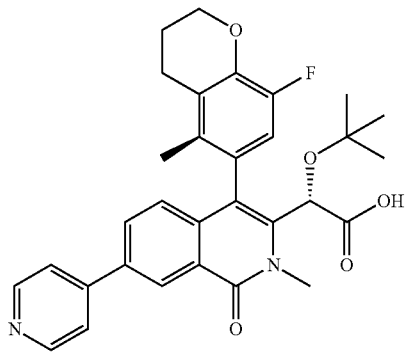

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and pyridin-4-ylboronic acid and was isolated as a bright yellow solid (13.6 mg, 59%) after reverse phase chromatography: $^1$H NMR (400 MHz, CHLOROFORM-d) δ=8.98 (d, J=1.6 Hz, 1 H), 8.91 (d, J=5.5 Hz, 2 H), 8.13 (d, J=5.9 Hz, 2 H), 7.85 (dd, J=2.0, 8.6 Hz, 1 H), 7.10 (d, J=8.6 Hz, 1 H), 6.86 (m, 1 H), 5.25 (s, 1 H), 4.33 (t, J=5.1 Hz, 2 H), 3.79 (s, 3 H), 2.75 (m, 2 H), 2.18 (m, 2 H), 1.94 (s, 3 H), 1.24 (s, 9 H); LC/MS (m/z) ES$^+$=531 (M+1).

Example 206

(2S)(M)-[(1,1-dimethylethyl)oxy][4-(8-fluoro-5-methyl-3,4-dihydro-2H-chromen-6-yl)-2-methyl-1-oxo-7-(3-pyridinyl)-1,2-dihydro-3-isoquinolinyl]ethanoic acid

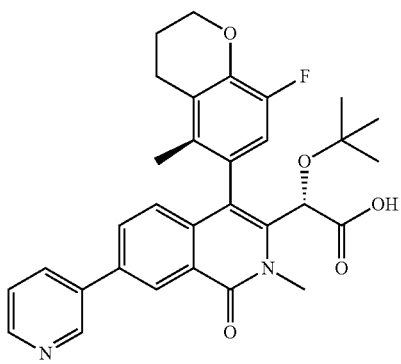

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and pyridin-3-ylboronic acid and was isolated as a white solid (16.1 mg, 70%) after reverse phase chromatography: $^1$H NMR (400 MHz, CHLOROFORM-d) δ=9.18 (m, 1 H), 8.84 (m, 1 H), 8.78 (s, 1 H), 8.62 (m, 1 H), 7.92 (m, 1 H), 7.78 (m, 1 H), 7.06 (m, 1 H), 6.86 (m, 1 H), 5.25 (s, 1 H), 4.38-4.25 (m, 2 H), 3.76 (s, 3 H), 2.74 (d, J=5.3 Hz, 2 H), 2.25-2.09 (m, 2 H), 1.93 (s, 3 H), 1.23 (s, 9 H); LC/MS (m/z) ES$^+$=531 (M+1).

Example 207

(2S)(M)-[(1,1-dimethylethyl)oxy][7-(3,5-dimethyl-4-isoxazolyl)-4-(8-fluoro-5-methyl-3,4-dihydro-2H-chromen-6-yl)-2-methyl-1-oxo-1,2-dihydro-3-isoquinolinyl]ethanoic acid

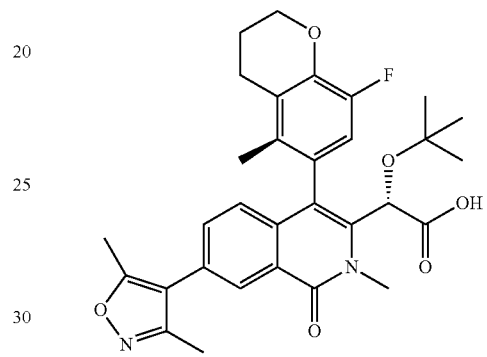

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 3,5-dimethyl-4-(4,4,5,5-tetramethyl-1,3,2-dioxaborolan-2-yl)isoxazole and was isolated after reverse phase chromatography (8.1 mg, 43%): $^1$H NMR (400 MHz, CHLOROFORM-d) δ=8.40 (d, J=1.8 Hz, 1 H), 7.41 (dd, J=2.0, 8.4 Hz, 1 H), 6.95 (d, J=8.4 Hz, 1 H), 6.87 (m, 1 H), 5.24 (s, 1 H), 4.32 (m, 2 H), 3.75 (s, 3 H), 2.79-2.68 (m, 2 H), 2.45 (s, 3 H), 2.31 (s, 3 H), 2.21-2.09 (m, 2 H), 1.98 (s, 3 H), 1.24 (s, 9 H); LC/MS (m/z) ES$^+$=549 (M+1).

Example 208

(2S)(M)-[(1,1-dimethylethyl)oxy]{4-(8-fluoro-5-methyl-3,4-dihydro-2H-chromen-6-yl)-2-methyl-7-[6-(methyloxy)-2-pyridinyl]-1-oxo-1,2-dihydro-3-isoquinolinyl}ethanoic acid

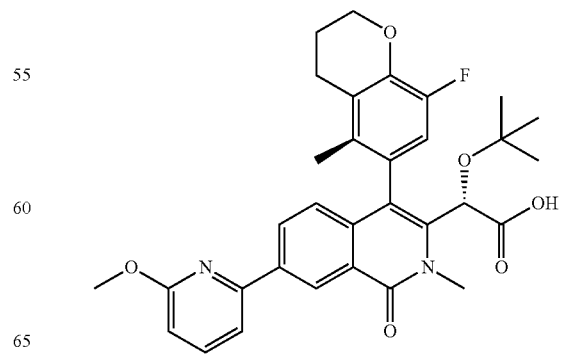

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 2-methoxy-6-(4,4,5,5-tetramethyl-1,3,2-dioxaborolan-2-yl)pyridine and was isolated as a white solid (12.4 mg, 38%) after reverse phase chromatography: $^1$H NMR (400 MHz, CHLOROFORM-d) δ=9.08 (d, J=1.8 Hz, 1 H), 8.33 (dd, J=2.0, 8.6 Hz, 1 H), 7.75-7.59 (m, 1 H), 7.52 (m, 1 H), 6.96 (d, J=8.6 Hz, 1 H), 6.87 (m, 1 H), 6.72 (m, 1 H), 5.24 (s, 1 H), 4.37-4.24 (m, 2 H), 4.03 (s, 3 H), 3.76 (s, 3 H), 2.76-2.66 (m, 2 H), 2.22-2.06 (m, 2 H), 1.93 (s, 3 H), 1.31-1.19 (m, 9 H); LC/MS (m/z) ES$^+$=561 (M+1).

Example 209

(S)(M)-2-(tert-butoxy)-2-(4-(8-fluoro-5-methylchroman-6-yl)-7-(4-fluorophenyl)-2-methyl-1-oxo-1,2-dihydroisoquinolin-3-yl)acetic acid

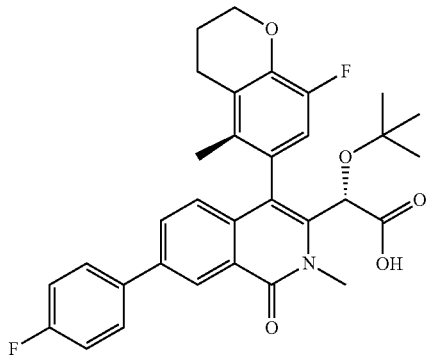

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 4-fluoroboronic acid. Following hydrolysis and purification by reverse phase HPLC, the title compound was isolated (6 mg, 9.97 μmol, 18.16% yield) as a white solid: $^1$H NMR (400 MHz, CHLOROFORM-d)=8.65 (s, 1 H), 7.74 (d, J=8.4 Hz, 1 H), 7.52 (t, J=7.8 Hz, 1 H), 7.41-7.30 (m, 1 H), 7.26-7.20 (m, 1 H), 7.16 (t, J=9.5 Hz, 1 H), 6.93 (d, J=8.5 Hz, 1 H), 6.87 (d, J=11.1 Hz, 1 H), 5.22 (s, 1 H), 4.31 (t, J=4.6 Hz, 2 H), 3.78 (s, 3 H), 2.70 (br. s., 2 H), 2.20-2.09 (m, 2 H), 1.88 (s, 3 H), 1.22 (s, 9 H); ES$^+$ MS: 548 (M+1).

Example 210

(S)(M)-2-(tert-butoxy)-2-(4-(8-fluoro-5-methylchroman-6-yl)-7-(3-fluorophenyl)-2-methyl-1-oxo-1,2-dihydroisoquinolin-3-yl)acetic acid

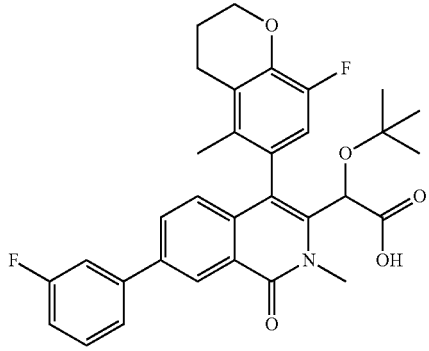 [SMILES: Cc1c(-c2c(C(OC(C)(C)C)C(=O)O)n(C)c(=O)c3cc(-c4cccc(F)c4)ccc23)cc(F)c2c1CCCO2]

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 3-fluoroboronic acid. Following hydrolysis and purification by reverse phase HPLC, the title compound was isolated (6 mg, 10.19 μmol, 18.56% yield) as a colorless residue: $^1$H NMR (400 MHz, CHLOROFORM-d) δ=8.71 (d, J=1.6 Hz, 1 H), 7.73 (dd, J=1.9, 8.5 Hz, 1 H), 7.52-7.32 (m, 3 H), 7.07 (t, J=8.2 Hz, 1 H), 6.94 (d, J=8.5 Hz, 1 H), 6.86 (d, J=11.1 Hz, 1 H), 5.22 (s, 1 H), 4.40-4.24 (m, 2 H), 3.78 (s, 3 H), 2.81-2.58 (m, 2 H), 2.22-2.09 (m, 2 H), 1.88 (s, 2 H), 1.22 (s, 9 H); ES$^+$ MS: 548 (M+1).

Example 211

(S)(M)-2-(tert-butoxy)-2-(4-(8-fluoro-5-methylchroman-6-yl)-7-(2-fluorophenyl)-2-methyl-1-oxo-1,2-dihydroisoquinolin-3-yl)acetic acid

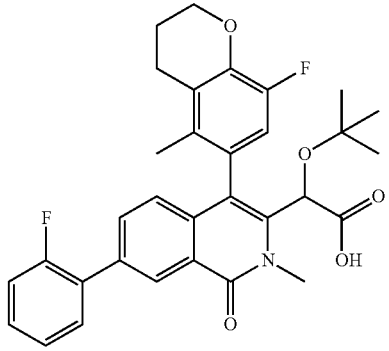 [SMILES: Cc1c(-c2c(C(OC(C)(C)C)C(=O)O)n(C)c(=O)c3cc(-c4ccccc4F)ccc23)cc(F)c2c1CCCO2]

The title compound was prepared in two steps in a manner similar to that described in Example 191 from (S)(M)-methyl 2-(7-bromo-4-(8-fluoro-5-methylchroman-6-yl)-2-methyl-1-oxo-1,2-dihydroisoquinolin-3-yl)-2-(tert-butoxy)acetate and 2-fluoroboronic acid. Following hydrolysis and purification by reverse phase HPLC, the title compound was isolated (11.2 mg, 0.020 mmol, 37.3% yield) as a colorless residue: $^1$H NMR (400 MHz, CHLOROFORM-d) δ=8.67 (s, 1 H), 7.70 (dd, J=1.9, 8.4 Hz, 1 H), 7.67-7.58 (m, 2 H), 7.14 (t, J=8.7 Hz, 2 H), 6.92 (d, J=8.5 Hz, 1 H), 6.86 (d, J=11.1 Hz, 1 H), 5.21 (s, 1 H), 4.36-4.27 (m, 2 H), 3.76 (s, 3 H), 2.78-2.62 (m, 2 H), 2.20-2.09 (m, 2 H), 1.90 (s, 3 H), 1.21 (s, 9 H); ES$^+$ MS: 548 (M+1).

Scheme 12: General Route for Synthesis of Examples with a R⁴ Nitrogen Linker
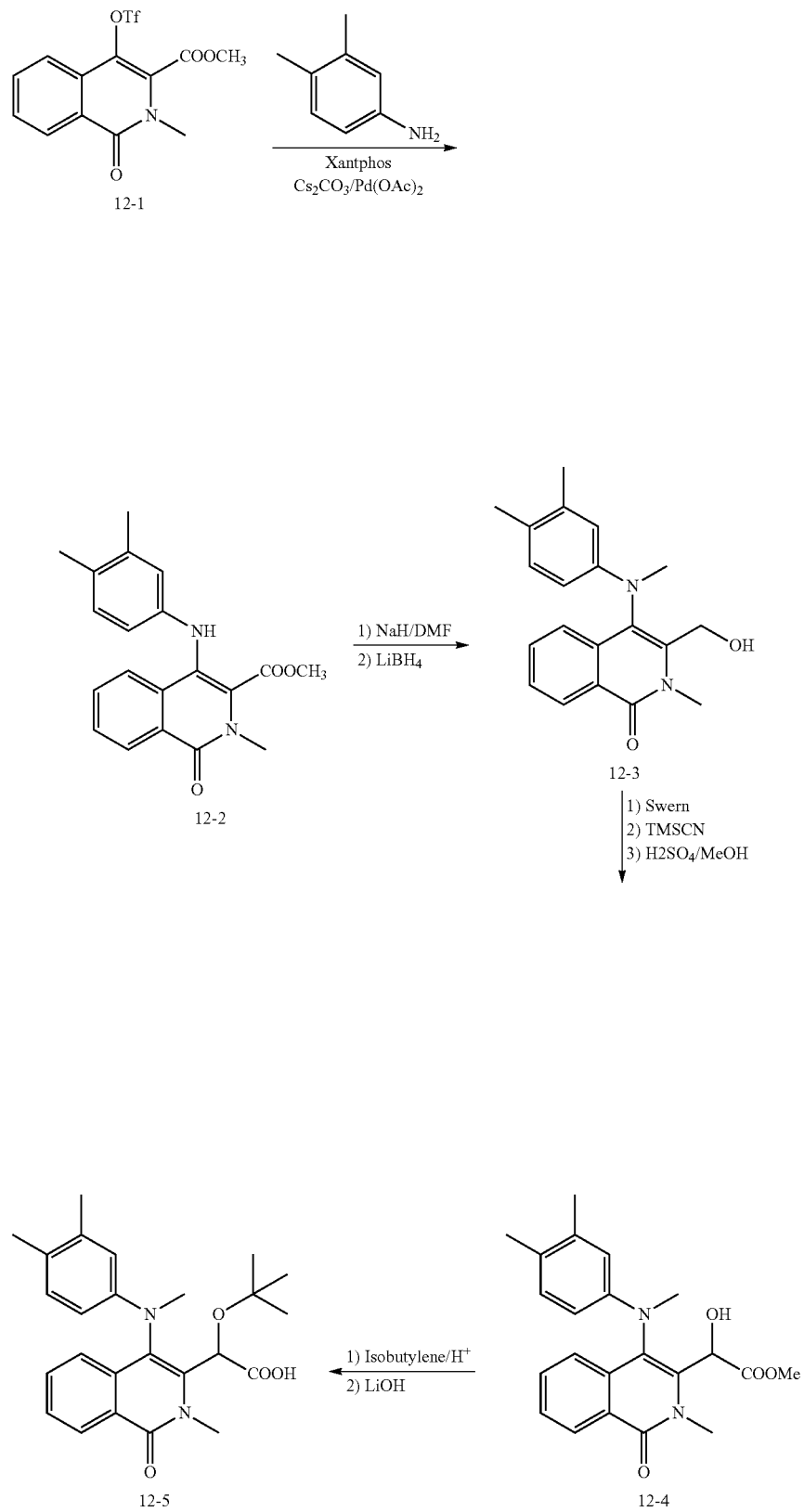

Example 212

2-(tert-Butoxy)-2-(4-((3,4-dimethylphenyl)(methyl)amino)-2-methyl-1-oxo-1,2-dihydroisoquinolin-3-yl)acetic acid

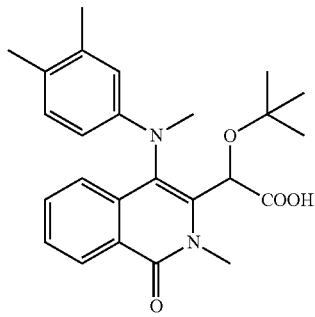 [SMILES: Cc1ccc(N(C)c2c(C(OC(C)(C)C)C(=O)O)n(C)c(=O)c3ccccc23)cc1C]

Step A

Methyl 4-[(3,4-dimethylphenyl)amino]-2-methyl-1-oxo-1,2-dihydro-3-isoquinolinecarboxylate

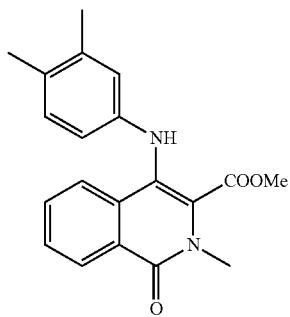 [SMILES: COC(=O)c1c(Nc2ccc(C)c(C)c2)c2ccccc2c(=O)n1C]

To a solution of methyl 2-methyl-1-oxo-4-{[(trifluoromethyl)sulfonyl]oxy}-1,2-dihydro-3-isoquinolinecarboxylate (0.84 g, 2.3 mmol) and (3,4-dimethylphenyl)amine (0.362 g, 2.99 mmol) in 1,4-dioxane (25 mL) under nitrogen was added cesium carbonate (1.124 g, 3.45 mmol), dimethylbisdiphenylphosphinoxanthene (0.103 g, 0.172 mmol) and Pd(OAc)$_2$ (0.026 g, 0.115 mmol) and the mixture was stirred at 100° C. for 16 hours. The mixture was diluted with diethyl ether, filtered through Celite and the filter cake was washed with diethyl ether. The crude product was purified on silica using EtOAc/hexanes 10-30% to provide the title compound as a yellow solid (0.59 g, 74%). $^1$H NMR (400 MHz, CDCl$_3$) δ ppm 8.48 (dd, J=1.2, 5.9 Hz, 1 H), 7.69-7.52 (m, 3 H), 6.89 (d, J=8.2 Hz, 1 H), 6.55-6.29 (m, 2 H), 5.66 (s, 1 H), 3.86 (s, 3 H), 3.62-3.51 (m, 3 H), 3.57 (s, 4 H), 2.14 (s, 9 H), 2.24-2.07 (m, 6 H), 1.56 (s, 3 H);); ES-LCMS: 337.3 (M+1).

Step B

Methyl 4-[(3,4-dimethylphenyl)(methyl)amino]-2-methyl-1-oxo-1,2-dihydro-3-isoquinolinecarboxylate

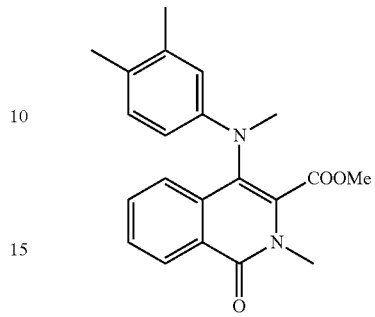

To a solution of methyl 4-[(3,4-dimethylphenyl)amino]-2-methyl-1-oxo-1,2-dihydro-3-isoquinolinecarboxylate (2.03 g, 6.03 mmol) in DMF (40 mL) at 0° C. was added sodium hydride (0.362 g, 9.05 mmol) followed by methyl iodide (5.66 mL, 91 mmol). The mixture was stirred at room temperature for 18 hours. 1M HCl/water was added and the mixture was extracted with EtOAc. The organic phase was washed with brine, dried over sodium sulfate and evaporated in vacuo. The crude product was purified on silica using EtOAc/hexanes 30-50% to provide the title compound as an off-white solid (2 g, 95%): $^1$H NMR (400 MHz, CDCl$_3$) δ ppm 8.56-8.37 (m, 1 H), 8.03 (s, 1 H), 7.62-7.47 (m, 2 H), 6.93 (d, J=8.4 Hz, 1 H), 6.48 (d, J=2.3 Hz, 1 H), 6.40 (dd, J=2.5, 8.2 Hz, 1 H), 3.77 (s, 3 H), 3.57 (s, 3 H), 3.24 (s, 3 H), 3.04-2.95 (m, 2 H), 2.89 (s, 2 H), 2.17 (d, J=8.8 Hz, 6 H);); ES-LCMS: 351.3 (M+1).

Step C

4-[(3,4-Dimethylphenyl)(methyl)amino]-3-(hydroxymethyl)-2-methyl-1(2H)-isoquinolinone

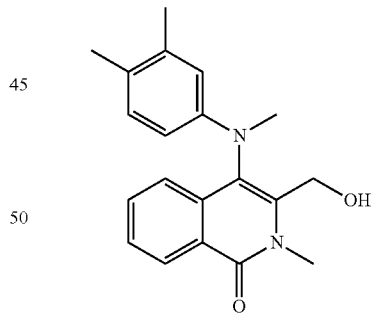

To a stirred solution of methyl 4-[(3,4-dimethylphenyl)(methyl)amino]-2-methyl-1-oxo-1,2-dihydro-3-isoquinolinecarboxylate (2.11 g, 6.02 mmol) in toluene (12 mL) was added dropwise 2 M lithium borohydride/THF (3.06 mL, 6.11 mmol). The mixture was stirred at 70° C. for 6 hours, quenched with 1M HCl/water and partitioned between EtOAc and aq. NaHCO$_3$. The organic phase was dried over sodium sulfate, evaporated in vacuo and purified on silica using EtOAc/hexanes 20-50% to provide the title compound as an off-white solid (0.94 g, 48%). $^1$H NMR (400 MHz, CDCl$_3$) δ ppm 8.51 (br. s., 1 H), 7.57 (br. s., 2 H), 6.96 (br. s., 1 H), 6.44 (br. s., 2 H), 4.80-4.48 (m, 2 H), 3.80 (br. s., 3 H), 3.27 (br. s., 3 H), 2.16 (d, 11 H), 2.29-2.06 (m, 6 H); ES-LCMS: 323.4 (M+1); ES-LCMS: 323.4 (M+1).

Step D

4-[(3,4-Dimethylphenyl)(methyl)amino]-2-methyl-1-oxo-1,2-dihydro-3-isoquinolinecarbaldehyde

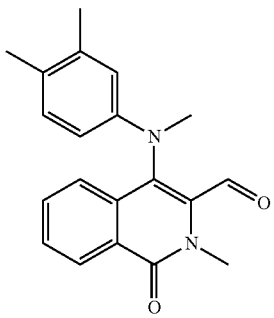 [SMILES: Cc1ccc(N(C)c2c(C=O)n(C)c(=O)c3ccccc23)cc1C]

To a solution of oxalyl chloride (0.015 mL, 0.172 mmol) in DCM (5 mL) at −70° C. was added dropwise DMSO (0.024 mL, 0.344 mmol). After 15 min a solution of 4-[(3,4-dimethylphenyl)(methyl)amino]-3-(hydroxymethyl)-2-methyl-1 (2H)-isoquinolinone (25 mg, 0.078 mmol) in DCM (1 mL) was added slowly, and the mixture was kept at −78° C. for 30 min. Then NEt$_3$ (38 uL) was added and the reaction was kept at −78° C. for 1 hour. The mixture was quenched with aq. NaHCO$_3$ and extracted with dichloromethane. The organic phase was dried over sodium sulfate and evaporated to give the crude title compound as yellow oil (16.9 mg, 61.4%). $^1$H NMR (400 MHz, CDCl$_3$) δ ppm 9.97-9.78 (m, 1 H), 8.64-8.46 (m, 1 H), 7.75-7.54 (m, 2 H), 7.51-7.42 (m, 1 H), 7.07-6.92 (m, 1 H), 6.59-6.38 (m, 2 H), 3.87 (s, 3 H), 3.40 (s, 3 H), 2.18 (d, J=6.3 Hz, 6 H); ES-LCMS: 321.1 (M+1).

Step 5

Methyl 2-(4-((3,4-dimethylphenyl)(methyl)amino)-2-methyl-1-oxo-1,2-dihydroisoquinolin-3-yl)-2-hydroxyacetate

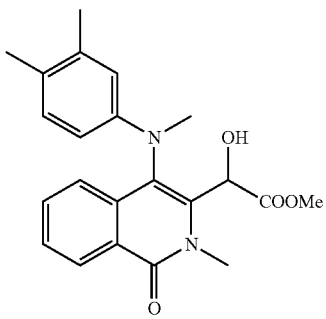 [SMILES: COC(=O)C(O)c1c(N(C)c2ccc(C)c(C)c2)c2ccccc2c(=O)n1C]

To a solution of 4-[(3,4-dimethylphenyl)(methyl)amino]-2-methyl-1-oxo-1,2-dihydro-3-isoquinolinecarbaldehyde (0.17 g, 0.531 mmol) in DCM (6 mL) at 0° C. was added ZnI$_2$ (0.339 g, 1.061 mmol), followed by TMSCN (0.711 mL, 5.31 mmol). The mixture was stirred at room temperature for 1 hour, then quenched with water and extracted with DCM. The organic phase was washed with brine, dried over sodium sulfate, filtered and concentrated to give the crude intermediate used in the next step.

To a solution of [2-methyl-1-oxo-4-(phenylmethyl)-1,2-dihydro-3-isoquinolinyl][(trimethylsilyl)oxy]acetonitrile in MeOH (6 mL) was added H$_2$SO$_4$ (1.69 mL) dropwise. The mixture was stirred at 80° C. for 3 hours, quenched with ice water and extracted with EtOAc. The organic phase was washed with brine, dried over sodium sulfate and evaporated in vacuo. The crude product was purified on silica using EtOAc/hexanes 0-40% to provide the title compound as a clear oil (90 mg, 44.6%). $^1$H NMR (400 MHz, CDCl$_3$) δ ppm 8.57-8.44 (m, 1 H), 7.60-7.44 (m, 2 H), 7.29-7.17 (m, 2 H), 7.05-6.90 (m, 1 H), 6.46 (br. s., 2 H), 5.57 (s, 0 H), 3.82-3.77 (m, 1 H), 3.72 (s, 1 H), 3.64-3.56 (m, 1 H), 3.50-3.41 (m, 1 H), 3.39-3.28 (m, 2 H), 3.24 (s, 2 H), 2.24-2.12 (m, 6 H); ES-LCMS: 381.3 (M+1).

Step 6

2-(tert-Butoxy)-2-(4-((3,4-dimethylphenyl)(methyl)amino)-2-methyl-1-oxo-1,2-dihydroisoquinolin-3-yl) acetic acid

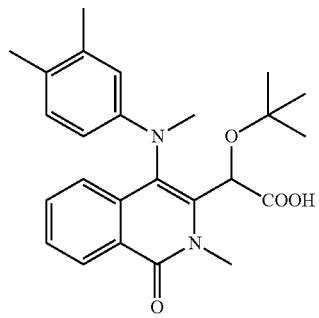 [SMILES: Cc1ccc(N(C)c2c(C(OC(C)(C)C)C(=O)O)n(C)c(=O)c3ccccc23)cc1C]

To a mixture of methyl 2-(4-((3,4-dimethylphenyl)(methyl)amino)-2-methyl-1-oxo-1,2-dihydroisoquinolin-3-yl)-2-hydroxyacetate (90 mg, 0.237 mmol) and amberlyst 15 resin (45 mg, 0.237 mmol) in DCM (3 mL) at −70° C. was bubbled a stream of isobutylene until the volume doubles. The tube was sealed, and the reaction was stirred at room temperature for 10 hours. The mixture was filtered through a short pad of silica gel, washed with DCM and EtOAc, and the filtrate was concentrated. The mixture was purified on silica using EtOAc/hexanes 0-40% to give the intermediate methyl ester as an off-white solid (41.6 mg, 39%). $^1$H NMR (400 MHz, CDCl$_3$) δ ppm 8.56-8.44 (m, 1 H), 7.59-7.42 (m, 3 H), 7.26-7.14 (m, 1 H), 7.05-6.93 (m, 1 H), 6.03-5.82 (m, 2 H), 3.74-3.67 (m, 7 H), 3.33 (s, 4 H), 2.23-2.12 (m, 6 H), 1.38-1.22 (m, 4 H), 1.12-1.00 (m, 9 H); ES-LCMS: 437.4 (M+1).

To a solution of methyl 2-(tert-butoxy)-2-(4-((3,4-dimethylphenyl)(methyl)amino)-2-methyl-1-oxo-1,2-dihydroisoquinolin-3-yl)acetate (41.6 mg) in THF (3.0 mL) and MeOH (1 mL) was added a solution of LiOH/water (1.183 mL, 1.183 mmol). The mixture was stirred at room temperature for 18 hours. The mixture was cooled to 0° C. and 1N HCl/water was added to pH~3 and the mixture was purified by reverse phase HPLC on a C$_{18}$ column using MeCN/water 10-90% containing 0.05% TFA to provide the title compound as an off-white solid (19.5 mg, 19%). $^1$H NMR (400 MHz, CDCl$_3$) ppm 8.58-8.42 (m, 1 H), 7.62-7.45 (m, 2 H), 7.21-7.12 (m, 1 H), 7.02-6.58 (m, 2 H), 6.02 (s, 1 H), 3.79-3.63 (m, 3 H), 3.41 (s, 3 H), 2.30-2.07 (m, 6 H), 1.27-1.08 (m, 9 H); ES-LCMS: 423.4 (M+1).

Scheme 13: General Route for Synthesis of Examples with Carboxylic Acid Isosteres

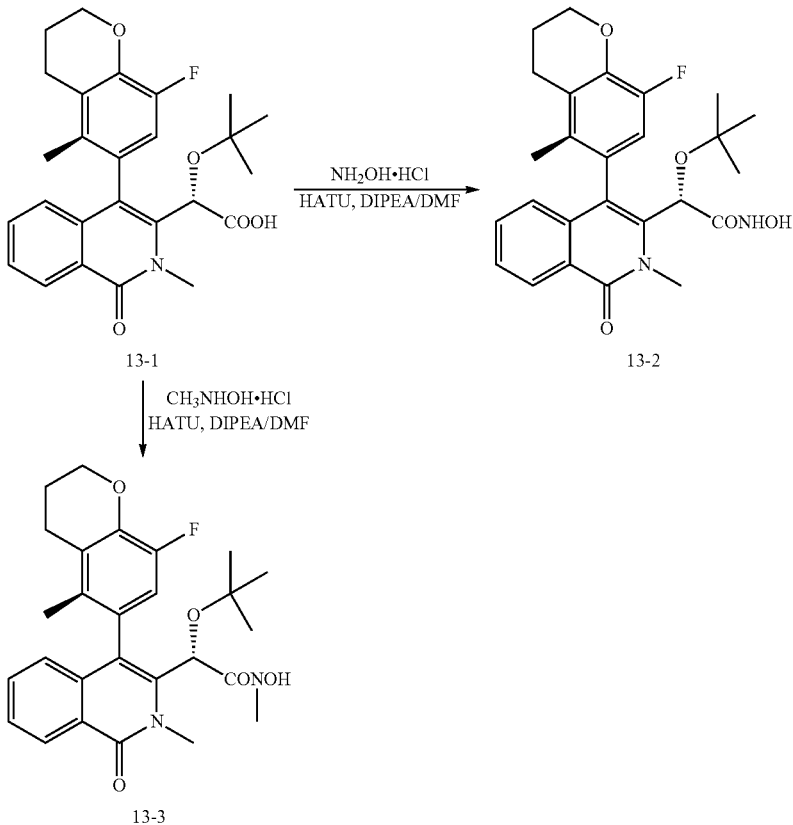

Example 213

(S)(M)-2-(tert-butoxy)-2-(4-(8-fluoro-5-methylchroman-6-yl)-2-methyl-1-oxo-1,2-dihydroisoquinolin-3-yl)-N-hydroxyacetamide

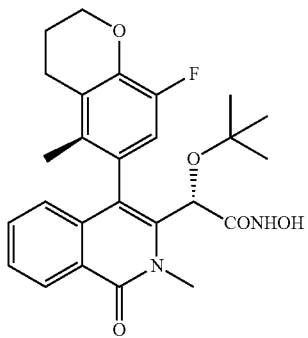

A solution of (S)(M)-2-(tert-butoxy)-2-(4-(8-fluoro-5-methylchroman-6-yl)-2-methyl-1-oxo-1,2-dihydroisoquinolin-3-yl)acetic acid (22.3 mg, 0.049 mmol), HATU (28.0 mg, 0.074 mmol) and DIPEA (0.030 mL, 0.172 mmol) in DMF (0.7 mL) was stirred at room temperature for 30 min and then hydroxylamine hydrochloride (6.83 mg, 0.098 mmol) was added. The mixture was stirred at room temperature for 2 hours, quenched with water and extracted with EtOAc. The organic phase was evaporated in vacuo and purified by reverse phase HPLC on a $C_{18}$ column using MeCN/water 10-90% containing 0.05% trifluoroacetic acid to provide the title compound as off-white solid (7.9 mg, 32.6%). $^1$H NMR (400 MHz, METHANOL-$d_4$) δ ppm 8.56-8.14 (m, 1H), 7.64-7.44 (m, 2H), 6.90-6.79 (m, 2H), 5.25-5.16 (m, 1H), 4.28-4.17 (m, 2H), 3.73 (s, 3H), 2.78-2.63 (m, 2H), 2.16-2.02 (m, 2H), 1.96-1.87 (m, 3H), 1.16 (s, 9H); ES-LCMS: 468.2 (M+1).

Example 214

(S)(M)-2-(tert-butoxy)-2-(4-(8-fluoro-5-methylchroman-6-yl)-2-methyl-1-oxo-1,2-dihydroisoquinolin-3-yl)-N-hydroxy-N-methylacetamide

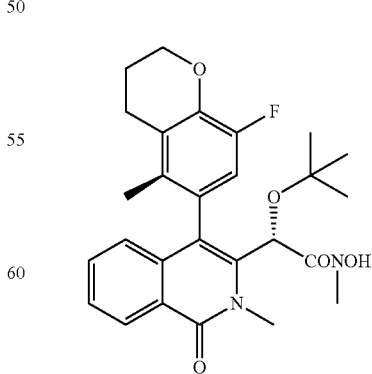

A solution of (S)(M)-2-(tert-butoxy)-2-(4-(8-fluoro-5-methylchroman-6-yl)-2-methyl-1-oxo-1,2-dihydroisoquinolin- 3-yl)acetic acid (25.2 mg, 0.056 mmol), DIPEA (0.034 mL, 0.194 mmol) and HATU (31.7 mg, 0.083 mmol) in DMF (0.7 mL) was stirred at room temperature for 30 min and then N-methylhydroxylamine hydrochloride (9.28 mg, 0.111 mmol) was added. The mixture was stirred at room temperature overnight, quenched with water and extracted with EtOAc. The organic phase was evaporated in vacuo and purified by reverse phase HPLC on a C$_{18}$ column using MeCN/water 10-90% containing 0.05% trifluoroacetic acid to provide the title compound as off-white solid (14.6 mg, 54.4%). $^1$H NMR (400 MHz, METHANOL-d$_4$) δ ppm 8.35 (s, 1 H), 7.50 (s, 2 H), 6.88 (s, 2 H), 5.75 (br. s., 1 H), 4.24 (br. s., 2 H), 3.88 (s, 3 H), 2.78-2.65 (m, 2 H), 2.16-2.05 (m, 2 H), 1.69 (s, 3 H), 1.12 (s, 9 H); ES-LCMS: 483.4 (M+1).

Example 215

(2S)(M)-2-[(1,1-dimethylethyl)oxy]-2-[4-(8-fluoro-5-methyl-3,4-dihydro-2H-chromen-6-yl)-2-methyl-1-oxo-1,2-dihydro-3-isoquinolinyl]-N-(methylsulfonyl)ethanamide

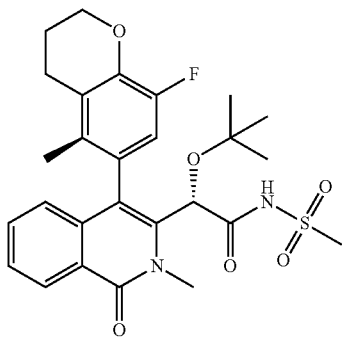

An ice cold mixture of (S)(M)-2-(tert-butoxy)-2-(4-(8-fluoro-5-methylchroman-6-yl)-2-methyl-1-oxo-1,2-dihydroisoquinolin-3-yl)acetic acid (20.00 mg, 0.044 mmol) in dichloromethane (DCM) (1.0 mL) was treated with oxalyl chloride (5.68 µL, 0.066 mmol) and DMF (one drop). The mixture was warmed to ambient temperature, stirred for several minutes and then concentrated to dryness. A mixture of the crude acid chloride in dichloromethane (DCM) (1.0 mL) was treated with methanesulfonamide (15.00 mg, 0.158 mmol) and stirred at ambient temperature for 30 minutes. LCMS indicated that no reaction had occurred. 1,2-dichloroethane (DCE) (1.000 mL) was added and the mixture was heated to 80° C. for 2 hours. LCMS indicated complete consumption of the desired product and significant conversion to the desired product. The mixture was cooled, concentrated to dryness and then purified by reverse phase chromatography to give a colorless residue. $^1$H NMR indicated that the sample contaminated with DMF. The residue was taken up in ethyl acetate, washed twice with water, once with brine, dried over sodium sulfate, filtered and concentrated to afford the title compound as a white solid (8.6 mg, 37%). $^1$H NMR (400 MHz, CHLOROFORM-d) δ=8.97 (m, 1 H), 8.50 (m, 1 H), 7.60-7.43 (m, 2 H), 6.91-6.76 (m, 2 H), 5.23 (s, 1 H), 4.42-4.18 (m, 2 H), 3.80-3.55 (m, 3 H), 3.32 (s, 3 H), 2.90-2.55 (m, 2 H), 2.30-2.04 (m, 2 H), 1.94 (s, 3 H), 1.23 (s, 9 H); LC/MS (m/z) ES$^+$=531 (M+1).

Scheme 14: General Route for Synthesis of Examples with R$^3$ = Alkyl

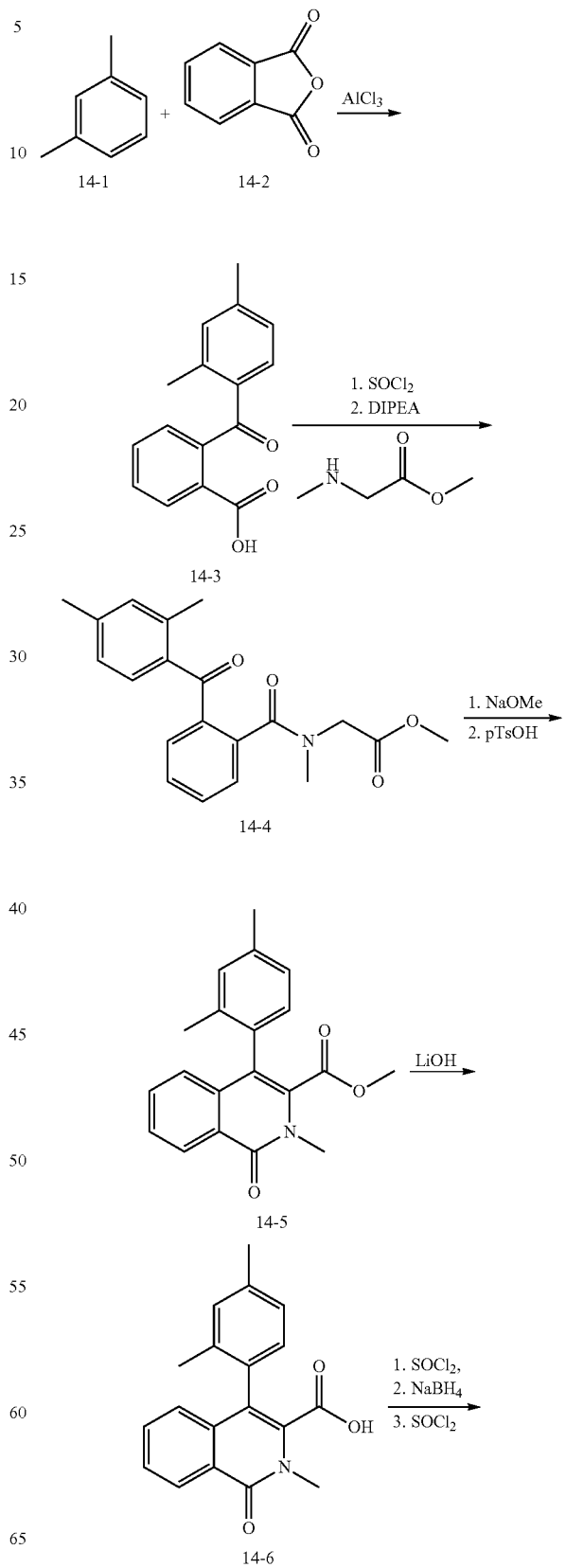

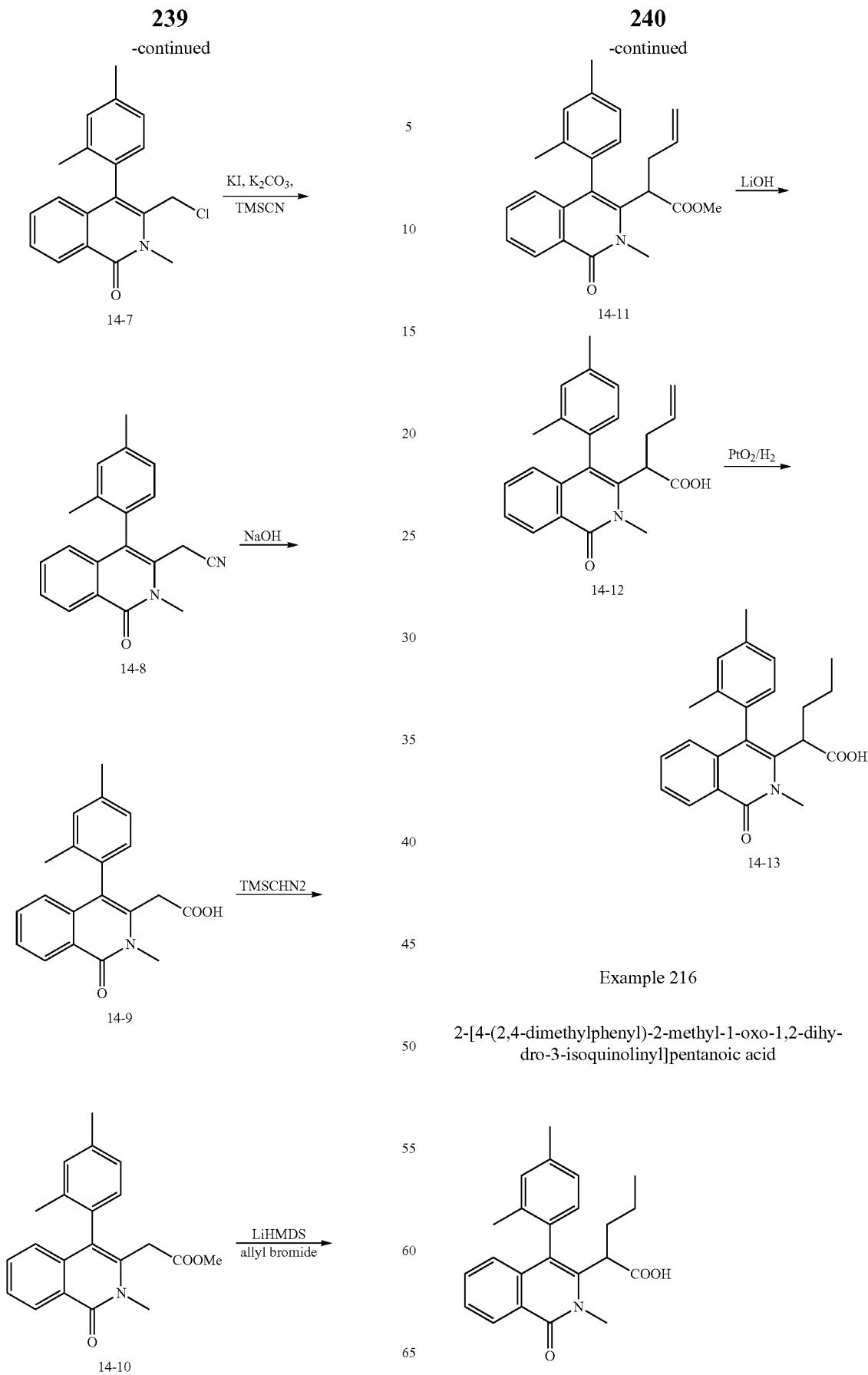
Example 216
2-[4-(2,4-dimethylphenyl)-2-methyl-1-oxo-1,2-dihydro-3-isoquinolinyl]pentanoic acid

Step A

2-[(2,4-dimethylphenyl)carbonyl]benzoic acid

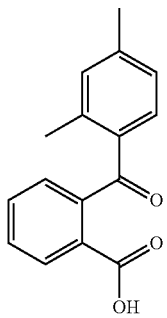

An ice/salt cold mixture of m-xylene (114 g, 1073 mmol) was treated with aluminium chloride (59.4 g, 446 mmol) (in three portions), followed by 2-benzofuran-1,3-dione (30 g, 203 mmol) (in three portions). The mixture was warmed to room temperature and stirred for 3 hours after which time the mixture turned to a thick white suspension. The mixture was heated to 55° C. for 2 hours, and cooled to room temperature. The thick mixture was slowly poured into ice cold 20% HCl and collected on filter paper. The filtered material was allowed to dry to give the desired product as a white solid (50 g, 97%). $^1$H NMR (400 MHz, CHLOROFORM-d) δ ppm 7.98-8.07 (m, 1 H) 7.60-7.69 (m, 1 H) 7.51-7.59 (m, 1 H) 7.38-7.45 (m, 1 H) 7.01-7.13 (m, 2 H) 6.86-6.94 (m, 1 H) 2.61 (s, 3 H) 2.33 (s, 3 H); LC/MS (m/z) ES$^+$=255 (M+1).

Step B

Methyl N-({2-[(2,4-dimethylphenyl)carbonyl]phenyl}carbonyl)-N-methylglycinate

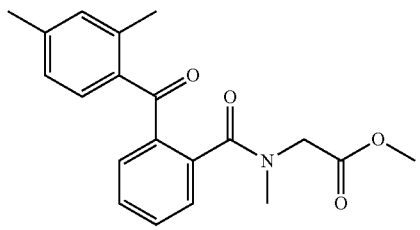

A mixture of 2-(2,4-dimethylbenzoyl)benzoic acid (50 g, 197 mmol) and thionyl chloride (215 mL, 2949 mmol) was heated at 70° C. for 1.5 hours. The mixture was concentrated, dissolved in tetrahydrofuran (THF) (200 mL) and N,N-dimethylformamide (DMF) (40 mL) and treated with methyl N-methylglycinate (27.4 g, 197 mmol). The mixture was cooled to 0° C. and treated with Hunig's base (103 mL, 590 mmol). The mixture was heated to 70° C. for 1 hour, cooled to ambient temperature and then diluted with ethyl acetate. The organic phase was washed with 1N HCl, water, then brine, dried over sodium sulfate, filtered and concentrated to a brown thick oil (60 g, 90%) which was used without further purification. LC/MS (m/z) ES$^+$=340 (M+1).

Step C methyl 4-(2,4-dimethylphenyl)-2-methyl-1-oxo-1,2-dihydro-3-isoquinolinecarboxylate

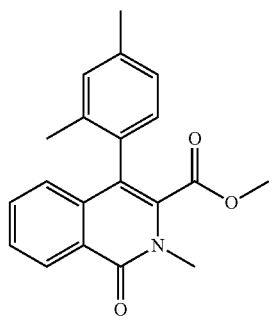 [SMILES: COC(=O)c1c(-c2ccc(C)cc2C)c2ccccc2c(=O)n1C]

An ice cold mixture of methyl 2-(2-(2,4-dimethylbenzoyl)-N-methylbenzamido)acetate (60 g, 177 mmol) in methanol (400 mL) was treated with sodium methoxide (42.0 g, 194 mmol) and the resultant was allowed to stir at ambient temperature for 1 hour. The mixture was cooled to 0° C., treated with HCl (21.78 mL, 265 mmol) and then concentrated. The residue was dissolved in ethyl acetate, washed with water, brine, dried over Na$_2$SO$_4$, filtered and concentrated. The crude intermediate was treated with Toluene (400 mL) and pTsOH (16.81 g, 88 mmol) and the mixture was heated at 120° C. for 1 hour. Additional pTsOH (16.81 g, 88 mmol) was added and the mixture was stirred at 120° C. overnight. LCMS indicated complete reaction. The mixture was concentrated and the residue was dissolved in ethyl acetate. The organic phase was washed with water, then brine, dried over Na$_2$SO$_4$, filtered and concentrated. The residue was purified on silica gel (0-60% EA on hexane) to give the desired product as a white solid (24 g, 53%). $^1$H NMR (400 MHz, CHLOROFORM-d) δ ppm 8.48-8.57 (m, 1 H) 7.50-7.58 (m, 2 H) 7.10-7.14 (m, 1 H) 7.04 (s, 3 H) 3.61 (s, 3 H) 3.54 (s, 3 H) 2.39 (s, 3 H) 2.04 (s, 3 H); LC/MS (m/z) ES$^+$=322 (M+1).

Step D 4-(2,4-dimethylphenyl)-2-methyl-1-oxo-1,2-dihydro-3-isoquinolinecarboxylic acid

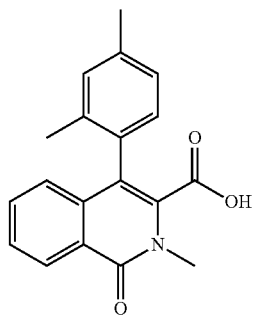 [SMILES: Cc1ccc(-c2c(C(=O)O)n(C)c(=O)c3ccccc23)c(C)c1]

A mixture of methyl 4-(2,4-dimethylphenyl)-2-methyl-1-oxo-1,2-dihydroisoquinoline-3-carboxylate (30 g, 74.7 mmol) in tetrahydrofuran (THF) (400 mL) was treated with lithium hydroxide (8.94 g, 373 mmol) and stirred at reflux overnight. The mixture was concentrated and used crude in the next step (21.6 g, 94%). $^1$H NMR (400 MHz, DMSO-$d_6$) δ ppm 13.81-14.14 (m, 1 H) 8.28-8.37 (m, 1 H) 7.62-7.69 (m, 1 H) 7.53-7.61 (m, 1 H) 7.13-7.19 (m, 1 H) 7.01-7.12 (m, 2 H) 6.82-6.91 (m, 1 H) 3.52 (s, 3 H) 2.34 (s, 3 H) 1.97 (s, 3 H); LC/MS (m/z) ES$^+$=308 (M+1).

Step E 3-(chloromethyl)-4-(2,4-dimethylphenyl)-2-methyl-1(2H)-isoquinolinone

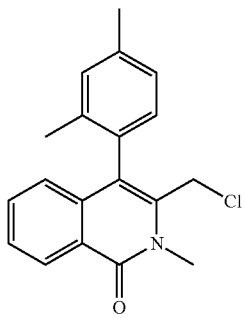 [SMILES: Cc1ccc(-c2c(CCl)n(C)c(=O)c3ccccc23)c(C)c1]

A suspension of 4-(2,4-dimethylphenyl)-2-methyl-1-oxo-1,2-dihydroisoquinoline-3-carboxylic acid (21.6 g) in thionyl chloride (218 mL, 2987 mmol) was heated at 70° C. for 2 hours. The mixture was concentrated, dissolved in tetrahydrofuran (THF) (15 mL), and treated with sodium borohydride (0.929 g, 24.56 mmol). The resulting mixture was heated to 70° C. for 2 hours until LCMS indicated complete reaction. The mixture was cooled to 0° C. and methanol was added until gas evolution ceased. The mixture was concentrated, diluted with water and then extracted three times with dichloromethane. The combined extracts were washed with brine, dried over Na$_2$SO$_4$, filtered and concentrated. The residue was treated with thionyl chloride (20 mL) and heated at 70° C. for 2 hours. The mixture was concentrated and then purified on silica gel (0-70% EA/Hexane) to afford the title compound (1.17 g, 76%). $^1$H NMR (400 MHz, CHLOROFORM-d) δ ppm 8.46-8.59 (m, 1 H) 7.47-7.57 (m, 2 H) 7.05-7.24 (m, 3 H) 6.87-6.99 (m, 1 H) 4.43-4.55 (m, 1 H) 4.31-4.41 (m, 1 H) 3.86 (s, 3 H) 2.43 (s, 3 H) 2.01 (s, 3 H). LC/MS (m/z) ES$^+$=312 (M+1).

Step F

[4-(2,4-dimethylphenyl)-2-methyl-1-oxo-1,2-dihydro-3-isoquinolinyl]acetonitrile

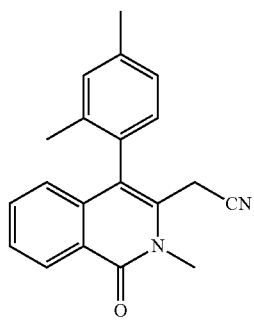 [SMILES: Cc1ccc(-c2c(CC#N)n(C)c(=O)c3ccccc23)c(C)c1]

A solution of 3-(chloromethyl)-4-(2,4-dimethylphenyl)-2-methylisoquinolin-1(2H)-one (1.17 g, 3.75 mmol, 76% yield) in Acetonitrile (15.00 mL) was treated with potassium carbonate (1.018 g, 7.37 mmol), potassium iodide (1.223 g, 7.37 mmol) and TMSCN (0.988 mL, 7.37 mmol) and then stirred at room temperature for 3 hours. The mixture was diluted with dichloromethane, washed with saturated NaHCO$_3$ solution and brine, dried over Na$_2$SO$_4$, filtered and concentrated. The residue was purified on silica gel (0-70% EA/Hexane) to afford the title compound (1.05 g, 93%). $^1$H NMR (400 MHz, CHLOROFORM-d) δ ppm 8.45-8.57 (m, 1 H) 7.47-7.59 (m, 2 H) 7.20-7.24 (m, 1 H) 7.13-7.19 (m, 1 H) 7.03-7.11 (m, 1 H) 6.86-6.98 (m, 1 H) 3.86 (s, 3 H) 3.48-3.67 (m, 2 H) 2.44 (s, 3 H) 2.02 (s, 3 H). LC/MS (m/z) ES$^+$=303 (M+1).

Step G

[4-(2,4-dimethylphenyl)-2-methyl-1-oxo-1,2-dihydro-3-isoquinolinyl]acetic acid

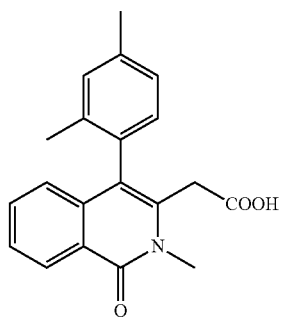 [SMILES: Cc1ccc(-c2c(CC(=O)O)n(C)c(=O)c3ccccc23)c(C)c1]

A solution of 2-(4-(2,4-dimethylphenyl)-2-methyl-1-oxo-1,2-dihydroisoquinolin-3-yl)acetonitrile (1.05 g, 3.47 mmol, 70.7% yield) in ethanol (15.00 mL) was treated with 2 mL 20% NaOH solution and heated in a sealed tube at 110° C. overnight. The mixture was cooled to room temperature and then concentrated. The resultant was cooled to 0° C., acidified to pH 1.0 with HCl (4 M), then filtered to afford the title compound (835 mg, 75%). $^1$H NMR (400 MHz, DMSO-$d_6$) δ ppm 12.70-12.89 (m, 1 H) 8.24-8.35 (m, 1 H) 7.53-7.63 (m, 1 H) 7.44-7.53 (m, 1 H) 7.19-7.26 (m, 1 H) 7.08-7.17 (m, 1 H)

6.93-7.00 (m, 1 H) 6.71-6.82 (m, 1 H) 3.62-3.71 (m, 1 H) 3.56 (s, 2 H) 3.41-3.49 (m, 1 H) 2.36 (s, 3 H) 1.91 (s, 3 H). LC/MS (m/z) ES$^+$=322 (M+1).

Step H

Methyl [4-(2,4-dimethylphenyl)-2-methyl-1-oxo-1,2-dihydro-3-isoquinolinyl]acetate

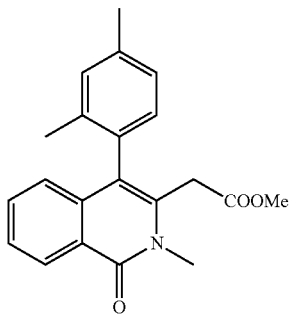 [SMILES: COC(=O)Cc1c(-c2ccc(C)cc2C)c2ccccc2c(=O)n1C]

A solution of 2-(4-(2,4-dimethylphenyl)-2-methyl-1-oxo-1,2-dihydroisoquinolin-3-yl)acetic acid (1.1 g, 3.42 mmol, 69.7% yield) in diethyl ether (15.00 mL) was treated with TMS-diazomethane (3.68 mL, 7.37 mmol) and the resultant was allowed to stir at room temperature for 30 minutes. The mixture was quenched with acetic acid and then extracted with ethyl acetate. The combined extracts were washed with saturated NaHCO$_3$ solution and brine, dried over Na$_2$SO$_4$, filtered and concentrated. The residue was purified on silica gel (0-70% EA/Hexane) (830 mg, 96%) to afford the title compound. $^1$H NMR (400 MHz, CHLOROFORM-d) δ ppm 8.46-8.54 (m, 1 H) 7.42-7.54 (m, 2 H) 7.13-7.20 (m, 1 H) 7.06-7.13 (m, 1 H) 6.99-7.05 (m, 1 H) 6.84-6.94 (m, 1 H) 3.66 (s, 3 H) 3.65 (s, 3 H) 2.41 (s, 3 H) 1.97 (s, 3 H). LC/MS (m/z) ES$^+$=336 (M+1).

Step I methyl 2-[4-(2,4-dimethylphenyl)-2-methyl-1-oxo-1,2-dihydro-3-isoquinolinyl]-4-pentenoate

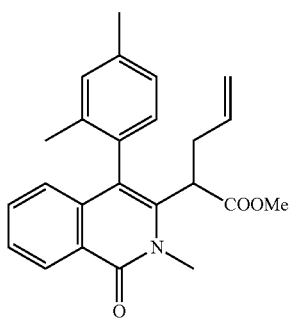 [SMILES: C=CCC(C(=O)OC)c1c(-c2ccc(C)cc2C)c2ccccc2c(=O)n1C]

A solution of methyl 2-(4-(2,4-dimethylphenyl)-2-methyl-1-oxo-1,2-dihydroisoquinolin-3-yl)acetate (60 mg, 0.179 mmol) in tetrahydrofuran (THF) (2 mL) was treated with LiHMDS (0.358 mL, 0.358 mmol) and allyl bromide (0.232 mL, 2.68 mmol) at 0° C. The mixture was warmed to room temperature and stirred for 1 hour. The mixture was quenched with saturated NH$_4$Cl solution and extracted with ethyl acetate. The combined extracts were washed with saturated NaHCO$_3$ solution and brine, dried over Na$_2$SO$_4$, filtered and concentrated. The material was used crude in the next step (64 mg, 95%). $^1$H NMR (400 MHz, CHLOROFORM-d) δ ppm 8.44-8.54 (m, 1 H) 7.41-7.56 (m, 2 H) 7.06-7.19 (m, 2 H) 6.97-7.05 (m, 1 H) 6.80-6.91 (m, 1 H) 5.40-5.70 (m, 1 H) 4.85-5.06 (m, 2 H) 3.89-4.05 (m, 1 H) 3.68 (s, 3 H) 3.53 (s, 3 H) 2.91-3.06 (m, 1 H) 2.43-2.55 (m, 1 H) 2.41 (s, 3 H) 2.03 (s, 3 H). LC/MS (m/z) ES$^+$=376 (M+1).

Step J

2-[4-(2,4-dimethylphenyl)-2-methyl-1-oxo-1,2-dihydro-3-isoquinolinyl]-4-pentenoic acid

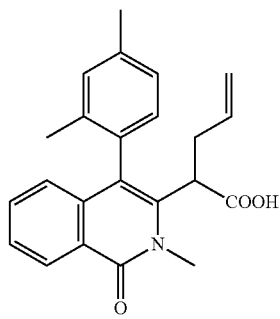 [SMILES: C=CCC(C(=O)O)c1c(-c2ccc(C)cc2C)c2ccccc2c(=O)n1C]

A solution of methyl 2-(4-(2,4-dimethylphenyl)-2-methyl-1-oxo-1,2-dihydroisoquinolin-3-yl)pent-4-enoate (71 mg, 0.170 mmol, 95% yield) in tetrahydrofuran (THF) (2 mL) was treated with lithium hydroxide (1 mL, 2.0 mmol) and heated to 70° C. overnight. The mixture was cooled to room temperature, quenched with saturated NH$_4$Cl solution and acidified with HCl (1M) to pH 2.0. The mixture was then extracted with ethyl acetate, washed with saturated NaHCO$_3$ solution and brine, dried over Na$_2$SO$_4$, filtered and concentrated. The material was used crude in the next step (59 mg, 96%). $^1$H NMR (400 MHz, CHLOROFORM-d) δ ppm 8.40-8.57 (m, 1 H) 7.41-7.56 (m, 2 H) 6.97-7.22 (m, 3 H) 6.82-6.92 (m, 1 H) 5.44-5.72 (m, 1 H) 4.86-5.06 (m, 2 H) 3.95-4.12 (m, 1 H) 3.60 (br. s., 3 H) 2.88-3.05 (m, 1 H) 2.42 (s, 3 H) 1.93-2.10 (m, 3 H). LC/MS (m/z) ES$^+$=362 (M+1).

Step K

2-[4-(2,4-dimethylphenyl)-2-methyl-1-oxo-1,2-dihydro-3-isoquinolinyl]pentanoic acid

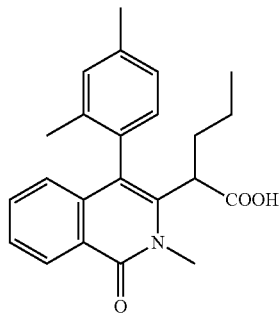 [SMILES: CCCC(C(=O)O)c1c(-c2ccc(C)cc2C)c2ccccc2c(=O)n1C]

A solution of 2-(4-(2,4-dimethylphenyl)-2-methyl-1-oxo-1,2-dihydroisoquinolin-3-yl)pent-4-enoic acid (69 mg, 0.162 mmol,) in ethyl acetate (2 mL) was treated with platinum(IV) oxide (8.12 mg, 0.036 mmol) and the mixture was stirred at room temperature under an atmosphere of $H_2$ for 1 hour. The mixture was filtered and the filtrate was purified by reverse phase hplc afford the title compound (31 mg, 52%). $^1$H NMR (400 MHz, CHLOROFORM-d) δ ppm 8.45-8.52 (m, 1 H) 7.43-7.54 (m, 2 H) 7.07-7.23 (m, 2 H) 6.97-7.03 (m, 1 H) 6.81-6.92 (m, 1 H) 3.79-3.97 (m, 1 H) 3.59 (s, 3 H) 2.42 (s, 3 H) 1.94-2.10 (m, 3 H) 1.54-1.74 (m, 2 H) 1.19-1.30 (m, 2 H) 0.72-0.88 (m, 3 H). LC/MS (m/z) ES$^+$=364 (M+1).

Example 217

Step A

Methyl 2-[4-(2,4-dimethylphenyl)-2-methyl-1-oxo-1,2-dihydro-3-isoquinolinyl]-4-methyl-4-pentenoate

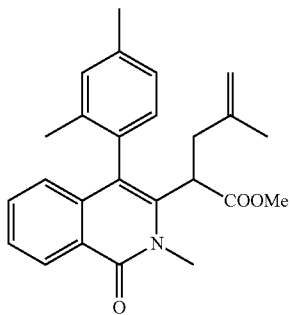 [SMILES: C=C(C)CC(C(=O)OC)c1c(-c2ccc(C)cc2C)c2ccccc2c(=O)n1C]

A solution of methyl 2-(4-(2,4-dimethylphenyl)-2-methyl-1-oxo-1,2-dihydroisoquinolin-3-yl)acetate (60 mg, 0.179 mmol) in tetrahydrofuran (THF) (2 mL) was treated with LiHMDS (0.447 mL, 0.447 mmol, 1.0M in THF) and 3-bromo-2-methylpropene (0.271 mL, 2.68 mmol) at 0° C. The mixture was stirred at room temperature for 1 hour and then quenched with saturated $NH_4Cl$ solution. The mixture was extracted with ethyl acetate, washed with saturated $NaHCO_3$ and brine, dried over $Na_2SO_4$, filtered and concentrated. The residue was used crude in the next step (65 mg, 94%). $^1$H NMR (400 MHz, CHLOROFORM-d) δ ppm 8.43-8.56 (m, 1 H) 7.40-7.57 (m, 2 H) 7.09-7.20 (m, 1 H) 6.95-7.08 (m, 2 H) 6.78-6.86 (m, 1 H) 4.68-4.75 (m, 1 H) 4.44-4.54 (m, 1 H) 3.91-4.03 (m, 1 H) 3.68 (s, 3 H) 3.53 (s, 3 H) 2.40 (br. s., 3 H) 2.04 (s, 3 H) 1.59-1.68 (m, 2 H) 1.49 (br. s., 3 H). LC/MS (m/z) ES$^+$=390 (M+1).

Step B

Methyl 2-[4-(2,4-dimethylphenyl)-2-methyl-1-oxo-1,2-dihydro-3-isoquinolinyl]-4-methylpentanoate

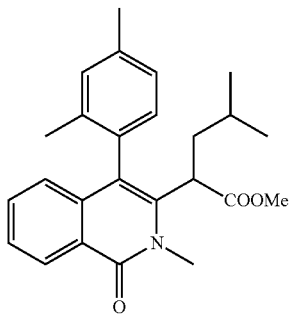 [SMILES: COC(=O)C(CC(C)C)c1c(-c2ccc(C)cc2C)c2ccccc2c(=O)n1C]

A solution of methyl 2-(4-(2,4-dimethylphenyl)-2-methyl-1-oxo-1,2-dihydroisoquinolin-3-yl)-4-methylpent-4-enoate (87 mg, 0.168 mmol, 94% yield) in ethyl acetate (2 mL) was treated with platinum(IV) oxide (8.12 mg, 0.036 mmol) and stirred for one hour at room temperature under an atmosphere of $H_2$. The mixture was filtered and concentrated. The residue was used crude in the next step (62 mg, 98%). $^1$H NMR (400 MHz, CHLOROFORM-d) δ ppm 8.43-8.57 (m, 1 H) 7.46 (td, J=4.59, 1.76 Hz, 2 H) 7.14-7.22 (m, 1 H) 7.06-7.13 (m, 1 H) 6.95-7.02 (m, 1 H) 6.78-6.91 (m, 1 H) 3.77-3.88 (m, 1 H) 3.67 (s, 3 H) 3.52 (s, 3 H) 2.40 (s, 3 H) 2.16-2.29 (m, 1 H) 2.05 (s, 3 H) 1.65-1.77 (m, 1 H) 1.39-1.52 (m, 1 H) 0.84-0.98 (m, 1 H) 0.77 (d, J=6.44 Hz, 3 H) 0.63 (d, J=6.44 Hz, 3 H); LC/MS (m/z) ES$^+$=392 (M+1).

Step C

2-[4-(2,4-dimethylphenyl)-2-methyl-1-oxo-1,2-dihydro-3-isoquinolinyl]-4-methylpentanoic acid

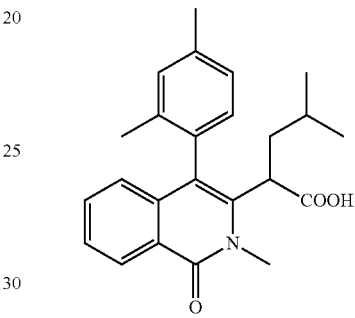

A solution of methyl methyl 2-(4-(2,4-dimethylphenyl)-2-methyl-1-oxo-1,2-dihydroisoquinolin-3-yl)-4-methylpentanoate (86 mg, 0.165 mmol, 92% yield) in tetrahydrofuran (THF) (2 mL) was treated with lithium hydroxide (1 mL, 2.000 mmol) and heated to 70° C. for 2 days. The mixture was cooled to room temperature and then quenched with saturated $NH_4Cl$ solution. The mixture was extracted with ethyl acetate, washed with saturated $NaHCO_3$ solution and brine, dried over $Na_2SO_4$, filtered and concentrated. The residue was purified by reverse phase hplc to afford the title product (42 mg, 68%). $^1$H NMR (400 MHz, CHLOROFORM-d) δ ppm 8.44-8.55 (m, 1 H) 7.42-7.53 (m, 2 H) 7.06-7.20 (m, 2 H) 6.96-7.03 (m, 1 H) 6.80-6.94 (m, 1 H) 3.86-4.09 (m, 1 H) 3.59 (s, 3 H) 2.41 (s, 3 H) 2.15-2.29 (m, 1 H) 1.92-2.12 (m, 3 H) 1.65-1.83 (m, 1 H) 1.18-1.25 (m, 1 H) 0.71-0.82 (m, 3 H) 0.51-0.68 (m, 3 H). LC/MS (m/z) ES$^+$=378 (M+1).

Scheme 15: General Route for Synthesis of Examples with $R^3$ = Alkoxy besides tert-Butoxy and Methylcyclobutoxy

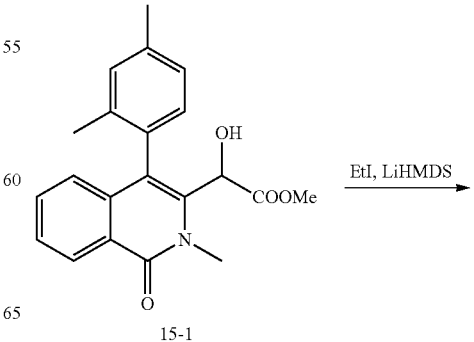

15-1

-continued

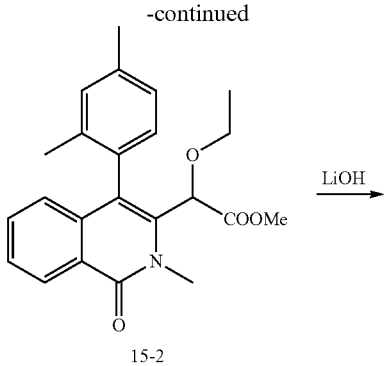

15-2

↓ LiOH

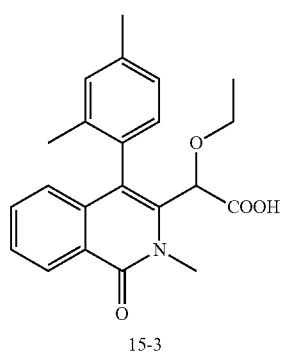

15-3

Example 218

Step A

Methyl [4-(2,4-dimethylphenyl)-2-methyl-1-oxo-1,2-dihydro-3-isoquinolinyl](ethyloxy)acetate

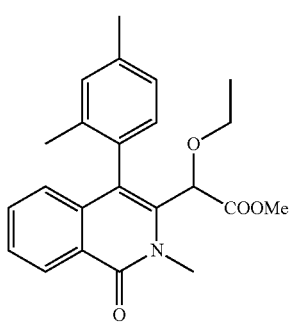 [SMILES: CCOC(C(=O)OC)c1c(-c2ccc(C)cc2C)c2ccccc2c(=O)n1C]

A solution of methyl 2-(4-(2,4-dimethylphenyl)-2-methyl-1-oxo-1,2-dihydroisoquinolin-3-yl)-2-hydroxyacetate (50 mg, 0.142 mmol) in Tetrahydrofuran (THF) (1 mL) was treated with LiHMDS (0.213 mL, 0.213 mmol) and iodoethane (0.069 mL, 0.854 mmol) at 0° C. The mixture was stirred at room temperature for 1 hour and then quenched with saturated $NH_4Cl$ solution. The mixture was extracted with ethyl acetate, washed with saturated $NaHCO_3$ solution and brine, dried over $Na_2SO_4$, filtered and concentrated. The residue was used crude in the next step without further purification (44 mg, 82%). $^1$H NMR (400 MHz, CHLOROFORM-d) δ ppm 8.47-8.55 (m, 1 H) 7.46-7.55 (m, 2 H) 7.06-7.21 (m, 3 H) 6.85-6.96 (m, 1 H) 4.87-4.98 (m, 1 H) 3.65-3.68 (m, 2 H) 3.66 (s, 3 H) 2.86-3.00 (m, 3 H) 2.42 (s, 3 H) 2.02 (s, 3 H) 1.10-1.24 (m, 3 H). LC/MS (m/z) $ES^+$=380 (M+1).

Step B

[4-(2,4-dimethylphenyl)-2-methyl-1-oxo-1,2-dihydro-3-isoquinolinyl](ethyloxy)acetic acid

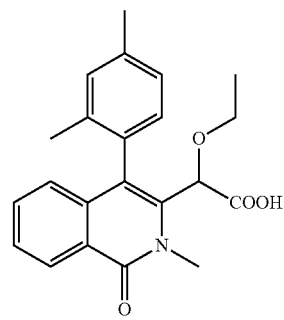 [SMILES: CCOC(C(=O)O)c1c(-c2ccc(C)cc2C)c2ccccc2c(=O)n1C]

A solution of methyl 2-(4-(2,4-dimethylphenyl)-2-methyl-1-oxo-1,2-dihydroisoquinolin-3-yl)-2-ethoxyacetate (52 mg, 0.116 mmol, 82% yield) in Tetrahydrofuran (THF) (1 mL) was treated with lithium borohydride (2 mL, 4.00 mmol), and heated at 70° C. for 2 days. The mixture was cooled to room temperature and quenched with saturated $NH_4Cl$. The mixture was acidified with HCl (1M) to pH 2.0, then extracted with ethyl acetate. The extracts were washed with saturated $NaHCO_3$ solution and brine, dried over $Na_2SO_4$, filtered and concentrated. The residue was purified by reverse phase HPLC to afford the title compound (33 mg, 77%). $^1$H NMR (400 MHz, CHLOROFORM-d) δ ppm 8.44-8.58 (m, 1 H) 7.46-7.63 (m, 2 H) 7.15-7.25 (m, 1 H) 7.03-7.15 (m, 2 H) 6.85-7.00 (m, 1 H) 4.94-5.13 (m, 1 H) 3.70 (d, J=2.73 Hz, 3 H) 3.41-3.55 (m, 2 H) 2.42 (s, 3 H) 1.95-2.13 (m, 3 H) 1.22 (t, J=6.93 Hz, 6 H). LC/MS (m/z) $ES^+$=366 (M+1).

Scheme 16: General Route for Synthesis of Examples with $R^7$ = Triazole using Click Chemistry

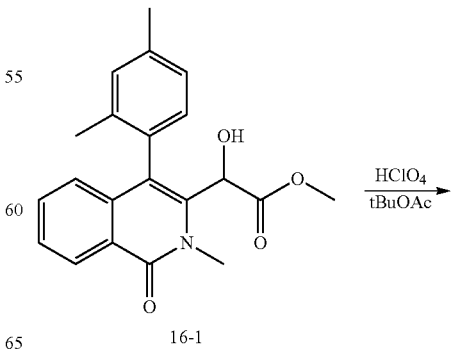

16-1

251
-continued

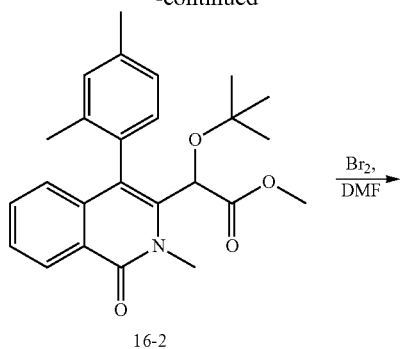
16-2

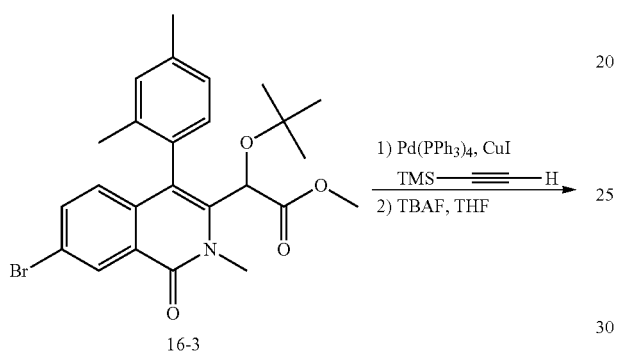
16-3

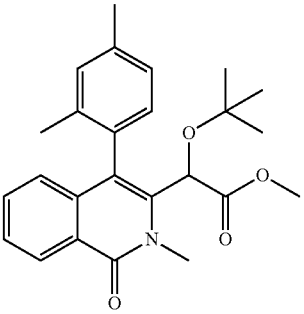
16-4

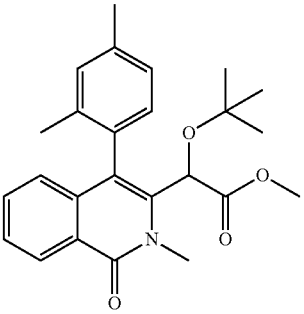
16-5

252
Example 219

[(1,1-dimethylethyl)oxy]{4-(2,4-dimethylphenyl)-7-[1-(2-hydroxyethyl)-1H-1,2,3-triazol-4-yl]-2-methyl-1-oxo-1,2-dihydro-3-isoquinolinyl}acetic acid

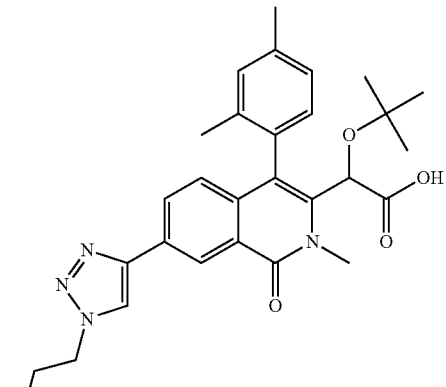

Step A methyl [(1,1-dimethylethyl)oxy][4-(2,4-dimethylphenyl)-2-methyl-1-oxo-1,2-dihydro-3-isoquinolinyl]acetate

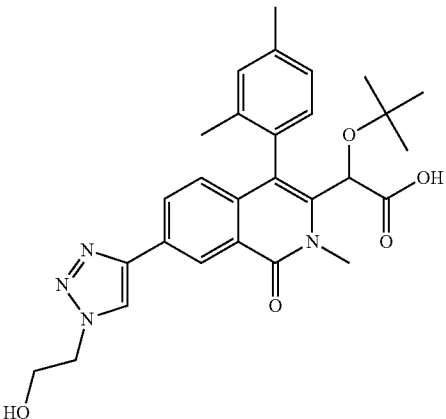 [SMILES: Cc1ccc(-c2c(C(OC(C)(C)C)C(=O)O)n(C)c(=O)c3cc(-c4cn(CCO)nn4)ccc23)c(C)c1]

A mixture of methyl 2-(4-(2,4-dimethylphenyl)-2-methyl-1-oxo-1,2-dihydroisoquinolin-3-yl)-2-hydroxyacetate (858 mg, 2.442 mmol) in t-butyl acetate (20 mL) was treated with perchloric acid (0.147 mL, 2.442 mmol) and stirred at ambient temperature overnight. LCMS indicated only 45% conversion to the desired product. The mixture was made basic by adding 3N sodium hydroxide and then extracted with ethyl acetate. The extracts were washed with water, then brine, dried over sodium sulfate, filtered and concentrated. The residue was purified on silica gel (0-50% ethyl acetate/hexanes gradient) to afford the desired product as a colorless residue (383 mg, 39%). LC/MS (m/z) ES+=408 (M+1).

Step B

[7-bromo-4-(2,4-dimethylphenyl)-2-methyl-1-oxo-1,2-dihydro-3-isoquinolinyl][(1,1-dimethylethyl)oxy]acetic acid

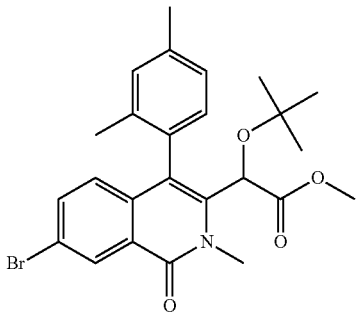 [SMILES: COC(=O)C(OC(C)(C)C)c1c(-c2ccc(C)cc2C)c2ccc(Br)cc2c(=O)n1C]

An ice cold mixture of methyl 2-(tert-butoxy)-2-(4-(2,4-dimethylphenyl)-2-methyl-1-oxo-1,2-dihydroisoquinolin-3-yl)acetate (383 mg, 0.940 mmol) in N,N-dimethylformamide (DMF) (5.0 mL) was treated slowly with a solution of bromine (0.053 mL, 1.034 mmol) in dichloromethane (dichloromethane) (280 µl) to give an orange solution. The ice bath was removed and the mixture, which was excluded from light by wrapping the reaction vessel with aluminum foil, was stirred at ambient temperature overnight. The mixture was cooled to 0° C., quenched with saturated sodium bicarbonate and extracted with ethyl acetate. The extracts were washed with water, then brine, dried over sodium sulfate, filtered and concentrated. The residue was purified on silica gel (0-50% ethyl acetate/hexanes gradient) to give the impure desired product as a white solid. The solid was re-purified by reverse phase chromatography to afford the desired product as a white solid (128 mg, 28%). LC/MS (m/z) ES+=486 (M+1).

Step C

[(1,1-dimethylethyl)oxy][4-(3,4-dimethylphenyl)-7-ethynyl-2-methyl-1-oxo-1,2-dihydro-3-isoquinolinyl]acetic acid

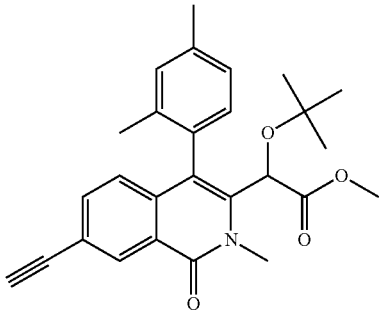 [SMILES: C#Cc1ccc2c(-c3ccc(C)cc3C)c(C(OC(C)(C)C)C(=O)OC)n(C)c(=O)c2c1]

A mixture of methyl [7-bromo-4-(2,4-dimethylphenyl)-2-methyl-1-oxo-1,2-dihydro-3-isoquinolinyl][(1,1-dimethylethyl)oxy]acetic acid (46.0 mg, 0.095 mmol), trimethylsilylacetylene (0.067 mL, 0.473 mmol), copper(I) iodide (3.60 mg, 0.019 mmol) and Hunig's base (0.066 mL, 0.378 mmol) in acetonitrile (1.5 mL) was treated with Pd(PPh$_3$)$_4$ (10.93 mg, 9.46 µmol) and then irradiated in the microwave at 120° C. for 20 minutes. LCMS indicated only 20% conversion to the desired product. N,N-dimethylformamide (DMF) (1.0 mL), trimethylsilylacetylene (0.067 mL, 0.473 mmol) and Pd(PPh$_3$)$_4$ (10.93 mg, 9.46 µmol) were added and the mixture was irradiated in the microwave at 120° C. for 30 minutes. LCMS indicated near complete conversion to the desired product. The mixture was diluted with ethyl acetate and washed successively with saturated sodium sulfate, water, and then brine. The organic phase was dried over sodium sulfate, filtered and concentrated to give a dark residue. The crude residue in tetrahydrofuran (THF) (1.500 mL) was treated with tetrabutylammoniumfluoride (0.142 mL, 0.142 mmol, 1 M solution in THF) at 0° C. and then stirred at ambient temperature for 5 minutes. The mixture was concentrated and purified by reverse phase chromatography to afford the title compound as a tan solid (26 mg, 64%). LC/MS (m/z) ES+=432 (M+1).

Step D 2-azidoethyl acetate

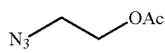

A mixture of 2-bromoethyl acetate (500 µl, 4.54 mmol) in N,N-dimethylformamide (DMF) (2.0 mL) was treated with sodium azide (295 mg, 4.54 mmol) and then heated to 70° C. for 2 hours. The mixture was diluted with water and then extracted with ether. The extracts were washed with water, then brine, dried over sodium sulfate, filtered and concentrated to afford the title compound as a colorless liquid. $^1$H NMR (400 MHz, CHLOROFORM-d) d=4.29-4.19 (m, 2 H), 3.53-3.44 (m, 2 H), 2.11 (s, 3 H).

Step E

[(1,1-dimethylethyl)oxy]{4-(2,4-dimethylphenyl)-7-[1-(2-hydroxyethyl)-1H-1,2,3-triazol-4-yl]-2-methyl-1-oxo-1,2-dihydro-3-isoquinolinyl}acetic acid

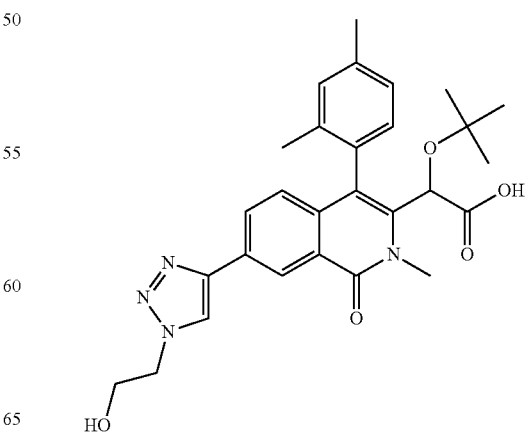

A mixture of methyl 2-(tert-butoxy)-2-(4-(2,4-dimethylphenyl)-7-ethynyl-2-methyl-1-oxo-1,2-dihydroisoquinolin-3-yl)acetate (26.0 mg, 0.060 mmol), 2-azidoethyl acetate (10.11 mg, 0.078 mmol), ascorbic acid (2.123 mg, 0.012 mmol) and copper sulfate monohydrate (1.923 mg, 0.012 mmol) in Ethanol (1.2 mL) and Water (0.2 mL) was irradiated in the microwave at 120° C. for 10 minutes. The mixture was diluted with ethyl acetate, then washed with saturated sodium bicarbonate and brine. The organic phase was dried over sodium sulfate, filtered and concentrated. The resulting crude residue in methanol (1.0 mL), tetrahydrofuran (THF) (1.0 mL) and water (0.2 mL) was treated with lithium hydroxide (28.8 mg, 1.205 mmol) and then heated to 60° C. for 90 minutes. The mixture was concentrated to dryness, water was added and the mixture was adjusted to pH 3-4 with 1N hydrochloric acid. The mixture was extracted with ethyl acetate; the extracts were washed with brine, dried over sodium sulfate, filtered and concentrated. The residue was purified by reverse phase chromatography to afford the desired product as a white solid. $^1$H NMR (400 MHz, CHLOROFORM-d) (atropisomers) δ=8.75-8.54 (m, 1 H), 8.14 (br. s., 2 H), 7.43 (d, J=7.6 Hz, 1 H), 7.15 (d, J=14.6 Hz, 2 H), 7.04-6.85 (m, 1 H), 5.44-5.15 (m, 1 H), 4.56 (m, 2 H), 4.14 (m, 2 H), 3.83-3.64 (m, 3 H), 2.43 (s, 3 H), 2.15-1.83 (m, 3 H), 1.29-0.97 (m, 9 H); LC/MS (m/z) ES$^+$=505 (M+1).

Administration and Formulation

In another embodiment, there is provided a pharmaceutical composition comprising a pharmaceutically acceptable diluent and a therapeutically effective amount of a compound of Formula (I) or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formulas I, II, or III may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, Na$_2$CO$_3$, K$_2$CO$_3$, NaH, and potassium-t-butoxide.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed., Mack Publishing Company, Easton, Pa., 1985, p. 1418, the disclosure of which is hereby incorporated by reference only with regards to the lists of suitable salts.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. D$_2$O, d$_6$-acetone, d$_6$-DMSO.

Compounds of Formula (I) containing one or more asymmetric carbon atoms can exist as two or more stereoisomers. Where a compound of Formula (I) contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labelled compounds of formula (I) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be administered as prodrugs. Thus, certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used, the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %. Representative pharmaceutical compositions containing at least one chemical entity described herein are described below.

The following examples serve to more fully describe the manner of making and using the above-described invention. It is understood that these examples in no way serve to limit the true scope of the invention, but rather are presented for illustrative purposes.

Biological Examples

Example 220

Anti-HIV Activity

MT4 Assay

Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", *Antimicrob. Agents Chemother.* 2007, 51: 3147-3154; and Pauwels et al., "Sensitive and rapid assay on MT-4 cells for the detection of antiviral compounds against the AIDS virus", *J. of Virological Methods* 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer glo (Promega, Madison, Wis.). $IC_{50}$s were determined from a 10 point dose response curve using 3-4-fold serial dilution for each compound, which spans a concentration range >1000 fold.

These values are plotted against the molar compound concentrations using the standard four parameter logistic equation:

$$y=((V\max*x\string^n)/(K\string^n+x\string^n))+Y2$$

Where:
Y2=minimum y n=slope factor
Vmax=maximum y x=compound concentration [M]
$K=EC_{50}$
When tested in the MT4 assay, certain compounds of Table 1 were found to have $IC_{50}$ values listed in Table 3

TABLE 3

| Example No. | HIV MT4 Assay $IC_{50}$ (μM) |
| --- | --- |
| 1 | 6.59 |
| 2 | 2.55 |
| 3 | 0.44 |
| 4 | 3.70 |
| 5 | 41.67 |
| 6 | 10.59 |
| 7 | 0.70 |
| 8 | 1.30 |
| 9 | 1.33 |
| 10 | 10.52 |
| 11 | 14.79 |
| 12 | 36.67 |
| 13 | 23.77 |
| 14 | 2.57 |
| 15 | 8.59 |
| 16 | 20.70 |
| 17 | 18.45 |
| 18 | 3.58 |
| 19 | 0.41 |
| 20 | 3.79 |
| 21 | 3.50 |
| 24 | 25.00 |
| 25 | 0.67 |
| 26 | 1.90 |
| 27 | 50.00 |
| 28 | 6.13 |
| 29 | 8.30 |
| 30 | 38.33 |
| 31 | 1.72 |
| 33 | 21.68 |
| 34 | 0.41 |
| 35 | 1.89 |
| 36 | 15.02 |
| 37 | 33.25 |
| 38 | 2.41 |
| 39 | 1.88 |
| 40 | 2.18 |
| 41 | 50.00 |
| 42 | 33.33 |
| 43 | 0.37 |
| 44 | 38.88 |
| 45 | 50.00 |
| 46 | 1.57 |
| 47 | 1.85 |
| 48 | 50.00 |
| 49 | 15.61 |
| 50 | 25.55 |
| 51 | 5.30 |
| 52 | 3.12 |
| 53 | 2.46 |
| 54 | 12.32 |
| 55 | 2.56 |
| 56 | 1.68 |
| 57 | 1.65 |
| 58 | 0.37 |
| 59 | 2.18 |
| 60 | 1.29 |
| 61 | 8.70 |
| 62 | 11.10 |
| 63 | 1.69 |
| 64 | 8.70 |
| 65 | 1.46 |
| 66 | 3.60 |
| 67 | 0.12 |
| 68 | 2.45 |
| 69 | 0.57 |
| 70 | 1.23 |
| 71 | 1.45 |
| 72 | 0.40 |
| 75 | 0.39 |
| 76 | 0.12 |
| 77 | 0.49 |
| 78 | 41.63 |
| 79 | 0.20 |
| 80 | 50.00 |
| 81 | 0.44 |
| 82 | 7.40 |
| 83 | 0.50 |
| 84 | 25.97 |
| 85 | 7.63 |
| 86 | 4.38 |
| 87 | 0.74 |
| 88 | 0.11 |
| 89 | 0.40 |
| 90 | 0.51 |
| 91 | 0.44 |
| 92 | 0.14 |
| 93 | 0.08 |
| 94 | 0.02 |
| 95 | 0.09 |
| 96 | 0.07 |
| 97 | 0.37 |
| 98 | 0.09 |
| 99 | 0.13 |
| 100 | 0.27 |
| 101 | 0.29 |
| 102 | 0.33 |
| 103 | 0.05 |
| 104 | 0.06 |
| 105 | 0.10 |
| 106 | 0.04 |
| 107 | 0.02 |
| 108 | 0.03 |
| 109 | 0.02 |
| 110 | 0.04 |
| 111 | 0.03 |
| 112 | 0.05 |
| 113 | 0.03 |
| 114 | 0.42 |
| 115 | 0.02 |
| 116 | 33.25 |

TABLE 3-continued

| Example No. | HIV MT4 Assay IC$_{50}$ (µM) |
|---|---|
| 117 | 4.09 |
| 118 | 41.63 |
| 119 | 2.13 |
| 120 | 0.23 |
| 121 | 0.94 |
| 122 | 50.00 |
| 123 | 1.22 |
| 124 | 0.13 |
| 125 | 0.32 |
| 126 | 0.36 |
| 127 | 1.14 |
| 128 | 0.38 |
| 129 | 0.20 |
| 130 | 3.75 |
| 131 | 0.02 |
| 132 | 0.31 |
| 133 | 0.93 |
| 134 | 0.07 |
| 135 | 0.14 |
| 136 | 0.10 |
| 137 | 1.03 |
| 138 | 0.07 |
| 139 | 0.03 |
| 140 | 0.11 |
| 141 | 0.03 |
| 142 | 0.03 |
| 143 | 0.03 |
| 144 | 0.04 |
| 145 | 0.11 |
| 146 | 0.26 |
| 147 | 0.02 |
| 148 | 0.05 |
| 149 | 1.17 |
| 150 | 0.16 |
| 151 | 1.22 |
| 152 | 0.43 |
| 153 | 3.88 |
| 154 | 2.09 |
| 155 | 13.33 |
| 156 | 0.80 |
| 157 | 41.63 |
| 158 | 50.00 |
| 159 | 0.03 |
| 160 | 41.63 |
| 161 | 7.21 |
| 162 | 4.19 |
| 163 | 0.11 |
| 164 | 0.46 |
| 165 | 0.10 |
| 166 | 0.02 |
| 167 | 3.71 |
| 168 | 0.26 |
| 169 | 22.50 |
| 170 | — |
| 171 | 1.30 |
| 172 | 0.27 |
| 173 | 0.12 |
| 174 | 0.05 |
| 175 | 0.07 |
| 176 | 0.05 |
| 178 | 50.00 |
| 179 | 50.00 |
| 180 | 12.43 |
| 181 | 0.27 |
| 182 | 1.38 |
| 183 | 3.61 |
| 184 | 31.44 |
| 185 | 37.44 |
| 186 | 50.00 |
| 187 | 22.91 |
| 188 | 3.70 |
| 189 | 0.04 |
| 190 | 0.32 |
| 191 | 0.35 |
| 192 | 0.35 |
| 193 | 1.34 |
| 194 | 0.04 |
| 195 | 0.14 |
| 196 | 1.16 |
| 197 | 1.46 |
| 198 | 0.04 |
| 199 | 0.09 |
| 200 | 0.11 |
| 201 | 0.04 |
| 202 | 0.02 |
| 203 | 0.03 |
| 204 | 0.03 |
| 205 | 0.16 |
| 206 | 0.16 |
| 207 | 0.08 |
| 208 | 0.04 |
| 209 | 0.02 |
| 210 | 0.01 |
| 211 | 0.02 |
| 212 | 50.00 |
| 213 | 5.25 |
| 214 | 4.84 |
| 215 | 11.10 |
| 216 | 36.63 |
| 217 | 13.05 |
| 218 | 33.25 |
| 219 | 11.10 |

Formulation Examples

The following are representative pharmaceutical formulations containing a compound of Formula (I) or a pharmaceutically acceptable salt thereof.

Formulation Example 1

Tablet formulation

The following ingredients are mixed intimately and pressed into single tablets.

| Ingredient | Quantity per tablet (mg) |
|---|---|
| compound | 1-500 mg/tablet |
| cornstarch | 50 |
| croscarmellose sodium | 25 |
| lactose | 120 |
| magnesium stearate | 5 |

Formulation Example 2

Capsule Formulation

The following ingredients are mixed intimately and loaded into a hard-shell gelatin capsule.

| Ingredient | Quantity per capsule (mg) |
|---|---|
| compound | 1-500 mg/tablet |
| Lactose, spray-dried | 148 |
| magnesium stearate | 2 |

Formulation Example 3

Suspension Formulation

The following ingredients are mixed to form a suspension for oral administration.

| Ingredient | Amount |
| --- | --- |
| compound | 0.4 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. (quantity sufficient) to 100 mL |

Formulation Example 4

Injectable Formulation

The following ingredients are mixed to form an injectable formulation.

| Ingredient | Amount |
| --- | --- |
| compound | 1.0 mg-50 mg |
| sodium acetate buffer solution, | 0.4M 2.0 mL |
| HCl (1N) or NaOH (1N) | q.s. to suitable pH |
| water (distilled, sterile) | q.s. to 20 mL |

Formulation Example 5

Suppository Formulation

A suppository of total weight 2.5 g is prepared by mixing the compound with Witepsol® H-15 (triglycerides of saturated vegetable fatty acid; Riches-Nelson, Inc., New York), and has the following composition:

| Ingredient | Amount |
| --- | --- |
| compound | 500 mg |
| Witepsol ® H-15 | balance |

Although the invention has been shown and described above with reference to some embodiments, those skilled in the art will readily appreciate that the specific experiments detailed are only illustrative of the invention. It should be understood that various modifications can be made without departing from the spirit of the invention.

For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims. Accordingly, the invention is limited only by the following claims. All publications, issued patents, patent applications, books and journal articles, cited in this application are each herein incorporated by reference in their entirety.

What is claimed is:

1. A compound comprising the structure of Formula (II):

Formula II

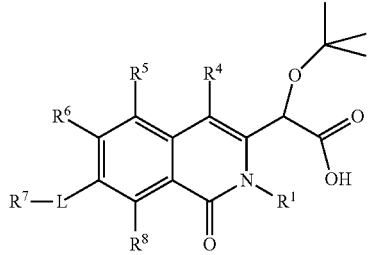

(II)

or a pharmaceutically acceptable salt thereof, wherein:

L is linker that is selected from the group consisting of a direct bond, methylene, —SO2—, and —C(O)NH—;

X is phenyl;

R4 is selected from the group consisting of phenyl, dihydrobenzopyranyl, naphthalenyl, pyridinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, and tetrahydropyridoquinolinyl;

R5, R6, and R7 are independently selected from H, methyl, ethyl, propyl, butyl, hydroxyl, fluoro, chloro, bromo, methoxy, ethoxy, propoxy, methoxyethoxy, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, and dimethylisoxazolyl;

R9 is independently selected from the group consisting of —H, methyl, ethyl, propyl, isopropyl, butyl, isobutyl, tert-butyl, pentyl, and septyl;

R10 is selected from the group consisting of —H, methyl, ethyl, propyl, isopropyl, butyl, isobutyl, tert-butyl, penty, and septyl;

R11, R12, and R13 are independently selected from the group consisting of —H, methyl, ethyl, methoxy, ethoxy, oxo, chloro, fluoro, bromo, trifluoromethyl, trifluoromethoxy, methylsulfonyl, —C(O)methyl, —C(O)R15, and methylmethoxy;

R14 is selected from the group consisting of chloro, fluoro, and bromo;

R15 is —N(R16)2;

R16 is independently selected from the group consisting of —H, methyl, ethyl, hydroxyl, methylsulfonyl, —SO2N(methyl)2, —C(O)NHmethyl, —C(O)R18, and —(X)(R11);

R17 is —OR9; and

R18 is —CO2R9.

2. A pharmaceutical composition comprising a pharmaceutically acceptable diluent and a therapeutically effective amount of a compound or salt as defined in claim 1.

3. A method for treating HIV a viral infection in a mammal comprising administering to a mammal, that has been diagnosed with said viral infection or is at risk of developing said viral infection, a compound or salt as defined in claim 1.

4. The method according to claim 3, further comprising administration of a therapeutically effective amount of one or more agents active against an HIV virus.

5. The method according to claim 4, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

* * * * *